US010357555B2

(12) United States Patent
Tupin et al.

(10) Patent No.: US 10,357,555 B2
(45) Date of Patent: Jul. 23, 2019

(54) MYCOBACTERIAL ANTIGEN VACCINE

(71) Applicant: TRANSGENE SA, Illkirch Graffenstaden (FR)

(72) Inventors: Emmanuel Tupin, Stockholm (SE); Romain Micol, Lyons (FR); Charles Antoine Coupet, Lyons (FR); Geneviève Inchauspe, Lyons (FR); Marie Gouanvic, Lyons (FR); Nathalie Silvestre, Ergersheim (FR); Jean-Baptiste Marchand, Obernai (FR); Cécile Beny, Cerisiers (FR)

(73) Assignee: TRANSGENE SA, Illkirch Graffenstaden (FR)

( * ) Notice: Subject to any disclaimer, the term of this patent is extended or adjusted under 35 U.S.C. 154(b) by 647 days.

(21) Appl. No.: 14/413,565

(22) PCT Filed: Jul. 10, 2013

(86) PCT No.: PCT/EP2013/064624
§ 371 (c)(1),
(2) Date: May 11, 2015

(87) PCT Pub. No.: WO2014/009438
PCT Pub. Date: Jan. 16, 2014

(65) Prior Publication Data
US 2015/0165014 A1 Jun. 18, 2015

(30) Foreign Application Priority Data

Jul. 10, 2012 (EP) .................................. 12305825
Dec. 7, 2012 (EP) .................................. 12306539
Jun. 3, 2013 (EP) .................................. 13305737

(51) Int. Cl.
*A61K 39/00* (2006.01)
*A61K 39/04* (2006.01)
*C07K 14/35* (2006.01)
*C07K 16/12* (2006.01)

(52) U.S. Cl.
CPC .............. *A61K 39/04* (2013.01); *C07K 14/35* (2013.01); *C07K 16/1289* (2013.01); *A61K 2039/51* (2013.01); *A61K 2039/53* (2013.01); *C07K 2319/00* (2013.01); *C07K 2319/40* (2013.01)

(58) Field of Classification Search
None
See application file for complete search history.

(56) References Cited

U.S. PATENT DOCUMENTS

| 6,204,026 | B1 * | 3/2001 | DesJardin | C12Q 1/689 435/6.1 |
|---|---|---|---|---|
| 6,892,139 | B2 * | 5/2005 | Eisenberg | G06F 19/18 435/6.16 |
| 7,670,609 | B2 * | 3/2010 | Shafferman | A61K 39/04 424/185.1 |
| 7,927,818 | B2 * | 4/2011 | Felgner | A61K 39/015 424/248.1 |
| 7,951,376 | B2 * | 5/2011 | Hill | C07K 14/465 424/184.1 |
| 8,114,614 | B2 * | 2/2012 | Felgner | A61K 39/015 424/248.1 |
| 8,252,288 | B2 * | 8/2012 | Hill | C07K 14/465 424/184.1 |
| 8,329,418 | B2 * | 12/2012 | Felgner | A61K 39/015 424/248.1 |
| 8,361,482 | B2 * | 1/2013 | Shafferman | A61K 39/04 424/185.1 |
| 8,445,662 | B2 * | 5/2013 | He | A61K 39/04 435/252.3 |

(Continued)

FOREIGN PATENT DOCUMENTS

WO WO 2003/000721 A1 1/2003
WO WO 2003/004520 A2 1/2003

(Continued)

OTHER PUBLICATIONS

Langermans et al, Vaccine 23 (2005) 2740-2750, Protection of macaques against Mycobacterium tuberculosis infection by a subunit vaccine based on a fusion protein of antigen 85B and ESAT-6, available online Dec. 15, 2004.*

(Continued)

*Primary Examiner* — Nita M. Minnifield
(74) *Attorney, Agent, or Firm* — Finnegan, Henderson, Farabow, Garrett & Dunner, L.L.P.

(57) ABSTRACT

The present invention relates generally to immunogenic combinations comprising at least five antigens of a *Mycobacterium* species as well as fusion thereof and nucleic acid molecules encoding such combined antigens and fusion. The present invention also relates to nucleic acid molecules, vectors, host cells and compositions comprising or encoding said combinations of mycobacterial antigens and fusion polypeptides as well as to methods for recombinantly producing them. The present invention also relates to methods of using said combinations of mycobacterial antigens, fusion polypeptides, vectors, host cells, compositions particularly for inducing or stimulating an immune response against a *Mycobacterium* infection or any disease caused by or associated with a *Mycobacterium* infection. The present invention also concerns antibodies directed to such mycobacterial antigens and fusion polypeptides that can be used in the diagnosis of a *Mycobacterium* infection and method of detection as well as kits of reagent comprising said combinations of mycobacterial antigens, fusion polypeptides, vectors, host cells, compositions or antibodies.

16 Claims, 16 Drawing Sheets
Specification includes a Sequence Listing.

(56) References Cited

U.S. PATENT DOCUMENTS

| | | | | |
|---|---|---|---|---|
| 8,486,414 | B2* | 7/2013 | Reed | A61K 39/04 424/192.1 |
| 8,703,151 | B2* | 4/2014 | Aagaard | A61K 39/04 424/184.1 |
| 8,883,431 | B2* | 11/2014 | Felgner | A61K 39/015 424/248.1 |
| 9,181,311 | B2* | 11/2015 | Spencer | C07K 14/435 |
| 9,339,534 | B2* | 5/2016 | Carroll | A61K 39/04 |
| 9,377,460 | B2* | 6/2016 | Lalvani | G01N 33/5695 |
| 9,494,586 | B2* | 11/2016 | Felgner | A61K 39/015 |
| 9,982,039 | B2* | 5/2018 | Carroll | A61K 39/04 |
| 10,004,793 | B2* | 6/2018 | Aagaard | A61K 39/04 |
| 10,010,595 | B2* | 7/2018 | Horwitz | A61K 39/04 |
| 2009/0110693 | A1* | 4/2009 | Hill | C07K 14/465 424/198.1 |
| 2009/0136534 | A1* | 5/2009 | Shafferman | A61K 39/04 424/190.1 |
| 2011/0117133 | A1* | 5/2011 | Shafferman | A61K 39/04 424/248.1 |
| 2012/0058162 | A1* | 3/2012 | Jin | A61K 39/12 424/400 |
| 2012/0282290 | A1* | 11/2012 | Spencer | C07K 14/435 424/190.1 |
| 2013/0142800 | A1* | 6/2013 | Carroll | A61K 39/04 424/139.1 |
| 2013/0344099 | A1* | 12/2013 | Luirink | C07K 14/245 424/192.1 |
| 2014/0212455 | A1* | 7/2014 | Dou | A61K 39/04 424/200.1 |
| 2014/0322264 | A1* | 10/2014 | Sadoff | A61K 39/04 424/199.1 |
| 2014/0377300 | A1* | 12/2014 | Anantha | C07K 14/35 424/190.1 |
| 2015/0165014 | A1* | 6/2015 | Tupin | A61K 39/04 424/190.1 |
| 2015/0211012 | A1* | 7/2015 | Joseph | C12N 15/70 424/200.1 |
| 2016/0213767 | A1* | 7/2016 | King | A61K 39/04 |
| 2016/0251415 | A1* | 9/2016 | Carroll | A61K 39/04 424/139.1 |
| 2016/0326236 | A1* | 11/2016 | Hall | A61K 39/04 |
| 2016/0331823 | A1* | 11/2016 | Marchand | A61K 39/04 |
| 2017/0246282 | A1* | 8/2017 | Nammalwar | A61K 39/04 |
| 2017/0269079 | A1* | 9/2017 | Vordermeier | G01N 33/5695 |
| 2017/0362284 | A1* | 12/2017 | Anantha | A61P 31/06 |
| 2018/0015158 | A1* | 1/2018 | Jin | A61K 39/12 |
| 2018/0016599 | A1* | 1/2018 | Evans | A61K 39/04 |
| 2018/0066043 | A1* | 3/2018 | Hall | A61K 39/04 |
| 2018/0161415 | A9* | 6/2018 | Jin | A61K 39/12 |

FOREIGN PATENT DOCUMENTS

| | | | |
|---|---|---|---|
| WO | WO 2003/035681 | A2 | 5/2003 |
| WO | WO 2004/006952 | A2 | 1/2004 |
| WO | WO 2006/053871 | A2 | 5/2006 |
| WO | WO 2006/072787 | A1 | 8/2006 |
| WO | WO 2006/104389 | A1 | 10/2006 |
| WO | WO 2006/136162 | A2 | 12/2006 |
| WO | WO 2008/124647 | A2 | 10/2008 |
| WO | WO 2009/070700 | | 6/2009 |
| WO | WO 2009/070700 | A1 * | 6/2009 |
| WO | WO-2009070700 | A1 * | 6/2009 ............ A61K 39/04 |
| WO | WO 2011/144951 | A1 | 11/2011 |
| WO | WO 2012/057904 | A1 | 5/2012 |

OTHER PUBLICATIONS

Morris et al, Vaccine 2000, 18:2155-2163.*

Aagaard, C., et al., "Protection and Polyfunctional T Cells Induced by Ag85B-TB10.4/IC31® against *Mycobacterium tuberculosis* Is Highly Dependent on the Antigen Dose," *PLoS One*, 4:1-8, (2009).

Aagaard, C., et al., "A multistage tuberculosis vaccine that confers efficient protection before and after exposure," *Nature Med.*, 17:189-94, (2011).

Abel, B., et al., "The Novel Tuberculosis Vaccine, AERAS-402, Induces Robust and Polyfuncitional $CD4^+$ and $CD8^+$ T Cells in Adults," *Am J Respir Crit Care Med*, 181:1407-1417, (2010).

Andersen, P., "Vaccine strategies against latent tuberculosis infection," *Trends in Microbiology*, 19:1-7, (2006).

Andersen, P., "Tuberculosis vaccines an update," *Nature*, 5:484, (2007).

Baldwin, S.L., et al., "Intradermal immunization improves protective efficacy of a novel TB vaccine candidate," *Vaccine*, 27:3063-3071, (2009).

Bertholet, S., et al., "Identification of Human T Cell Antigens for the Development of Vaccines against Mycobacterium tuberculosis[1]," *The Journal of Immunology*, 181:1407-1417, (2009).

Bertholet, S. et al., "A Defined Tuberculosis Vaccine Candidate Boosts BCG and Protects Against Multidrug Resistant Mycobacterium tuberculosis," *Sci Transl Med*, 2:1-29, (2010).

Chen, L., et al., "The development and preliminary evaluation of a new Mycobacterium tuberculosis vaccine comprising Ag85b, HspX and CFP-10:ESAT-6 fusion protein with CpG DNA and aluminum hydroxide adjuvants," *FEMS Immunol Med Microbiol*, 59:42-52, (2010).

Cole, S.T., et al., "Deciphering the biology of Mycobacterium tuberculosis from the complete genome sequence," *Nature*, 393:537-544, (1998).

Delogu, G. et al., "The quest for a new vaccine against tuberculosis," *J Infec Developing Countrie*, 3:5-15, (2009).

Dietrich, J., et al., "Synergistic Effect of Bacillus Calmette Guerin and a Tuberculosis Subunit Vaccine in Cationic Liposomes: Increased Immunogenicity and Protection," *The Journal of Immunology*, 178:3721-3730, (2007).

Goonetileke, N.P., et al., "Enhanced Immunogenicity and Protective Efficacy Against *Mycobacterium tuberculosis of* Bacille Calmette-Guérin Vaccine Using Mucosal Administration and Boosting with a Recombinant Modified Vaccinia Virus Ankara[1]," *The Journal of Immunology*, 171:1602-1609, (2003).

Grode, L., et al., "Increased vaccine efficacy against tuberculosis of recombinant *Mycobacterium bovis* bacille Calmette-Guérin mutants that secrete listeriolysin," *J Clin Invest*, 115:2472-2479, (2005).

Houghton, R.L., et al., "Use of Multiepitope Polyproteins in Serodiagnosis of Active Tuberculosis," *Clin & Diag Lab Immunol*, 9:883-891, (2002).

International Search Report for PCT/EP2013/064624 dated Feb. 18, 2014.

Langermans, J.A.M., et al., "Protection of macaques against *Mycobacterium tuberculosis* infection by a subunit vaccine based on a fusion protein of antigen 85B and ESAT-6," *Vaccine*, 23:2740-2750, (2005).

Lin, P.L., et al., "The multistage vaccine H56 boosts the effects of BCG to protect cynomolgus macaques against active tuberculosis and reactivation of latent *Mycobacterium tuberculosis* infection" *J Clin of Inves.*, 122:303-314, (2012).

Magalhaes, I., et al., "rBCG Induces Strong Antigen-Specific T Cell Responses in Rhesus Macaques in a Prime-Boost Setting with an Adenovirus 35 Tuberculosis Vaccine Vector," PLoS One, 3:e3790, (2008).

McShane, H., et al., "Recombinant modified vaccinia virus Ankara expressing antigen 85A boosts BCg-primed and naturally acquired antimycobacterial immunity in humans," *Nature Med*, 10:1240-2750, (2004).

Mollenkopf, H.J., et al., "Applicatoin of Mycobacterial Proteomic to Vaccine Design: Improved Protection by Mycobacterium bovis BCG Prime-Rv3407 DNA Boost Vaccination against Tuberculosis," *Infec & Immuno*, 72:6471-6479, (2004).

Ottenhoff, T.H., et al., "Vaccines against Tuberculosis: Where Are We and Where Do We Need to Go?," PLoS, 8:e1002607, (2012).

Radošević, K., et al., "Protective Immune Responses to a Recombinant Adenovirus Type 35 Tuberculosis Vaccine in Two Mouse Strains: CD4 and CD8 T-Cell Epitope Mapping and Role of Gamma Interferon," *Infec. & Immun.*, 75:4105-4115, (2007).

(56) References Cited

OTHER PUBLICATIONS

Rook, G.A.W, et al., "Immunotherapeutics for Tuberculosis in Experimental Animals: Is There a Common Pathway Activated by Effective Protocols?," *J Infec Dis*, 196:191-198, (2007).
Scriba, T.J., et al., "Modified vaccinia Ankara-expressing Ag85A, a novel tuberculosis vaccine, is safe in adolescents and children, and induces polyfunctional CD4+ T cells," *Eur J Immunol*, 40:279-290, (2010).
Thaiss, C.A., et al., "Toward Novel Vaccines Against Tuberculosis: Current Hopes and Obstacles," *Yale J of Biol & Med*, 83:209-215, (2010).
Van Dissel, J.T. et al., "Ag85B-ESAT-6 adjuvanted with IC31® promotes strong and long-lived Mycobacterium tuberculosis specific T cell responses in naïve human volunteers," Vaccine, 28:3571-3581, (2010).
Van Dissel, J.T. et al., Ag85B-EST-6 adjuvanted with IC31® promotes strong and long-lived Mycobacterium tuberculosis specific T cell responses in volunteers with previous BCG vaccination or tuberculosis infection, *Vaccine*, 29:2100-2109, (2011).
Von Eschen, K., et al., "The candidate tuberculosis vaccine Mtb72F/AS02A," *Human Vaccine*, 5:375-482, (2009).
Yeremeev, V.V., et al., "Proteins of the Rpf Family: Immune Cell reactivity and Vaccination Efficacy against Tuberculosis in Mice," *Infection and Immunity*, 71:4789-4794, (2003).

\* cited by examiner pTG18295: Flag-Rv0569-Rv1813-Rv3407-Rv3478-Rv1807-cMyc-His (cytoplasmic version of pTG18269): 112,9 KDa
pTG18296: Flag-Ag85B-TB10.4-ESAT6-cMyc-His (cytoplasmic version of pTG18266): 53,8 Kda
pTG18297: Flag-RpfB-Dhyb-Ag85B-TB10.4-ESAT6-cMyc-His (cytoplasmic version of pTG18268): 90 KDa
pTG18307: Flag-RpfB-Dhyb-cMyc-His (cytoplasmic version of pTG18267): 39,3 KDa pTG18268: SR-Flag-RpfB-Dhyb-Ag85B-TB10,4-ESAT6-cMyc-TMRv1-His/ MW: 99,7kDA
pTG18266: SR-Flag-Ag85B-TB10,4-ESAT6-cMyc-TMR-His MW:63,6kDa
pTG18296: Flag-Ag85B-TB10,4-ESAT6-cMyc-His (cassette2delSR-TMR) MW:53,8kDA
pTG18297: Flag-RpfB-Dhyb-Ag85B-TB10,4-ESAT6-cMyc-His (cassette4 delSR-TMR) MW: 90kDA
pTG18324: SF-Flag- Rv2029-TB10.4-ESAT6-Rv0111del1TM-cMyc-His/ MW:90,6 kDa
pTG18315: TB10,4 MW:13,5kDA

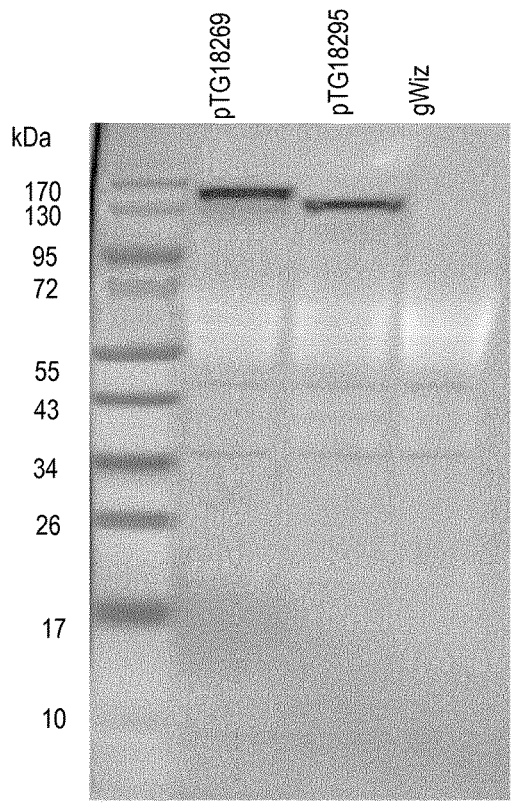
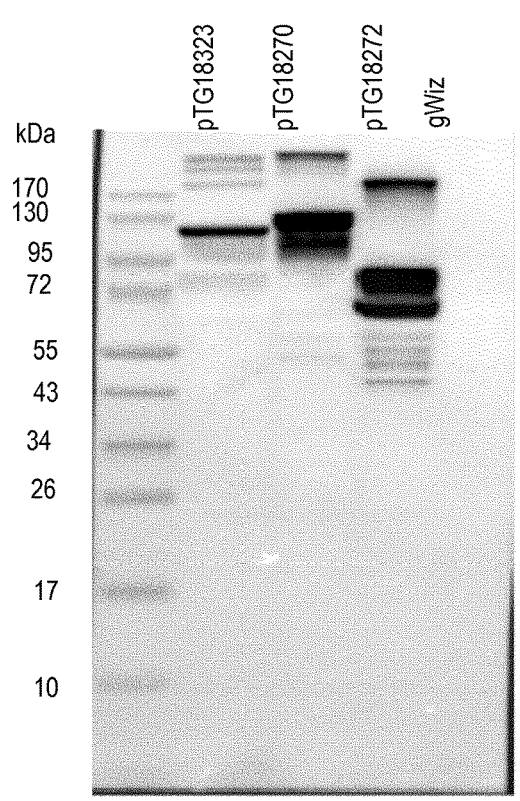
Fig. 4B
Fig. 4C
pTG18269: SR-Flag-Rv0569-Rv1813-Rv3407-RV3478-Rv1807-cMyc-TMRv2-His/ MW: 122kDA
pTG18295: Flag-Rv0569-Rv1813-RV3407-Rv3478-Rv1807-cMyc-His (cassettte5 del SR-TMR) MW: 112,9kDA
pTG18323: SF-Flag-Rv2029-Rv2626-Rv1733-Rv0111del1TM-cMyc-His/ MW:101,5kDa
pTG18270: SR-Flag-Ag85B-RV2626-RpfB-Dhyb-RV1733-cMyc-His/ MW:103,5kDa
pTG18272: SR-Flag-Ag85B-Rv2626-Rv1733-cMyc-His/ MW:67,3kDa
pTG18324: SF-Flag- Rv2029-TB10.4-ESAT6-Rv0111del1TM-cMyc-His/ MW:90,6 kDa

Fig. 9A  Rv2626
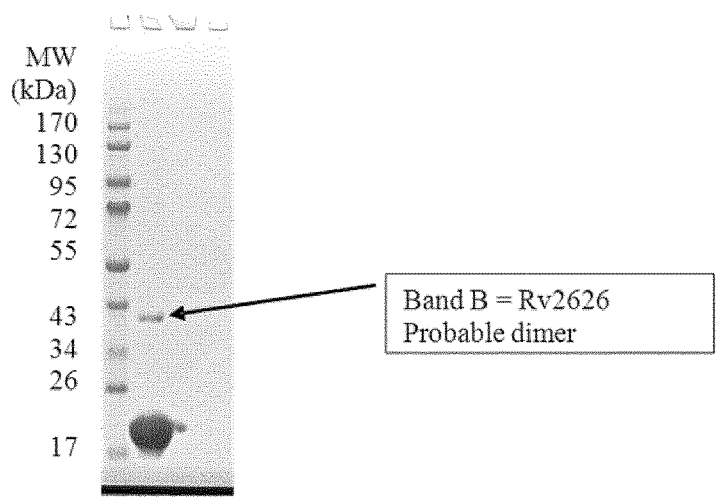
Fig. 9B  RPFB-Dhyb
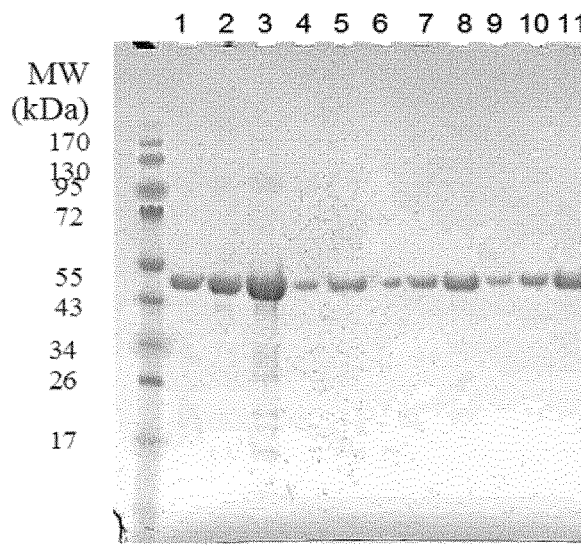
Lanes 1 to 8: intermediate fractions of purification
Lanes 9 to 11: final pool 5, 10 and 15 μL
Fig. 9C  TB10.4
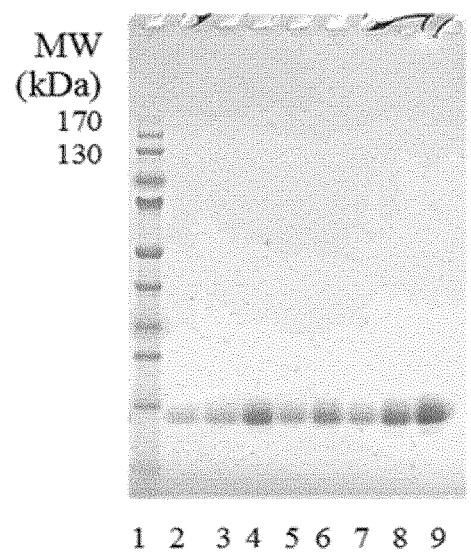
Lane 1: MW
Lanes 1 to 6: intermediate fractions of purification
Lanes 7 to 9: 1, 3 and 6 μL of the final pool Figure 10
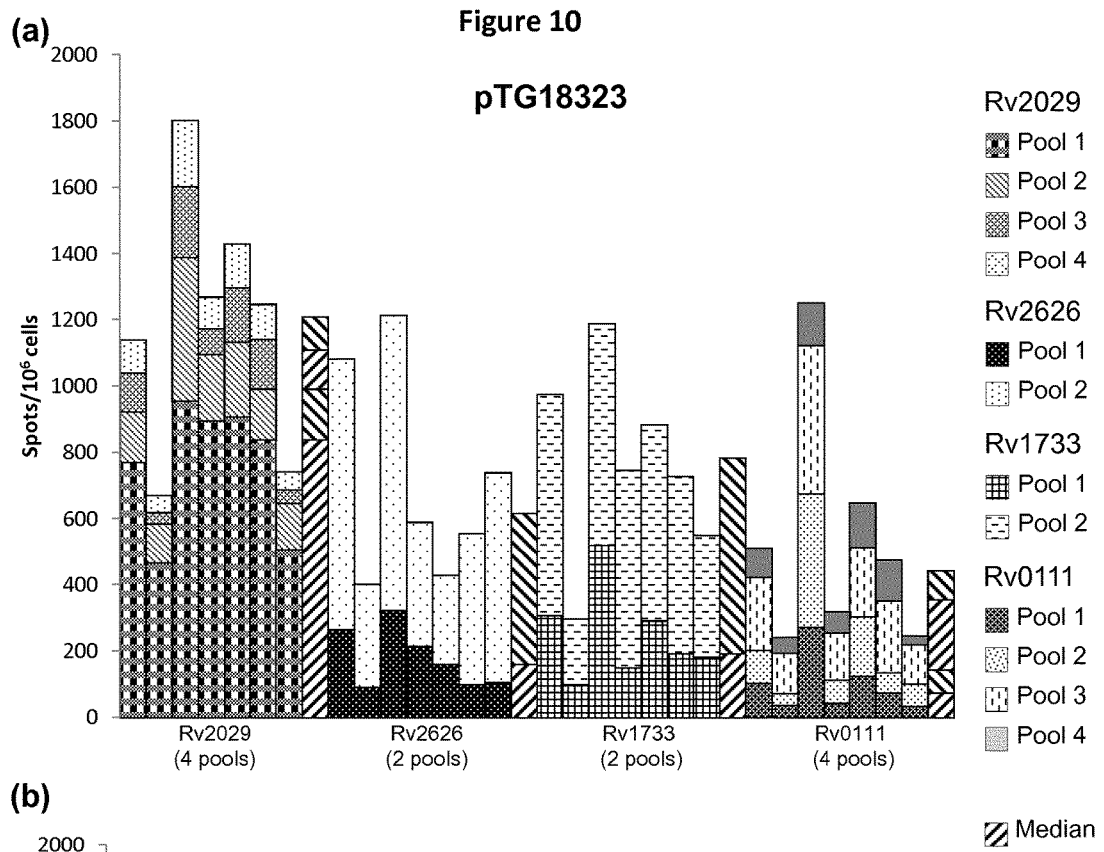
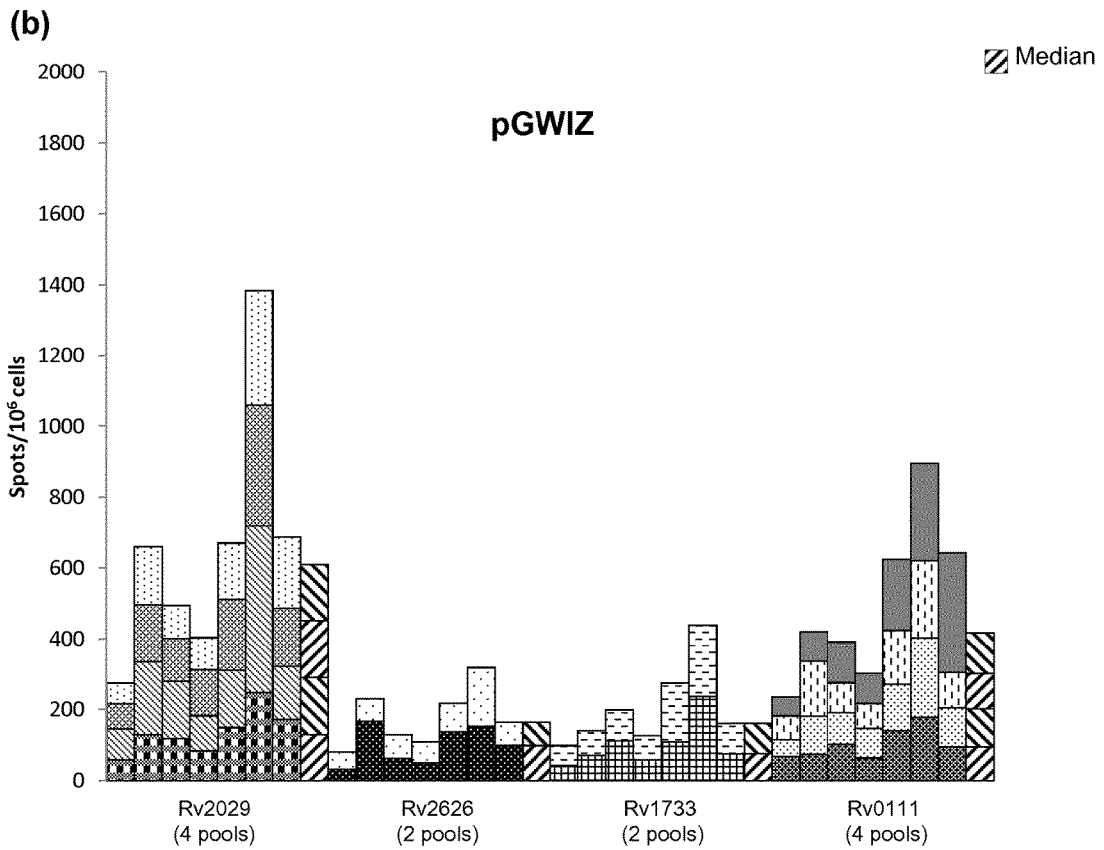

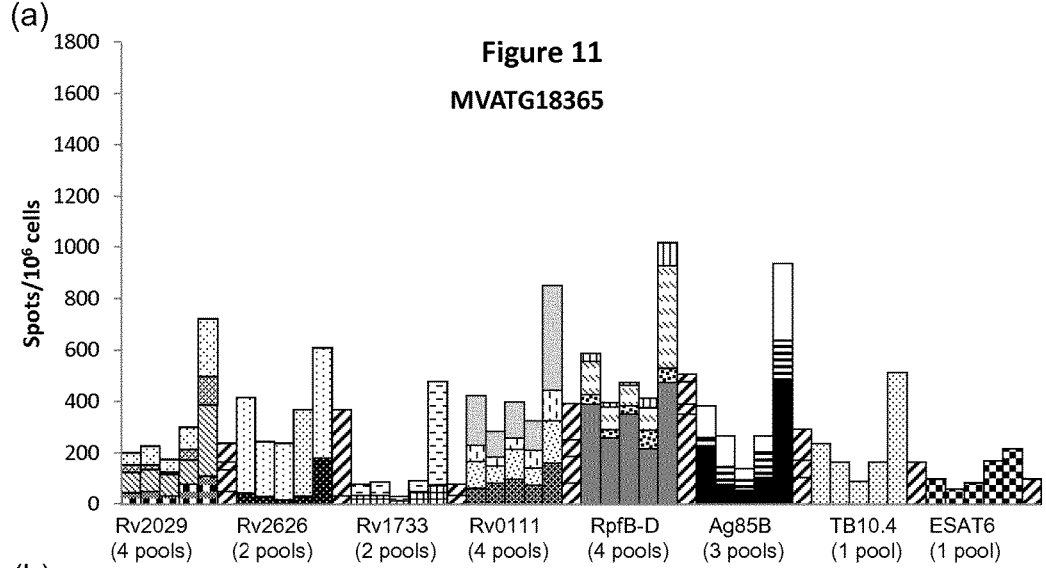
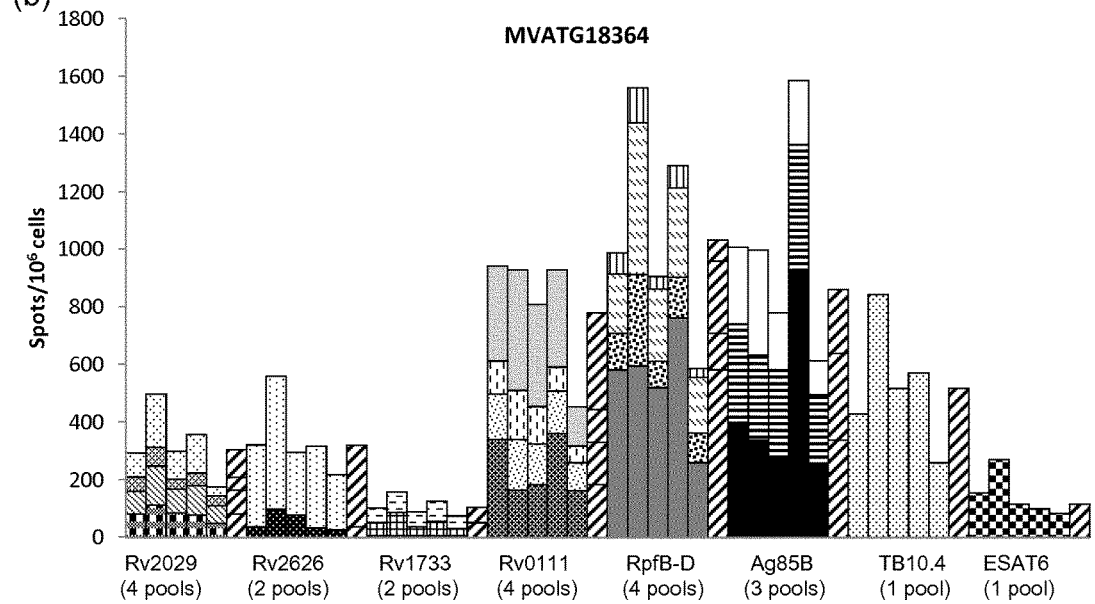
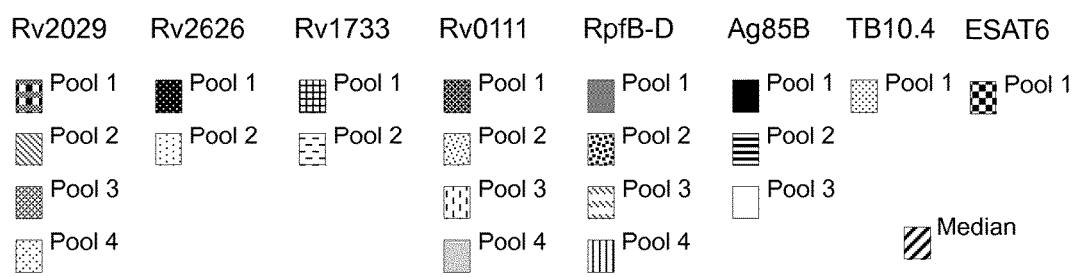
Figure 11

Figure 12

| | |
|---|---|
| - | Median < cut-off |
| + | x1 < median < x2 cut-off |
| ++ | x2 < median < x3 cut-off |
| +++ | median > x3 cut-off |

| | Vaccine | Latent | | | | | | | | Resuscitation | Active | | | |
|---|---|---|---|---|---|---|---|---|---|---|---|---|---|---|
| | | Rv1733 | Rv2029 | Rv2626 | Rv0111 | Rv0569 | Rv1807 | Rv1813 | Rv3407 | RpfB-D hyb | Rv3478 | Ag85B | ESAT6 | TB10.4 |
| by TB phase | MVATG18355 | - | - | ++ | - | | | | | | | | | |
| | MVATG18364 | - | - | ++ | +++ | | | | | +++ | | +++ | - | +++ |
| | MVATG18365 | - | - | +++ | - | | | | | +++ | | - | - | + |
| | MVATG18377 | - | + | ++ | ++ | - | + | + | ++ | +++ | +++ | ++ | + | ++ |
| | MVATG18379 | - | - | ++ | ++ | - | - | - | - | +++ | + | + | + | ++ |
| | MVATG18376 | - | - | + | + | - | + | - | + | +++ | ++ | ++ | + | +++ |
| | MVATG18378 | - | - | + | + | - | - | - | - | +++ | + | ++ | - | +++ |
| by biochemical rationale | MVATG18404 | - | + | +++ | ++ | | | | | | | +++ | ++ | ++ |
| | MVATG18417 | - | - | +++ | + | - | + | - | ++ | +++ | +++ | +++ | + | +++ |
| | MVATG18418 | - | - | +++ | +++ | - | + | - | + | +++ | + | +++ | + | +++ |

Figure 15

| | |
|---|---|
| - | Median < cut-off |
| + | x1 < median < x2 cut-off |
| ++ | x2 < median < x3 cut-off |
| +++ | median > x3 cut-off |

| | Vaccine | Latent | | | | | | | | Resuscitation | Active | | | |
|---|---|---|---|---|---|---|---|---|---|---|---|---|---|---|
| | | Rv1733 | Rv2029 | Rv2626 | Rv0111 | Rv0569 | Rv1807 | Rv1813 | Rv3407 | RpfB-D hyb | Rv3478 | Ag85B | ESAT6 | TB10.4 |
| HLA-A2 | MVATG18376 | - | - | - | - | + | + | + | + | +++ | + | +++ | + | - |
| HLA-A2 | MVATG18378 | - | - | - | + | + | + | ++ | - | +++ | + | +++ | +++ | + |
| C57BL/6 | MVATG18377 | - | - | - | - | - | +++ | - | - | +++ | ++ | +++ | + | - |
| C57BL/6 | MVATG18379 | - | - | - | - | + | ++ | - | - | ++ | + | +++ | ++ | + |
| C3H/HeN | MVATG18376 | - | + | + | - | - | - | - | - | - | - | - | - | - |
| C3H/HeN | MVATG18378 | - | ++ | ++ | - | - | - | - | - | - | - | - | - | - |
| C3H/HeN | MVATG18377 | + | +++ | +++ | - | - | + | + | + | + | - | - | - | - |
| C3H/HeN | MVATG18379 | + | +++ | ++ | - | - | - | - | - | - | - | - | - | - |

SEQUENCE LISTING

<160> NUMBER OF SEQ ID NOS: 102

<210> SEQ ID NO 1
<211> LENGTH: 685
<212> TYPE: PRT
<213> ORGANISM: Mycobacterium tuberculosis

<400> SEQUENCE: 1

```
Met Pro Ala Arg Ser Val Pro Arg Pro Arg Trp Val Ala Pro Val Arg
1               5                   10                  15

Arg Val Gly Arg Leu Ala Val Trp Asp Arg Pro Glu Arg Arg Ser Gly
            20                  25                  30

Ile Pro Ala Leu Asp Gly Leu Arg Ala Ile Ala Val Ala Leu Val Leu
        35                  40                  45

Ala Ser His Gly Gly Ile Pro Gly Met Gly Gly Phe Ile Gly Val
    50                  55                  60

Asp Ala Phe Phe Val Leu Ser Gly Phe Leu Ile Thr Ser Leu Leu Leu
65                  70                  75                  80

Asp Glu Leu Gly Arg Thr Gly Arg Ile Asp Leu Ser Gly Phe Trp Ile
                85                  90                  95

Arg Arg Ala Arg Arg Leu Leu Pro Ala Leu Val Leu Met Val Leu Thr
            100                 105                 110

Val Ser Ala Ala Arg Ala Leu Phe Pro Asp Gln Ala Leu Thr Gly Leu
        115                 120                 125

Arg Ser Asp Ala Ile Ala Ala Phe Leu Trp Thr Ala Asn Trp Arg Phe
    130                 135                 140

Val Ala Gln Asn Thr Asp Tyr Phe Thr Gln Gly Ala Pro Pro Ser Pro
145                 150                 155                 160

Leu Gln His Thr Trp Ser Leu Gly Val Glu Glu Gln Tyr Tyr Val Val
                165                 170                 175
```

-continued

```
Trp Pro Leu Leu Leu Ile Gly Ala Thr Leu Leu Ala Ala Arg Ala
            180                 185                 190

Arg Arg Arg Cys Arg Arg Ala Thr Val Gly Gly Val Arg Phe Ala Ala
        195                 200                 205

Phe Leu Ile Ala Ser Leu Gly Thr Met Ala Ser Ala Thr Ala Ala Val
    210                 215                 220

Ala Phe Thr Ser Ala Ala Thr Arg Asp Arg Ile Tyr Phe Gly Thr Asp
225                 230                 235                 240

Thr Arg Ala Gln Ala Leu Leu Ile Gly Ser Ala Ala Ala Leu Leu
                245                 250                 255

Val Arg Asp Trp Pro Ser Leu Asn Arg Gly Trp Cys Leu Ile Arg Thr
            260                 265                 270

Arg Trp Gly Arg Arg Ile Ala Arg Leu Leu Pro Phe Val Gly Leu Ala
        275                 280                 285

Gly Leu Ala Val Thr Thr His Val Ala Thr Gly Ser Val Gly Glu Phe
    290                 295                 300

Arg His Gly Leu Leu Ile Val Val Ala Gly Ala Ala Val Ile Val Val
305                 310                 315                 320

Ala Ser Val Ala Met Glu Gln Arg Gly Ala Val Ala Arg Ile Leu Ala
                325                 330                 335

Trp Arg Pro Leu Val Trp Leu Gly Thr Ile Ser Tyr Gly Val Tyr Leu
            340                 345                 350

Trp His Trp Pro Ile Phe Leu Ala Leu Asn Gly Gln Arg Thr Gly Trp
        355                 360                 365

Ser Gly Pro Ala Leu Phe Ala Ala Arg Cys Ala Ala Thr Val Val Leu
    370                 375                 380

Ala Gly Ala Ser Trp Trp Leu Ile Glu Gln Pro Ile Arg Arg Trp Arg
385                 390                 395                 400

Pro Ala Arg Val Pro Leu Leu Pro Leu Ala Ala Thr Val Ala Ser
                405                 410                 415

Ala Ala Ala Val Thr Met Leu Val Val Pro Val Gly Ala Gly Pro Gly
            420                 425                 430

Leu Arg Glu Ile Gly Leu Pro Pro Gly Val Ser Ala Val Ala Ala Val
        435                 440                 445

Ser Pro Ser Pro Pro Glu Ala Ser Gln Pro Ala Pro Gly Pro Arg Asp
    450                 455                 460

Pro Asn Arg Pro Phe Thr Val Ser Val Phe Gly Asp Ser Ile Gly Trp
465                 470                 475                 480

Thr Leu Met His Tyr Leu Pro Pro Thr Pro Gly Phe Arg Phe Ile Asp
                485                 490                 495

His Thr Val Ile Gly Cys Ser Leu Val Arg Gly Thr Pro Tyr Arg Tyr
            500                 505                 510

Ile Gly Gln Thr Leu Glu Gln Arg Ala Glu Cys Asp Gly Trp Pro Ala
        515                 520                 525

Arg Trp Ser Ala Gln Val Asn Arg Asp Gln Pro Asp Val Ala Leu Leu
    530                 535                 540

Ile Val Gly Arg Trp Glu Thr Val Asp Arg Val Asn Glu Gly Arg Trp
545                 550                 555                 560

Thr His Ile Gly Asp Pro Thr Phe Asp Ala Tyr Leu Asn Ala Glu Leu
                565                 570                 575

Gln Arg Ala Leu Ser Ile Val Gly Ser Thr Gly Val Arg Val Met Val
            580                 585                 590

Thr Thr Val Pro Tyr Ser Arg Gly Gly Glu Lys Pro Asp Gly Arg Leu
```

```
                    595                 600                 605

Tyr Pro Glu Asp Gln Pro Glu Arg Val Asn Lys Trp Asn Ala Met Leu
    610                 615                 620

His Asn Ala Ile Ser Gln His Ser Asn Val Gly Met Ile Asp Leu Asn
625                 630                 635                 640

Lys Lys Leu Cys Pro Asp Gly Val Tyr Thr Ala Lys Val Asp Gly Ile
                645                 650                 655

Lys Val Arg Ser Asp Gly Val His Leu Thr Gln Glu Gly Val Lys Trp
            660                 665                 670

Leu Ile Pro Trp Leu Glu Asp Ser Val Arg Val Ala Ser
        675                 680                 685

<210> SEQ ID NO 2
<211> LENGTH: 96
<212> TYPE: PRT
<213> ORGANISM: Mycobacterium tuberculosis

<400> SEQUENCE: 2

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

<210> SEQ ID NO 3
<211> LENGTH: 88
<212> TYPE: PRT
<213> ORGANISM: Mycobacterium tuberculosis

<400> SEQUENCE: 3

Met Lys Ala Lys Val Gly Asp Trp Leu Val Ile Lys Gly Ala Thr Ile
1               5                   10                  15

Asp Gln Pro Asp His Arg Gly Leu Ile Ile Glu Val Arg Ser Ser Asp
            20                  25                  30

Gly Ser Pro Pro Tyr Val Val Arg Trp Leu Glu Thr Asp His Val Ala
        35                  40                  45

Thr Val Ile Pro Gly Pro Asp Ala Val Val Thr Ala Glu Glu Gln
    50                  55                  60

Asn Ala Ala Asp Glu Arg Ala Gln His Arg Phe Gly Ala Val Gln Ser
65                  70                  75                  80

Ala Ile Leu His Ala Arg Gly Thr
                85

<210> SEQ ID NO 4
<211> LENGTH: 362
<212> TYPE: PRT
<213> ORGANISM: Mycobacterium tuberculosis

<400> SEQUENCE: 4

Met Leu Arg Leu Val Val Gly Ala Leu Leu Leu Val Leu Ala Phe Ala
1               5                   10                  15
```

Gly Gly Tyr Ala Val Ala Ala Cys Lys Thr Val Thr Leu Thr Val Asp
            20                  25                  30

Gly Thr Ala Met Arg Val Thr Thr Met Lys Ser Arg Val Ile Asp Ile
            35                  40                  45

Val Glu Glu Asn Gly Phe Ser Val Asp Asp Arg Asp Leu Tyr Pro
 50                  55                  60

Ala Ala Gly Val Gln Val His Asp Ala Asp Thr Ile Val Leu Arg Arg
 65                  70                  75                  80

Ser Arg Pro Leu Gln Ile Ser Leu Asp Gly His Asp Ala Lys Gln Val
                 85                  90                  95

Trp Thr Thr Ala Ser Thr Val Asp Glu Ala Leu Ala Gln Leu Ala Met
                100                 105                 110

Thr Asp Thr Ala Pro Ala Ala Ser Arg Ala Ser Arg Val Pro Leu
             115                 120                 125

Ser Gly Met Ala Leu Pro Val Val Ser Ala Lys Thr Val Gln Leu Asn
 130                 135                 140

Asp Gly Gly Leu Val Arg Thr Val His Leu Pro Ala Pro Asn Val Ala
 145                 150                 155                 160

Gly Leu Leu Ser Ala Ala Gly Val Pro Leu Leu Gln Ser Asp His Val
                 165                 170                 175

Val Pro Ala Ala Thr Ala Pro Ile Val Glu Gly Met Gln Ile Gln Val
             180                 185                 190

Thr Arg Asn Arg Ile Lys Lys Val Thr Glu Arg Leu Pro Leu Pro Pro
             195                 200                 205

Asn Ala Arg Arg Val Glu Asp Pro Glu Met Asn Met Ser Arg Glu Val
            210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
            275                 280                 285

Ala Gly Cys Glu Ala Gly Gly Asn Trp Ala Ile Asn Thr Gly Asn Gly
            290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
            325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
            355                 360

<210> SEQ ID NO 5
<211> LENGTH: 210
<212> TYPE: PRT
<213> ORGANISM: Mycobacterium tuberculosis

<400> SEQUENCE: 5

Met Ile Ala Thr Thr Arg Asp Arg Glu Gly Ala Thr Met Ile Thr Phe
 1               5                  10                  15

Arg Leu Arg Leu Pro Cys Arg Thr Ile Leu Arg Val Phe Ser Arg Asn

```
            20                  25                  30
Pro Leu Val Arg Gly Thr Asp Arg Leu Glu Ala Val Val Met Leu Leu
         35                  40                  45
Ala Val Thr Val Ser Leu Leu Thr Ile Pro Phe Ala Ala Ala Ala Gly
     50                  55                  60
Thr Ala Val Gln Asp Ser Arg Ser His Val Tyr Ala His Gln Ala Gln
 65                  70                  75                  80
Thr Arg His Pro Ala Thr Ala Thr Val Ile Asp His Glu Gly Val Ile
                 85                  90                  95
Asp Ser Asn Thr Thr Ala Thr Ser Ala Pro Pro Arg Thr Lys Ile Thr
             100                 105                 110
Val Pro Ala Arg Trp Val Val Asn Gly Ile Glu Arg Ser Gly Glu Val
         115                 120                 125
Asn Ala Lys Pro Gly Thr Lys Ser Gly Asp Arg Val Gly Ile Trp Val
     130                 135                 140
Asp Ser Ala Gly Gln Leu Val Asp Glu Pro Ala Pro Ala Arg Ala
145                 150                 155                 160
Ile Ala Asp Ala Ala Leu Ala Ala Leu Gly Leu Trp Leu Ser Val Ala
                 165                 170                 175
Ala Val Ala Gly Ala Leu Leu Ala Leu Thr Arg Ala Ile Leu Ile Arg
             180                 185                 190
Val Arg Asn Ala Ser Trp Gln His Asp Ile Asp Ser Leu Phe Cys Thr
         195                 200                 205
Gln Arg
    210

<210> SEQ ID NO 6
<211> LENGTH: 399
<212> TYPE: PRT
<213> ORGANISM: Mycobacterium tuberculosis

<400> SEQUENCE: 6

Leu Asp Phe Ala Thr Leu Pro Pro Glu Ile Asn Ser Ala Arg Met Tyr
 1               5                  10                  15
Ser Gly Ala Gly Ser Ala Pro Met Leu Ala Ala Ala Ser Ala Trp His
             20                  25                  30
Gly Leu Ser Ala Glu Leu Arg Ala Ser Ala Leu Ser Tyr Ser Ser Val
         35                  40                  45
Leu Ser Thr Leu Thr Gly Glu Glu Trp His Gly Pro Ala Ser Ala Ser
     50                  55                  60
Met Thr Ala Ala Ala Pro Tyr Val Ala Trp Met Ser Val Thr Ala
 65                  70                  75                  80
Val Arg Ala Glu Gln Ala Gly Ala Gln Ala Glu Ala Ala Ala Ala
                 85                  90                  95
Tyr Glu Ala Ala Phe Ala Ala Thr Val Pro Pro Val Ile Glu Ala
             100                 105                 110
Asn Arg Ala Gln Leu Met Ala Leu Ile Ala Thr Asn Val Leu Gly Gln
         115                 120                 125
Asn Ala Pro Ala Ile Ala Ala Thr Glu Ala Gln Tyr Ala Glu Met Trp
     130                 135                 140
Ser Gln Asp Ala Met Ala Met Tyr Gly Tyr Ala Gly Ala Ser Ala Ala
145                 150                 155                 160
Ala Thr Gln Leu Thr Pro Phe Thr Glu Pro Val Gln Thr Thr Asn Ala
                 165                 170                 175
```

```
Ser Gly Leu Ala Ala Gln Ser Ala Ile Ala His Ala Thr Gly Ala
            180                 185                 190

Ser Ala Gly Ala Gln Gln Thr Thr Leu Ser Gln Leu Ile Ala Ala Ile
        195                 200                 205

Pro Ser Val Leu Gln Gly Leu Ser Ser Thr Ala Ala Thr Phe Ala
    210                 215                 220

Ser Gly Pro Ser Gly Leu Leu Gly Ile Val Gly Ser Gly Ser Ser Trp
225                 230                 235                 240

Leu Asp Lys Leu Trp Ala Leu Leu Asp Pro Asn Ser Asn Phe Trp Asn
                245                 250                 255

Thr Ile Ala Ser Ser Gly Leu Phe Leu Pro Ser Asn Thr Ile Ala Pro
            260                 265                 270

Phe Leu Gly Leu Leu Gly Gly Val Ala Ala Asp Ala Ala Gly Asp
    275                 280                 285

Val Leu Gly Glu Ala Thr Ser Gly Gly Leu Gly Gly Ala Leu Val Ala
            290                 295                 300

Pro Leu Gly Ser Ala Gly Gly Leu Gly Gly Thr Val Ala Ala Gly Leu
305                 310                 315                 320

Gly Asn Ala Ala Thr Val Gly Thr Leu Ser Val Pro Pro Ser Trp Thr
                325                 330                 335

Ala Ala Ala Pro Leu Ala Ser Pro Leu Gly Ser Ala Leu Gly Gly Thr
            340                 345                 350

Pro Met Val Ala Pro Pro Ala Val Ala Gly Met Pro Gly Met
                355                 360                 365

Pro Phe Gly Thr Met Gly Gly Gln Gly Phe Gly Arg Ala Val Pro Gln
    370                 375                 380

Tyr Gly Phe Arg Pro Asn Phe Val Ala Arg Pro Pro Ala Ala Gly
385                 390                 395

<210> SEQ ID NO 7
<211> LENGTH: 143
<212> TYPE: PRT
<213> ORGANISM: Mycobacterium tuberculosis

<400> SEQUENCE: 7

Met Ile Thr Asn Leu Arg Arg Arg Thr Ala Met Ala Ala Ala Gly Leu
1               5                   10                  15

Gly Ala Ala Leu Gly Leu Gly Ile Leu Leu Val Pro Thr Val Asp Ala
                20                  25                  30

His Leu Ala Asn Gly Ser Met Ser Glu Val Met Met Ser Glu Ile Ala
            35                  40                  45

Gly Leu Pro Ile Pro Pro Ile Ile His Tyr Gly Ala Ile Ala Tyr Ala
        50                  55                  60

Pro Ser Gly Ala Ser Gly Lys Ala Trp His Gln Arg Thr Pro Ala Arg
65                  70                  75                  80

Ala Glu Gln Val Ala Leu Glu Lys Cys Gly Asp Lys Thr Cys Lys Val
                85                  90                  95

Val Ser Arg Phe Thr Arg Cys Gly Ala Val Ala Tyr Asn Gly Ser Lys
            100                 105                 110

Tyr Gln Gly Gly Thr Gly Leu Thr Arg Arg Ala Ala Glu Asp Asp Ala
        115                 120                 125

Val Asn Arg Leu Glu Gly Gly Arg Ile Val Asn Trp Ala Cys Asn
    130                 135                 140

<210> SEQ ID NO 8
```

```
<211> LENGTH: 325
<212> TYPE: PRT
<213> ORGANISM: Mycobacterium tuberculosis

<400> SEQUENCE: 8

Met Thr Asp Val Ser Arg Lys Ile Arg Ala Trp Gly Arg Arg Leu Met
1               5                   10                  15

Ile Gly Thr Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 9
<211> LENGTH: 339
<212> TYPE: PRT
<213> ORGANISM: Mycobacterium tuberculosis

<400> SEQUENCE: 9

Met Thr Glu Pro Ala Ala Trp Asp Glu Gly Lys Pro Arg Ile Ile Thr
1               5                   10                  15
```

Leu Thr Met Asn Pro Ala Leu Asp Ile Thr Thr Ser Val Asp Val Val
            20                  25                  30

Arg Pro Thr Glu Lys Met Arg Cys Gly Ala Pro Arg Tyr Asp Pro Gly
        35                  40                  45

Gly Gly Gly Ile Asn Val Ala Arg Ile Val His Val Leu Gly Gly Cys
    50                  55                  60

Ser Thr Ala Leu Phe Pro Ala Gly Gly Ser Thr Gly Ser Leu Leu Met
65                  70                  75                  80

Ala Leu Leu Gly Asp Ala Gly Val Pro Phe Arg Val Ile Pro Ile Ala
                85                  90                  95

Ala Ser Thr Arg Glu Ser Phe Thr Val Asn Gly Ser Arg Thr Ala Lys
            100                 105                 110

Gln Tyr Arg Phe Val Leu Pro Gly Pro Ser Leu Thr Val Ala Glu Gln
        115                 120                 125

Glu Gln Cys Leu Asp Glu Leu Arg Gly Ala Ala Ser Ala Ala Phe
    130                 135                 140

Val Val Ala Ser Gly Ser Leu Pro Pro Gly Val Ala Ala Asp Tyr Tyr
145                 150                 155                 160

Gln Arg Val Ala Asp Ile Cys Arg Arg Ser Ser Thr Pro Leu Ile Leu
                165                 170                 175

Asp Thr Ser Gly Gly Gly Leu Gln His Ile Ser Ser Gly Val Phe Leu
            180                 185                 190

Leu Lys Ala Ser Val Arg Glu Leu Arg Glu Cys Val Gly Ser Glu Leu
        195                 200                 205

Leu Thr Glu Pro Glu Gln Leu Ala Ala Ala His Glu Leu Ile Asp Arg
    210                 215                 220

Gly Arg Ala Glu Val Val Val Ser Leu Gly Ser Gln Gly Ala Leu
225                 230                 235                 240

Leu Ala Thr Arg His Ala Ser His Arg Phe Ser Ser Ile Pro Met Thr
                245                 250                 255

Ala Val Ser Gly Val Gly Ala Gly Asp Ala Met Val Ala Ala Ile Thr
            260                 265                 270

Val Gly Leu Ser Arg Gly Trp Ser Leu Ile Lys Ser Val Arg Leu Gly
        275                 280                 285

Asn Ala Ala Gly Ala Ala Met Leu Leu Thr Pro Gly Thr Ala Ala Cys
    290                 295                 300

Asn Arg Asp Asp Val Glu Arg Phe Phe Glu Leu Ala Ala Glu Pro Thr
305                 310                 315                 320

Glu Val Gly Gln Asp Gln Tyr Val Trp His Pro Ile Val Asn Pro Glu
                325                 330                 335

Ala Ser Pro

<210> SEQ ID NO 10
<211> LENGTH: 143
<212> TYPE: PRT
<213> ORGANISM: Mycobacterium tuberculosis

<400> SEQUENCE: 10

Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
            20                  25                  30

Ile Gly Ala Leu Pro Ile Cys Gly Asp Asp Arg Leu His Gly Met
        35                  40                  45

Leu Thr Asp Arg Asp Ile Val Ile Lys Gly Leu Ala Ala Gly Leu Asp
            50                  55                  60

Pro Asn Thr Ala Thr Ala Gly Glu Leu Ala Arg Asp Ser Ile Tyr Tyr
 65                  70                  75                  80

Val Asp Ala Asn Ala Ser Ile Gln Glu Met Leu Asn Val Met Glu Glu
                    85                  90                  95

His Gln Val Arg Arg Val Pro Val Ile Ser Glu His Arg Leu Val Gly
                100                 105                 110

Ile Val Thr Glu Ala Asp Ile Ala Arg His Leu Pro Glu His Ala Ile
            115                 120                 125

Val Gln Phe Val Lys Ala Ile Cys Ser Pro Met Ala Leu Ala Ser
        130                 135                 140

<210> SEQ ID NO 11
<211> LENGTH: 154
<212> TYPE: PRT
<213> ORGANISM: Mycobacterium tuberculosis

<400> SEQUENCE: 11

Met Thr Pro Gly Leu Leu Thr Thr Ala Gly Ala Gly Arg Pro Arg Asp
 1               5                  10                  15

Arg Cys Ala Arg Ile Val Cys Thr Val Phe Ile Glu Thr Ala Val Val
                20                  25                  30

Ala Thr Met Phe Val Ala Leu Leu Gly Leu Ser Thr Ile Ser Ser Lys
            35                  40                  45

Ala Asp Asp Ile Asp Trp Asp Ala Ile Ala Gln Cys Glu Ser Gly Gly
        50                  55                  60

Asn Trp Ala Ala Asn Thr Gly Asn Gly Leu Tyr Gly Gly Leu Gln Ile
 65                  70                  75                  80

Ser Gln Ala Thr Trp Asp Ser Asn Gly Val Gly Ser Pro Ala Ala
                85                  90                  95

Ala Ser Pro Gln Gln Gln Ile Glu Val Ala Asp Asn Ile Met Lys Thr
                100                 105                 110

Gln Gly Pro Gly Ala Trp Pro Lys Cys Ser Ser Cys Ser Gln Gly Asp
            115                 120                 125

Ala Pro Leu Gly Ser Leu Thr His Ile Leu Thr Phe Leu Ala Ala Glu
        130                 135                 140

Thr Gly Gly Cys Ser Gly Ser Arg Asp Asp
145                 150

<210> SEQ ID NO 12
<211> LENGTH: 99
<212> TYPE: PRT
<213> ORGANISM: Mycobacterium tuberculosis

<400> SEQUENCE: 12

Met Arg Ala Thr Val Gly Leu Val Glu Ala Ile Gly Ile Arg Glu Leu
 1               5                  10                  15

Arg Gln His Ala Ser Arg Tyr Leu Ala Arg Val Glu Ala Gly Glu Glu
                20                  25                  30

Leu Gly Val Thr Asn Lys Gly Arg Leu Val Ala Arg Leu Ile Pro Val
            35                  40                  45

Gln Ala Ala Glu Arg Ser Arg Glu Ala Leu Ile Glu Ser Gly Val Leu
        50                  55                  60

Ile Pro Ala Arg Arg Pro Gln Asn Leu Leu Asp Val Thr Ala Glu Pro
 65                  70                  75                  80

```
Ala Arg Gly Arg Lys Arg Thr Leu Ser Asp Val Leu Asn Glu Met Arg
                85                  90                  95

Asp Glu Gln
```

<210> SEQ ID NO 13
<211> LENGTH: 393
<212> TYPE: PRT
<213> ORGANISM: Mycobacterium tuberculosis

<400> SEQUENCE: 13

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
                20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
    50                  55                  60

Leu Met Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala Ala
                85                  90                  95

Ala Tyr Glu Thr Ala Tyr Arg Leu Thr Val Pro Pro Val Ile Ala
            100                 105                 110

Glu Asn Arg Thr Glu Leu Met Thr Leu Thr Ala Thr Asn Leu Leu Gly
        115                 120                 125

Gln Asn Thr Pro Ala Ile Glu Ala Asn Gln Ala Ala Tyr Ser Gln Met
    130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Ala Gln Gly Val Val Pro Ser Ser Lys Leu
    210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
        275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350
```

```
Ala Pro Gly His Met Leu Gly Gly Leu Pro Leu Gly His Ser Val Asn
            355                 360                 365

Ala Gly Ser Gly Ile Asn Asn Ala Leu Arg Val Pro Ala Arg Ala Tyr
        370                 375                 380

Ala Ile Pro Arg Thr Pro Ala Ala Gly
385                 390

<210> SEQ ID NO 14
<211> LENGTH: 95
<212> TYPE: PRT
<213> ORGANISM: Mycobacterium tuberculosis

<400> SEQUENCE: 14

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 15
<211> LENGTH: 293
<212> TYPE: PRT
<213> ORGANISM: artificial sequence
<220> FEATURE:
<223> OTHER INFORMATION: N-terminal truncated Rv0111 antigen (393-685)

<400> SEQUENCE: 15

Glu Gln Pro Ile Arg Arg Trp Arg Pro Ala Arg Val Pro Leu Leu Pro
1               5                   10                  15

Leu Ala Ala Ala Thr Val Ala Ser Ala Ala Ala Val Thr Met Leu Val
            20                  25                  30

Val Pro Val Gly Ala Gly Pro Gly Leu Arg Glu Ile Gly Leu Pro Pro
        35                  40                  45

Gly Val Ser Ala Val Ala Ala Val Ser Pro Ser Pro Pro Glu Ala Ser
    50                  55                  60

Gln Pro Ala Pro Gly Pro Arg Asp Pro Asn Arg Pro Phe Thr Val Ser
65                  70                  75                  80

Val Phe Gly Asp Ser Ile Gly Trp Thr Leu Met His Tyr Leu Pro Pro
                85                  90                  95

Thr Pro Gly Phe Arg Phe Ile Asp His Thr Val Ile Gly Cys Ser Leu
            100                 105                 110

Val Arg Gly Thr Pro Tyr Arg Tyr Ile Gly Gln Thr Leu Glu Gln Arg
        115                 120                 125

Ala Glu Cys Asp Gly Trp Pro Ala Arg Trp Ser Ala Gln Val Asn Arg
    130                 135                 140

Asp Gln Pro Asp Val Ala Leu Leu Ile Val Gly Arg Trp Glu Thr Val
145                 150                 155                 160

Asp Arg Val Asn Glu Gly Arg Trp Thr His Ile Gly Asp Pro Thr Phe
                165                 170                 175
```

Asp Ala Tyr Leu Asn Ala Glu Leu Gln Arg Ala Leu Ser Ile Val Gly
                180                 185                 190

Ser Thr Gly Val Arg Val Met Val Thr Thr Val Pro Tyr Ser Arg Gly
            195                 200                 205

Gly Glu Lys Pro Asp Gly Arg Leu Tyr Pro Glu Asp Gln Pro Glu Arg
        210                 215                 220

Val Asn Lys Trp Asn Ala Met Leu His Asn Ala Ile Ser Gln His Ser
225                 230                 235                 240

Asn Val Gly Met Ile Asp Leu Asn Lys Lys Leu Cys Pro Asp Gly Val
                245                 250                 255

Tyr Thr Ala Lys Val Asp Gly Ile Lys Val Arg Ser Asp Gly Val His
            260                 265                 270

Leu Thr Gln Glu Gly Val Lys Trp Leu Ile Pro Trp Leu Glu Asp Ser
        275                 280                 285

Val Arg Val Ala Ser
        290

<210> SEQ ID NO 16
<211> LENGTH: 254
<212> TYPE: PRT
<213> ORGANISM: artificial sequence
<220> FEATURE:
<223> OTHER INFORMATION: N and C-terminal truncated RpfB

<400> SEQUENCE: 16

Thr Val Asp Gly Thr Ala Met Arg Val Thr Thr Met Lys Ser Arg Val
1               5                   10                  15

Ile Asp Ile Val Glu Glu Asn Gly Phe Ser Val Asp Arg Asp Arg Asp
                20                  25                  30

Leu Tyr Pro Ala Ala Gly Val Gln Val His Asp Ala Asp Thr Ile Val
            35                  40                  45

Leu Arg Arg Ser Arg Pro Leu Gln Ile Ser Leu Asp Gly His Asp Ala
        50                  55                  60

Lys Gln Val Trp Thr Thr Ala Ser Thr Val Asp Glu Ala Leu Ala Gln
65                  70                  75                  80

Leu Ala Met Thr Asp Thr Ala Pro Ala Ala Ser Arg Ala Ser Arg
                85                  90                  95

Val Pro Leu Ser Gly Met Ala Leu Pro Val Val Ser Ala Lys Thr Val
            100                 105                 110

Gln Leu Asn Asp Gly Gly Leu Val Arg Thr Val His Leu Pro Ala Pro
        115                 120                 125

Asn Val Ala Gly Leu Leu Ser Ala Ala Gly Val Pro Leu Leu Gln Ser
130                 135                 140

Asp His Val Val Pro Ala Ala Thr Ala Pro Ile Val Glu Gly Met Gln
145                 150                 155                 160

Ile Gln Val Thr Arg Asn Arg Ile Lys Lys Val Thr Glu Arg Leu Pro
                165                 170                 175

Leu Pro Pro Asn Ala Arg Arg Val Glu Asp Pro Glu Met Asn Met Ser
            180                 185                 190

Arg Glu Val Val Glu Asp Pro Gly Val Pro Gly Thr Gln Asp Val Thr
        195                 200                 205

Phe Ala Val Ala Glu Val Asn Gly Val Glu Thr Gly Arg Leu Pro Val
    210                 215                 220

Ala Asn Val Val Val Thr Pro Ala His Glu Ala Val Arg Val Gly
225                 230                 235                 240

```
Thr Lys Pro Gly Thr Glu Val Pro Pro Val Ile Asp Gly Ser
                245                 250
```

<210> SEQ ID NO 17
<211> LENGTH: 148
<212> TYPE: PRT
<213> ORGANISM: artificial sequence
<220> FEATURE:
<223> OTHER INFORMATION: N-terminal truncated Rv1733 (63-210) without
      peptide signal

<400> SEQUENCE: 17

```
Ala Gly Thr Ala Val Gln Asp Ser Arg Ser His Val Tyr Ala His Gln
1               5                   10                  15

Ala Gln Thr Arg His Pro Ala Thr Ala Thr Val Ile Asp His Glu Gly
            20                  25                  30

Val Ile Asp Ser Asn Thr Thr Ala Thr Ser Ala Pro Pro Arg Thr Lys
        35                  40                  45

Ile Thr Val Pro Ala Arg Trp Val Val Asn Gly Ile Glu Arg Ser Gly
50                  55                  60

Glu Val Asn Ala Lys Pro Gly Thr Lys Ser Gly Asp Arg Val Gly Ile
65                  70                  75                  80

Trp Val Asp Ser Ala Gly Gln Leu Val Asp Glu Pro Ala Pro Pro Ala
                85                  90                  95

Arg Ala Ile Ala Asp Ala Ala Leu Ala Ala Leu Gly Leu Trp Leu Ser
            100                 105                 110

Val Ala Ala Val Ala Gly Ala Leu Leu Ala Leu Thr Arg Ala Ile Leu
        115                 120                 125

Ile Arg Val Arg Asn Ala Ser Trp Gln His Asp Ile Asp Ser Leu Phe
130                 135                 140

Cys Thr Gln Arg
145
```

<210> SEQ ID NO 18
<211> LENGTH: 339
<212> TYPE: PRT
<213> ORGANISM: artificial sequence
<220> FEATURE:
<223> OTHER INFORMATION: C-terminal truncated Rv1807 (1-339)

<400> SEQUENCE: 18

```
Leu Asp Phe Ala Thr Leu Pro Pro Glu Ile Asn Ser Ala Arg Met Tyr
1               5                   10                  15

Ser Gly Ala Gly Ser Ala Pro Met Leu Ala Ala Ser Ala Trp His
            20                  25                  30

Gly Leu Ser Ala Glu Leu Arg Ala Ser Ala Leu Ser Tyr Ser Ser Val
        35                  40                  45

Leu Ser Thr Leu Thr Gly Glu Glu Trp His Gly Pro Ala Ser Ala Ser
50                  55                  60

Met Thr Ala Ala Ala Pro Tyr Val Ala Trp Met Ser Val Thr Ala
65                  70                  75                  80

Val Arg Ala Glu Gln Ala Gly Ala Gln Ala Glu Ala Ala Ala Ala
                85                  90                  95

Tyr Glu Ala Ala Phe Ala Ala Thr Val Pro Pro Val Ile Glu Ala
            100                 105                 110

Asn Arg Ala Gln Leu Met Ala Leu Ile Ala Thr Asn Val Leu Gly Gln
        115                 120                 125

Asn Ala Pro Ala Ile Ala Ala Thr Glu Ala Gln Tyr Ala Glu Met Trp
```

```
                130                 135                 140
Ser Gln Asp Ala Met Ala Met Tyr Gly Tyr Ala Gly Ser Ala Ala
145                 150                 155                 160

Ala Thr Gln Leu Thr Pro Phe Thr Glu Pro Val Gln Thr Thr Asn Ala
                165                 170                 175

Ser Gly Leu Ala Ala Gln Ser Ala Ala Ile Ala His Ala Thr Gly Ala
                180                 185                 190

Ser Ala Gly Ala Gln Gln Thr Thr Leu Ser Gln Leu Ile Ala Ala Ile
                195                 200                 205

Pro Ser Val Leu Gln Gly Leu Ser Ser Thr Ala Ala Thr Phe Ala
210                 215                 220

Ser Gly Pro Ser Gly Leu Leu Gly Ile Val Gly Ser Gly Ser Ser Trp
225                 230                 235                 240

Leu Asp Lys Leu Trp Ala Leu Leu Asp Pro Asn Ser Asn Phe Trp Asn
                245                 250                 255

Thr Ile Ala Ser Ser Gly Leu Phe Leu Pro Ser Asn Thr Ile Ala Pro
                260                 265                 270

Phe Leu Gly Leu Leu Gly Gly Val Ala Ala Asp Ala Ala Gly Asp
                275                 280                 285

Val Leu Gly Glu Ala Thr Ser Gly Gly Leu Gly Gly Ala Leu Val Ala
                290                 295                 300

Pro Leu Gly Ser Ala Gly Gly Leu Gly Gly Thr Val Ala Ala Gly Leu
305                 310                 315                 320

Gly Asn Ala Ala Thr Val Gly Thr Leu Ser Val Pro Pro Ser Trp Thr
                325                 330                 335

Ala Ala Ala

<210> SEQ ID NO 19
<211> LENGTH: 109
<212> TYPE: PRT
<213> ORGANISM: artificial sequence
<220> FEATURE:
<223> OTHER INFORMATION: N-terminal truncated Rv1813 (35-143) without
      signal peptide

<400> SEQUENCE: 19

Ala Asn Gly Ser Met Ser Glu Val Met Met Ser Glu Ile Ala Gly Leu
1               5                   10                  15

Pro Ile Pro Pro Ile Ile His Tyr Gly Ala Ile Ala Tyr Ala Pro Ser
                20                  25                  30

Gly Ala Ser Gly Lys Ala Trp His Gln Arg Thr Pro Ala Arg Ala Glu
                35                  40                  45

Gln Val Ala Leu Glu Lys Cys Gly Asp Lys Thr Cys Lys Val Val Ser
                50                  55                  60

Arg Phe Thr Arg Cys Gly Ala Val Ala Tyr Asn Gly Ser Lys Tyr Gln
65                  70                  75                  80

Gly Gly Thr Gly Leu Thr Arg Arg Ala Ala Glu Asp Asp Ala Val Asn
                85                  90                  95

Arg Leu Glu Gly Gly Arg Ile Val Asn Trp Ala Cys Asn
                100                 105

<210> SEQ ID NO 20
<211> LENGTH: 286
<212> TYPE: PRT
<213> ORGANISM: artificial sequence
<220> FEATURE:
<223> OTHER INFORMATION: N-terminal truncated Ag85B (40-325) without
``` signal peptide

<400> SEQUENCE: 20

Ala Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65                  70                  75                  80

Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly
        275                 280                 285

<210> SEQ ID NO 21
<211> LENGTH: 313
<212> TYPE: PRT
<213> ORGANISM: artificial sequence
<220> FEATURE:
<223> OTHER INFORMATION: C-terminal truncated (2-314) and mutated D265N
      Rv2029

<400> SEQUENCE: 21

Thr Glu Pro Ala Ala Trp Asp Glu Gly Lys Pro Arg Ile Ile Thr Leu
1               5                   10                  15

Thr Met Asn Pro Ala Leu Asp Ile Thr Thr Ser Val Asp Val Val Arg
            20                  25                  30

Pro Thr Glu Lys Met Arg Cys Gly Ala Pro Arg Tyr Asp Pro Gly Gly
        35                  40                  45

Gly Gly Ile Asn Val Ala Arg Ile Val His Val Leu Gly Gly Cys Ser

```
                50                  55                  60
Thr Ala Leu Phe Pro Ala Gly Gly Ser Thr Gly Ser Leu Leu Met Ala
 65                  70                  75                  80

Leu Leu Gly Asp Ala Gly Val Pro Phe Arg Val Ile Pro Ile Ala Ala
                 85                  90                  95

Ser Thr Arg Glu Ser Phe Thr Val Asn Glu Ser Arg Thr Ala Lys Gln
            100                 105                 110

Tyr Arg Phe Val Leu Pro Gly Pro Ser Leu Thr Val Ala Glu Gln Glu
            115                 120                 125

Gln Cys Leu Asp Glu Leu Arg Gly Ala Ala Ser Ala Ala Phe Val
            130                 135                 140

Val Ala Ser Gly Ser Leu Pro Pro Gly Val Ala Ala Asp Tyr Tyr Gln
145                 150                 155                 160

Arg Val Ala Asp Ile Cys Arg Arg Ser Ser Thr Pro Leu Ile Leu Asp
                165                 170                 175

Thr Ser Gly Gly Gly Leu Gln His Ile Ser Ser Gly Val Phe Leu Leu
                180                 185                 190

Lys Ala Ser Val Arg Glu Leu Arg Glu Cys Val Gly Ser Glu Leu Leu
                195                 200                 205

Thr Glu Pro Glu Gln Leu Ala Ala His Glu Leu Ile Asp Arg Gly
            210                 215                 220

Arg Ala Glu Val Val Val Ser Leu Gly Ser Gln Gly Ala Leu Leu
225                 230                 235                 240

Ala Thr Arg His Ala Ser His Arg Phe Ser Ser Ile Pro Met Thr Ala
                245                 250                 255

Val Ser Gly Val Gly Ala Gly Asn Ala Met Val Ala Ala Ile Thr Val
                260                 265                 270

Gly Leu Ser Arg Gly Trp Ser Leu Ile Lys Ser Val Arg Leu Gly Asn
                275                 280                 285

Ala Ala Gly Ala Ala Met Leu Leu Thr Pro Gly Thr Ala Ala Cys Asn
            290                 295                 300

Arg Asp Asp Val Glu Arg Phe Phe Glu
305                 310

<210> SEQ ID NO 22
<211> LENGTH: 95
<212> TYPE: PRT
<213> ORGANISM: artificial sequence
<220> FEATURE:
<223> OTHER INFORMATION: catalytic domain RpfD

<400> SEQUENCE: 22

Ile Trp Asp Ala Ile Ala Gln Cys Lys Ser Gly Gly Asn Trp Ala Ala
  1               5                  10                  15

Asn Thr Gly Asn Gly Leu Tyr Gly Gly Leu Gln Ile Ser Gln Ala Ala
                 20                  25                  30

Trp Asp Ser Asn Gly Gly Val Gly Ser Pro Ala Ala Ser Pro Gln
             35                  40                  45

Gln Gln Ile Glu Val Ala Asp Asn Ile Met Lys Thr Ala Gly Pro Gly
         50                  55                  60

Ala Trp Pro Lys Cys Ser Ser Cys Ser Gln Gly Asp Ala Pro Leu Gly
 65                  70                  75                  80

Ser Leu Thr His Ile Leu Thr Phe Leu Ala Ala Glu Thr Gly Gly
                 85                  90                  95
```

```
<210> SEQ ID NO 23
<211> LENGTH: 65
<212> TYPE: PRT
<213> ORGANISM: artificial sequence
<220> FEATURE:
<223> OTHER INFORMATION: C-terminal truncated Rv3407 (2-66)

<400> SEQUENCE: 23

Arg Ala Thr Val Gly Leu Val Glu Ala Ile Gly Ile Arg Glu Leu Arg
1               5                   10                  15

Gln His Ala Ser Arg Tyr Leu Ala Arg Val Glu Ala Gly Glu Glu Leu
            20                  25                  30

Gly Val Thr Asn Lys Gly Arg Leu Val Ala Arg Leu Ile Pro Val Gln
        35                  40                  45

Ala Ala Glu Arg Ser Arg Glu Ala Leu Ile Glu Ser Gly Val Leu Ile
    50                  55                  60

Pro
65

<210> SEQ ID NO 24
<211> LENGTH: 352
<212> TYPE: PRT
<213> ORGANISM: artificial sequence
<220> FEATURE:
<223> OTHER INFORMATION: C-terminal truncated Rv3478 (2-353)

<400> SEQUENCE: 24

Val Asp Phe Gly Ala Leu Pro Pro Glu Ile Asn Ser Ala Arg Met Tyr
1               5                   10                  15

Ala Gly Pro Gly Ser Ala Ser Leu Val Ala Ala Ala Lys Met Trp Asp
            20                  25                  30

Ser Val Ala Ser Asp Leu Phe Ser Ala Ala Ser Ala Phe Gln Ser Val
        35                  40                  45

Val Trp Gly Leu Thr Val Gly Ser Trp Ile Gly Ser Ser Ala Gly Leu
    50                  55                  60

Met Ala Ala Ala Ser Pro Tyr Val Ala Trp Met Ser Val Thr Ala
65                  70                  75                  80

Gly Gln Ala Gln Leu Thr Ala Ala Gln Val Arg Val Ala Ala Ala Ala
            85                  90                  95

Tyr Glu Thr Ala Tyr Arg Leu Thr Val Pro Pro Val Ile Ala Glu
                100                 105                 110

Asn Arg Thr Glu Leu Met Thr Leu Thr Ala Thr Asn Leu Leu Gly Gln
            115                 120                 125

Asn Thr Pro Ala Ile Glu Ala Asn Gln Ala Ala Tyr Ser Gln Met Trp
        130                 135                 140

Gly Gln Asp Ala Glu Ala Met Tyr Gly Tyr Ala Ala Thr Ala Ala Thr
145                 150                 155                 160

Ala Thr Glu Ala Leu Leu Pro Phe Glu Asp Ala Pro Leu Ile Thr Asn
                165                 170                 175

Pro Gly Gly Leu Leu Glu Gln Ala Val Ala Val Glu Glu Ala Ile Asp
            180                 185                 190

Thr Ala Ala Ala Asn Gln Leu Met Asn Asn Val Pro Gln Ala Leu Gln
        195                 200                 205

Gln Leu Ala Gln Pro Ala Gln Gly Val Val Pro Ser Ser Lys Leu Gly
    210                 215                 220

Gly Leu Trp Thr Ala Val Ser Pro His Leu Ser Pro Leu Ser Asn Val
225                 230                 235                 240
```

```
Ser Ser Ile Ala Asn Asn His Met Ser Met Met Gly Thr Gly Val Ser
                245                 250                 255

Met Thr Asn Thr Leu His Ser Met Leu Lys Gly Leu Ala Pro Ala Ala
            260                 265                 270

Ala Gln Ala Val Glu Thr Ala Ala Glu Asn Gly Val Trp Ala Met Ser
        275                 280                 285

Ser Leu Gly Ser Gln Leu Gly Ser Ser Leu Gly Ser Ser Gly Leu Gly
    290                 295                 300

Ala Gly Val Ala Ala Asn Leu Gly Arg Ala Ala Ser Val Gly Ser Leu
305                 310                 315                 320

Ser Val Pro Pro Ala Trp Ala Ala Ala Asn Gln Ala Val Thr Pro Ala
                325                 330                 335

Ala Arg Ala Leu Pro Leu Thr Ser Leu Thr Ser Ala Ala Gln Thr Ala
            340                 345                 350
```

<210> SEQ ID NO 25
<211> LENGTH: 8
<212> TYPE: PRT
<213> ORGANISM: artificial sequence
<220> FEATURE:
<223> OTHER INFORMATION: FLAG tag

<400> SEQUENCE: 25

```
Asp Tyr Lys Asp Asp Asp Asp Lys
1               5
```

<210> SEQ ID NO 26
<211> LENGTH: 10
<212> TYPE: PRT
<213> ORGANISM: artificial sequence
<220> FEATURE:
<223> OTHER INFORMATION: MYC tag

<400> SEQUENCE: 26

```
Glu Gln Lys Leu Ile Ser Glu Glu Asp Leu
1               5                   10
```

<210> SEQ ID NO 27
<211> LENGTH: 6
<212> TYPE: PRT
<213> ORGANISM: artificial sequence
<220> FEATURE:
<223> OTHER INFORMATION: His tag

<400> SEQUENCE: 27

```
His His His His His His
1               5
```

<210> SEQ ID NO 28
<211> LENGTH: 589
<212> TYPE: PRT
<213> ORGANISM: artificial sequence
<220> FEATURE:
<223> OTHER INFORMATION: fusion "SS-Flag-Ag85B*-TB10.4-ESAT6-Myc-TM-His
      tag"

<400> SEQUENCE: 28

```
Met Val Pro Gln Ala Leu Leu Phe Val Pro Leu Leu Val Phe Pro Leu
1               5                   10                  15

Cys Phe Gly Lys Phe Pro Ile Asp Tyr Lys Asp Asp Asp Asp Lys Ala
            20                  25                  30

Phe Ser Arg Pro Gly Leu Pro Val Glu Tyr Leu Gln Val Pro Ser Pro
        35                  40                  45
```

```
Ser Met Gly Arg Asp Ile Lys Val Gln Phe Gln Ser Gly Gly Asn Asn
     50                  55                  60

Ser Pro Ala Val Tyr Leu Leu Asp Gly Leu Arg Ala Gln Asp Asp Tyr
 65                  70                  75                  80

Asn Gly Trp Asp Ile Asn Thr Pro Ala Phe Glu Trp Tyr Tyr Gln Ser
                 85                  90                  95

Gly Leu Ser Ile Val Met Pro Val Gly Gly Gln Ser Ser Phe Tyr Ser
                100                 105                 110

Asp Trp Tyr Ser Pro Ala Cys Gly Lys Ala Gly Cys Gln Thr Tyr Lys
            115                 120                 125

Trp Glu Thr Phe Leu Thr Ser Glu Leu Pro Gln Trp Leu Ser Ala Asn
        130                 135                 140

Arg Ala Val Lys Pro Thr Gly Ser Ala Ala Ile Gly Leu Ser Met Ala
145                 150                 155                 160

Gly Ser Ser Ala Met Ile Leu Ala Ala Tyr His Pro Gln Gln Phe Ile
                165                 170                 175

Tyr Ala Gly Ser Leu Ser Ala Leu Leu Asp Pro Ser Gln Gly Met Gly
            180                 185                 190

Pro Ser Leu Ile Gly Leu Ala Met Gly Asp Ala Gly Gly Tyr Lys Ala
        195                 200                 205

Ala Asp Met Trp Gly Pro Ser Ser Asp Pro Ala Trp Glu Arg Asn Asp
210                 215                 220

Pro Thr Gln Gln Ile Pro Lys Leu Val Ala Asn Asn Thr Arg Leu Trp
225                 230                 235                 240

Val Tyr Cys Gly Asn Gly Thr Pro Asn Glu Leu Gly Gly Ala Asn Ile
                245                 250                 255

Pro Ala Glu Phe Leu Glu Asn Phe Val Arg Ser Ser Asn Leu Lys Phe
            260                 265                 270

Gln Asp Ala Tyr Asn Ala Ala Gly Gly His Asn Ala Val Phe Asn Phe
        275                 280                 285

Pro Pro Asn Gly Thr His Ser Trp Glu Tyr Trp Gly Ala Gln Leu Asn
290                 295                 300

Ala Met Lys Gly Asp Leu Gln Ser Ser Leu Gly Ala Gly Ser Gln Ile
305                 310                 315                 320

Met Tyr Asn Tyr Pro Ala Met Leu Gly His Ala Gly Asp Met Ala Gly
                325                 330                 335

Tyr Ala Gly Thr Leu Gln Ser Leu Gly Ala Glu Ile Ala Val Glu Gln
            340                 345                 350

Ala Ala Leu Gln Ser Ala Trp Gln Gly Asp Thr Gly Ile Thr Tyr Gln
        355                 360                 365

Ala Trp Gln Ala Gln Trp Asn Gln Ala Met Glu Asp Leu Val Arg Ala
370                 375                 380

Tyr His Ala Met Ser Ser Thr His Glu Ala Asn Thr Met Ala Met Met
385                 390                 395                 400

Ala Arg Asp Thr Ala Glu Ala Ala Lys Trp Gly Thr Glu Gln Gln
                405                 410                 415

Trp Asn Phe Ala Gly Ile Glu Ala Ala Ala Ser Ala Ile Gln Gly Asn
            420                 425                 430

Val Thr Ser Ile His Ser Leu Leu Asp Glu Gly Lys Gln Ser Leu Thr
        435                 440                 445

Lys Leu Ala Ala Ala Trp Gly Gly Ser Gly Ser Glu Ala Tyr Gln Gly
450                 455                 460
```

```
Val Gln Gln Lys Trp Asp Ala Thr Ala Thr Glu Leu Asn Asn Ala Leu
465                 470                 475                 480

Gln Asn Leu Ala Arg Thr Ile Ser Glu Ala Gly Gln Ala Met Ala Ser
                485                 490                 495

Thr Glu Gly Asn Val Thr Gly Met Phe Ala Glu Gln Lys Leu Ile Ser
                500                 505                 510

Glu Glu Asp Leu Ser Tyr Val Leu Leu Ser Ala Gly Ala Leu Thr Ala
            515                 520                 525

Leu Met Leu Ile Ile Phe Leu Met Thr Cys Cys Arg Arg Val Asn Arg
530                 535                 540

Ser Glu Pro Thr Gln His Asn Leu Arg Gly Thr Gly Arg Glu Val Ser
545                 550                 555                 560

Val Thr Pro Gln Ser Gly Lys Ile Ile Ser Ser Trp Glu Ser His Lys
                565                 570                 575

Ser Gly Gly Glu Thr Arg Leu His His His His His
                580                 585

<210> SEQ ID NO 29
<211> LENGTH: 500
<212> TYPE: PRT
<213> ORGANISM: artificial sequence
<220> FEATURE:
<223> OTHER INFORMATION: fusion "Flag-Ag85B*-TB10.4-ESAT6-Myc-His tag"

<400> SEQUENCE: 29

Met Asp Tyr Lys Asp Asp Asp Lys Ala Phe Ser Arg Pro Gly Leu
1               5                   10                  15

Pro Val Glu Tyr Leu Gln Val Pro Ser Pro Ser Met Gly Arg Asp Ile
                20                  25                  30

Lys Val Gln Phe Gln Ser Gly Gly Asn Asn Ser Pro Ala Val Tyr Leu
            35                  40                  45

Leu Asp Gly Leu Arg Ala Gln Asp Asp Tyr Asn Gly Trp Asp Ile Asn
50                  55                  60

Thr Pro Ala Phe Glu Trp Tyr Tyr Gln Ser Gly Leu Ser Ile Val Met
65                  70                  75                  80

Pro Val Gly Gly Gln Ser Ser Phe Tyr Ser Asp Trp Tyr Ser Pro Ala
                85                  90                  95

Cys Gly Lys Ala Gly Cys Gln Thr Tyr Lys Trp Glu Thr Phe Leu Thr
            100                 105                 110

Ser Glu Leu Pro Gln Trp Leu Ser Ala Asn Arg Ala Val Lys Pro Thr
        115                 120                 125

Gly Ser Ala Ala Ile Gly Leu Ser Met Ala Gly Ser Ser Ala Met Ile
    130                 135                 140

Leu Ala Ala Tyr His Pro Gln Gln Phe Ile Tyr Ala Gly Ser Leu Ser
145                 150                 155                 160

Ala Leu Leu Asp Pro Ser Gln Gly Met Gly Pro Ser Leu Ile Gly Leu
                165                 170                 175

Ala Met Gly Asp Ala Gly Gly Tyr Lys Ala Ala Asp Met Trp Gly Pro
            180                 185                 190

Ser Ser Asp Pro Ala Trp Glu Arg Asn Asp Pro Thr Gln Gln Ile Pro
        195                 200                 205

Lys Leu Val Ala Asn Asn Thr Arg Leu Trp Val Tyr Cys Gly Asn Gly
    210                 215                 220

Thr Pro Asn Glu Leu Gly Gly Ala Asn Ile Pro Ala Glu Phe Leu Glu
225                 230                 235                 240
```

Asn Phe Val Arg Ser Ser Asn Leu Lys Phe Gln Asp Ala Tyr Asn Ala
                245                 250                 255

Ala Gly Gly His Asn Ala Val Phe Asn Phe Pro Pro Asn Gly Thr His
            260                 265                 270

Ser Trp Glu Tyr Trp Gly Ala Gln Leu Asn Ala Met Lys Gly Asp Leu
        275                 280                 285

Gln Ser Ser Leu Gly Ala Gly Ser Gln Ile Met Tyr Asn Tyr Pro Ala
    290                 295                 300

Met Leu Gly His Ala Gly Asp Met Ala Gly Tyr Ala Gly Thr Leu Gln
305                 310                 315                 320

Ser Leu Gly Ala Glu Ile Ala Val Glu Gln Ala Leu Gln Ser Ala
                325                 330                 335

Trp Gln Gly Asp Thr Gly Ile Thr Tyr Gln Ala Trp Gln Ala Gln Trp
            340                 345                 350

Asn Gln Ala Met Glu Asp Leu Val Arg Ala Tyr His Ala Met Ser Ser
        355                 360                 365

Thr His Glu Ala Asn Thr Met Ala Met Met Ala Arg Asp Thr Ala Glu
    370                 375                 380

Ala Ala Lys Trp Gly Gly Thr Glu Gln Gln Trp Asn Phe Ala Gly Ile
385                 390                 395                 400

Glu Ala Ala Ala Ser Ala Ile Gln Gly Asn Val Thr Ser Ile His Ser
                405                 410                 415

Leu Leu Asp Glu Gly Lys Gln Ser Leu Thr Lys Leu Ala Ala Ala Trp
            420                 425                 430

Gly Gly Ser Gly Ser Glu Ala Tyr Gln Gly Val Gln Gln Lys Trp Asp
        435                 440                 445

Ala Thr Ala Thr Glu Leu Asn Asn Ala Leu Gln Asn Leu Ala Arg Thr
    450                 455                 460

Ile Ser Glu Ala Gly Gln Ala Met Ala Ser Thr Glu Gly Asn Val Thr
465                 470                 475                 480

Gly Met Phe Ala Glu Gln Lys Leu Ile Ser Glu Glu Asp Leu His His
                485                 490                 495

His His His His
        500

<210> SEQ ID NO 30
<211> LENGTH: 463
<212> TYPE: PRT
<213> ORGANISM: artificial sequence
<220> FEATURE:
<223> OTHER INFORMATION: fusion "SS-Flag-RPFB-Dhyb-Myc-TM-His tag"

<400> SEQUENCE: 30

Met Val Pro Gln Ala Leu Leu Leu Val Pro Leu Leu Gly Phe Ser Leu
1               5                   10                  15

Cys Phe Gly Lys Phe Pro Ile Asp Tyr Lys Asp Asp Asp Lys Thr
            20                  25                  30

Val Asp Gly Thr Ala Met Arg Val Thr Thr Met Lys Ser Arg Val Ile
        35                  40                  45

Asp Ile Val Glu Glu Asn Gly Phe Ser Val Asp Arg Asp Leu
    50                  55                  60

Tyr Pro Ala Ala Gly Val Gln Val His Asp Ala Asp Thr Ile Val Leu
65                  70                  75                  80

Arg Arg Ser Arg Pro Leu Gln Ile Ser Leu Asp Gly His Asp Ala Lys
                85                  90                  95

Gln Val Trp Thr Thr Ala Ser Thr Val Asp Glu Ala Leu Ala Gln Leu
            100                 105                 110

Ala Met Thr Asp Thr Ala Pro Ala Ala Ser Arg Ala Ser Arg Val
    115                 120                 125

Pro Leu Ser Gly Met Ala Leu Pro Val Val Ser Ala Lys Thr Val Gln
    130                 135                 140

Leu Asn Asp Gly Gly Leu Val Arg Thr Val His Leu Pro Ala Pro Asn
145                 150                 155                 160

Val Ala Gly Leu Leu Ser Ala Ala Gly Val Pro Leu Leu Gln Ser Asp
                165                 170                 175

His Val Val Pro Ala Ala Thr Ala Pro Ile Val Glu Gly Met Gln Ile
            180                 185                 190

Gln Val Thr Arg Asn Arg Ile Lys Lys Val Thr Glu Arg Leu Pro Leu
        195                 200                 205

Pro Pro Asn Ala Arg Arg Val Glu Asp Pro Glu Met Asn Met Ser Arg
    210                 215                 220

Glu Val Val Glu Asp Pro Gly Val Pro Gly Thr Gln Asp Val Thr Phe
225                 230                 235                 240

Ala Val Ala Glu Val Asn Gly Val Glu Thr Gly Arg Leu Pro Val Ala
                245                 250                 255

Asn Val Val Val Thr Pro Ala His Glu Ala Val Val Arg Val Gly Thr
            260                 265                 270

Lys Pro Gly Thr Glu Val Pro Pro Val Ile Asp Gly Ser Ile Trp Asp
        275                 280                 285

Ala Ile Ala Gln Cys Lys Ser Gly Gly Asn Trp Ala Ala Asn Thr Gly
    290                 295                 300

Asn Gly Leu Tyr Gly Gly Leu Gln Ile Ser Gln Ala Ala Trp Asp Ser
305                 310                 315                 320

Asn Gly Gly Val Gly Ser Pro Ala Ala Ala Ser Pro Gln Gln Gln Ile
                325                 330                 335

Glu Val Ala Asp Asn Ile Met Lys Thr Ala Gly Pro Gly Ala Trp Pro
            340                 345                 350

Lys Cys Ser Ser Cys Ser Gln Gly Asp Ala Pro Leu Gly Ser Leu Thr
        355                 360                 365

His Ile Leu Thr Phe Leu Ala Ala Glu Thr Gly Gly Glu Gln Lys Leu
    370                 375                 380

Ile Ser Glu Glu Asp Leu Ser Tyr Val Leu Leu Ser Ala Gly Thr Leu
385                 390                 395                 400

Ile Ala Leu Met Leu Ile Ile Phe Leu Ile Thr Cys Cys Lys Arg Val
                405                 410                 415

Asp Arg Pro Glu Ser Thr Gln Arg Ser Leu Arg Gly Thr Gly Arg Asn
            420                 425                 430

Val Ser Val Thr Ser Gln Ser Gly Lys Phe Ile Ser Ser Trp Glu Ser
        435                 440                 445

His Lys Ser Gly Gly Glu Thr Arg Leu His His His His His
    450                 455                 460

<210> SEQ ID NO 31
<211> LENGTH: 374
<212> TYPE: PRT
<213> ORGANISM: artificial sequence
<220> FEATURE:
<223> OTHER INFORMATION: fusion "Flag-RPFB-Dhyb-Myc-His tag"

<400> SEQUENCE: 31

Met Asp Tyr Lys Asp Asp Asp Lys Thr Val Asp Gly Thr Ala Met
1               5                   10                  15

Arg Val Thr Thr Met Lys Ser Arg Val Ile Asp Ile Val Glu Glu Asn
            20                  25                  30

Gly Phe Ser Val Asp Asp Arg Asp Leu Tyr Pro Ala Ala Gly Val
        35                  40                  45

Gln Val His Asp Ala Asp Thr Ile Val Leu Arg Arg Ser Arg Pro Leu
50                  55                  60

Gln Ile Ser Leu Asp Gly His Asp Ala Lys Gln Val Trp Thr Thr Ala
65                  70                  75                  80

Ser Thr Val Asp Glu Ala Leu Ala Gln Leu Ala Met Thr Asp Thr Ala
                85                  90                  95

Pro Ala Ala Ala Ser Arg Ala Ser Arg Val Pro Leu Ser Gly Met Ala
                100                 105                 110

Leu Pro Val Val Ser Ala Lys Thr Val Gln Leu Asn Asp Gly Gly Leu
            115                 120                 125

Val Arg Thr Val His Leu Pro Ala Pro Asn Val Ala Gly Leu Leu Ser
130                 135                 140

Ala Ala Gly Val Pro Leu Leu Gln Ser Asp His Val Val Pro Ala Ala
145                 150                 155                 160

Thr Ala Pro Ile Val Glu Gly Met Gln Ile Gln Val Thr Arg Asn Arg
                165                 170                 175

Ile Lys Lys Val Thr Glu Arg Leu Pro Leu Pro Asn Ala Arg Arg
            180                 185                 190

Val Glu Asp Pro Glu Met Asn Met Ser Arg Glu Val Val Glu Asp Pro
            195                 200                 205

Gly Val Pro Gly Thr Gln Asp Val Thr Phe Ala Val Ala Glu Val Asn
210                 215                 220

Gly Val Glu Thr Gly Arg Leu Pro Val Ala Asn Val Val Thr Pro
225                 230                 235                 240

Ala His Glu Ala Val Val Arg Val Gly Thr Lys Pro Gly Thr Glu Val
                245                 250                 255

Pro Pro Val Ile Asp Gly Ser Ile Trp Asp Ala Ile Ala Gln Cys Lys
            260                 265                 270

Ser Gly Gly Asn Trp Ala Ala Asn Thr Gly Asn Gly Leu Tyr Gly Gly
            275                 280                 285

Leu Gln Ile Ser Gln Ala Ala Trp Asp Ser Asn Gly Gly Val Gly Ser
            290                 295                 300

Pro Ala Ala Ala Ser Pro Gln Gln Gln Ile Glu Val Ala Asp Asn Ile
305                 310                 315                 320

Met Lys Thr Ala Gly Pro Gly Ala Trp Pro Lys Cys Ser Ser Cys Ser
                325                 330                 335

Gln Gly Asp Ala Pro Leu Gly Ser Leu Thr His Ile Leu Thr Phe Leu
            340                 345                 350

Ala Ala Glu Thr Gly Gly Glu Gln Lys Leu Ile Ser Glu Glu Asp Leu
            355                 360                 365

His His His His His His
        370

<210> SEQ ID NO 32
<211> LENGTH: 938
<212> TYPE: PRT
<213> ORGANISM: artificial sequence
<220> FEATURE:
<223> OTHER INFORMATION: fusion "SS-Flag-RFPB-Dhyb-Ag85B*-TB10.4-ESAT6-

Myc-TM-His tag"

<400> SEQUENCE: 32

```
Met Val Pro Gln Ala Leu Leu Leu Val Pro Leu Leu Gly Phe Ser Leu
1               5                   10                  15

Cys Phe Gly Lys Phe Pro Ile Asp Tyr Lys Asp Asp Asp Asp Lys Thr
            20                  25                  30

Val Asp Gly Thr Ala Met Arg Val Thr Thr Met Lys Ser Arg Val Ile
            35                  40                  45

Asp Ile Val Glu Glu Asn Gly Phe Ser Val Asp Asp Arg Asp Asp Leu
        50                  55                  60

Tyr Pro Ala Ala Gly Val Gln Val His Asp Ala Asp Thr Ile Val Leu
65                  70                  75                  80

Arg Arg Ser Arg Pro Leu Gln Ile Ser Leu Asp Gly His Asp Ala Lys
                85                  90                  95

Gln Val Trp Thr Thr Ala Ser Thr Val Asp Glu Ala Leu Ala Gln Leu
            100                 105                 110

Ala Met Thr Asp Thr Ala Pro Ala Ala Ser Arg Ala Ser Arg Val
            115                 120                 125

Pro Leu Ser Gly Met Ala Leu Pro Val Val Ser Ala Lys Thr Val Gln
        130                 135                 140

Leu Asn Asp Gly Gly Leu Val Arg Thr Val His Leu Pro Ala Pro Asn
145                 150                 155                 160

Val Ala Gly Leu Leu Ser Ala Ala Gly Val Pro Leu Leu Gln Ser Asp
                165                 170                 175

His Val Val Pro Ala Ala Thr Ala Pro Ile Val Glu Gly Met Gln Ile
            180                 185                 190

Gln Val Thr Arg Asn Arg Ile Lys Lys Val Thr Glu Arg Leu Pro Leu
        195                 200                 205

Pro Pro Asn Ala Arg Arg Val Glu Asp Pro Glu Met Asn Met Ser Arg
210                 215                 220

Glu Val Val Glu Asp Pro Gly Val Pro Gly Thr Gln Asp Val Thr Phe
225                 230                 235                 240

Ala Val Ala Glu Val Asn Gly Val Glu Thr Gly Arg Leu Pro Val Ala
                245                 250                 255

Asn Val Val Thr Pro Ala His Glu Ala Val Arg Val Gly Thr
            260                 265                 270

Lys Pro Gly Thr Glu Val Pro Pro Val Ile Asp Gly Ser Ile Trp Asp
            275                 280                 285

Ala Ile Ala Gln Cys Lys Ser Gly Gly Asn Trp Ala Ala Asn Thr Gly
        290                 295                 300

Asn Gly Leu Tyr Gly Gly Leu Gln Ile Ser Gln Ala Ala Trp Asp Ser
305                 310                 315                 320

Asn Gly Gly Val Gly Ser Pro Ala Ala Ala Ser Pro Gln Gln Ile
                325                 330                 335

Glu Val Ala Asp Asn Ile Met Lys Thr Ala Gly Pro Gly Ala Trp Pro
            340                 345                 350

Lys Cys Ser Ser Cys Ser Gln Gly Asp Ala Pro Leu Gly Ser Leu Thr
            355                 360                 365

His Ile Leu Thr Phe Leu Ala Ala Glu Thr Gly Gly Ala Phe Ser Arg
        370                 375                 380

Pro Gly Leu Pro Val Glu Tyr Leu Gln Val Pro Ser Pro Ser Met Gly
385                 390                 395                 400
```

```
Arg Asp Ile Lys Val Gln Phe Gln Ser Gly Asn Asn Ser Pro Ala
            405                 410                 415

Val Tyr Leu Leu Asp Gly Leu Arg Ala Gln Asp Tyr Asn Gly Trp
            420                 425                 430

Asp Ile Asn Thr Pro Ala Phe Glu Trp Tyr Tyr Gln Ser Gly Leu Ser
            435                 440                 445

Ile Val Met Pro Val Gly Gly Gln Ser Ser Phe Tyr Ser Asp Trp Tyr
450                 455                 460

Ser Pro Ala Cys Gly Lys Ala Gly Cys Gln Thr Tyr Lys Trp Glu Thr
465                 470                 475                 480

Phe Leu Thr Ser Glu Leu Pro Gln Trp Leu Ser Ala Asn Arg Ala Val
            485                 490                 495

Lys Pro Thr Gly Ser Ala Ala Ile Gly Leu Ser Met Ala Gly Ser Ser
            500                 505                 510

Ala Met Ile Leu Ala Ala Tyr His Pro Gln Gln Phe Ile Tyr Ala Gly
            515                 520                 525

Ser Leu Ser Ala Leu Leu Asp Pro Ser Gln Gly Met Gly Pro Ser Leu
            530                 535                 540

Ile Gly Leu Ala Met Gly Asp Ala Gly Gly Tyr Lys Ala Ala Asp Met
545                 550                 555                 560

Trp Gly Pro Ser Ser Asp Pro Ala Trp Glu Arg Asn Asp Pro Thr Gln
                565                 570                 575

Gln Ile Pro Lys Leu Val Ala Asn Asn Thr Arg Leu Trp Val Tyr Cys
            580                 585                 590

Gly Asn Gly Thr Pro Asn Glu Leu Gly Gly Ala Asn Ile Pro Ala Glu
            595                 600                 605

Phe Leu Glu Asn Phe Val Arg Ser Ser Asn Leu Lys Phe Gln Asp Ala
            610                 615                 620

Tyr Asn Ala Ala Gly Gly His Asn Ala Val Phe Asn Phe Pro Pro Asn
625                 630                 635                 640

Gly Thr His Ser Trp Glu Tyr Trp Gly Ala Gln Leu Asn Ala Met Lys
                645                 650                 655

Gly Asp Leu Gln Ser Ser Leu Gly Ala Gly Ser Gln Ile Met Tyr Asn
            660                 665                 670

Tyr Pro Ala Met Leu Gly His Ala Gly Asp Met Ala Gly Tyr Ala Gly
            675                 680                 685

Thr Leu Gln Ser Leu Gly Ala Glu Ile Ala Val Glu Gln Ala Ala Leu
            690                 695                 700

Gln Ser Ala Trp Gln Gly Asp Thr Gly Ile Thr Tyr Gln Ala Trp Gln
705                 710                 715                 720

Ala Gln Trp Asn Gln Ala Met Glu Asp Leu Val Arg Ala Tyr His Ala
                725                 730                 735

Met Ser Ser Thr His Glu Ala Asn Thr Met Ala Met Met Ala Arg Asp
                740                 745                 750

Thr Ala Glu Ala Ala Lys Trp Gly Gly Thr Gln Gln Trp Asn Phe
            755                 760                 765

Ala Gly Ile Glu Ala Ala Ser Ala Ile Gln Gly Asn Val Thr Ser
            770                 775                 780

Ile His Ser Leu Leu Asp Glu Lys Gln Ser Leu Thr Lys Leu Ala
785                 790                 795                 800

Ala Ala Trp Gly Gly Ser Gly Ser Glu Ala Tyr Gln Gly Val Gln Gln
                805                 810                 815

Lys Trp Asp Ala Thr Ala Thr Glu Leu Asn Asn Ala Leu Gln Asn Leu
```

```
            820                 825                 830
Ala Arg Thr Ile Ser Glu Ala Gly Gln Ala Met Ala Ser Thr Glu Gly
            835                 840                 845

Asn Val Thr Gly Met Phe Ala Glu Gln Lys Leu Ile Ser Glu Glu Asp
        850                 855                 860

Leu Ser Tyr Val Leu Leu Ser Ala Gly Thr Leu Ile Ala Leu Met Leu
865                 870                 875                 880

Ile Ile Phe Leu Ile Thr Cys Cys Lys Arg Val Asp Arg Pro Glu Ser
                885                 890                 895

Thr Gln Arg Ser Leu Arg Gly Thr Gly Arg Asn Val Ser Val Thr Ser
            900                 905                 910

Gln Ser Gly Lys Phe Ile Ser Ser Trp Glu Ser His Lys Ser Gly Gly
        915                 920                 925

Glu Thr Arg Leu His His His His His His
            930                 935

<210> SEQ ID NO 33
<211> LENGTH: 849
<212> TYPE: PRT
<213> ORGANISM: artificial sequence
<220> FEATURE:
<223> OTHER INFORMATION: fusion "Flag-RPFB-Dhyb-Ag85B*-TB10.4-ESAT6-Myc-
      His tag"

<400> SEQUENCE: 33

Met Asp Tyr Lys Asp Asp Asp Lys Thr Val Asp Gly Thr Ala Met
1               5                   10                  15

Arg Val Thr Thr Met Lys Ser Arg Val Ile Asp Ile Val Glu Glu Asn
                20                  25                  30

Gly Phe Ser Val Asp Asp Arg Asp Asp Leu Tyr Pro Ala Ala Gly Val
            35                  40                  45

Gln Val His Asp Ala Asp Thr Ile Val Leu Arg Arg Ser Arg Pro Leu
        50                  55                  60

Gln Ile Ser Leu Asp Gly His Asp Ala Lys Gln Val Trp Thr Thr Ala
65                  70                  75                  80

Ser Thr Val Asp Glu Ala Leu Ala Gln Leu Ala Met Thr Asp Thr Ala
                85                  90                  95

Pro Ala Ala Ala Ser Arg Ala Ser Arg Val Pro Leu Ser Gly Met Ala
            100                 105                 110

Leu Pro Val Val Ser Ala Lys Thr Val Gln Leu Asn Asp Gly Gly Leu
        115                 120                 125

Val Arg Thr Val His Leu Pro Ala Pro Asn Val Ala Gly Leu Leu Ser
130                 135                 140

Ala Ala Gly Val Pro Leu Leu Gln Ser Asp His Val Val Pro Ala Ala
145                 150                 155                 160

Thr Ala Pro Ile Val Glu Gly Met Gln Ile Gln Val Thr Arg Asn Arg
                165                 170                 175

Ile Lys Lys Val Thr Glu Arg Leu Pro Leu Pro Asn Ala Arg Arg
            180                 185                 190

Val Glu Asp Pro Glu Met Asn Met Ser Arg Glu Val Val Glu Asp Pro
        195                 200                 205

Gly Val Pro Gly Thr Gln Asp Val Thr Phe Ala Val Ala Glu Val Asn
    210                 215                 220

Gly Val Glu Thr Gly Arg Leu Pro Val Ala Asn Val Val Val Thr Pro
225                 230                 235                 240
```

```
Ala His Glu Ala Val Arg Val Gly Thr Lys Pro Gly Thr Glu Val
            245                 250                 255

Pro Pro Val Ile Asp Gly Ser Ile Trp Asp Ala Ile Ala Gln Cys Lys
        260                 265                 270

Ser Gly Gly Asn Trp Ala Ala Asn Thr Gly Asn Gly Leu Tyr Gly Gly
        275                 280                 285

Leu Gln Ile Ser Gln Ala Ala Trp Asp Ser Asn Gly Gly Val Gly Ser
        290                 295                 300

Pro Ala Ala Ala Ser Pro Gln Gln Ile Glu Val Ala Asp Asn Ile
305                 310                 315                 320

Met Lys Thr Ala Gly Pro Gly Ala Trp Pro Lys Cys Ser Ser Cys Ser
                325                 330                 335

Gln Gly Asp Ala Pro Leu Gly Ser Leu Thr His Ile Leu Thr Phe Leu
                340                 345                 350

Ala Ala Glu Thr Gly Gly Ala Phe Ser Arg Pro Gly Leu Pro Val Glu
                355                 360                 365

Tyr Leu Gln Val Pro Ser Pro Ser Met Gly Arg Asp Ile Lys Val Gln
        370                 375                 380

Phe Gln Ser Gly Gly Asn Asn Ser Pro Ala Val Tyr Leu Leu Asp Gly
385                 390                 395                 400

Leu Arg Ala Gln Asp Asp Tyr Asn Gly Trp Asp Ile Asn Thr Pro Ala
                405                 410                 415

Phe Glu Trp Tyr Tyr Gln Ser Gly Leu Ser Ile Val Met Pro Val Gly
                420                 425                 430

Gly Gln Ser Ser Phe Tyr Ser Asp Trp Tyr Ser Pro Ala Cys Gly Lys
                435                 440                 445

Ala Gly Cys Gln Thr Tyr Lys Trp Glu Thr Phe Leu Thr Ser Glu Leu
        450                 455                 460

Pro Gln Trp Leu Ser Ala Asn Arg Ala Val Lys Pro Thr Gly Ser Ala
465                 470                 475                 480

Ala Ile Gly Leu Ser Met Ala Gly Ser Ser Ala Met Ile Leu Ala Ala
                485                 490                 495

Tyr His Pro Gln Gln Phe Ile Tyr Ala Gly Ser Leu Ser Ala Leu Leu
                500                 505                 510

Asp Pro Ser Gln Gly Met Gly Pro Ser Leu Ile Gly Leu Ala Met Gly
        515                 520                 525

Asp Ala Gly Gly Tyr Lys Ala Ala Asp Met Trp Gly Pro Ser Ser Asp
        530                 535                 540

Pro Ala Trp Glu Arg Asn Asp Pro Thr Gln Gln Ile Pro Lys Leu Val
545                 550                 555                 560

Ala Asn Asn Thr Arg Leu Trp Val Tyr Cys Gly Asn Gly Thr Pro Asn
                565                 570                 575

Glu Leu Gly Gly Ala Asn Ile Pro Ala Glu Phe Leu Glu Asn Phe Val
                580                 585                 590

Arg Ser Ser Asn Leu Lys Phe Gln Asp Ala Tyr Asn Ala Ala Gly Gly
        595                 600                 605

His Asn Ala Val Phe Asn Phe Pro Pro Asn Gly Thr His Ser Trp Glu
        610                 615                 620

Tyr Trp Gly Ala Gln Leu Asn Ala Met Lys Gly Asp Leu Gln Ser Ser
625                 630                 635                 640

Leu Gly Ala Gly Ser Gln Ile Met Tyr Asn Tyr Pro Ala Met Leu Gly
                645                 650                 655

His Ala Gly Asp Met Ala Gly Tyr Ala Gly Thr Leu Gln Ser Leu Gly
```

```
            660                 665                 670
Ala Glu Ile Ala Val Glu Gln Ala Ala Leu Gln Ser Ala Trp Gln Gly
            675                 680                 685

Asp Thr Gly Ile Thr Tyr Gln Ala Trp Gln Ala Gln Trp Asn Gln Ala
            690                 695                 700

Met Glu Asp Leu Val Arg Ala Tyr His Ala Met Ser Ser Thr His Glu
705                 710                 715                 720

Ala Asn Thr Met Ala Met Met Ala Arg Asp Thr Ala Glu Ala Ala Lys
                725                 730                 735

Trp Gly Gly Thr Glu Gln Gln Trp Asn Phe Ala Gly Ile Glu Ala Ala
                740                 745                 750

Ala Ser Ala Ile Gln Gly Asn Val Thr Ser Ile His Ser Leu Leu Asp
            755                 760                 765

Glu Gly Lys Gln Ser Leu Thr Lys Leu Ala Ala Ala Trp Gly Gly Ser
            770                 775                 780

Gly Ser Glu Ala Tyr Gln Gly Val Gln Gln Lys Trp Asp Ala Thr Ala
785                 790                 795                 800

Thr Glu Leu Asn Asn Ala Leu Gln Asn Leu Ala Arg Thr Ile Ser Glu
                805                 810                 815

Ala Gly Gln Ala Met Ala Ser Thr Glu Gly Asn Val Thr Gly Met Phe
                820                 825                 830

Ala Glu Gln Lys Leu Ile Ser Glu Glu Asp Leu His His His His
            835                 840                 845

His

<210> SEQ ID NO 34
<211> LENGTH: 1198
<212> TYPE: PRT
<213> ORGANISM: artificial sequence
<220> FEATURE:
<223> OTHER INFORMATION: fusion "SS-Flag-Rv0569-Rv1813*-Rv3407-Rv3478-
      Rv1807-Myc-TM-His tag"

<400> SEQUENCE: 34

Met Val Pro Gln Ala Leu Leu Phe Val Pro Leu Leu Val Phe Pro Leu
1               5                   10                  15

Cys Phe Gly Lys Phe Pro Ile Asp Tyr Lys Asp Asp Asp Asp Lys Lys
                20                  25                  30

Ala Lys Val Gly Asp Trp Leu Val Ile Lys Gly Ala Thr Ile Asp Gln
            35                  40                  45

Pro Asp His Arg Gly Leu Ile Ile Glu Val Arg Ser Ser Asp Gly Ser
50                  55                  60

Pro Pro Tyr Val Val Arg Trp Leu Glu Thr Asp His Val Ala Thr Val
65                  70                  75                  80

Ile Pro Gly Pro Asp Ala Val Val Thr Ala Glu Glu Gln Asn Ala
                85                  90                  95

Ala Asp Glu Arg Ala Gln His Arg Phe Gly Ala Val Gln Ser Ala Ile
            100                 105                 110

Leu His Ala Arg Gly Thr Ala Asn Gly Ser Met Ser Glu Val Met Met
            115                 120                 125

Ser Glu Ile Ala Gly Leu Pro Ile Pro Ile Ile His Tyr Gly Ala
            130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
```

```
                165                 170                 175
Thr Cys Lys Val Val Ser Arg Phe Thr Arg Cys Gly Ala Val Ala Tyr
                180                 185                 190

Asn Gly Ser Lys Tyr Gln Gly Gly Thr Gly Leu Thr Arg Arg Ala Ala
                195                 200                 205

Glu Asp Asp Ala Val Asn Arg Leu Glu Gly Gly Arg Ile Val Asn Trp
            210                 215                 220

Ala Cys Asn Arg Ala Thr Val Gly Leu Val Glu Ala Ile Gly Ile Arg
225                 230                 235                 240

Glu Leu Arg Gln His Ala Ser Arg Tyr Leu Ala Arg Val Glu Ala Gly
                245                 250                 255

Glu Glu Leu Gly Val Thr Asn Lys Gly Arg Leu Val Ala Arg Leu Ile
                260                 265                 270

Pro Val Gln Ala Ala Glu Arg Ser Arg Glu Ala Leu Ile Glu Ser Gly
                275                 280                 285

Val Leu Ile Pro Ala Arg Arg Pro Gln Asn Leu Leu Asp Val Thr Ala
            290                 295                 300

Glu Pro Ala Arg Gly Arg Lys Arg Thr Leu Ser Asp Val Leu Asn Glu
305                 310                 315                 320

Met Arg Asp Glu Gln Val Asp Phe Gly Ala Leu Pro Pro Glu Ile Asn
                325                 330                 335

Ser Ala Arg Met Tyr Ala Gly Pro Gly Ser Ala Ser Leu Val Ala Ala
                340                 345                 350

Ala Lys Met Trp Asp Ser Val Ala Ser Asp Leu Phe Ser Ala Ala Ser
                355                 360                 365

Ala Phe Gln Ser Val Val Trp Gly Leu Thr Val Gly Ser Trp Ile Gly
            370                 375                 380

Ser Ser Ala Gly Leu Met Ala Ala Ala Ser Pro Tyr Val Ala Trp
385                 390                 395                 400

Met Ser Val Thr Ala Gly Gln Ala Gln Leu Thr Ala Ala Gln Val Arg
                405                 410                 415

Val Ala Ala Ala Ala Tyr Glu Thr Ala Tyr Arg Leu Thr Val Pro Pro
                420                 425                 430

Pro Val Ile Ala Glu Asn Arg Thr Glu Leu Met Thr Leu Thr Ala Thr
            435                 440                 445

Asn Leu Leu Gly Gln Asn Thr Pro Ala Ile Glu Ala Asn Gln Ala Ala
            450                 455                 460

Tyr Ser Gln Met Trp Gly Gln Asp Ala Glu Ala Met Tyr Gly Tyr Ala
465                 470                 475                 480

Ala Thr Ala Ala Thr Ala Thr Glu Ala Leu Leu Pro Phe Glu Asp Ala
                485                 490                 495

Pro Leu Ile Thr Asn Pro Gly Gly Leu Leu Glu Gln Ala Val Ala Val
            500                 505                 510

Glu Glu Ala Ile Asp Thr Ala Ala Ala Asn Gln Leu Met Asn Asn Val
            515                 520                 525

Pro Gln Ala Leu Gln Gln Leu Ala Gln Pro Ala Gln Gly Val Val Pro
            530                 535                 540

Ser Ser Lys Leu Gly Gly Leu Trp Thr Ala Val Ser Pro His Leu Ser
545                 550                 555                 560

Pro Leu Ser Asn Val Ser Ser Ile Ala Asn Asn His Met Ser Met Met
                565                 570                 575

Gly Thr Gly Val Ser Met Thr Asn Thr Leu His Ser Met Leu Lys Gly
            580                 585                 590
```

```
Leu Ala Pro Ala Ala Ala Gln Ala Val Glu Thr Ala Ala Glu Asn Gly
            595                 600                 605
Val Trp Ala Met Ser Ser Leu Gly Ser Gln Leu Gly Ser Ser Leu Gly
610                 615                 620
Ser Ser Gly Leu Gly Ala Gly Val Ala Ala Asn Leu Gly Arg Ala Ala
625                 630                 635                 640
Ser Val Gly Ser Leu Ser Val Pro Pro Ala Trp Ala Ala Ala Asn Gln
            645                 650                 655
Ala Val Thr Pro Ala Ala Arg Ala Leu Pro Leu Thr Ser Leu Thr Ser
            660                 665                 670
Ala Ala Gln Thr Ala Pro Gly His Met Leu Gly Gly Leu Pro Leu Gly
            675                 680                 685
His Ser Val Asn Ala Gly Ser Gly Ile Asn Asn Ala Leu Arg Val Pro
            690                 695                 700
Ala Arg Ala Tyr Ala Ile Pro Arg Thr Pro Ala Ala Gly Asp Phe Ala
705                 710                 715                 720
Thr Leu Pro Pro Glu Ile Asn Ser Ala Arg Met Tyr Ser Gly Ala Gly
            725                 730                 735
Ser Ala Pro Met Leu Ala Ala Ser Ala Trp His Gly Leu Ser Ala
            740                 745                 750
Glu Leu Arg Ala Ser Ala Leu Ser Tyr Ser Ser Val Leu Ser Thr Leu
            755                 760                 765
Thr Gly Glu Glu Trp His Gly Pro Ala Ser Ala Ser Met Thr Ala Ala
            770                 775                 780
Ala Ala Pro Tyr Val Ala Trp Met Ser Val Thr Ala Val Arg Ala Glu
785                 790                 795                 800
Gln Ala Gly Ala Gln Ala Glu Ala Ala Ala Ala Tyr Glu Ala Ala
            805                 810                 815
Phe Ala Ala Thr Val Pro Pro Val Ile Glu Ala Asn Arg Ala Gln
            820                 825                 830
Leu Met Ala Leu Ile Ala Thr Asn Val Leu Gly Gln Asn Ala Pro Ala
            835                 840                 845
Ile Ala Ala Thr Glu Ala Gln Tyr Ala Glu Met Trp Ser Gln Asp Ala
            850                 855                 860
Met Ala Met Tyr Gly Tyr Ala Gly Ala Ser Ala Ala Thr Gln Leu
865                 870                 875                 880
Thr Pro Phe Thr Glu Pro Val Gln Thr Thr Asn Ala Ser Gly Leu Ala
            885                 890                 895
Ala Gln Ser Ala Ala Ile Ala His Ala Thr Gly Ala Ser Ala Gly Ala
            900                 905                 910
Gln Gln Thr Thr Leu Ser Gln Leu Ile Ala Ala Ile Pro Ser Val Leu
            915                 920                 925
Gln Gly Leu Ser Ser Ser Thr Ala Ala Thr Phe Ala Ser Gly Pro Ser
            930                 935                 940
Gly Leu Leu Gly Ile Val Gly Ser Gly Ser Ser Trp Leu Asp Lys Leu
945                 950                 955                 960
Trp Ala Leu Leu Asp Pro Asn Ser Asn Phe Trp Asn Thr Ile Ala Ser
            965                 970                 975
Ser Gly Leu Phe Leu Pro Ser Asn Thr Ile Ala Pro Phe Leu Gly Leu
            980                 985                 990
Leu Gly Gly Val Ala Ala Ala Asp  Ala Ala Gly Asp Val  Leu Gly Glu
            995                 1000                1005
```

-continued

Ala Thr Ser Gly Gly Leu Gly Gly Ala Leu Val Ala Pro Leu Gly
    1010                1015                1020

Ser Ala Gly Gly Leu Gly Gly Thr Val Ala Ala Gly Leu Gly Asn
    1025                1030                1035

Ala Ala Thr Val Gly Thr Leu Ser Val Pro Pro Ser Trp Thr Ala
    1040                1045                1050

Ala Ala Pro Leu Ala Ser Pro Leu Gly Ser Ala Leu Gly Gly Thr
    1055                1060                1065

Pro Met Val Ala Pro Pro Ala Val Ala Ala Gly Met Pro Gly
    1070                1075                1080

Met Pro Phe Gly Thr Met Gly Gly Gln Gly Phe Gly Arg Ala Val
    1085                1090                1095

Pro Gln Tyr Gly Phe Arg Pro Asn Phe Val Ala Arg Pro Pro Ala
    1100                1105                1110

Ala Gly Glu Gln Lys Leu Ile Ser Glu Glu Asp Leu Ser Tyr Val
    1115                1120                1125

Leu Leu Ser Ala Gly Thr Leu Ile Ala Leu Met Leu Ile Ile Phe
    1130                1135                1140

Leu Ile Thr Cys Cys Lys Arg Val Asp Arg Pro Glu Ser Thr Gln
    1145                1150                1155

Arg Ser Leu Arg Gly Thr Gly Arg Asn Val Ser Val Thr Ser Gln
    1160                1165                1170

Ser Gly Lys Phe Ile Ser Ser Trp Glu Ser His Lys Ser Gly Gly
    1175                1180                1185

Glu Thr Arg Leu His His His His His His
    1190                1195

<210> SEQ ID NO 35
<211> LENGTH: 1109
<212> TYPE: PRT
<213> ORGANISM: artificial sequence
<220> FEATURE:
<223> OTHER INFORMATION: fusion "Flag-Rv0569-Rv1813*-Rv3407-Rv3478-
      Rv1807-Myc-His tag"

<400> SEQUENCE: 35

Met Asp Tyr Lys Asp Asp Asp Asp Lys Lys Ala Lys Val Gly Asp Trp
1               5                   10                  15

Leu Val Ile Lys Gly Ala Thr Ile Asp Gln Pro Asp His Arg Gly Leu
                20                  25                  30

Ile Ile Glu Val Arg Ser Ser Asp Gly Ser Pro Pro Tyr Val Val Arg
            35                  40                  45

Trp Leu Glu Thr Asp His Val Ala Thr Val Ile Pro Gly Pro Asp Ala
    50                  55                  60

Val Val Val Thr Ala Glu Gln Asn Ala Ala Asp Glu Arg Ala Gln
65                  70                  75                  80

His Arg Phe Gly Ala Val Gln Ser Ala Ile Leu His Ala Arg Gly Thr
                85                  90                  95

Ala Asn Gly Ser Met Ser Glu Val Met Met Ser Glu Ile Ala Gly Leu
            100                 105                 110

Pro Ile Pro Pro Ile Ile His Tyr Gly Ala Ile Ala Tyr Ala Pro Ser
        115                 120                 125

Gly Ala Ser Gly Lys Ala Trp His Gln Arg Thr Pro Ala Arg Ala Glu
    130                 135                 140

Gln Val Ala Leu Glu Lys Cys Gly Asp Lys Thr Cys Lys Val Val Ser
145                 150                 155                 160

```
Arg Phe Thr Arg Cys Gly Ala Val Ala Tyr Asn Gly Ser Lys Tyr Gln
            165                 170                 175

Gly Gly Thr Gly Leu Thr Arg Arg Ala Ala Glu Asp Asp Ala Val Asn
            180                 185                 190

Arg Leu Glu Gly Gly Arg Ile Val Asn Trp Ala Cys Asn Arg Ala Thr
            195                 200                 205

Val Gly Leu Val Glu Ala Ile Gly Ile Arg Glu Leu Arg Gln His Ala
            210                 215                 220

Ser Arg Tyr Leu Ala Arg Val Glu Ala Gly Glu Leu Gly Val Thr
225                 230                 235                 240

Asn Lys Gly Arg Leu Val Ala Arg Leu Ile Pro Val Gln Ala Ala Glu
            245                 250                 255

Arg Ser Arg Glu Ala Leu Ile Glu Ser Gly Val Leu Ile Pro Ala Arg
            260                 265                 270

Arg Pro Gln Asn Leu Leu Asp Val Thr Ala Glu Pro Ala Arg Gly Arg
            275                 280                 285

Lys Arg Thr Leu Ser Asp Val Leu Asn Glu Met Arg Asp Glu Gln Val
            290                 295                 300

Asp Phe Gly Ala Leu Pro Pro Glu Ile Asn Ser Ala Arg Met Tyr Ala
305                 310                 315                 320

Gly Pro Gly Ser Ala Ser Leu Val Ala Ala Lys Met Trp Asp Ser
            325                 330                 335

Val Ala Ser Asp Leu Phe Ser Ala Ala Ser Ala Phe Gln Ser Val Val
            340                 345                 350

Trp Gly Leu Thr Val Gly Ser Trp Ile Gly Ser Ser Ala Gly Leu Met
            355                 360                 365

Ala Ala Ala Ser Pro Tyr Val Ala Trp Met Ser Val Thr Ala Gly
            370                 375                 380

Gln Ala Gln Leu Thr Ala Ala Gln Val Arg Val Ala Ala Ala Tyr
385                 390                 395                 400

Glu Thr Ala Tyr Arg Leu Thr Val Pro Pro Pro Val Ile Ala Glu Asn
            405                 410                 415

Arg Thr Glu Leu Met Thr Leu Thr Ala Thr Asn Leu Leu Gly Gln Asn
            420                 425                 430

Thr Pro Ala Ile Glu Ala Asn Gln Ala Ala Tyr Ser Gln Met Trp Gly
            435                 440                 445

Gln Asp Ala Glu Ala Met Tyr Gly Tyr Ala Ala Thr Ala Thr Ala
450                 455                 460

Thr Glu Ala Leu Leu Pro Phe Glu Asp Ala Pro Leu Ile Thr Asn Pro
465                 470                 475                 480

Gly Gly Leu Leu Glu Gln Ala Val Ala Val Glu Glu Ala Ile Asp Thr
            485                 490                 495

Ala Ala Ala Asn Gln Leu Met Asn Asn Val Pro Gln Ala Leu Gln Gln
            500                 505                 510

Leu Ala Gln Pro Ala Gln Gly Val Pro Ser Ser Lys Leu Gly Gly
            515                 520                 525

Leu Trp Thr Ala Val Ser Pro His Leu Ser Pro Leu Ser Asn Val Ser
            530                 535                 540

Ser Ile Ala Asn Asn His Met Ser Met Met Gly Thr Gly Val Ser Met
545                 550                 555                 560

Thr Asn Thr Leu His Ser Met Leu Lys Gly Leu Ala Pro Ala Ala Ala
            565                 570                 575
```

Gln Ala Val Glu Thr Ala Ala Glu Asn Gly Val Trp Ala Met Ser Ser
                580                 585                 590

Leu Gly Ser Gln Leu Gly Ser Ser Leu Gly Ser Ser Gly Leu Gly Ala
            595                 600                 605

Gly Val Ala Ala Asn Leu Gly Arg Ala Ala Ser Val Gly Ser Leu Ser
        610                 615                 620

Val Pro Pro Ala Trp Ala Ala Asn Gln Ala Val Thr Pro Ala Ala
625                 630                 635                 640

Arg Ala Leu Pro Leu Thr Ser Leu Thr Ser Ala Ala Gln Thr Ala Pro
                645                 650                 655

Gly His Met Leu Gly Gly Leu Pro Leu Gly His Ser Val Asn Ala Gly
            660                 665                 670

Ser Gly Ile Asn Asn Ala Leu Arg Val Pro Ala Arg Ala Tyr Ala Ile
        675                 680                 685

Pro Arg Thr Pro Ala Ala Gly Asp Phe Ala Thr Leu Pro Pro Glu Ile
    690                 695                 700

Asn Ser Ala Arg Met Tyr Ser Gly Ala Gly Ser Ala Pro Met Leu Ala
705                 710                 715                 720

Ala Ala Ser Ala Trp His Gly Leu Ser Ala Glu Leu Arg Ala Ser Ala
                725                 730                 735

Leu Ser Tyr Ser Ser Val Leu Ser Thr Leu Thr Gly Glu Glu Trp His
            740                 745                 750

Gly Pro Ala Ser Ala Ser Met Thr Ala Ala Ala Pro Tyr Val Ala
        755                 760                 765

Trp Met Ser Val Thr Ala Val Arg Ala Glu Gln Ala Gly Ala Gln Ala
770                 775                 780

Glu Ala Ala Ala Ala Tyr Glu Ala Ala Phe Ala Ala Thr Val Pro
785                 790                 795                 800

Pro Pro Val Ile Glu Ala Asn Arg Ala Gln Leu Met Ala Leu Ile Ala
                805                 810                 815

Thr Asn Val Leu Gly Gln Asn Ala Pro Ala Ile Ala Ala Thr Glu Ala
            820                 825                 830

Gln Tyr Ala Glu Met Trp Ser Gln Asp Ala Met Ala Met Tyr Gly Tyr
        835                 840                 845

Ala Gly Ala Ser Ala Ala Ala Thr Gln Leu Thr Pro Phe Thr Glu Pro
850                 855                 860

Val Gln Thr Thr Asn Ala Ser Gly Leu Ala Ala Gln Ser Ala Ala Ile
865                 870                 875                 880

Ala His Ala Thr Gly Ala Ser Ala Gly Ala Gln Gln Thr Thr Leu Ser
                885                 890                 895

Gln Leu Ile Ala Ala Ile Pro Ser Val Leu Gln Gly Leu Ser Ser Ser
            900                 905                 910

Thr Ala Ala Thr Phe Ala Ser Gly Pro Ser Gly Leu Leu Gly Ile Val
        915                 920                 925

Gly Ser Gly Ser Ser Trp Leu Asp Lys Leu Trp Ala Leu Leu Asp Pro
    930                 935                 940

Asn Ser Asn Phe Trp Asn Thr Ile Ala Ser Ser Gly Leu Phe Leu Pro
945                 950                 955                 960

Ser Asn Thr Ile Ala Pro Phe Leu Gly Leu Gly Gly Val Ala Ala
                965                 970                 975

Ala Asp Ala Ala Gly Asp Val Leu Gly Glu Ala Thr Ser Gly Gly Leu
            980                 985                 990

Gly Gly Ala Leu Val Ala Pro Leu  Gly Ser Ala Gly Gly  Leu Gly Gly

```
                995              1000             1005
Thr Val Ala Ala Gly Leu Gly Asn Ala Ala Thr Val Gly Thr Leu
       1010             1015             1020

Ser Val Pro Pro Ser Trp Thr Ala Ala Pro Leu Ala Ser Pro
   1025            1030             1035

Leu Gly Ser Ala Leu Gly Gly Thr Pro Met Val Ala Pro Pro Pro
   1040            1045             1050

Ala Val Ala Ala Gly Met Pro Gly Met Pro Phe Gly Thr Met Gly
   1055            1060             1065

Gly Gln Gly Phe Gly Arg Ala Val Pro Gln Tyr Gly Phe Arg Pro
   1070            1075             1080

Asn Phe Val Ala Arg Pro Pro Ala Ala Gly Glu Gln Lys Leu Ile
   1085            1090             1095

Ser Glu Glu Asp Leu His His His His His His
   1100            1105
```

<210> SEQ ID NO 36
<211> LENGTH: 973
<212> TYPE: PRT
<213> ORGANISM: artificial sequence
<220> FEATURE:
<223> OTHER INFORMATION: fusion "SS-Flag-Ag85B*-Rv2626-RPFB-Dhyb-Rv1733*-Myc-His tag"

<400> SEQUENCE: 36

```
Met Val Pro Gln Ala Leu Leu Phe Val Pro Leu Leu Val Phe Pro Leu
1               5                   10                  15

Cys Phe Gly Lys Phe Pro Ile Asp Tyr Lys Asp Asp Asp Lys Ala
            20                  25                  30

Phe Ser Arg Pro Gly Leu Pro Val Glu Tyr Leu Gln Val Pro Ser Pro
        35                  40                  45

Ser Met Gly Arg Asp Ile Lys Val Gln Phe Gln Ser Gly Gly Asn Asn
50                  55                  60

Ser Pro Ala Val Tyr Leu Leu Asp Gly Leu Arg Ala Gln Asp Asp Tyr
65                  70                  75                  80

Asn Gly Trp Asp Ile Asn Thr Pro Ala Phe Glu Trp Tyr Tyr Gln Ser
                85                  90                  95

Gly Leu Ser Ile Val Met Pro Val Gly Gly Gln Ser Ser Phe Tyr Ser
            100                 105                 110

Asp Trp Tyr Ser Pro Ala Cys Gly Lys Ala Gly Cys Gln Thr Tyr Lys
        115                 120                 125

Trp Glu Thr Phe Leu Thr Ser Glu Leu Pro Gln Trp Leu Ser Ala Asn
    130                 135                 140

Arg Ala Val Lys Pro Thr Gly Ser Ala Ala Ile Gly Leu Ser Met Ala
145                 150                 155                 160

Gly Ser Ser Ala Met Ile Leu Ala Ala Tyr His Pro Gln Gln Phe Ile
                165                 170                 175

Tyr Ala Gly Ser Leu Ser Ala Leu Leu Asp Pro Ser Gln Gly Met Gly
            180                 185                 190

Pro Ser Leu Ile Gly Leu Ala Met Gly Asp Ala Gly Gly Tyr Lys Ala
        195                 200                 205

Ala Asp Met Trp Gly Pro Ser Ser Asp Pro Ala Trp Glu Arg Asn Asp
    210                 215                 220

Pro Thr Gln Gln Ile Pro Lys Leu Val Ala Asn Asn Thr Arg Leu Trp
225                 230                 235                 240
```

-continued

Val Tyr Cys Gly Asn Gly Thr Pro Asn Glu Leu Gly Ala Asn Ile
            245                 250                 255

Pro Ala Glu Phe Leu Glu Asn Phe Val Arg Ser Ser Asn Leu Lys Phe
            260                 265                 270

Gln Asp Ala Tyr Asn Ala Ala Gly Gly His Asn Ala Val Phe Asn Phe
        275                 280                 285

Pro Pro Asn Gly Thr His Ser Trp Glu Tyr Trp Gly Ala Gln Leu Asn
290                 295                 300

Ala Met Lys Gly Asp Leu Gln Ser Ser Leu Gly Ala Gly Thr Thr Ala
305                 310                 315                 320

Arg Asp Ile Met Asn Ala Gly Val Thr Cys Val Gly Glu His Glu Thr
                325                 330                 335

Leu Thr Ala Ala Ala Gln Tyr Met Arg Glu His Asp Ile Gly Ala Leu
                340                 345                 350

Pro Ile Cys Gly Asp Asp Asp Arg Leu His Gly Met Leu Thr Asp Arg
            355                 360                 365

Asp Ile Val Ile Lys Gly Leu Ala Ala Gly Leu Asp Pro Asn Thr Ala
370                 375                 380

Thr Ala Gly Glu Leu Ala Arg Asp Ser Ile Tyr Tyr Val Asp Ala Asn
385                 390                 395                 400

Ala Ser Ile Gln Glu Met Leu Asn Val Met Glu Glu His Gln Val Arg
                405                 410                 415

Arg Val Pro Val Ile Ser Glu His Arg Leu Val Gly Ile Val Thr Glu
            420                 425                 430

Ala Asp Ile Ala Arg His Leu Pro Glu His Ala Ile Val Gln Phe Val
            435                 440                 445

Lys Ala Ile Cys Ser Pro Met Ala Leu Ala Ser Thr Val Asp Gly Thr
450                 455                 460

Ala Met Arg Val Thr Thr Met Lys Ser Arg Val Ile Asp Ile Val Glu
465                 470                 475                 480

Glu Asn Gly Phe Ser Val Asp Asp Arg Asp Leu Tyr Pro Ala Ala
                485                 490                 495

Gly Val Gln Val His Asp Ala Asp Thr Ile Val Leu Arg Arg Ser Arg
            500                 505                 510

Pro Leu Gln Ile Ser Leu Asp Gly His Asp Ala Lys Gln Val Trp Thr
            515                 520                 525

Thr Ala Ser Thr Val Asp Glu Ala Leu Ala Gln Leu Ala Met Thr Asp
530                 535                 540

Thr Ala Pro Ala Ala Ser Arg Ala Ser Arg Val Pro Leu Ser Gly
545                 550                 555                 560

Met Ala Leu Pro Val Val Ser Ala Lys Thr Val Gln Leu Asn Asp Gly
                565                 570                 575

Gly Leu Val Arg Thr His Leu Pro Ala Pro Asn Val Ala Gly Leu
            580                 585                 590

Leu Ser Ala Ala Gly Val Pro Leu Leu Gln Ser Asp His Val Val Pro
        595                 600                 605

Ala Ala Thr Ala Pro Ile Val Glu Gly Met Gln Ile Gln Val Thr Arg
        610                 615                 620

Asn Arg Ile Lys Lys Val Thr Glu Arg Leu Pro Leu Pro Asn Ala
625                 630                 635                 640

Arg Arg Val Glu Asp Pro Glu Met Asn Met Ser Arg Glu Val Val Glu
                645                 650                 655

Asp Pro Gly Val Pro Gly Thr Gln Asp Val Thr Phe Ala Val Ala Glu

```
                    660               665                670
Val Asn Gly Val Glu Thr Gly Arg Leu Pro Val Ala Asn Val Val
                675                680                685

Thr Pro Ala His Glu Ala Val Arg Val Gly Thr Lys Pro Gly Thr
            690                695                700

Glu Val Pro Pro Val Ile Asp Gly Ser Ile Trp Asp Ala Ile Ala Gln
705                710                715                720

Cys Lys Ser Gly Gly Asn Trp Ala Ala Asn Thr Gly Asn Gly Leu Tyr
                725                730                735

Gly Gly Leu Gln Ile Ser Gln Ala Ala Trp Asp Ser Asn Gly Gly Val
            740                745                750

Gly Ser Pro Ala Ala Ser Pro Gln Gln Ile Glu Val Ala Asp
            755                760                765

Asn Ile Met Lys Thr Ala Gly Pro Gly Ala Trp Pro Lys Cys Ser Ser
            770                775                780

Cys Ser Gln Gly Asp Ala Pro Leu Gly Ser Leu Thr His Ile Leu Thr
785                790                795                800

Phe Leu Ala Ala Glu Thr Gly Gly Ala Gly Thr Ala Val Gln Asp Ser
                805                810                815

Arg Ser His Val Tyr Ala His Gln Ala Gln Thr Arg His Pro Ala Thr
                820                825                830

Ala Thr Val Ile Asp His Glu Gly Val Ile Asp Ser Asn Thr Thr Ala
                835                840                845

Thr Ser Ala Pro Pro Arg Thr Lys Ile Thr Val Pro Ala Arg Trp Val
850                855                860

Val Asn Gly Ile Glu Arg Ser Gly Glu Val Asn Ala Lys Pro Gly Thr
865                870                875                880

Lys Ser Gly Asp Arg Val Gly Ile Trp Val Asp Ser Ala Gly Gln Leu
                885                890                895

Val Asp Glu Pro Ala Pro Pro Arg Ala Ile Ala Asp Ala Ala Leu
            900                905                910

Ala Ala Leu Gly Leu Trp Leu Ser Val Ala Val Ala Gly Ala Leu
            915                920                925

Leu Ala Leu Thr Arg Ala Ile Leu Ile Arg Val Arg Asn Ala Ser Trp
            930                935                940

Gln His Asp Ile Asp Ser Leu Phe Cys Thr Gln Arg Glu Gln Lys Leu
945                950                955                960

Ile Ser Glu Glu Asp Leu Ser His His His His His His
                965                970

<210> SEQ ID NO 37
<211> LENGTH: 624
<212> TYPE: PRT
<213> ORGANISM: artificial sequence
<220> FEATURE:
<223> OTHER INFORMATION: fusion "SS-Flag-Ag85B*-Rv2626-Rv1733*-Myc-His
      tag"

<400> SEQUENCE: 37

Met Val Pro Gln Ala Leu Leu Phe Val Pro Leu Leu Val Phe Pro Leu
1               5                   10                  15

Cys Phe Gly Lys Phe Pro Ile Asp Tyr Lys Asp Asp Asp Lys Ala
                20                  25                  30

Phe Ser Arg Pro Gly Leu Pro Val Glu Tyr Leu Gln Val Pro Ser Pro
            35                  40                  45
```

```
Ser Met Gly Arg Asp Ile Lys Val Gln Phe Gln Ser Gly Gly Asn Asn
    50                  55                  60

Ser Pro Ala Val Tyr Leu Leu Asp Gly Leu Arg Ala Gln Asp Asp Tyr
65                  70                  75                  80

Asn Gly Trp Asp Ile Asn Thr Pro Ala Phe Glu Trp Tyr Tyr Gln Ser
                85                  90                  95

Gly Leu Ser Ile Val Met Pro Val Gly Gln Ser Ser Phe Tyr Ser
                100                 105                 110

Asp Trp Tyr Ser Pro Ala Cys Gly Lys Ala Gly Cys Gln Thr Tyr Lys
            115                 120                 125

Trp Glu Thr Phe Leu Thr Ser Glu Leu Pro Gln Trp Leu Ser Ala Asn
130                 135                 140

Arg Ala Val Lys Pro Thr Gly Ser Ala Ala Ile Gly Leu Ser Met Ala
145                 150                 155                 160

Gly Ser Ser Ala Met Ile Leu Ala Ala Tyr His Pro Gln Gln Phe Ile
                165                 170                 175

Tyr Ala Gly Ser Leu Ser Ala Leu Leu Asp Pro Ser Gln Gly Met Gly
            180                 185                 190

Pro Ser Leu Ile Gly Leu Ala Met Gly Asp Ala Gly Gly Tyr Lys Ala
        195                 200                 205

Ala Asp Met Trp Gly Pro Ser Ser Asp Pro Ala Trp Glu Arg Asn Asp
210                 215                 220

Pro Thr Gln Gln Ile Pro Lys Leu Val Ala Asn Asn Thr Arg Leu Trp
225                 230                 235                 240

Val Tyr Cys Gly Asn Gly Thr Pro Asn Glu Leu Gly Gly Ala Asn Ile
                245                 250                 255

Pro Ala Glu Phe Leu Glu Asn Phe Val Arg Ser Ser Asn Leu Lys Phe
            260                 265                 270

Gln Asp Ala Tyr Asn Ala Ala Gly Gly His Asn Ala Val Phe Asn Phe
        275                 280                 285

Pro Pro Asn Gly Thr His Ser Trp Glu Tyr Trp Gly Ala Gln Leu Asn
    290                 295                 300

Ala Met Lys Gly Asp Leu Gln Ser Ser Leu Gly Ala Gly Thr Thr Ala
305                 310                 315                 320

Arg Asp Ile Met Asn Ala Gly Val Thr Cys Val Gly Glu His Glu Thr
                325                 330                 335

Leu Thr Ala Ala Ala Gln Tyr Met Arg Glu His Asp Ile Gly Ala Leu
            340                 345                 350

Pro Ile Cys Gly Asp Asp Arg Leu His Gly Met Leu Thr Asp Arg
        355                 360                 365

Asp Ile Val Ile Lys Gly Leu Ala Ala Gly Leu Asp Pro Asn Thr Ala
370                 375                 380

Thr Ala Gly Glu Leu Ala Arg Asp Ser Ile Tyr Tyr Val Asp Ala Asn
385                 390                 395                 400

Ala Ser Ile Gln Glu Met Leu Asn Val Met Glu His Gln Val Arg
                405                 410                 415

Arg Val Pro Val Ile Ser Glu His Arg Leu Val Gly Ile Val Thr Glu
            420                 425                 430

Ala Asp Ile Ala Arg His Leu Pro Glu His Ala Ile Val Gln Phe Val
        435                 440                 445

Lys Ala Ile Cys Ser Pro Met Ala Leu Ala Ser Ala Gly Thr Ala Val
450                 455                 460

Gln Asp Ser Arg Ser His Val Tyr Ala His Gln Ala Gln Thr Arg His
```

```
            465                 470                 475                 480
        Pro Ala Thr Ala Thr Val Ile Asp His Glu Gly Val Ile Asp Ser Asn
                        485                 490                 495
        Thr Thr Ala Thr Ser Ala Pro Pro Arg Thr Lys Ile Thr Val Pro Ala
                        500                 505                 510
        Arg Trp Val Val Asn Gly Ile Glu Arg Ser Gly Glu Val Asn Ala Lys
                        515                 520                 525
        Pro Gly Thr Lys Ser Gly Asp Arg Val Gly Ile Trp Val Asp Ser Ala
        530                 535                 540
        Gly Gln Leu Val Asp Glu Pro Ala Pro Pro Ala Arg Ala Ile Ala Asp
        545                 550                 555                 560
        Ala Ala Leu Ala Ala Leu Gly Leu Trp Leu Ser Val Ala Ala Val Ala
                        565                 570                 575
        Gly Ala Leu Leu Ala Leu Thr Arg Ala Ile Leu Ile Arg Val Arg Asn
                        580                 585                 590
        Ala Ser Trp Gln His Asp Ile Asp Ser Leu Phe Cys Thr Gln Arg Glu
                        595                 600                 605
        Gln Lys Leu Ile Ser Glu Glu Asp Leu Ser His His His His His His
                        610                 615                 620

<210> SEQ ID NO 38
<211> LENGTH: 949
<212> TYPE: PRT
<213> ORGANISM: artificial sequence
<220> FEATURE:
<223> OTHER INFORMATION: fusion "SS-Flag-Rv2029*-Rv2626-Rv1733*-Rv0111*-
      Myc-His tag"

<400> SEQUENCE: 38

Met Gly Leu Lys Val Asn Val Ser Ala Ile Phe Met Ala Val Leu Leu
        1               5                   10                  15
        Thr Leu Gln Thr Pro Thr Gly Gln Ile His Trp Gly Asp Tyr Lys Asp
                        20                  25                  30
        Asp Asp Asp Lys Thr Glu Pro Ala Ala Trp Asp Glu Gly Lys Pro Arg
                        35                  40                  45
        Ile Ile Thr Leu Thr Met Asn Pro Ala Leu Asp Ile Thr Thr Ser Val
                50                  55                  60
        Asp Val Val Arg Pro Thr Glu Lys Met Arg Cys Gly Ala Pro Arg Tyr
        65                  70                  75                  80
        Asp Pro Gly Gly Gly Gly Ile Asn Val Ala Arg Ile Val His Val Leu
                        85                  90                  95
        Gly Gly Cys Ser Thr Ala Leu Phe Pro Ala Gly Gly Ser Thr Gly Ser
                        100                 105                 110
        Leu Leu Met Ala Leu Leu Gly Asp Ala Gly Val Pro Phe Arg Val Ile
                        115                 120                 125
        Pro Ile Ala Ala Ser Thr Arg Glu Ser Phe Thr Val Asn Glu Ser Arg
        130                 135                 140
        Thr Ala Lys Gln Tyr Arg Phe Val Leu Pro Gly Pro Ser Leu Thr Val
        145                 150                 155                 160
        Ala Glu Gln Glu Gln Cys Leu Asp Glu Leu Arg Gly Ala Ala Ala Ser
                        165                 170                 175
        Ala Ala Phe Val Val Ala Ser Gly Ser Leu Pro Pro Gly Val Ala Ala
                        180                 185                 190
        Asp Tyr Tyr Gln Arg Val Ala Asp Ile Cys Arg Arg Ser Ser Thr Pro
                        195                 200                 205
```

```
Leu Ile Leu Asp Thr Ser Gly Gly Leu Gln His Ile Ser Ser Gly
    210                 215                 220

Val Phe Leu Leu Lys Ala Ser Val Arg Glu Leu Arg Glu Cys Val Gly
225                 230                 235                 240

Ser Glu Leu Leu Thr Glu Pro Glu Gln Leu Ala Ala His Glu Leu
            245                 250                 255

Ile Asp Arg Gly Arg Ala Glu Val Val Val Ser Leu Gly Ser Gln
            260                 265                 270

Gly Ala Leu Leu Ala Thr Arg His Ala Ser His Arg Phe Ser Ser Ile
            275                 280                 285

Pro Met Thr Ala Val Ser Gly Val Gly Ala Gly Asn Ala Met Val Ala
290                 295                 300

Ala Ile Thr Val Gly Leu Ser Arg Gly Trp Ser Leu Ile Lys Ser Val
305                 310                 315                 320

Arg Leu Gly Asn Ala Ala Gly Ala Ala Met Leu Leu Thr Pro Gly Thr
            325                 330                 335

Ala Ala Cys Asn Arg Asp Asp Val Glu Arg Phe Phe Glu Thr Thr Ala
            340                 345                 350

Arg Asp Ile Met Asn Ala Gly Val Thr Cys Val Gly Glu His Glu Thr
            355                 360                 365

Leu Thr Ala Ala Ala Gln Tyr Met Arg Glu His Asp Ile Gly Ala Leu
    370                 375                 380

Pro Ile Cys Gly Asp Asp Arg Leu His Gly Met Leu Thr Asp Arg
385                 390                 395                 400

Asp Ile Val Ile Lys Gly Leu Ala Ala Gly Leu Asp Pro Asn Thr Ala
            405                 410                 415

Thr Ala Gly Glu Leu Ala Arg Asp Ser Ile Tyr Tyr Val Asp Ala Asn
            420                 425                 430

Ala Ser Ile Gln Glu Met Leu Asn Val Met Glu Glu His Gln Val Arg
    435                 440                 445

Arg Val Pro Val Ile Ser Glu His Arg Leu Val Gly Ile Val Thr Glu
450                 455                 460

Ala Asp Ile Ala Arg His Leu Pro Glu His Ala Ile Val Gln Phe Val
465                 470                 475                 480

Lys Ala Ile Cys Ser Pro Met Ala Leu Ala Ser Ala Gly Thr Ala Val
            485                 490                 495

Gln Asp Ser Arg Ser His Val Tyr Ala His Gln Ala Gln Thr Arg His
            500                 505                 510

Pro Ala Thr Ala Thr Val Ile Asp His Glu Gly Val Ile Asp Ser Asn
            515                 520                 525

Thr Thr Ala Thr Ser Ala Pro Pro Arg Thr Lys Ile Thr Val Pro Ala
    530                 535                 540

Arg Trp Val Val Asn Gly Ile Glu Arg Ser Gly Glu Val Asn Ala Lys
545                 550                 555                 560

Pro Gly Thr Lys Ser Gly Asp Arg Val Gly Ile Trp Val Asp Ser Ala
            565                 570                 575

Gly Gln Leu Val Asp Glu Pro Ala Pro Ala Arg Ala Ile Ala Asp
            580                 585                 590

Ala Ala Leu Ala Leu Gly Leu Trp Leu Ser Val Ala Val Ala
            595                 600                 605

Gly Ala Leu Leu Ala Leu Thr Arg Ala Ile Leu Ile Arg Val Arg Asn
            610                 615                 620

Ala Ser Trp Gln His Asp Ile Asp Ser Leu Phe Cys Thr Gln Arg Glu
```

```
            625                 630                 635                 640
        Gln Pro Ile Arg Arg Trp Arg Pro Ala Arg Val Pro Leu Leu Pro Leu
                        645                 650                 655

Ala Ala Ala Thr Val Ala Ser Ala Ala Ala Val Thr Met Leu Val Val
                        660                 665                 670

Pro Val Gly Ala Gly Pro Gly Leu Arg Glu Ile Gly Leu Pro Pro Gly
                        675                 680                 685

Val Ser Ala Val Ala Ala Val Ser Pro Ser Pro Glu Ala Ser Gln
            690                 695                 700

Pro Ala Pro Gly Pro Arg Asp Pro Asn Arg Pro Phe Thr Val Ser Val
        705                 710                 715                 720

Phe Gly Asp Ser Ile Gly Trp Thr Leu Met His Tyr Leu Pro Pro Thr
                        725                 730                 735

Pro Gly Phe Arg Phe Ile Asp His Thr Val Ile Gly Cys Ser Leu Val
                        740                 745                 750

Arg Gly Thr Pro Tyr Arg Tyr Ile Gly Gln Thr Leu Glu Gln Arg Ala
                        755                 760                 765

Glu Cys Asp Gly Trp Pro Ala Arg Trp Ser Ala Gln Val Asn Arg Asp
                        770                 775                 780

Gln Pro Asp Val Ala Leu Leu Ile Val Gly Arg Trp Glu Thr Val Asp
        785                 790                 795                 800

Arg Val Asn Glu Gly Arg Trp Thr His Ile Gly Asp Pro Thr Phe Asp
                        805                 810                 815

Ala Tyr Leu Asn Ala Glu Leu Gln Arg Ala Leu Ser Ile Val Gly Ser
                        820                 825                 830

Thr Gly Val Arg Val Met Val Thr Thr Val Pro Tyr Ser Arg Gly Gly
                        835                 840                 845

Glu Lys Pro Asp Gly Arg Leu Tyr Pro Glu Asp Gln Pro Glu Arg Val
                        850                 855                 860

Asn Lys Trp Asn Ala Met Leu His Asn Ala Ile Ser Gln His Ser Asn
        865                 870                 875                 880

Val Gly Met Ile Asp Leu Asn Lys Lys Leu Cys Pro Asp Gly Val Tyr
                        885                 890                 895

Thr Ala Lys Val Asp Gly Ile Lys Val Arg Ser Asp Gly Val His Leu
                        900                 905                 910

Thr Gln Glu Gly Val Lys Trp Leu Ile Pro Trp Leu Glu Asp Ser Val
                        915                 920                 925

Arg Val Ala Ser Glu Gln Lys Leu Ile Ser Glu Glu Asp Leu Ser His
        930                 935                 940

His His His His His
        945

<210> SEQ ID NO 39
<211> LENGTH: 848
<212> TYPE: PRT
<213> ORGANISM: artificial sequence
<220> FEATURE:
<223> OTHER INFORMATION: fusion "SS-Flag-Rv2029*-TB10.4-ESAT6-Rv0111*-
      Myc-His tag"

<400> SEQUENCE: 39

Met Gly Leu Lys Val Asn Val Ser Ala Ile Phe Met Ala Val Leu Leu
        1               5                   10                  15

Thr Leu Gln Thr Pro Thr Gly Gln Ile His Trp Gly Asp Tyr Lys Asp
                        20                  25                  30
```

Asp Asp Asp Lys Thr Glu Pro Ala Trp Asp Glu Gly Lys Pro Arg
            35                  40                  45

Ile Ile Thr Leu Thr Met Asn Pro Ala Leu Asp Ile Thr Thr Ser Val
 50                  55                  60

Asp Val Val Arg Pro Thr Glu Lys Met Arg Cys Gly Ala Pro Arg Tyr
 65                  70                  75                  80

Asp Pro Gly Gly Gly Ile Asn Val Ala Arg Ile Val His Val Leu
            85                  90                  95

Gly Gly Cys Ser Thr Ala Leu Phe Pro Ala Gly Gly Ser Thr Gly Ser
            100                 105                 110

Leu Leu Met Ala Leu Leu Gly Asp Ala Gly Val Pro Phe Arg Val Ile
            115                 120                 125

Pro Ile Ala Ala Ser Thr Arg Glu Ser Phe Thr Val Asn Glu Ser Arg
130                 135                 140

Thr Ala Lys Gln Tyr Arg Phe Val Leu Pro Gly Pro Ser Leu Thr Val
145                 150                 155                 160

Ala Glu Gln Glu Gln Cys Leu Asp Glu Leu Arg Gly Ala Ala Ala Ser
                165                 170                 175

Ala Ala Phe Val Val Ala Ser Gly Ser Leu Pro Pro Gly Val Ala Ala
            180                 185                 190

Asp Tyr Tyr Gln Arg Val Ala Asp Ile Cys Arg Arg Ser Ser Thr Pro
            195                 200                 205

Leu Ile Leu Asp Thr Ser Gly Gly Leu Gln His Ile Ser Ser Gly
            210                 215                 220

Val Phe Leu Leu Lys Ala Ser Val Arg Glu Leu Arg Glu Cys Val Gly
225                 230                 235                 240

Ser Glu Leu Leu Thr Glu Pro Glu Gln Leu Ala Ala His Glu Leu
                245                 250                 255

Ile Asp Arg Gly Arg Ala Glu Val Val Val Ser Leu Gly Ser Gln
            260                 265                 270

Gly Ala Leu Leu Ala Thr Arg His Ala Ser His Arg Phe Ser Ser Ile
            275                 280                 285

Pro Met Thr Ala Val Ser Gly Val Gly Ala Gly Asn Ala Met Val Ala
290                 295                 300

Ala Ile Thr Val Gly Leu Ser Arg Gly Trp Ser Leu Ile Lys Ser Val
305                 310                 315                 320

Arg Leu Gly Asn Ala Ala Gly Ala Ala Met Leu Leu Thr Pro Gly Thr
                325                 330                 335

Ala Ala Cys Asn Arg Asp Asp Val Glu Arg Phe Phe Glu Ser Gln Ile
            340                 345                 350

Met Tyr Asn Tyr Pro Ala Met Leu Gly His Ala Gly Asp Met Ala Gly
            355                 360                 365

Tyr Ala Gly Thr Leu Gln Ser Leu Gly Ala Glu Ile Ala Val Glu Gln
            370                 375                 380

Ala Ala Leu Gln Ser Ala Trp Gln Gly Asp Thr Gly Ile Thr Tyr Gln
385                 390                 395                 400

Ala Trp Gln Ala Gln Trp Asn Gln Ala Met Glu Asp Leu Val Arg Ala
                405                 410                 415

Tyr His Ala Met Ser Ser Thr His Glu Ala Asn Thr Met Ala Met Met
            420                 425                 430

Ala Arg Asp Thr Ala Glu Ala Lys Trp Gly Gly Thr Glu Gln Gln
            435                 440                 445

Trp Asn Phe Ala Gly Ile Glu Ala Ala Ala Ser Ala Ile Gln Gly Asn

```
                450                 455                 460
Val Thr Ser Ile His Ser Leu Leu Asp Glu Gly Lys Gln Ser Leu Thr
465                 470                 475                 480

Lys Leu Ala Ala Ala Trp Gly Gly Ser Gly Ser Glu Ala Tyr Gln Gly
                485                 490                 495

Val Gln Gln Lys Trp Asp Ala Thr Thr Glu Leu Asn Asn Ala Leu
            500                 505                 510

Gln Asn Leu Ala Arg Thr Ile Ser Glu Ala Gly Gln Ala Met Ala Ser
            515                 520                 525

Thr Glu Gly Asn Val Thr Gly Met Phe Ala Glu Gln Pro Ile Arg Arg
            530                 535                 540

Trp Arg Pro Ala Arg Val Pro Leu Leu Pro Leu Ala Ala Ala Thr Val
545                 550                 555                 560

Ala Ser Ala Ala Ala Val Thr Met Leu Val Val Pro Val Gly Ala Gly
                565                 570                 575

Pro Gly Leu Arg Glu Ile Gly Leu Pro Pro Gly Val Ser Ala Val Ala
            580                 585                 590

Ala Val Ser Pro Ser Pro Pro Glu Ala Ser Gln Pro Ala Pro Gly Pro
            595                 600                 605

Arg Asp Pro Asn Arg Pro Phe Thr Val Ser Val Phe Gly Asp Ser Ile
            610                 615                 620

Gly Trp Thr Leu Met His Tyr Leu Pro Pro Thr Pro Gly Phe Arg Phe
625                 630                 635                 640

Ile Asp His Thr Val Ile Gly Cys Ser Leu Val Arg Gly Thr Pro Tyr
                645                 650                 655

Arg Tyr Ile Gly Gln Thr Leu Glu Gln Arg Ala Glu Cys Asp Gly Trp
            660                 665                 670

Pro Ala Arg Trp Ser Ala Gln Val Asn Arg Asp Gln Pro Asp Val Ala
            675                 680                 685

Leu Leu Ile Val Gly Arg Trp Glu Thr Val Asp Arg Val Asn Glu Gly
            690                 695                 700

Arg Trp Thr His Ile Gly Asp Pro Thr Phe Asp Ala Tyr Leu Asn Ala
705                 710                 715                 720

Glu Leu Gln Arg Ala Leu Ser Ile Val Gly Ser Thr Gly Val Arg Val
            725                 730                 735

Met Val Thr Thr Val Pro Tyr Ser Arg Gly Gly Glu Lys Pro Asp Gly
            740                 745                 750

Arg Leu Tyr Pro Glu Asp Gln Pro Glu Arg Val Asn Lys Trp Asn Ala
            755                 760                 765

Met Leu His Asn Ala Ile Ser Gln His Ser Asn Val Gly Met Ile Asp
770                 775                 780

Leu Asn Lys Lys Leu Cys Pro Asp Gly Val Tyr Thr Ala Lys Val Asp
785                 790                 795                 800

Gly Ile Lys Val Arg Ser Asp Gly Val His Leu Thr Gln Glu Gly Val
                805                 810                 815

Lys Trp Leu Ile Pro Trp Leu Glu Asp Ser Val Arg Val Ala Ser Glu
            820                 825                 830

Gln Lys Leu Ile Ser Glu Glu Asp Leu Ser His His His His His
            835                 840                 845

<210> SEQ ID NO 40
<211> LENGTH: 1770
<212> TYPE: DNA
<213> ORGANISM: artificial sequence
```

<220> FEATURE:
<223> OTHER INFORMATION: nucleotide sequence encoding fusion n?2
"SS-Flag-Ag85B*-TB10.4-ESAT6-Myc-TM-His tag" (pTG18266)

<400> SEQUENCE: 40

| | |
|---|---|
| atggttcctc aggctctcct gtttgtaccc cttctggttt ttccattgtg ttttgggaaa | 60 |
| ttccctattg attacaagga tgacgacgat aaggccttct ctagacctgg cctgccgtg | 120 |
| gaatacctgc aggtcccaag ccccagcatg ggccgggata tcaaggtgca gtttcagagc | 180 |
| ggcggcaaca acagccctgc cgtgtatctg ctggatggcc tgagagccca ggacgactac | 240 |
| aacggctggg acatcaacac ccctgccttc gagtggtact accagagcgg cctgtccatc | 300 |
| gtgatgcctg tgggcggcca gagcagcttc tacagcgact ggtacagccc cgcctgtggc | 360 |
| aaagccggct gccagaccta caagtgggag acattcctga cctccgagct gccccagtgg | 420 |
| ctgagcgcca atagagccgt gaagcctaca ggctctgccg ccatcggact gagcatggcc | 480 |
| ggaagctctg ccatgatcct ggccgcctat caccctcagc agttcatcta cgccggcagc | 540 |
| ctgtctgccc tgctggaccc ttctcagggc atggcccctt ctctgatcgg actggctatg | 600 |
| ggcgacgctg gcggatacaa ggccgccgat atgtggggcc tagcagcga tcctgcctgg | 660 |
| gagagaaacg accccaccca gcagatcccc aagctggtgg ccaacaacac ccggctgtgg | 720 |
| gtgtactgcg gcaacggcac ccctaatgaa ctgggcggag ccaatatccc cgccgagttc | 780 |
| ctggaaaact tcgtgcggag cagcaacctg aagttccagg atgcctacaa cgccgctggc | 840 |
| ggccacaacg ccgtgttcaa cttccctccc aatggcaccc acagctggga gtactgggga | 900 |
| gcccagctga acgccatgaa gggcgatctg cagtcctctc tgggagccgg cagccagatc | 960 |
| atgtacaact accccgccat gctgggccac gccggcgata tggctggata tgccggcaca | 1020 |
| ctgcagagcc tgggtgccga gattgccgtg aacaggctg ccctccagtc tgcctggcag | 1080 |
| ggcgataccg gcatcacata ccaggcttgg caggcccagt ggaaccaggc catggaagat | 1140 |
| ctcgtgcggg cctaccacgc catgagcagc acacacgagg ccaacaccat ggccatgatg | 1200 |
| gcccgggata cagccgaggc cgctaagtgg ggaggaaccg agcagcagtg gaacttcgcc | 1260 |
| ggaattgagg ccgctgccag cgccatccag ggcaacgtga catccatcca gcctgctg | 1320 |
| gacgagggca agcagagcct gacaaaactg gctgctgcct ggggcggctc tggctctgaa | 1380 |
| gcttatcagg gcgtgcagca gaagtgggac gccaccgcca ccgagctgaa caacgccctg | 1440 |
| cagaacctgg cccggacaat ctctgaagcc ggacaggcca tggccagcac cgagggcaat | 1500 |
| gtgaccggca tgtttgccga acaaaaactc atctcagaag aggatctgag ctatgtatta | 1560 |
| ctgagtgcag gggccctgac tgccttgatg ttgataattt tcctgatgac atgttgtaga | 1620 |
| agagtcaatc gatcagaacc tacgcaacac aatctcagag ggacagggag ggaggtgtca | 1680 |
| gtcactcccc aaagcgggaa gatcatatct tcatgggaat cacacaagag tgggggtgag | 1740 |
| accagactgc atcatcatca tcatcattga | 1770 |

<210> SEQ ID NO 41
<211> LENGTH: 1503
<212> TYPE: DNA
<213> ORGANISM: artificial sequence
<220> FEATURE:
<223> OTHER INFORMATION: nt sequence encoding fusion n?10
"Flag-Ag85B*-TB10.4-ESAT6-Myc-His tag" (pTG18296)

<400> SEQUENCE: 41

| | |
|---|---|
| atggattaca aggatgacga cgataaggcc ttctctagac ctggcctgcc cgtggaatac | 60 |

```
ctgcaggtcc caagcccag catgggccgg gatatcaagg tgcagtttca gagcggcggc    120
aacaacagcc ctgccgtgta tctgctggat ggcctgagag cccaggacga ctacaacggc    180
tgggacatca acacccctgc cttcgagtgg tactaccaga gcggcctgtc catcgtgatg    240
cctgtgggcg ccagagcag cttctacagc gactggtaca gccccgcctg tggcaaagcc    300
ggctgccaga cctacaagtg ggagacattc ctgacctccg agctgcccca gtggctgagc    360
gccaatagag ccgtgaagcc tacaggctct gccgccatcg gactgagcat ggccggaagc    420
tctgccatga tcctggccgc ctatcaccct cagcagttca tctacgccgg cagcctgtct    480
gccctgctgg acccttctca gggcatgggc ccttctctga tcggactggc tatgggcgac    540
gctggcggat acaaggccgc cgatatgtgg ggccctagca gcgatcctgc ctgggagaga    600
aacgacccca cccagcagat ccccaagctg gtggccaaca caccccggct gtgggtgtac    660
tgcggcaacg gcacccctaa tgaactgggc ggagccaata tccccgccga gttcctggaa    720
aacttcgtgc ggagcagcaa cctgaagttc aggatgcct acaacgccgc tggcggccac    780
aacgccgtgt tcaacttccc tcccaatggc acccacagct gggagtactg gggagcccag    840
ctgaacgcca tgaagggcga tctgcagtcc tctctgggag ccggcagcca gatcatgtac    900
aactaccccg ccatgctggg ccacgccggc gatatggctg gatatgccgg cacactgcag    960
agcctgggtg ccgagattgc cgtggaacag gctgccctcc agtctgcctg gcagggcgat   1020
accggcatca cataccaggc ttggcaggcc cagtggaacc aggccatgga agatctcgtg   1080
cgggcctacc acgccatgag cagcacacac gaggccaaca ccatggccat gatggcccgg   1140
gatacagccg aggccgctaa gtggggagga accgagcagc agtggaactt cgccggaatt   1200
gaggccgctg ccagcgccat ccagggcaac gtgacatcca tccacagcct gctggacgag   1260
ggcaagcaga gcctgacaaa actggctgct gcctggggcg gctctggctc tgaagcttat   1320
cagggcgtgc agcagaagtg ggacgccacc gccaccgagc tgaacaacgc cctgcagaac   1380
ctggcccgga caatctctga agccggacag gccatggcca gcaccgaggg caatgtgacc   1440
ggcatgtttg ccgaacaaaa actcatctca gaagaggatc tgcatcatca tcatcatcat   1500
tga                                                                 1503
```

<210> SEQ ID NO 42
<211> LENGTH: 1392
<212> TYPE: DNA
<213> ORGANISM: artificial sequence
<220> FEATURE:
<223> OTHER INFORMATION: nt sequence encoding fusion n?3 "SS-Flag-RPFB-
      Dhyb-Myc-TM-His tag" (pTG18267)

<400> SEQUENCE: 42

```
atggtaccac aagcgctgtt acttgtccca ctgcttggtt tctctttatg ttttggaaaa     60
ttcccaatag attacaagga tgacgacgat aagaccgtgg acggcaccgc catgagagtg    120
accaccatga agtccagagt gatcgacatc gtggaagaga acggcttcag cgtgacgac    180
cgggacgacc tgtatcctgc tgctggagtg caggtccacg acgccgatac aatcgtgctg    240
cggagaagca gaccccctgca gatcagcctg gatggcacg acgccaagca ggtctggacc    300
acagccagca cagtggatga agccctggcc cagctgccat gaccgatac agctccagcc    360
gccgctagca gagctagcag agtgcctctg tctggcatgg ccctgcctgt ggtgtctgcc    420
aagaccgtgc agctgaacga tggcggcctc gtgcggacag tgcatctgcc tgctcctaat    480
gtggccggcc tgctgtctgc agcaggcgtg ccactgctgc agagcgatca tgtggtgcct    540
```

```
gccgccacag cccctatcgt ggaaggcatg cagatccagg tcacacggaa ccggatcaag    600
aaagtgaccg agcggctgcc cctgcctccc aacgctagaa gagtggaaga tcccgagatg    660
aacatgagca gagaggtggt cgaggaccct ggcgtgccag gcacacagga tgtgacattc    720
gccgtggcca agtgaacgg cgtggaaacc ggcagactgc ccgtggccaa tgtggtggtc     780
acaccagccc atgaggccgt cgtcagagtg gcacaaagc ctggcacaga ggtgccaccc     840
gtgatcgacg gcagcatctg ggatgccatt gcccagtgca gagcggcgg aaactgggcc     900 gccaataccg gcaatggcct ctatggcggc ctgcagatct ctcaggccgc ctgggattct    960
aatggcggcg tgggatctcc tgccgctgcc tctccacagc agcagatcga ggtggccgac   1020
aacatcatga agacagccgg acctggcgcc tggcccaagt gtagcagttg ttctcagggc   1080
gacgcccctc tgggcagcct gacacacatc ctgacatttc tggccgccga cacaggcgga   1140
gaacaaaaac tcatctcaga gaggatctg agctatgttc ttctctctgc tggaacttta    1200
atagctttaa tgttaataat attcttaata acgtgctgta aagggtaga ccgtccagag    1260 tcaactcagc gcagccttag gggtactggg agaaatgttt ccgtgacatc acagagtgga   1320
aaatttatct cgtcttggga atctcataag agtggaggcg aaacacgtct tcatcatcat   1380
catcatcatt ga                                                        1392

<210> SEQ ID NO 43
<211> LENGTH: 1125
<212> TYPE: DNA
<213> ORGANISM: artificial sequence
<220> FEATURE:
<223> OTHER INFORMATION: nt sequence encoding fusion n?12 "Flag-RPFB-
      Dhyb-Myc-His tag" (pTG18307)

<400> SEQUENCE: 43
atggattaca aggatgacga cgataagacc gtggacggca ccgccatgag agtgaccacc     60
atgaagtcca gagtgatcga catcgtggaa gagaacggct tcagcgtgga cgaccgggac    120
gacctgtatc ctgctgctgg agtgcaggtc cacgacgccg atacaatcgt gctgcggaga    180
agcagacccc tgcagatcag cctggatggc cacgacgcca gcaggtctg gaccacagcc     240 agcacagtgg atgaagccct ggcccagctg gccatgaccg atacagctcc agccgccgct    300
agcagagcta gcagagtgcc tctgtctggc atggccctgc ctgtggtgtc tgccaagacc    360
gtgcagctga cgatggcgg cctcgtgcgg acagtgcatc tgcctgctcc taatgtggcc    420
ggcctgctgt ctgcagcagg cgtgccactg ctgcagagcg atcatgtggt gcctgccgcc    480
acagccccta tcgtggaagg catgcagatc caggtcacac ggaaccggat caagaaagtg    540
accgagcggc tgcccctgcc tcccaacgct agaagagtgg aagatcccga tgaacatg      600 agcagagagg tggtcgagga ccctggcgtg ccaggcacac aggatgtgac attcgccgtg    660
gccgaagtga acggcgtgga aaccggcaga ctgcccgtgg ccaatgtggt ggtcacacca    720
gcccatgagg ccgtcgtcag agtgggcaca aagcctggca cagaggtgcc acccgtgatc   780
gacggcagca tctgggatgc cattgcccag tgcagagcg cggaaactg gccgccaat      840 accggcaatg gcctctatgg cggcctgcag atctctcagg ccgcctggga ttctaatggc    900
ggcgtgggat ctcctgccgc tgcctctcca gcagcagaga tcgaggtggc cgacaacatc    960
atgaagacag ccggacctgg cgcctggccc aagtgtagca gttgttctca gggcgacgcc   1020
cctctgggca gcctgacaca catcctgaca tttctggccg ccgagacagg cggagaacaa   1080
aaactcatct cagaagagga tctgcatcat catcatcatc attga                    1125
```

<210> SEQ ID NO 44
<211> LENGTH: 2817
<212> TYPE: DNA
<213> ORGANISM: artificial sequence
<220> FEATURE:
<223> OTHER INFORMATION: nt sequence encoding fusion n?4
"SS-Flag-RPFB-Dhyb-Ag85B*-TB10.4-ESAT6-Myc-TM-His tag" (pTG18268)

<400> SEQUENCE: 44

| | | | | |
|---|---|---|---|---|
| atggtaccac aagcgctgtt acttgtccca ctgcttggtt tctctttatg ttttggaaaa | 60 |
| ttcccaatag attacaagga tgacgacgat aagaccgtgg acggcaccgc catgagagtg | 120 |
| accaccatga agtccagagt gatcgacatc gtggaagaga acggcttcag cgtgacgac | 180 |
| cgggacgacc tgtatcctgc tgctggagtg caggtccacg acgccgatac aatcgtgctg | 240 |
| cggagaagca gaccctgca gatcagcctg gatggcacg acgccaagca ggtctggacc | 300 |
| acagccagca cagtggatga agccctggcc cagctggcca tgaccgatac agctccagcc | 360 |
| gccgctagca gagctagcag agtgcctctg tctggcatgg ccctgcctgt ggtgtctgcc | 420 |
| aagaccgtgc agctgaacga tggcggcctc gtgcggacag tgcatctgcc tgctcctaat | 480 |
| gtggccggcc tgctgtctgc agcaggcgtg ccactgctgc agagcgatca tgtggtgcct | 540 |
| gccgccacag cccctatcgt ggaaggcatg cagatccagg tcacacggaa ccggatcaag | 600 |
| aaagtgaccg agcggctgcc cctgcctccc aacgctagaa gagtggaaga tcccgagatg | 660 |
| aacatgagca gagaggtggt cgaggaccct ggcgtgccag gcacacagga tgtgacattc | 720 |
| gccgtggccg aagtgaacgg cgtggaaacc ggcagactgc ccgtggccaa gtggtggtc | 780 |
| acaccagccc atgaggccgt cgtcagagtg ggcacaaagc ctggcacaga ggtgccaccc | 840 |
| gtgatcgacg cagcatctg gatgccatt gcccagtgca gagcggcgg aaactgggcc | 900 |
| gccaataccg gcaatggcct ctatggcggc ctgcagatct ctcaggccgc ctgggattct | 960 |
| aatggcggcg tgggatctcc tgccgctgcc tctccacagc agcagatcga ggtggccgac | 1020 |
| aacatcatga gacagccgg acctggcgcc tggcccaagt gtagcagttg ttctcagggc | 1080 |
| gacgcccctc tgggcagcct gacacacatc ctgacatttc tggccgccga cacaggcgga | 1140 |
| gccttctcta gacctggcct gcccgtggaa tacctgcagg tcccaagccc cagcatgggc | 1200 |
| cgggatatca aggtgcagtt tcagagcggc ggcaacaaca gccctgccgt gtatctgctg | 1260 |
| gatggcctga gagcccagga cgactacaac ggctgggaca tcaacacccc tgccttcgag | 1320 |
| tggtactacc agagcggcct gtccatcgtg atgcctgtgg gcggccagag cagcttctac | 1380 |
| agcgactggt acagccccgc ctgtggcaaa gccggctgcc agacctacaa gtgggagaca | 1440 |
| ttcctgacct ccgagctgcc ccagtggctg agcgccaata gagccgtgaa gcctacaggc | 1500 |
| tctgccgcca tcggactgag catggccgga agctctgcca tgatcctggc cgcctatcac | 1560 |
| cctcagcagt tcatctacgc cggcagcctg tctgccctgc tggacccttc tcagggcatg | 1620 |
| ggccttctc tgatcggact ggctatgggc gacgctggcg atacaaggc cgccgatatg | 1680 |
| tggggcccta gcagcgatcc tgcctgggag agaaacgacc ccacccagca gatccccaag | 1740 |
| ctggtggcca acaacacccg gctgtgggtg tactgcggca acggcacccc taatgaactg | 1800 |
| ggcggagcca atatccccgc cgagttcctg gaaaacttcg tgcggagcag caacctgaag | 1860 |
| ttccaggatg cctacaacgc cgctggcggc cacaacgccg tgttcaactt ccctcccaat | 1920 |
| ggcacccaca gctgggagta ctggggagcc cagctgaacg ccatgaaggg cgatctgcag | 1980 |
| tcctctctgg agccggcag ccagatcatg tacaactacc ccgccatgct gggccacgcc | 2040 |

-continued

```
ggcgatatgg ctggatatgc cggcacactg cagagcctgg gtgccgagat tgccgtggaa     2100
caggctgccc tccagtctgc ctggcagggc gataccggca tcacatacca ggcttggcag     2160
gcccagtgga accaggccat ggaagatctc gtgcgggcct accacgccat gagcagcaca     2220
cacgaggcca acaccatggc catgatggcc cgggatacag ccgaggccgc taagtgggga     2280
ggaaccgagc agcagtggaa cttcgccgga attgaggccg ctgccagcgc catccagggc     2340
aacgtgacat ccatccacag cctgctggac gagggcaagc agagcctgac aaaactggct     2400
gctgctgggg gcggctctgg ctctgaagct tatcagggcg tgcagcagaa gtgggacgcc     2460
accgccaccg agctgaacaa cgccctgcag aacctggccc ggacaatctc tgaagccgga     2520
caggccatgg ccagcaccga gggcaatgtg accggcatgt ttgccgaaca aaaactcatc     2580
tcagaagagg atctgagcta tgttcttctc tctgctggaa cttttaatagc tttaatgtta     2640 ataatattct taataacgtg ctgtaaaagg gtagaccgtc cagagtcaac tcagcgcagc     2700
cttaggggta ctgggagaaa tgtttccgtg acatcacaga gtggaaaatt tatctcgtct     2760
tgggaatctc ataagagtgg aggcgaaaca cgtcttcatc atcatcatca tcattga       2817
```

<210> SEQ ID NO 45
<211> LENGTH: 2550
<212> TYPE: DNA
<213> ORGANISM: artificial sequence
<220> FEATURE:
<223> OTHER INFORMATION: nt sequence encoding fusion n?11
    "Flag-RPFB-Dhyb-Ag85B*-TB10.4-ESAT6-Myc-His tag" (pTG18297)

<400> SEQUENCE: 45

```
atggattaca aggatgacga cgataagacc gtggacggca ccgccatgag agtgaccacc       60
atgaagtcca gagtgatcga catcgtggaa gagaacggct tcagcgtgga cgaccgggac      120
gacctgtatc ctgctgctgg agtgcaggtc cacgacgccg atacaatcgt gctgcggaga      180
agcagacccc tgcagatcag cctggatggc cacgacgcca gcaggtctg gaccacagcc      240 agcacagtgg atgaagccct ggcccagctg gccatgaccg atacagctcc agccgccgct      300
agcagagcta gcagagtgcc tctgtctggc atggccctgc ctgtggtgtc tgccaagacc      360
gtgcagctga acgatggcgg cctcgtgcgg acagtgcatc tgcctgctcc taatgtggcc      420
ggcctgctgt ctgcagcagg cgtgccactg ctgcagagcg atcatgtggt gcctgccgcc      480
acagccccta tcgtggaagg catgcagatc caggtcacac ggaaccggat caagaaagtg      540
accgagcggc tgcccctgcc tcccaacgct agaagagtgg aagatcccga gatgaacatg      600
agcagagagg tggtcgagga ccctggccgt gccaggcacac aggatgtgac attcgccgtg      660
gccgaagtga acggcgtgga aaccggcaga ctgcccgtgg ccaatgtggt ggtcacacca      720
gcccatgagg ccgtcgtcag agtgggcaca aagcctggca cagaggtgcc acccgtgatc      780
gacggcagca tctgggatgc cattgcccag tgcaagagcg gcggaaactg gccgccaat      840 accggcaatg gcctctatgg cggcctgcag atctctcagg ccgcctggga ttctaatggc      900
ggcgtgggat ctcctgccgc tgcctctcca cagcagcaga tcgaggtggc cgacaacatc      960
atgaagacag ccggacctgg cgcctggccc aagtgtagca gttgttctca gggcgacgcc     1020
cctctgggca gcctgacaca catcctgaca tttctggccg ccagacagg cggagccttc     1080 tctagacctg gcctgcccgt ggaatacctg caggtcccaa gccccagcat gggccgggat     1140
atcaaggtgc agtttcagag cggcggcaac aacagccctg ccgtgtatct gctggatggc     1200
ctgagagccc aggacgacta caacggctgg gacatcaaca cccctgcctt cgagtggtac     1260
```

| | |
|---|---:|
| taccagagcg gcctgtccat cgtgatgcct gtgggcggcc agagcagctt ctacagcgac | 1320 |
| tggtacagcc ccgcctgtgg caaagccggc tgccagacct acaagtggga gacattcctg | 1380 |
| acctccgagc tgccccagtg gctgagcgcc aatagagccg tgaagcctac aggctctgcc | 1440 |
| gccatcggac tgagcatggc cggaagctct gccatgatcc tggccgccta tcaccctcag | 1500 |
| cagttcatct acgccggcag cctgtctgcc ctgctggacc cttctcaggg catgggccct | 1560 |
| tctctgatcg gactggctat gggcgacgct ggcggataca aggccgccga tatgtggggc | 1620 |
| cctagcagcg atcctgcctg ggagagaaac gaccccaccc agcagatccc caagctggtg | 1680 |
| gccaacaaca cccggctgtg ggtgtactgc ggcaacggca ccctaatgaa actgggcgga | 1740 |
| gccaatatcc ccgccgagtt cctggaaaac ttcgtgcgga gcagcaacct gaagttccag | 1800 |
| gatgcctaca cgccgctgg cggccacaac gccgtgttca acttccctcc aatggcacc | 1860 |
| cacagctggg agtactgggg agcccagctg aacgccatga agggcgatct gcagtcctct | 1920 |
| ctggagccg gcagccagat catgtacaac taccccgcca tgctgggcca cgccggcgat | 1980 |
| atggctggat atgccggcac actgcagagc ctgggtgccg agattgccgt ggaacaggct | 2040 |
| gccctccagt ctgcctggca gggcgatacc ggcatcacat accaggcttg gcaggcccag | 2100 |
| tggaaccagg ccatggaaga tctcgtgcgg gcctaccacg ccatgagcag cacacacgag | 2160 |
| gccaacacca tggccatgat ggcccgggat acagccgagg ccgctaagtg gggaggaacc | 2220 |
| gagcagcagt ggaacttcgc cggaattgag gccgctgcca cgccatcca gggcaacgtg | 2280 |
| acatccatcc acagcctgct ggacgagggc aagcagagcc tgacaaaact ggctgctgcc | 2340 |
| tggggcggct ctggctctga agcttatcag ggcgtgcagc agaagtggga cgccaccgcc | 2400 |
| accgagctga caacgcct gcagaacctg gcccggacaa tctctgaagc cggacaggcc | 2460 |
| atggccagca ccgagggcaa tgtgaccggc atgtttgccg aacaaaaact catctcagaa | 2520 |
| gaggatctgc atcatcatca tcatcattga | 2550 |

<210> SEQ ID NO 46
<211> LENGTH: 3597
<212> TYPE: DNA
<213> ORGANISM: artificial sequence
<220> FEATURE:
<223> OTHER INFORMATION: nt sequence encoding fusion n?5
"SS-Flag-Rv0569-Rv1813*-Rv3407-Rv3478-Rv1807-Myc-TM-His tag"
(pTG18269)

<400> SEQUENCE: 46

| | |
|---|---:|
| atggtaccgc aagccctgct attcgtacct ttattggtct ttcccctctg tttcggtaag | 60 |
| tttcctatag attacaagga tgacgacgat aagaaggcca aagtcggcga ctggctggtc | 120 |
| atcaagggcg ccaccatcga ccagcccgat cacagaggcc tgatcatcga agtgcggagc | 180 |
| agcgacggca gccctcctta cgtcgtcaga tggctggaaa ccgaccacgt ggccaccgtg | 240 |
| atccctggac ctgatgccgt ggtggtcacc gccgaggaac agaatgccgc cgatgagaga | 300 |
| gcccagcaca gattcggagc cgtgcagagc gccatcctgc acgccagagg aacagccaac | 360 |
| ggcagcatga gcgaagtgat gatgagcgag atcgccggcc tgcccatccc tcccatcatc | 420 |
| cactatggcg ccattgccta cgcccctagc ggcgcctctg aaaagcctg caccagaga | 480 |
| acacccgcca gagccgaaca ggtggccctg aaaagtgcg gcgacaagac ctgcaaggtg | 540 |
| gtgtcccggt tcaccagatg tggcgccgtg gcctacaacg gctccaagta tcagggcggc | 600 |
| accgcctga caagaagggc cgctgaggac gacgccgtga acagactgga aggcggcaga | 660 |
| atcgtgaact gggcctgcaa cagagccacc gtgggactgg tggaagccat cggcatcaga | 720 |

```
gagctgagac agcacgccag cagatacctg gccagagtgg aagccggcga ggaactgggc    780
gtgaccaaca agggcagact ggtggccaga ctgatccctg tgcaggccgc cgagagaagc    840
agagaggccc tgattgagag cggcgtgctg atccctgcca gacggcctca gaacctgctg    900
gatgtgacag ccgagcccgc cagaggccgg aagagaaccc tgagcgacgt gctgaacgag    960
atgcgggatg aacaggtgga cttcggcgcc ctgcctcccg agattaatag cgccaggatg   1020
tacgccggcc ctggcagcgc ttctctggtg ccgctgcca agatgtggga tagcgtggcc   1080
agcgacctgt tctctgccgc cagcgcattt cagagcgtcg tgtggggact cactgtgggc   1140
tcttggatcg gatcttctgc cggtctgatg ccgctgctg cctctcctta tgtggcctgg   1200
atgagcgtga ccgccggaca ggcacagctg acagctgcac aggtccgagt ggctgccgcc   1260
gcttacgaga cagcctacag actgacagtg cctccacccg tgatcgccga aatcggacc    1320 gagctcatga ccctgaccgc caccaatctg ctcggccaga cacccctgc catcgaggcc    1380 aatcaggccg cctactctca aatgtggggc caagatgccg aggctatgta cggctatgca   1440
gccacagccg ccactgctac agaagccctg ctgcccttcg aagatgcccc tctgatcaca   1500
aaccctggcg gcctgctgga acaggccgtg gctgtggaag aggccatcga taccgctgcc   1560
gccaaccaac tcatgaacaa cgtgccacag gccctccagc agctggctca gcctgctcag   1620
ggcgtggtgc cttctagcaa gctcggcgga ctgtggaccg ccgtgtctcc tcatctgagc   1680
cctctgagca acgtgtcctc tatcgccaac aaccacatga gcatgatggg caccggcgtg   1740
tccatgacca caccctgca cagcatgctg aagggactgg ccctgctgc tgcccaggct   1800 gtggaaacag ccgccgaaaa tggcgtgtgg gccatgagca gcctgggctc tcagctggga   1860
agctccctcg gttcttctgg actgggagct ggcgtggccg ccaatctggg aagagctgct   1920
tctgtcggca gcctgtctgt gcctcctgct tgggccgctg ctaaccaggc tgtgacacca   1980
gctgctagag ccctgcctct gaccagcctg acatctgccg tcagacagc ccctggccac   2040 atgctgggag gactgcctct gggccactct gtgaatgccg gcagcggcat caacaacgcc   2100
ctgagagtgc ctgccagagc ctacgccatc cccagaactc cagccgctgg cgattttgcc   2160
accctcccac ctgagatcaa ttccgctaga atgtatagcg gagccgggtc tgctcctatg   2220
ctggctgctg cttctgcctg gcacggactg tctgccgaac tgagagccag cgccctgagc   2280
tacagcagcg tgctgagtac cctgaccggc gaagagtggc acggacctgc cagcgcctct   2340
atgacagcag ccgctgcccc atatgtcgca tggatgtcag tcactgcagt gcgggccgaa   2400
caggcaggcg ctcaggctga agctgcagca gcagcttatg aagccgcctt tgccgctaca   2460 gtcccaccctc ctgtcattga ggccaaccgg gcccagctga tggctctgat tgccacaaac   2520
gtgctgggac agaatgcccc agccattgcc gctacagaag cccagtatgc cgagatgtgg   2580
tcccaggacg ctatggcaat gtatgggtat gctggcgcct ccgccgctgc cacacagctg   2640
acacctttca ccgagcccgt gcagaccacc aatgcctctg gactggccgc cagtctgcc   2700 gccattgctc atgctacagg cgcctctgct ggggctcagc agacaacact gtcccagctg   2760
atcgccgcca tccctagcgt gctgcaggga ctgagcagct ctaccgccgc cacatttgcc   2820
tctggcccta gcggactgct gggcatcgtg gcagtggaa gctcctggct ggataagctg   2880
tgggccctgc tggaccccaa cagcaacttc tggaacacaa tcgccagctc cggcctgttt   2940
ctgcccagca acaccattgc cccatttctg ggcctgctgg gcgagtggc tgctgcagat   3000 gctgctgggg atgtgctggg cgaagccaca agcggaggac tgggaggcgc tctggtggca   3060
```

```
cctctgggat ctgcaggcgg actcggagga acagtggctg caggactggg caatgctgcc    3120
acagtgggca cactgagcgt gccaccatct tggacagctg ccgcccctct ggcttctcct    3180
ctcggatctg ctctgggcgg cacccctatg gtggctccac ctcctgctgt ggctgccgga    3240
atgcctggca tgcctttcgg cacaatgggc ggacagggct tcggcagagc cgtgcctcag    3300
tacggcttcc ggcctaactt cgtggccaga cctcctgcag ctggcgaaca aaaactcatc    3360
tcagaagagg atctgagcta cgtactgcta tcggcaggca cgttgatcgc actaatgctt    3420
atcatcttcc taataacctg ctgcaagcgg gttgataggc ccgaaagtac ccaaaggtcc    3480
ttgagaggta ccggacgcaa cgtatcggta acgtcgcaaa gcggcaagtt cattagcagt    3540
tgggagtcgc acaaatcagg tggagagacc cgcctgcatc atcatcatca tcattga      3597
```

<210> SEQ ID NO 47
<211> LENGTH: 3330
<212> TYPE: DNA
<213> ORGANISM: artificial sequence
<220> FEATURE:
<223> OTHER INFORMATION: nt sequence encoding fusion n?9
    "Flag-Rv0569-Rv1813*-Rv3407-Rv3478-Rv1807-Myc-His tag" (pTG18295)

<400> SEQUENCE: 47

```
atggattaca aggatgacga cgataagaag gccaaagtcg gcgactggct ggtcatcaag      60
ggcgccacca tcgaccagcc cgatcacaga ggcctgatca tcgaagtgcg gagcagcgac     120
ggcagccctc cttacgtcgt cagatggctg gaaaccgacc acgtggccac cgtgatccct     180
ggacctgatg ccgtggtggt caccgccgag gaacagaatg ccgccgatga gagagcccag     240
cacagattcg gagccgtgca gagcgccatc ctgcacgcca gaggaacagc caacggcagc     300
atgagcgaag tgatgatgag cgagatcgcc ggcctgccca tccctcccat catccactat     360
ggcgccattg cctacgcccc tagcggcgcc tctggaaaag cctggcacca gagaacaccc     420
gccagagccg aacaggtggc cctgaaaaag tgcggcgaca agacctgcaa ggtggtgtcc     480
cggttcacca gatgtggcgc cgtggcctac aacggctcca gtatcagggg cggcaccggc     540
ctgacaagaa gggccgctga ggacgacgcc gtgaacagac tggaaggcgg cagaatcgtg     600
aactgggcct gcaacagagc caccgtggga ctggtggaag ccatcggcat cagagagctg     660
agacagcacg ccagcagata cctggccaga gtgaagccgg cgaggaact  gggcgtgacc     720 aacaagggca gactggtggc cagactgatc cctgtgcagg ccgccgagag aagcagagag     780
gccctgattg agagcggcgt gctgatccct gccagacggc ctcagaacct gctggatgtg     840
acagccgagc cgccagagg ccggaagaga accctgagcg acgtgctgaa cgagatgcgg     900
gatgaacagg tggacttcgg cgccctgcct cccgagatta atagcgccag gatgtacgcc     960
ggccctggca gcgcttctct ggtggccgct gccaagatgt gggatagcgt ggccagcgac    1020
ctgttctctg ccgccagcgc atttcagagc gtcgtgtggg gactcactgt gggctcttgg    1080
atcggatctt ctgccggtct gatggccgct gctgcctctc cttatgtggc ctggatgagc    1140
gtgaccgccg acaggcaca gctgacagct gcacaggtcc gagtggctgc cgccgcttac    1200
gagacagcct acagactgac agtgcctcca cccgtgatcg ccgagaatcg gaccgagctc    1260
atgaccctga ccgccaccaa tctgctcggc cagaacaccc ctgccatcga ggccaatcag    1320
gccgcctact ctcaaatgtg gggccaagat gccgaggcta tgtacggcta tgcagccaca    1380
gccgccactg ctacagaagc cctgctgccc ttcgaagatg cccctctgat cacaaaccct    1440
ggcggcctgc tggaacaggc cgtggctgtg aagaggcca tcgataccgc tgccgccaac    1500
```

-continued

```
caactcatga acaacgtgcc acaggccctc cagcagctgg ctcagcctgc tcagggcgtg      1560
gtgccttcta gcaagctcgg cggactgtgg accgccgtgt ctcctcatct gagccctctg      1620
agcaacgtgt cctctatcgc caacaaccac atgagcatga tgggcaccgg cgtgtccatg      1680
accaacaccc tgcacagcat gctgaaggga ctggcccctg ctgctgccca ggctgtggaa      1740
acagccgccg aaaatggcgt gtgggccatg agcagcctgg gctctcagct gggaagctcc      1800
ctcggttctt ctggactggg agctggcgtg ccgccaatc tgggaagagc tgcttctgtc       1860
ggcagcctgt ctgtgcctcc tgcttgggcc gctgctaacc aggctgtgac cagctgct       1920 agagccctgc ctctgaccag cctgacatct gccgctcaga cagcccctgg ccacatgctg      1980
ggaggactgc tctgggcca ctctgtgaat gccggcagcg catcaacaa cgccctgaga        2040 gtgcctgcca gagcctacgc catccccaga actccagccg ctggcgattt tgccaccctc      2100
ccacctgaga tcaattccgc tagaatgtat agcggagccg gtctgctcc tatgctggct       2160 gctgcttctg cctggcacgg actgtctgcc gaactgagag ccagcgccct gagctacagc      2220
agcgtgctga gtaccctgac cggcgaagag tggcacggac ctgccagcgc ctctatgaca      2280
gcagccgctg ccccatatgt cgcatggatg tcagtcactg cagtgcgggc cgaacaggca      2340
ggcgctcagg ctgaagctgc agcagcagct tatgaagccg cctttgccgc tacagtccca      2400
cctcctgtca ttgaggccaa ccgggcccag ctgatggctc tgattgccac aaacgtgctg      2460
ggacagaatg cccagccat tgccgctaca gaagcccagt atgccgagat gtggtcccag       2520
gacgctatgg caatgtatgg gtatgctggc gcctccgccg ctgccacaca gctgacacct      2580
ttcaccgagc ccgtgcagac caccaatgcc tctggactgg ccgcccagtc tgccgccatt      2640
gctcatgcta caggcgcctc tgctggggct cagcagacaa cactgtccca gctgatcgcc      2700
gccatcccta gcgtgctgca gggactgagc agctctaccg ccgccacatt tgcctctggc      2760
cctagcggac tgctgggcat cgtgggcagt ggaagctcct ggctggataa gctgtgggcc      2820
ctgctggacc caacagcaa cttctggaac acaatcgcca gctccggcct gtttctgccc       2880
agcaacacca ttgccccatt tctgggcctg ctgggcggag tggctgctgc agatgctgct      2940
ggggatgtgc tgggcgaagc cacaagcgga ggactgggag cgctctggt ggcacctctg       3000 ggatctgcag gcggactcgg aggaacagtg gctgcaggac tgggcaatgc tgccacagtg      3060
ggcacactga gcgtgccacc atcttggaca gctgccgccc ctctggcttc tcctctcgga      3120
tctgctctgg gcggcacccc tatggtggct ccacctcctg ctgtggctgc cggaatgcct      3180
ggcatgcctt tcggcacaat gggcggacag ggcttcggca gagccgtgcc tcagtacggc      3240
ttccggccta acttcgtggc cagacctcct gcagctggcg aacaaaaact catctcagaa      3300
gaggatctgc atcatcatca tcatcattga                                       3330
```

<210> SEQ ID NO 48
<211> LENGTH: 2922
<212> TYPE: DNA
<213> ORGANISM: artificial sequence
<220> FEATURE:
<223> OTHER INFORMATION: nt sequence encoding fusion n°6
      "SS-Flag-Ag85B*-Rv2626-RPFB-Dhyb-Rv1733*-Myc-His tag" (pTG18270)

<400> SEQUENCE: 48

```
atggttcctc aggctctcct gtttgtaccc cttctggttt tccattgtg ttttgggaaa       60 ttccctattg attacaagga tgacgacgat aaggccttct ctagacctgg cctgcccgtg      120
gaatacctgc aggtcccaag ccccagcatg ggccgggata tcaaggtgca gtttcagagc      180
```

| | |
|---|---|
| ggcggcaaca acagccctgc cgtgtatctg ctggatggcc tgagagccca ggacgactac | 240 |
| aacggctggg acatcaacac ccctgccttc gagtggtact accagagcgg cctgtccatc | 300 |
| gtgatgcctg tgggcggcca gagcagcttc tacagcgact ggtacagccc cgcctgtggc | 360 |
| aaagccggct gccagaccta caagtgggag acattcctga cctccgagct gccccagtgg | 420 |
| ctgagcgcca atagagccgt gaagcctaca ggctctgccg ccatcggact gagcatggcc | 480 |
| ggaagctctg ccatgatcct ggccgcctat caccctcagc agttcatcta cgccggcagc | 540 |
| ctgtctgccc tgctggaccc ttctcagggc atgggccctt ctctgatcgg actggctatg | 600 |
| ggcgacgctg gcggatacaa ggccgccgat atgtggggcc ctagcagcga tcctgcctgg | 660 |
| gagagaaacg accccaccca gcagatcccc aagctggtgg ccaacaacac ccggctgtgg | 720 |
| gtgtactgcg gcaacggcac ccctaatgaa ctgggcggag ccaatatccc cgccgagttc | 780 |
| ctggaaaact tcgtgcggag cagcaacctg aagttccagg atgcctacaa cgccgctggc | 840 |
| ggccacaacg ccgtgttcaa cttccctccc aatggcaccc acagctggga gtactgggga | 900 |
| gcccagctga acgccatgaa gggcgatctg cagtcctctc tgggagccgg cacaaccgcc | 960 |
| agagacatca tgaacgccgg cgtgacctgt gtgggcgagc acgagacact gacagccgcc | 1020 |
| gctcagtaca tgagagagca cgacatcggc gccctgccca tctgcggcga cgatgataga | 1080 |
| ctgcacggca tgctgaccga ccgggacatc gtgatcaagg gcctggctgc tggcctggac | 1140 |
| cccaatactg ctacagctgg cgagctggca agagacagca tctactacgt ggacgccaac | 1200 |
| gccagcatcc aggaaatgct gaacgtgatg gaagaacacc aggtccgacg ggtgcccgtg | 1260 |
| atcagcgaac acagactcgt gggcatcgtg accgaggccg atatcgccag acatctgccc | 1320 |
| gagcacgcca tcgtgcagtt cgtgaaggcc atctgcagcc ccatggccct ggcctctacc | 1380 |
| gtggacggca ccgccatgag agtgaccacc atgaagtcca gagtgatcga catcgtggaa | 1440 |
| gagaacggct tcagcgtgga cgaccgggac gacctgtatc ctgctgctgg agtgcaggtc | 1500 |
| cacgacgccg atacaatcgt gctgcggaga agcagacccc tgcagatcag cctggatggc | 1560 |
| cacgacgcca agcaggtctg gaccacagcc agcacagtgg atgaagccct ggcccagctg | 1620 |
| gccatgaccg atacagctcc agccgccgct agcagagcta gcagagtgcc tctgtctggc | 1680 |
| atggccctgc ctgtggtgtc tgccaagacc gtgcagctga cgatggcgg cctcgtgcgg | 1740 |
| acagtgcatc tgcctgctcc taatgtggcc ggcctgctgt ctgcagcagg cgtgccactg | 1800 |
| ctgcagagcg atcatgtggt gcctgccgcc acagccccta tcgtggaagg catgcagatc | 1860 |
| caggtcacac ggaaccggat caagaaagtg accgagcggc tgccctgcc tcccaacgct | 1920 |
| agaagagtgg aagatcccga gatgaacatg agcagagagg tggtcgagga ccctggcgtg | 1980 |
| ccaggcacac aggatgtgac attcgccgtg gccgaagtga acggcgtgga aaccggcaga | 2040 |
| ctgcccgtgg ccaatgtggt ggtcacacca gcccatgagg ccgtcgtcag agtgggcaca | 2100 |
| aagcctggca cagaggtgcc accccgtgatc gacggcagca tctgggatgc cattgcccag | 2160 |
| tgcaagagcg gcggaaactg gccgccaat accggcaatg cctctatgg cggcctgcag | 2220 |
| atctctcagg ccgcctggga ttctaatggc ggcgtgggat ctcctgccgc tgcctctcca | 2280 |
| cagcagcaga tcgaggtggc cgacaacatc atgaagacag ccggacctgg cgcctggccc | 2340 |
| aagtgtagca gttgttctca gggcgacgcc cctctgggca gcctgacaca catcctgaca | 2400 |
| tttctggccg ccgagacagg cggagctgga acagccgtgc aggatagccg gtcccacgtg | 2460 |
| tacgctcacc aggcccagac aagacaccct gccacagcca ccgtgatcga ccacgagggc | 2520 |
| gtgatcgaca gcaacaccac cgccacatct gccccacccc ggaccaagat cacagtgcct | 2580 |

```
gctagatggg tggtcaacgg catcgagcgg agcggcgaag tgaatgccaa gcccggcacc    2640
aagagcggcg acagagtggg aatctgggtg gactctgccg gccagctggt ggatgaacct    2700
gccCctcctg ccagagccat tgccgatgct gctctggctg cactgggcct gtggctgtct    2760
gtggcagctg tggctggcgc actgctggct ctgacaagag ccatcctgat cagagtgcgg    2820
aacgccagtt ggcagcacga tatcgacagc ctgttctgca cccagcggga acaaaaactc    2880
atctcagaag aggatctgag ccatcatcat catcatcatt ga                       2922
```

<210> SEQ ID NO 49
<211> LENGTH: 1875
<212> TYPE: DNA
<213> ORGANISM: artificial sequence
<220> FEATURE:
<223> OTHER INFORMATION: nt sequence encoding fusion n?8
    "SS-Flag-Ag85B*-Rv2626-Rv1733*-Myc-His tag" (pTG18272)

<400> SEQUENCE: 49

```
atggttcctc aggctctcct gtttgtaccc cttctggttt ttccattgtg ttttgggaaa      60
ttccctattg attacaagga tgacgacgat aaggccttct ctagacctgg cctgcccgtg    120
gaatacctgc aggtcccaag ccccagcatg ggccgggata tcaaggtgca gtttcagagc    180
ggcggcaaca acagccctgc cgtgtatctg ctggatggcc tgagagccca ggacgactac    240
aacggctggg acatcaacac ccctgccttc gagtggtact accagagcgg cctgtccatc    300
gtgatgcctg tgggcggcca gagcagcttc tacagcgact ggtacagccc cgcctgtggc    360
aaagccggct gccagaccta caagtgggag acattcctga cctccgagct gccccagtgg    420
ctgagcgcca atagagccgt gaagcctaca ggctctgccg ccatcggact gagcatggcc    480
ggaagctctg ccatgatcct ggccgcctat acccctcagc agttcatcta cgccggcagc    540
ctgtctgccc tgctggaccc ttctcagggc atgggccctt ctctgatcgg actggctatg    600
ggcgacgctg gcggatacaa ggccgccgat atgtggggcc ctagcagcga tcctgcctgg    660
gagagaaacg accccaccca gcagatcccc aagctggtgg ccaacaacac ccggctgtgg    720
gtgtactgcg gcaacggcac ccctaatgaa ctgggcggag ccaatatccc cgccgagttc    780
ctggaaaact tcgtgcggag cagcaacctg aagttccagg atgcctacaa cgccgctggc    840
ggccacaacg ccgtgttcaa cttccctccc aatggcaccc acagctggga gtactgggga    900
gcccagctga acgccatgaa gggcgatctg cagtcctctc tgggagccgg cacaaccgcc    960
agagacatca tgaacgccgg cgtgacctgt gtgggcgagc acgagacact gacagccgcc    1020
gctcagtaca tgagagagca cgacatcggc gccctgccca tctgcggcga cgatgataga    1080
ctgcacggca tgctgaccga ccgggacatc gtgatcaagg gcctggctgc tggcctggac    1140
cccaatactg ctacagctgg cgagctggca agagacagca tctactacgt ggacgccaac    1200
gccagcatcc aggaaatgct gaacgtgatg aagaacacc aggtccgacg ggtgcccgtg    1260
atcagcgaac acagactcgt gggcatcgtg accgaggccg atatcgccag acatctgccc    1320
gagcacgcca tcgtgcagtt cgtgaaggcc atctgcagcc ccatggccct ggcctctgct    1380
ggaacagccg tgcaggatag ccggtcccac gtgtacgctc accaggccca gacaagacac    1440
cctgccacag ccaccgtgat cgaccacgag ggcgtgatcg acagcaacac caccgccaca    1500
tctgccccac cccggaccaa gatcacagtg cctgctagat gggtggtcaa cggcatcgag    1560
cggagcggca agtgaatgc caagcccggc accaagagcg cgacagagt gggaatctgg    1620 gtggactctg ccggccagct ggtggatgaa cctgcccctc tgccagagc cattgccgat    1680
```

<210> SEQ ID NO 50
<211> LENGTH: 2845
<212> TYPE: DNA
<213> ORGANISM: artificial sequence
<220> FEATURE:
<223> OTHER INFORMATION: nt sequence encoding fusion N?13
"SS-Flag-Rv2029*-Rv2626-Rv1733*-Rv0111*-Myc-His tag" (pTG18323)

<400> SEQUENCE: 50

```
gctgctctgg ctgcactggg cctgtggctg tctgtggcag ctgtggctgg cgcactgctg      1740
gctctgacaa gagccatcct gatcagagtg cggaacgcca gttggcagca cgatatcgac      1800
agcctgttct gcacccagcg ggaacaaaaa ctcatctcag aagaggatct gagccatcat      1860
catcatcatc attga                                                       1875 atgggtctca aggtgaacgt ctctgccata ttcatggcag tactgttaac tctccaaaca        60
cccaccggtc aaatccattg gggcgattac aaggatgacg acgataagac cgagcctgcc       120
gcctgggatg agggcaagcc cagaatcatc accctgacca tgaacccccgc cctggacatc      180
accaccagcg tggacgtcgt gcggcccacc gagaagatga atgtggcgc ccctagatac        240
gaccctggcg gcggaggaat caacgtggcc agaatcgtgc acgtgctggg cggctgtagc       300
accgccctgt ttccagctgg cggctctaca ggctctctgc tgatggccct gctgggagat       360
gccggcgtgc ccttcagagt gatccctatc gccgccagca cccgcgagag cttcaccgtg       420
aatgagagcc ggaccgccaa gcagtacaga ttcgtgctgc ctggccccag cctgacagtg       480
gccgaacagg aacagtgcct ggacgagctg agaggcgccg ctgcctctgc tgcttttgtg       540
gtggcctctg gctctctgcc tcctggcgtg gccgccgact actatcagag agtggccgac       600
atctgccggc ggagcagcac acctctgatc ctggatacaa gcggcggagg cctgcagcat       660
atcagcagcg gagtgttcct gctgaaggcc agcgtccgcg agctgaggga atgtgtggga       720
agcgagctgc tgaccgagcc cgaacagctg gccgctgccc acgagctgat cgatagaggc       780
agagccgagg tggtggtggt gtctctggga tctcagggcg ctctgctggc acaagacac        840
gccagccacc ggttcagcag catccctatg acagccgtgt ctggcgtggg agccggcaat       900
gctatggtgg ccgccatcac agtgggcctg tctagaggct ggtccctgat caagtctgtg       960
cggctgggca atgccgctgg cgctgctatg ctgctgacac ctggaaccgc cgcctgcaac      1020
agggacgacg tggaacggtt cttcgagaca accgccagag acatcatgaa cgccggcgtg      1080
acctgtgtgg gcgagcacga gacactgaca gccgccgctc agtacatgag agagcacgac      1140
atcggcgccc tgcccatctg cggcgacgat gatagactgc acggcatgct gaccgaccgg      1200
gacatcgtga tcaagggcct ggctgctggc ctggaccccca atactgctac agctggcgag      1260
ctggcaagag acagcatcta ctacgtggac gccaacgcca gcatccagga aatgctgaac      1320
gtgatggaag aacaccaggt ccgacgggtg ccgtgatca gcgaacacag actcgtgggc       1380
atcgtgaccg aggccgatat cgccagacat ctgcccgagc acgccatcgt gcagttcgtg      1440
aaggccatct gcagccccat ggccctggcc tctgctggaa cagccgtgca ggatagccgg      1500
tcccacgtgt acgctcacca ggcccagaca agacaccctg ccacagccac cgtgatcgac      1560
cacgagggcg tgatcgacag caacaccacc gccacatctg ccccaccccg gaccaagatc      1620
acagtgcctg ctagatgggt ggtcaacggc atcgagcgga gcgcgaagt gaatgccaag       1680
cccggcacca gagcggcga cagagtggga atctgggtgg actctgccgg ccagctggtg      1740
gatgaacctg ccctcctgc cagagccatt gccgatgctg ctctggctgc actgggcctg      1800
```

| | | |
|---|---|---|
| tggctgtctg tggcagctgt ggctggcgca ctgctggctc tgacaagagc catcctgatc | | 1860 |
| agagtgcgga acgccagttg gcagcacgat atcgacagcc tgttctgcac ccagcgggag | | 1920 |
| cagcccatca agaatggcg gcctgccaga gtgccactgc tgccactggc tgctgctaca | | 1980 |
| gtggcttctg ccgccgctgt gaccatgctg gtggtgcctg tgggagctgg acctggcctg | | 2040 |
| agagagatcg gactgccacc aggcgtgtca gccgtggctg ctgtgtctcc tagccctcct | | 2100 |
| gaagcctctc agcctgcccc tggcccaaga gatcccaaca gacccttcac cgtgtccgtg | | 2160 |
| ttcggcgaca gcatcggctg gaccctgatg cactacctgc ctcccacccc tggcttccgg | | 2220 |
| ttcatcgacc acacagtgat cggctgcagt ctcgtgcggg gcaccccta cagatatatc | | 2280 |
| ggccagaccc tggaacagcg ggccgagtgt gatggatggc ctgctaggtg gtccgcccag | | 2340 |
| gtcaacagag atcagcccga cgtggcactg ctgatcgtgg gcagatggga gacagtggac | | 2400 |
| agagtgaacg agggccggtg gacccacatc ggcgacccta cctttgacgc ctacctgaac | | 2460 |
| gccgagctgc agcgggccct gtctatcgtg ggaagcacag cgtcagagt gatggtcacc | | 2520 |
| accgtgccct acagcagagg cggcgagaag cctgacggca gactgtaccc tgaggaccag | | 2580 |
| cccgagcgcg tgaacaagtg gaacgccatg ctgcacaacg ccatcagcca gcacagcaac | | 2640 |
| gtgggcatga tcgacctgaa caagaagctg tgccccgacg gcgtgtacac cgccaaggtg | | 2700 |
| gacggaatca agtgcggag cgacggcgtg cacctgaccc aggaaggcgt gaagtggctg | | 2760 |
| atcccctggc tggaagatag cgtgcgggtg gcctctgaac aaaaactcat ctcagaagag | | 2820 |
| gatctgagcc atcatcatca tcatc | | 2845 |

<210> SEQ ID NO 51
<211> LENGTH: 2547
<212> TYPE: DNA
<213> ORGANISM: artificial sequence
<220> FEATURE:
<223> OTHER INFORMATION: nt sequence encoding fusion n?14
      "SS-Flag-Rv2029*-TB10.4-ESAT6-Rv0111*-Myc-His tag" (pTG18324)

<400> SEQUENCE: 51

| | | |
|---|---|---|
| atgggtctca aggtgaacgt ctctgccata ttcatggcag tactgttaac tctccaaaca | | 60 |
| cccaccggtc aaatccattg gggcgattac aaggatgacg acgataagac cgagcctgcc | | 120 |
| gcctgggatg agggcaagcc cagaatcatc accctgacca tgaaccccgc cctggacatc | | 180 |
| accaccagcg tggacgtcgt gcggcccacc gagaagatga gatgtggcgc ccctagatac | | 240 |
| gaccctggcg gcgaggaat caacgtggcc agaatcgtgc acgtgctggg cggctgtagc | | 300 |
| accgccctgt ttccagctgg cggctctaca ggctctctgc tgatggccct gctgggagat | | 360 |
| gccggcgtgc ccttcagagt gatccctatc gccgccagca cccgcgagag cttcaccgtg | | 420 |
| aatgagagcc ggaccgccaa gcagtacaga ttcgtgctgc ctggccccag cctgacagtg | | 480 |
| gccgaacagg aacagtgcct ggacgagctg agaggcgccg ctgcctctgc tgcttttgtg | | 540 |
| gtggcctctg gctctctgcc tcctggcgtg gccgccgact actatcagag agtggccgac | | 600 |
| atctgccggc ggagcagcac acctctgatc ctggatacaa gcggcggagg cctgcagcat | | 660 |
| atcagcagcg gagtgttcct gctgaaggcc agcgtccgcg agctgaggga atgtgtggga | | 720 |
| agcgagctgc tgaccgagcc cgaacagctg gccgctgccc acgagctgat cgatagaggc | | 780 |
| agagccgagg tggtggtggt gtctctggga tctcagggcg ctctgctggc acaagacac | | 840 |
| gccagccacc ggttcagcag catccctatg acagccgtgt ctggcgtggg agccggcaat | | 900 |
| gctatggtgg ccgccatcac agtgggcctg tctagaggct ggtccctgat caagtctgtg | | 960 |

```
cggctgggca atgccgctgg cgctgctatg ctgctgacac ctggaaccgc cgcctgcaac    1020
agggacgacg tggaacggtt cttcgagagc cagatcatgt acaactaccc cgccatgctg    1080
ggccacgccg gcgatatggc tggatatgcc ggcacactgc agagcctggg tgccgagatt    1140
gccgtggaac aggctgccct ccagtctgcc tggcagggcg ataccggcat cacataccag    1200
gcttggcagg cccagtggaa ccaggccatg aagatctcg tgcgggccta ccacgccatg    1260
agcagcacac acgaggccaa caccatggcc atgatggccc gggatacagc cgaggccgct    1320
aagtggggag gaaccgagca gcagtggaac ttcgccggaa ttgaggccgc tgccagcgcc    1380
atccagggca acgtgacatc catccacagc ctgctgacg agggcaagca gagcctgaca    1440
aaactggctg ctgcctgggg cggctctggc tctgaagctt atcagggcgt gcagcagaag    1500
tgggacgcca ccgccaccga gctgaacaac gccctgcaga acctggcccg gacaatctct    1560
gaagccggac aggccatggc cagcaccgag ggcaatgtga ccggcatgtt tgccgagcag    1620
cccatcagaa gatggcggcc tgccagagtg ccactgctgc cactggctgc tgctacagtg    1680
gcttctgccg ccgctgtgac catgctggtg gtgcctgtgg gagctggacc tggcctgaga    1740
gagatcggac tgccaccagg cgtgtcagcc gtggctgctg tgtctcctag ccctcctgaa    1800
gcctctcagc ctgcccctgg cccaagagat cccaacagac ccttcaccgt gtccgtgttc    1860
ggcgacagca tcggctggac cctgatgcac tacctgcctc ccaccctgg cttccggttc    1920 atcgaccaca cagtgatcgg ctgcagtctc gtgcggggca ccccttacag atatatcggc    1980
cagaccctgg aacagcgggc cgagtgtgat ggatggcctg ctaggtggtc cgcccaggtc    2040
aacagagatc agcccgacgt ggcactgctg atcgtgggca gatgggagac agtggacaga    2100
gtgaacgagg gccggtggac ccacatcggc gaccctacct ttgacgccta cctgaacgcc    2160
gagctgcagc gggccctgtc tatcgtggga agcacaggc tcagagtgat ggtcaccacc    2220
gtgccctaca gcagaggcgg cgagaagcct gacggcagac tgtaccctga ggaccagccc    2280
gagcgcgtga acaagtggaa cgccatgctg cacaacgcca tcagccagca cagcaacgtg    2340
ggcatgatcg acctgaacaa gaagctgtgc cccgacggcg tgtacaccgc caaggtggac    2400
ggaatcaaag tgcggagcga cggcgtgcac ctgacccagg aaggcgtgaa gtggctgatc    2460
ccctggctgg aagatagcgt gcgggtggcc tctgaacaaa aactcatctc agaagaggat    2520
ctgagccatc atcatcatca tcattga                                       2547
```

<210> SEQ ID NO 52
<211> LENGTH: 34
<212> TYPE: DNA
<213> ORGANISM: artificial sequence
<220> FEATURE:
<223> OTHER INFORMATION: primer

<400> SEQUENCE: 52
cgcggccgca ccatggatta caaggatgac gacg                              34

<210> SEQ ID NO 53
<211> LENGTH: 34
<212> TYPE: DNA
<213> ORGANISM: artificial sequence
<220> FEATURE:
<223> OTHER INFORMATION: primer

<400> SEQUENCE: 53
cgtcgtcatc cttgtaatcc atggtgcggc cgcg                              34

```
<210> SEQ ID NO 54
<211> LENGTH: 39
<212> TYPE: DNA
<213> ORGANISM: artificial sequence
<220> FEATURE:
<223> OTHER INFORMATION: primer

<400> SEQUENCE: 54
catctcagaa gaggatctgc atcatcatca tcatcattg                          39

<210> SEQ ID NO 55
<211> LENGTH: 39
<212> TYPE: DNA
<213> ORGANISM: artificial sequence
<220> FEATURE:
<223> OTHER INFORMATION: primer

<400> SEQUENCE: 55
caatgatgat gatgatgatg cagatcctct tctgagatg                          39

<210> SEQ ID NO 56
<211> LENGTH: 40
<212> TYPE: DNA
<213> ORGANISM: artificial sequence
<220> FEATURE:
<223> OTHER INFORMATION: primer

<400> SEQUENCE: 56
gatgacgacg ataaggctag cagagccacc gtgggactgg                         40

<210> SEQ ID NO 57
<211> LENGTH: 41
<212> TYPE: DNA
<213> ORGANISM: artificial sequence
<220> FEATURE:
<223> OTHER INFORMATION: primer

<400> SEQUENCE: 57
gatgagtttt tgttcgctag cctgttcatc ccgcatctcg t                       41

<210> SEQ ID NO 58
<211> LENGTH: 37
<212> TYPE: DNA
<213> ORGANISM: artificial sequence
<220> FEATURE:
<223> OTHER INFORMATION: primer

<400> SEQUENCE: 58
gatgacgacg ataaggctag caaggccaaa gtcggcg                            37

<210> SEQ ID NO 59
<211> LENGTH: 37
<212> TYPE: DNA
<213> ORGANISM: artificial sequence
<220> FEATURE:
<223> OTHER INFORMATION: primer

<400> SEQUENCE: 59
gatgagtttt tgttcgctag ctgttcctct ggcgtgc                            37

<210> SEQ ID NO 60
<211> LENGTH: 41
<212> TYPE: DNA
<213> ORGANISM: artificial sequence
<220> FEATURE:
<223> OTHER INFORMATION: primer
```

<400> SEQUENCE: 60
gatgacgacg ataaggctag cgattttgcc accctcccac c           41

<210> SEQ ID NO 61
<211> LENGTH: 43
<212> TYPE: DNA
<213> ORGANISM: artificial sequence
<220> FEATURE:
<223> OTHER INFORMATION: primer

<400> SEQUENCE: 61
gagatgagtt tttgttcgct agcgccagct gcaggaggtc tgg         43

<210> SEQ ID NO 62
<211> LENGTH: 40
<212> TYPE: DNA
<213> ORGANISM: artificial sequence
<220> FEATURE:
<223> OTHER INFORMATION: primer

<400> SEQUENCE: 62
gatgacgacg ataaggctag cgccaacggc agcatgagcg             40

<210> SEQ ID NO 63
<211> LENGTH: 43
<212> TYPE: DNA
<213> ORGANISM: artificial sequence
<220> FEATURE:
<223> OTHER INFORMATION: primer

<400> SEQUENCE: 63
gagatgagtt tttgttcgct agcgttgcag gcccagttca cga         43

<210> SEQ ID NO 64
<211> LENGTH: 40
<212> TYPE: DNA
<213> ORGANISM: artificial sequence
<220> FEATURE:
<223> OTHER INFORMATION: primer

<400> SEQUENCE: 64
gatgacgacg ataaggctag cgtggacttc ggcgccctgc             40

<210> SEQ ID NO 65
<211> LENGTH: 43
<212> TYPE: DNA
<213> ORGANISM: artificial sequence
<220> FEATURE:
<223> OTHER INFORMATION: primer

<400> SEQUENCE: 65
gagatgagtt tttgttcgct agcgccagcg gctggagttc tgg         43

<210> SEQ ID NO 66
<211> LENGTH: 42
<212> TYPE: DNA
<213> ORGANISM: artificial sequence
<220> FEATURE:
<223> OTHER INFORMATION: primer

<400> SEQUENCE: 66
gatgacgacg ataaggctag cacaaccgcc agagacatca tg          42

<210> SEQ ID NO 67

```
<211> LENGTH: 40
<212> TYPE: DNA
<213> ORGANISM: artificial sequence
<220> FEATURE:
<223> OTHER INFORMATION: primer

<400> SEQUENCE: 67
gatgagtttt tgttcgctag cagaggccag ggccatgggg                            40

<210> SEQ ID NO 68
<211> LENGTH: 35
<212> TYPE: DNA
<213> ORGANISM: artificial sequence
<220> FEATURE:
<223> OTHER INFORMATION: primer

<400> SEQUENCE: 68
gttttggaaa attcccaata accgtggacg gcacc                                 35

<210> SEQ ID NO 69
<211> LENGTH: 35
<212> TYPE: DNA
<213> ORGANISM: artificial sequence
<220> FEATURE:
<223> OTHER INFORMATION: primer

<400> SEQUENCE: 69
ggtgccgtcc acggttattg ggaattttcc aaaac                                 35

<210> SEQ ID NO 70
<211> LENGTH: 35
<212> TYPE: DNA
<213> ORGANISM: artificial sequence
<220> FEATURE:
<223> OTHER INFORMATION: primer

<400> SEQUENCE: 70
gaccggcatg tttgccagct atgttcttct ctctg                                 35

<210> SEQ ID NO 71
<211> LENGTH: 35
<212> TYPE: DNA
<213> ORGANISM: artificial sequence
<220> FEATURE:
<223> OTHER INFORMATION: primer

<400> SEQUENCE: 71
cagagagaag aacatagctg gcaaacatgc cggtc                                 35

<210> SEQ ID NO 72
<211> LENGTH: 38
<212> TYPE: DNA
<213> ORGANISM: artificial sequence
<220> FEATURE:
<223> OTHER INFORMATION: primer

<400> SEQUENCE: 72
gtttcggtaa gtttcctata aaggccaaag tcggcgac                              38

<210> SEQ ID NO 73
<211> LENGTH: 38
<212> TYPE: DNA
<213> ORGANISM: artificial sequence
<220> FEATURE:
<223> OTHER INFORMATION: primer

<400> SEQUENCE: 73
```
gtcgccgact ttggccttta taggaaactt accgaaac                                        38

<210> SEQ ID NO 74
<211> LENGTH: 32
<212> TYPE: DNA
<213> ORGANISM: artificial sequence
<220> FEATURE:
<223> OTHER INFORMATION: primer

<400> SEQUENCE: 74
cctcctgcag ctggcagcta cgtactgcta tc                                              32

<210> SEQ ID NO 75
<211> LENGTH: 32
<212> TYPE: DNA
<213> ORGANISM: artificial sequence
<220> FEATURE:
<223> OTHER INFORMATION: primer

<400> SEQUENCE: 75
gatagcagta cgtagctgcc agctgcagga gg                                              32

<210> SEQ ID NO 76
<211> LENGTH: 36
<212> TYPE: DNA
<213> ORGANISM: artificial sequence
<220> FEATURE:
<223> OTHER INFORMATION: primer

<400> SEQUENCE: 76
gttttgggaa attccctatt gccttctcta gacctg                                          36

<210> SEQ ID NO 77
<211> LENGTH: 36
<212> TYPE: DNA
<213> ORGANISM: artificial sequence
<220> FEATURE:
<223> OTHER INFORMATION: primer

<400> SEQUENCE: 77
caggtctaga gaaggcaata gggaatttcc caaaac                                          36

<210> SEQ ID NO 78
<211> LENGTH: 44
<212> TYPE: DNA
<213> ORGANISM: artificial sequence
<220> FEATURE:
<223> OTHER INFORMATION: primer

<400> SEQUENCE: 78
gatcagatat cgcggccgcc gtacgaccat ggtaccacaa gcgc                                 44

<210> SEQ ID NO 79
<211> LENGTH: 32
<212> TYPE: DNA
<213> ORGANISM: artificial sequence
<220> FEATURE:
<223> OTHER INFORMATION: primer

<400> SEQUENCE: 79
ggcggcaggc tcggtgcccc aatggatttg ac                                              32

<210> SEQ ID NO 80
<211> LENGTH: 124
<212> TYPE: DNA

```
<213> ORGANISM: artificial sequence
<220> FEATURE:
<223> OTHER INFORMATION: promoter p7.5K

<400> SEQUENCE: 80
ccacccactt tttatagtaa gttttcacc cataaataat aaatacaata attaatttct      60
cgtaaaagta gaaatatat tctaatttat tgcacggtaa ggaagtagaa tcataaagaa     120
cagt                                                                 124

<210> SEQ ID NO 81
<211> LENGTH: 30
<212> TYPE: DNA
<213> ORGANISM: artificial sequence
<220> FEATURE:
<223> OTHER INFORMATION: primer

<400> SEQUENCE: 81
gctggtagat ctcccaccca cttttatag                                       30

<210> SEQ ID NO 82
<211> LENGTH: 42
<212> TYPE: DNA
<213> ORGANISM: artificial sequence
<220> FEATURE:
<223> OTHER INFORMATION: primer

<400> SEQUENCE: 82
ccttgagacc catggtggac tgttctttat gattctactt cc                        42

<210> SEQ ID NO 83
<211> LENGTH: 43
<212> TYPE: DNA
<213> ORGANISM: artificial sequence
<220> FEATURE:
<223> OTHER INFORMATION: primer

<400> SEQUENCE: 83
gtagaatcat aaagaacagt ccaccatggg tctcaaggtg aac                       43

<210> SEQ ID NO 84
<211> LENGTH: 55
<212> TYPE: DNA
<213> ORGANISM: artificial sequence
<220> FEATURE:
<223> OTHER INFORMATION: primer

<400> SEQUENCE: 84
gagtcattct cgacttgcgg ccgcacaaaa atcaagaggc cacccgcacg ctatc          55

<210> SEQ ID NO 85
<211> LENGTH: 114
<212> TYPE: DNA
<213> ORGANISM: artificial sequence
<220> FEATURE:
<223> OTHER INFORMATION: promoter pH5R

<400> SEQUENCE: 85
tttattctat acttaaaaaa tgaaaataaa tacaaaggtt cttgagggtt gtgttaaatt     60
gaaagcgaga aataatcata aattatttca ttatcgcgat atccgttaag tttg          114

<210> SEQ ID NO 86
<211> LENGTH: 56
<212> TYPE: DNA
<213> ORGANISM: artificial sequence
```

<220> FEATURE:
<223> OTHER INFORMATION: primer

<400> SEQUENCE: 86
cctcttgatt tttgtgcggc cgctttattc tatacttaaa aaatgaaaat aaatac        56

<210> SEQ ID NO 87
<211> LENGTH: 39
<212> TYPE: DNA
<213> ORGANISM: artificial sequence
<220> FEATURE:
<223> OTHER INFORMATION: primer

<400> SEQUENCE: 87
ggacattaat taacaaactt aacggatatc gcgataatg                            39

<210> SEQ ID NO 88
<211> LENGTH: 36
<212> TYPE: DNA
<213> ORGANISM: artificial sequence
<220> FEATURE:
<223> OTHER INFORMATION: primer

<400> SEQUENCE: 88
ggcacttaat taaccaccat ggtaccacaa gcgctg                               36

<210> SEQ ID NO 89
<211> LENGTH: 48
<212> TYPE: DNA
<213> ORGANISM: artificial sequence
<220> FEATURE:
<223> OTHER INFORMATION: primer

<400> SEQUENCE: 89
gttaacgcta gcctcgagac aaaaatcaaa gacgtgtttc gcctccac                  48

<210> SEQ ID NO 90
<211> LENGTH: 42
<212> TYPE: DNA
<213> ORGANISM: artificial sequence
<220> FEATURE:
<223> OTHER INFORMATION: primer

<400> SEQUENCE: 90
ggcacttaat taaccaccat gaccgtggac ggcaccgcca tg                        42

<210> SEQ ID NO 91
<211> LENGTH: 51
<212> TYPE: DNA
<213> ORGANISM: artificial sequence
<220> FEATURE:
<223> OTHER INFORMATION: primer

<400> SEQUENCE: 91
gttaacgcta gcctcgagac aaaaatcagg caaacatgcc ggtcacattg c              51

<210> SEQ ID NO 92
<211> LENGTH: 100
<212> TYPE: DNA
<213> ORGANISM: artificial sequence
<220> FEATURE:
<223> OTHER INFORMATION: promoter B2R

<400> SEQUENCE: 92
tatattatta agtgtggtgt ttggtcgatg taaaattttt gtcgataaaa attaaaaaat    60
aacttaattt attattgatc tcgtgtgtac aaccgaaatc    100

<210> SEQ ID NO 93
<211> LENGTH: 35
<212> TYPE: DNA
<213> ORGANISM: artificial sequence
<220> FEATURE:
<223> OTHER INFORMATION: primer

<400> SEQUENCE: 93
ggatcctcga gtatattatt aagtgtggtg tttgg    35

<210> SEQ ID NO 94
<211> LENGTH: 48
<212> TYPE: DNA
<213> ORGANISM: artificial sequence
<220> FEATURE:
<223> OTHER INFORMATION: primer

<400> SEQUENCE: 94
cttgcggtac catggtgggc tagcgatttc ggttgtacac acgagatc    48

<210> SEQ ID NO 95
<211> LENGTH: 45
<212> TYPE: DNA
<213> ORGANISM: artificial sequence
<220> FEATURE:
<223> OTHER INFORMATION: primer

<400> SEQUENCE: 95
gtgtgtacaa ccgaaatcgc tagcccacca tggtaccgca agccc    45

<210> SEQ ID NO 96
<211> LENGTH: 34
<212> TYPE: DNA
<213> ORGANISM: artificial sequence
<220> FEATURE:
<223> OTHER INFORMATION: primer

<400> SEQUENCE: 96
ctttccggat ccacaaaaat cacaggcggg tctc    34

<210> SEQ ID NO 97
<211> LENGTH: 52
<212> TYPE: DNA
<213> ORGANISM: artificial sequence
<220> FEATURE:
<223> OTHER INFORMATION: primer

<400> SEQUENCE: 97
gtgtgtacaa ccgaaatcgc tagcccacca tgaaggccaa agtcggcgac tg    52

<210> SEQ ID NO 98
<211> LENGTH: 33
<212> TYPE: DNA
<213> ORGANISM: artificial sequence
<220> FEATURE:
<223> OTHER INFORMATION: primer

<400> SEQUENCE: 98
gagtcggatc cacaaaaatc agccagctgc agg    33

```
<210> SEQ ID NO 99
<211> LENGTH: 49
<212> TYPE: DNA
<213> ORGANISM: artificial sequence
<220> FEATURE:
<223> OTHER INFORMATION: primer

<400> SEQUENCE: 99
gagtcattct cgacttgcgg ccgcacaaaa atcaagaggc cacccgcac            49

<210> SEQ ID NO 100
<211> LENGTH: 40
<212> TYPE: DNA
<213> ORGANISM: artificial sequence
<220> FEATURE:
<223> OTHER INFORMATION: primer

<400> SEQUENCE: 100
gctggtggat cccacccact ttttatagta agtttttcac                     40

<210> SEQ ID NO 101
<211> LENGTH: 37
<212> TYPE: DNA
<213> ORGANISM: artificial sequence
<220> FEATURE:
<223> OTHER INFORMATION: primer

<400> SEQUENCE: 101
ggcacttaat taaccaccat ggttcctcag gctctcc                         37

<210> SEQ ID NO 102
<211> LENGTH: 44
<212> TYPE: DNA
<213> ORGANISM: artificial sequence
<220> FEATURE:
<223> OTHER INFORMATION: primer

<400> SEQUENCE: 102
gttaacgcta gcctcgagac aaaaatcacc gctgggtgca gaac                 44
```

MYCOBACTERIAL ANTIGEN VACCINE

FIELD OF THE INVENTION

The present invention relates generally to novel immunogenic combinations comprising at least five antigens of a *Mycobacterium* species as well as fusion thereof and nucleic acid molecules encoding such combined antigens and fusion, where the antigens are from a *Mycobacterium* species, particularly a *Mycobacterium* of the tuberculosis complex such as *Mycobacterium tuberculosis* (Mtb). The present invention also relates to vectors, host cells and compositions comprising or encoding said combinations of mycobacterial antigens and fusion polypeptides as well as to methods for expressing and producing them. The present invention also relates to methods of using said combinations of mycobacterial antigens, fusion polypeptides, vectors, host cells, compositions particularly for inducing or stimulating an immune response with the goal of providing a protective response against a *Mycobacterium* infection or any disease caused by or associated with a *Mycobacterium* infection. The present invention also concerns antibodies directed to the mycobacterial antigens and fusion polypeptides in use in this invention that can be used in the diagnosis of a *Mycobacterium* infection and diagnosis kits comprising said combinations of mycobacterial antigens, fusion polypeptides, vectors, host cells and compositions.

BACKGROUND OF THE INVENTION

With an estimated one third of the world's population infected with *Mycobacterium tuberculosis* (Mtb) (i.e. more than two billion individuals) and 9 to 10 million new cases and 2 million deaths every year, tuberculosis (TB) is a global and worldwide health problem. *Mycobacterium tuberculosis* (Mtb) *bacillus*, the causative agent of TB, possesses a circular genome of 4 411 529 base pairs (bp) which was fully sequenced in 1998 (Cole et al., 1998, Nature 393: 537-44). Mtb encodes approximately 4000 genes; however the function and role in Mtb life cycle and pathogenesis of the majority of these genes have not yet been elucidated yet. It has been hypothesized for a long time that separate sets of genes are expressed during distinct and sequential infection phases, namely the active phase followed by the latent state and, when conditions are gathered, the resuscitation phase leading to a novel active phase. Recent evidence has shaken this classical dogma and the field is now acknowledging that a certain "leakiness" is taking place, i.e. expression of genes can happen in a phase-independent manner although to various thresholds. Moreover the latent nature of Mtb is also disputed: are bacteria mostly dormant, non-replicating, or do they continue to replicate and sometimes even escape from the infected cells into adjacent airways, thereby inducing recurring immune responses? (Ehlers et al., 2009, Infection 37: 87-95).

Generally, person-to-person transmission occurs by aerosolized droplets generated by a person suffering from pulmonary TB (active disease). Among those infected (an estimated 30% of exposed individuals), only 5-10% will develop active TB disease within 2 years post-exposure (known as primary TB). However, the majority of infected individuals develop latent infection (LTBI) which can last decades without clinical signs or symptoms of disease. LTBI represents a state of equilibrium in which the infected subject is able to control the infection but not completely eradicate the bacteria. Reactivation (active TB after remote infection) may occur at a later stage, particularly in the elderly or in immunocompromised individuals as in the case of HIV infection and treatment with TNF inhibitors. The risk of TB reactivation is estimated as 10% per lifetime and impaired immunity increases the risk to 10% per year.

There are several lines of evidence suggesting that stimulation of the cellular immune system plays a role in controlling TB disease (Rook et al. 2007, J Infect Dis 196:191-8). The central role of CD4 T lymphocytes to control the pathogen and prevent progression to disease (approximately 90% of Mtb infected subjects) is well established. For instance, HIV/AIDS patients with low $CD4^+$ T cells count are more susceptible to progression to TB disease while antiviral treatments that elevate $CD4^+$ T cells reduce progression to TB disease. However, CD4 T cells do not operate alone and are supported by CD8 T cells and other T cell subsets. In this respect, experience with tumor necrosis factor-alpha (TNFa) blockers and genetic polymorphisms such as interferon-gamma (IFNg) and other receptor deficiencies demonstrate the importance of specific cytokines and cytokine networks in controlling the disease, implicating the cellular immune nature of TB control in humans (Cooper et al., 2009, Annu Rev Immunol 27: 393-422).

The Mtb-caused million deaths every year are particularly dramatic considering that both vaccine (Bacille-Calmette-Guerin (BCG)) and antibiotics exist and are widely used. However, if BCG appears to be effective at preventing disease in newborns and toddlers, it does not protect adults and fails to prevent Mtb reactivation in latently infected persons. On the other hand, treatment of active TB with various antibiotic combinations appears efficacious but requires strong patient compliance with daily administrations of different drugs over several months. Moreover, while antibiotics are very efficient against wild type Mtb strains when taken properly, there is an alarming rate of appearance of drug resistant Mtb strains (e.g."MultiDrug Resistant" (MDR), "eXtensively Drug-Resistant" (XDR) and "Totally Drug Resistant" (TDR) strains), mostly because of improper observance of this lengthy and costly drug regimen treatment. Development of effective TB vaccines is therefore a priority in this worrying context and two main approaches are being investigated for the last decade: replacement of BCG and BCG booster. More than a dozen vaccine candidates are now in clinical trials (for a review see Ottenhoff and Kaufmann, 2012, PLoS 8(5): e1002607). In addition, the field has also more recently considered using novel vaccine formulations to help in the treatment of Mtb infection, so called "therapeutic vaccines" to be used as novel stand-alone treatment or alternatively to adjunct to standard therapy, in particular for the treatment of drug resistant strains.

BCG replacement candidates aim at improving BCG efficacy and safety and are mainly based on live attenuated bacteria such as genetically modified BCG or Mtb strains engineered to express new sets of antigens that are absent from BCG or to overexpress Mtb antigens that BCG expresses but at a likely insufficient level or still to delete virulence genes and their regulators. Various recombinant BCG constructs have entered clinical trials to test their ability to substitute BCG. The most advanced VPM1002 currently in a Phase II trial is a urease-deficient rBCG that expresses the thiol-activated, cholesterol-binding listeriolysin (hly) from *Listeria monocytogenes* that has been shown to be safer than BCG in immunocompromised animals and to provide a superior protection in mice against challenge with Mtb (erode et al., 2005, J Clin Invest 115: 2472-9). Two additional rBCG have recently entered clinical assessment, respectively rBCG30 expressing Ag85B and AERAS422 expressing Ag85A, Ag85B and Rv3407 together with perfringolysin.

BCG boosters aim at inducing cellular and/or humoral immune responses and generally rely on recombinant vaccines designed for providing TB antigens, either as protein composition generally admixed with potent Th1-activating adjuvants or through viral expressing vectors, (for a review see Thaissa et al., 2010, Yale J. of Biol. and Medicine 83: 209-15; Andersen, 2007, Nature 5: 484 and Kaufman, 2012, Trend in Immunology 241: 1-7). Among the 4000 potential TB antigens, a number of them proved immunogenic in preclinical models.

One of the most advanced protein-based candidates is the hybrid 1 (H1) protein which consists of Ag85B fused to ESAT-6 (Langermans et al., 2005, Vaccine 23: 2740-50; Dietrich et al., 2007, J. Immunol. 178: 3721-30). A strong CD4+Th1 IFNg-mediated response was observed in humans when administered with IC31 adjuvant (Van Dissel et al., 2010, Vaccine 28: 3571-81). More recently, this vaccine was found to boost immune responses previously induced by either BCG or latent Mtb infection (Van Dissel, 2011, Vaccine 29: 2100-9). Another fusion protein Hyvac 4 (H4), which consists of Ag85B fused to the TB10.4 (Aagaard et al., PLoS One 4: 1-8) is in a parallel development program. The GSK's M72 fusion protein made of Rv1196 inserted in the middle of the serine protease Rv0125 showed a favourable clinical profile in terms of safety and immunogenicity when administered with different synthetic adjuvants (Von Eschen et al., 2009, Hum Vaccine 5: 475-82). One may also cite the so-called ID fusion proteins (WO2008/124647) such as ID83 made of Rv1813, Rv3620 and Rv2608 (Baldwin et al., 2009, Vaccine 27: 3063-71) and ID93 including Rv3619 fused to the three ID83 antigens (Bertholet et al., 2010, Sci Transl Med 2(53): 53ra74).

Viral-vectored TB vaccines that are being tested in clinical trials include the modified vaccinia virus Ankara (MVA) expressing the Ag85A antigen (MVA85A/Aeras-485; WO2006/72787), and the replication-deficient adenovirus (Ad) 35 expressing Ag85A, Ag85B and TB10.4 antigens (Crucell Ad35/Aeras-402; WO2006/053871). MVA85A has proved immunogenic in both naïve as well as BCG primed individuals, inducing high CD4+ T cell response (Mc Shane et al., 2004, Nat Med 10: 1240-4; Scriba et al., 2010, Eur J Immunol 40: 279-90) whereas Aeras-402 seemed to favor CD8 T cell and IFNg responses (Radosevic et al., 2007, Infect Immunol 75: 4105-15; Magalhaes et al., 2008, PLoS One 3, e3790; Abel et al., 2010 Am J Respir Crit Care Med 181: 1407-17).

More recent studies now focus on multi-phasic compositions (see e.g. WO2008/124647 and WO2011/144951). Some of these vaccine candidates have produced results in preclinical and clinical studies that demonstrate an ability to induce a robust cellular mediated immune response against Mtb (Thaissa et al., 2010, Yale J. of Biol. and Medicine 83: 209-15; Delogu et al., 2009, J Infect Developing Countries 3: 5-15). For example, the H56 fusion protein combining the latent Mtb Rv2660 together with the active Ag85B and ESAT-6 antigens showed potentially promising BCG booster activity although it has not yet reached clinical trials (Aagaard et al, 2011, Nature Med 17: 189-94; Lin et al., 2012, J Clin Invest 122: 303-14). However, these studies have highlighted the influence of various factors on the T cell response and protective efficacy such as the antigen doses (e.g. Aagaard et al., PLoS One 4: 1-8) and administration routes (Goonetilleke et al., 2003, J. Immunol. 171: 1602-9).

Tuberculosis is far from being controlled for different reasons: poor patient compliance with the prescribed standard-of-care in areas with limited resources, exacerbation of TB epidemics due to HIV coinfection, poor performance of BCG vaccination which is ineffective in protecting adults. In view of the increasing worldwide threat of TB and the inherent complexity of the Mtb infection and anti-mycobacterial immune response, there remains a need for improved vaccine strategies for diagnosing, preventing and treating tuberculosis, especially in endemic regions.

The present invention fulfils this and other needs by providing an immunogenic combination of Mtb antigens that is tailored for all phases of the natural course of infection.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

BRIEF SUMMARY OF THE INVENTION

The present invention relates generally to an immunogenic combination comprising at least 5 different antigens or nucleic acid molecules encoding the at least 5 antigens, wherein said antigens are independently obtained from a *Mycobacterium* species, particularly from a *Mycobacterium* species of the tuberculosis complex such as *Mycobacterium tuberculosis* (Mtb). A data mining scoring system was developed and used to classify a panel of Mtb antigens based on their immunogenicity and protection properties. Upon sequence alignment, biochemical and bioinformatics prediction studies, 14 Mtb antigens were selected and combined into antigen/vector combination and fusion polypeptides.

In one aspect of the invention, the antigen combination of the invention is multiphasic where the at least 5 mycobacterial antigens are from two or the three phases of the natural course of a *Mycobacterium* infection, namely the active, latent and resuscitation phases. The mycobacterial antigens can be employed/expressed in the form of mixture or in one or more fusion polypeptide(s) as described herein.

The present invention also concerns fusion polypeptides of specific mycobacterial antigens, nucleic acid molecules and vectors encoding/expressing such fusion polypeptides and compositions comprising or encoding said fusion polypeptides as well as methods of preparing said fusions, vectors and compositions. The present invention also relates to antibodies against such mycobacterial antigens and fusion polypeptides. It further relates to the use of such immunogenic combinations, fusion polypeptides, nucleic acid molecules, vectors, compositions or antibodies for the purpose of the diagnosis, prevention, or treatment of a *Mycobacterium* infection or ameliorating a condition associated with a *Mycobacterium* infection.

A further aspect of the present invention includes a method of treating, preventing or inhibiting a *Mycobacterium* infection or ameliorating a condition associated with *Mycobacterium* infection in a subject in need thereof, comprising providing or administering this immunogenic combination, fusion polypeptide, nucleic acid molecule, vector or composition.

Still a further aspect of the present invention concerns a method of eliciting an immune response in a subject in need thereof, comprising providing or administering this immunogenic combination, fusion polypeptide, nucleic acid molecule, vector or composition, for the purpose of inducing or stimulating an immune response in this subject or for preventing or treating a *Mycobacterium* infection.

Still yet aspect of the present invention provides a kit of parts comprising a plurality of containers and instructions for providing or administering to a subject this immunogenic combination, fusion polypeptide, nucleic acid molecule, vector or composition.

Still yet more aspect of the present invention provides a kit of reagents for antibody assay for diagnosis of a *Mycobacterium* infection (e.g. tuberculosis) comprising this immunogenic combination, fusion polypeptide, nucleic acid molecule, vector or composition.

The antigen combination provided by the invention offers improved and unexpected immunogenic properties (e.g. level, quality and/or scope of the immunogenic response) as compared to the individual antigens.

The present invention is particularly useful in the context of immunotherapy as stand alone or as BCG booster for preventive or therapeutic purposes in the *Mycobacterium* infection field, e.g. preventing Mtb infection and/or prevention of primary TB and/or prevention of reactivation in latently infected subjects. It can also be used in association with standard (e.g. antibiotic-therapy) or any other novel treatment that is currently developed (e.g. small direct or indirect inhibitor molecules; antibodies or immunotherapeutics, etc). The present invention is also useful in the veterinary field, for example to reduce or abolish the risk of *Mycobacterium* infection and/or active disease in animals, especially in bovine and goat breedings.

DETAILED DESCRIPTION OF THE INVENTION

The present invention relates generally to an immunogenic combination comprising at least 5 antigens of a *Mycobacterium* species or nucleic acid molecules encoding said at least 5 antigens.

Definitions

As used herein throughout the entire application, the terms "a" and "an" are used in the sense that they mean "at least one", "at least a first", "one or more" or "a plurality" of the referenced compounds or steps, unless the context dictates otherwise.

The term "and/or" wherever used herein includes the meaning of "and", "or" and "all or any other combination of the elements connected by said term".

The term "about" or "approximately" as used herein means within 10%, preferably within 8%, and more preferably within 5% of a given value or range.

The terms "amino acids", "residues" and "amino acid residues" are synonyms and encompass natural amino acids as well as amino acid analogs (e.g. non-natural, synthetic and modified amino acids, including D or L optical isomers).

The term "polypeptide" refers to a polymer of amino acid residues which comprises at least nine or more amino acids bonded via covalent peptide bonds. The polypeptide can be linear, branched or cyclic and may comprise naturally occurring and/or amino acid analogs. It may be chemically modified by being glycosylated, lipidated, acetylated, cleaved, cross-linked by disulfide bridges and/or phosphorylated, or still by containing additional amino acids such as tag (his, myc, Flag, etc) or a targeting peptide (signal peptide, trans-membrane domain, etc). It will be understood that the term "polypeptide" encompasses proteins (usually employed for polypeptides comprising 50 or more amino acid residues), oligopeptides, and peptides (usually employed for polypeptides comprising less than 50 amino acid residues). Each polypeptide may thus be characterized by specific amino acids and be encoded by specific nucleic acid sequences.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues (e.g. tag and targeting peptides as mentioned herein). "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

The term "identity" refers to an amino acid to amino acid or nucleotide to nucleotide correspondence between two polypeptide or nucleic acid sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoffed, 1981, Suppl., 3: 482-9). Programs for determining identity between nucleotide sequences are also available in specialized data base (e.g. Genbank, the Wisconsin Sequence Analysis Package, BESTFIT, FASTA and GAP programs). For illustrative purposes, "at least 80% identity" means 80%, 81%, 82%, 83%, 84%, 85%, 86%, 87%, 88%, 89%, 90%, 91%, 92%, 93%, 94%, 95%, 96%, 97%, 98%, 99% or 100%.

As used herein, "operably linked" means that the elements being linked are arranged so that they function in concert for their intended purposes. For example a promoter is operably linked to a nucleic acid molecule if the promoter effects transcription from the transcription initiation to the terminator resulting in the expression of the coding sequence present in the nucleic acid molecule in a permissive host cell.

As used herein, the terms "*Mycobacterium*", "*Mycobacterium* species" and "mycobacterial" are used interchangeably to refer to any member of the genus of *Actinobacteria* belonging to the Mycobacteriaceae family. The terms encompass laboratory strains as well as clinical isolates.

A "*Mycobacterium* infection" refers to the exposure of a subject to a *Mycobacterium* species followed by a colonization of the subject or the subject's tissue(s) by the bacterium. The colonization can cause serious diseases (e.g.

tuberculosis, leprosy, Bureli ulcer etc, depending on the *Mycobacterium*), or can result in no adverse signs (asymptomatic or latent infection).

The term "combination" as used herein refers to any arrangement possible of various components (e.g. mycobacterial antigens and/or encoding nucleic acid molecules). Such an arrangement includes mixture of mycobacterial antigens (e.g. mixture of individual antigens and/or fusion of antigens) or mixture of nucleic acid molecules (e.g. carried by one or more vector) as well as mixture of polypeptide(s) and nucleic acid molecule(s). The present invention encompasses combinations comprising equal molar concentrations of each component as well as combinations with very different concentrations. It is appreciated that optimal concentration of each *Mycobacterium* component can be determined by the artisan skilled in the art.

The term "immunogenic" refers to the ability to induce or stimulate a measurable T and/or B cell-mediated immune response in a subject into which the component qualified as immunogenic has been introduced. For example, the antigenic combination of the invention is immunogenic in the sense as it is capable of inducing or stimulating an immune response in a subject which can be innate and/or specific (i.e. against at least one mycobacterial antigen/epitope comprised in or expressed by said immunogenic combination), humoral and/or cellular (e.g. production of antibodies and/or cytokines and/or the activation of cytotoxic T cells, B, T lymphocytes, antigen presenting cells, helper T cells, dendritic cells, NK cells, etc) and usually results in a protective response in the administered subject. A vast variety of direct or indirect biological assays are available in the art to evaluate the immunogenic nature of a component either in vivo (animal or human being), or in vitro (e.g. in a biological sample) as described herein.

As used herein, the term "mycobacterial antigen" refers to a polypeptide present in or obtained from a *Mycobacterium* species or fragment thereof (e.g. an epitope) capable of being bound by an antibody or a T cell receptor. Typically, such an antigen contains one or more B and/or T epitope(s), in particular CTL or $T_H$ epitope(s) or both, involved in recognition by a particular antibody or T-cell receptor in the context of the Major Histocompatibility Complex (MHC). In the context of the invention, this term encompasses native mycobacterial polypeptide as well as fragment and modified version thereof (i.e. variant) as described hereinafter.

An "epitope" corresponds to a minimal peptide motif (usually a set of 8-25 amino acid residues) that forms a site recognized by an antibody, a T-cell receptor or a HLA molecule. Those residues can be consecutive (linear epitope) or not (conformational epitope that includes residues that are not immediately adjacent to one another).

The term "treating" (and any form of treating such as "treatment", "treat") as used herein encompasses prophylaxis (e.g. prevention of a subject at risk of being infected with a *Mycobacterium*) and/or therapy (e.g. a subject diagnosed as being infected with a *Mycobacterium*). Treatment requires administer externally or internally to a subject an active agent (e.g. the immunogenic combination, fusion polypeptide, nucleic acid molecule, vector and/or composition described herein), eventually in association with conventional therapeutic modalities, especially the one currently used in the treatment of active *Mycobacterium* disease (e.g. TB).

The term "subject" generally refers to a vertebrate that would benefit from induction or stimulation of an immune response against a *Mycobacterium* species and particularly a mammalian selected from the group consisting of domestic animals, farm animals, sport animals, and primates. Preferably, the subject is a human who has been diagnosed as being or at risk of being infected with a *Mycobacterium* and especially Mtb and thus is susceptible of having or at risk of having a disease or condition caused by or associated with a *Mycobacterium* infection (e.g. active or latent tuberculosis).

"Protective response" has its usual meaning, that the treatment provides a benefit to the treated subject as compared to the response in a non-treated subject; e.g. induction or stimulation of an immune response, protection from contracting a *Mycobacterium* infection, or increased resistance to an active disease or prevention against reactivation of a latent *Mycobacterium* infection or even curing after active disease development.

As used herein, the term "isolated" refers to a component (e.g. a polypeptide, nucleic acid molecule, vector, etc) that is removed from its natural environment (i.e. separated from at least one other component(s) with which it is naturally associated).

The term "obtained from", "originating" or "originate" is used to identify the original source of a component (e.g. polypeptide, nucleic acid molecule) but is not meant to limit the method by which the component is made which can be, for example, by chemical synthesis or recombinant means.

*Mycobacterium* Species

As defined above, the mycobacterial antigens comprised/ encoded by the immunogenic combination of the invention can independently be obtained from any member of a *Mycobacterium* (M.) species identified at present time. A vast number of Mycobacteria for use in the context of the invention are described in the art. Exemplary *Mycobacterium* species include without limitation *M. phlei, M. smegmatis, M. africanum, M. canetti, M fortuitum, M. marinum, M. ulcerans, M. tuberculosis* (Mtb), *M. paratuberculosis, M. bovis, M. microti, M celatum M. avium, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae, M. caprae, M. pinnipedii* and *M. shimoidei*.

In a preferred embodiment, the mycobacterial antigens in use in this invention are obtained from a *Mycobacterium* species of the tuberculosis complex which includes those species traditionally considered as causing the disease tuberculosis, as well as *Mycobacterium* environmental and opportunistic species that cause tuberculosis and pulmonary disease in immune compromised subjects (e.g. HIV-infected patients). Exemplary species of the tuberculosis complex for use herein include without limitation *M. tuberculosis* (Mtb), *M. bovis, M. bovis* BCG, *M. africanum, M. canetti, M. caprae,* and *M. microti*. A preferred embodiment is directed to Mtb including the Mtb laboratory strains such as H37Rv and H37Ra and clinical isolates such as KZN4207, T85, CDC1551 (isolated in the US), F11 (isolated in South Africa), C, K85 (isolated in Netherland), CPHL-A, as well as the MDR or XDR isolates such as TN5904, Haarlem, KZN1435, Bejing and KZN605. Other preferred species for mycobacterial antigen sources are *M. bovis, M. bovis* BCG and *M. caprae*, especially for veterinary use. However, one would indeed expect cross-reactivity given the high percentage of homology existing between the M. species at the amino acid and nucleotide levels. For example, Rv1733 antigens of Mtb and *M. bovis* are 100% identical whereas *M. africanum* Rv1733 shares 209 amino acids in common out of 210 with that of Mtb. Thus, a combination of Mtb antigens is likely to be useful for treating both Mtb-infected (human use), *M. bovis-* and *M. caprae-*(veterinary use) infected subjects.

Amino acid sequences of the suitable mycobacterial antigens and the encoding nucleotide sequences are readily available in specialized data banks (and in the literature. For example, Mtb sequences can be found in Cole et al. (1998, Nature 393: 537) or at websites such as those maintained by the Wellcome Trust Sanger Institute, Institut Pasteur and others (e.g. TB database (@tbdb.org) and tuberculist (@tuberculist.epfl.ch)). However, the present invention is not limited to these exemplary *Mycobacterium* species. Indeed the nucleotide and amino acid sequences can vary between different isolates and strains and this natural genetic variation is included within the scope of the invention as well as non-natural modification(s) such as those described below.

Immunogenic Combination

As used herein, "at least five" is a number comprised within a range going from 5 to 50 (i.e. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, etc.), desirably from 5 to 33, preferably from 7 to 20, and more preferably from 8 to 18 with a specific preference for 10 to 15 (e.g. 12, 13 or 14). Preferably the combination of the present invention comprises approximately 10 to 15 Mtb antigens or corresponding nucleic acid molecules.

In the context of the present invention the "at least 5 mycobacterial antigens" are different from each other (e.g. multiple copies of the same mycobacterial antigen can be used provided that the combination comprises/encodes at least 5 different mycobacterial antigens).

Alternatively or in addition, each of the at least 5 mycobacterial antigens may be a native mycobacterial antigen (e.g. a full length antigen) or a modified version (fragment or variant) thereof.

A "native" mycobacterial antigen can be found, isolated, obtained from a source of *Mycobacterium* in nature. Such sources include biological samples (e.g. blood, plasma, sera, saliva, sputum, tissue sections, biopsy specimen etc.) collected from a subject infected or that has been exposed to a *Mycobacterium*, cultured cells as well as recombinant materials available in depositary institutions (e.g. ATCC or TB institutions), libraries or described in the literature (e.g. *Mycobacterium* isolates, *Mycobacterium* genomes, genomic fragments, genomic RNA or cDNA as well as any plasmid and vector known in the art to include such elements).

A modified mycobacterial antigen (e.g. a variant) typically differs from a polypeptide specifically disclosed herein or a native one in one or more position(s). Any modification(s) can be envisaged, including substitution, insertion, addition and/or deletion of one or more amino acid residue(s), non-natural arrangements and any combination of these possibilities. Amino acid substitution can be conservative or not. When several modifications are contemplated, they can concern consecutive residues and/or non-consecutive residues. Modification(s) can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by synthetic techniques (e.g. resulting in a synthetic nucleic acid molecule encoding the desired polypeptide variant).

Whatever their origin (native or modified), it is preferred that each of the mycobacterial antigen comprised in or encoded by the immunogenic combination of the invention retains one or more immunogenic portions of the corresponding native antigen including B and/or T cell epitope(s). Methods to identify such relevant immunogenic portions are well known in the art. For example, T cell epitopes can be identified by implementing biological assays (e.g. IFNg assays using libraries of synthetic overlapping oligopeptides) or available prediction programs.

In one embodiment, the immunogenic combination of the present invention comprises or encodes mycobacterial antigens from at least 2 different infection phases selected from the group consisting of active, resuscitation and latent phases (e.g. active and resuscitation, active and latent or resuscitation and latent phases). A preferred combination is "multiphasic" comprising or encoding mycobacterial antigens, and particularly Mtb antigens, from the three infection phases, with at least one antigen from the active infection phase, at least one antigen from the resuscitation infection phase and at least one antigen from the latent infection phase.

"Antigens of the active phase" are typically the set of proteins that are mainly expressed when *Mycobacterium* is actively growing and replicating in vivo. A vast number of active mycobacterial antigens for use in this invention are described in the literature (e.g. Bertholet et al., 2008, J. Immunol. 181: 7948-57; Bertholet and al., 2010, Sci Transl Med 2: 53ra74). Particularly appropriate antigen(s) of the active phase is/are selected from the group consisting of ESAT-6 (Rv3875), CFP-10 (Rv3874), TB10.4 (Rv0288), Ag85A (Rv3804), Ag85B (Rv1886), Rv3619, Rv3620 and PPE family proteins Rv3478 and Rv2608 and any combination thereof. A preferred immunogenic combination comprises or encodes at least ESAT-6 (Rv3875), Ag85B (Rv1886) and TB10.4 (Rv0288).

"Antigens of the latent phase" are mainly expressed during the dormant (or latent) phase of the *Mycobacterium* infection, a reversible state of low metabolic activity in which the *Mycobacterium* can persist for extended periods. A vast number of latent mycobacterial antigens for use in the present invention are described in the literature. Exemplary Mtb latent antigens are those encoded by the DosR regulon which mediates the bacteria response to hypoxia and starvation antigens that are up-regulated upon depletion of nutrients (Voskuil et al., 2003, J. Exp Med 198: 705-13; Leyten et al., 2006, Microbes Inf. 8: 2052-60; Roupie et al., 2007, Infection and Immunity 75: 941-9; Black et al., 2009, Clin Vaccine Immunol 16: 1203-12; Schuck et al., 2009, PLoS One 4: e5590; Vipond et al., 2006, Vaccine 24: 6340-50; Vipond et al., 2007, Tuberculosis 86: 218-24; Bertholet et al., 2008, J. Immunol. 181: 7948-57; Bertholet et al., 2010, Sci Transl Med 2: 53ra74, Mollenkopf et al., 2004, Infect Immun 72: 6471-9); WO03/000721; WO03/004520; WO03/035681; WO2004/006952 and WO2006/104389). Particularly appropriate antigen(s) of the latent phase is/are selected from the group consisting of Rv0081, Rv0111, Rv0198, Rv0569, Rv1733c, Rv1735, Rv1737, Rv1806, Rv1807, Rv1813, Rv2005c, Rv2029c, Rv2032, Rv2626, Rv2627, Rv2628, Rv2660c, Rv3407 and Rv3812 and Rv3478 and any combination thereof; and more preferably from the group consisting of Rv0111, Rv1733, Rv2029 and Rv2626 or from Rv0569, Rv1807, Rv1813, Rv3407 and Rv3478 or from both Rv0111, Rv1733, Rv2029, Rv2626, Rv0569, Rv1807, Rv1813, Rv3407 and Rv3478.

"Antigens of the resuscitation phase" refer to any antigen mainly expressed or involved into the transition between the dormancy state and active growth and replication (active state of *Mycobacterium* infection). The resuscitation antigens for use in this invention are described in the literature (e.g. Mukamolova et al., 2002, Mol Microbiol 46: 623-35;

Yeremeev et al., 2003, Infection and Immunity 71: 4789-94; Mukamolova et al., 2006, Mol Microbiol 59: 84-98; Tufariello et al., 2006, Infect Immun 74: 2985-95; Biketov et al., 2007, MMC Infect Dis 7: 146; Kana et al., 2008, Mol Microbiol 67: 672-84; Kana et al., 2009, FEMS Immunol Med Microbiol 58: 39-50; Russel-Goldman et al., 2008, Infect Immun 76: 4269-81; Gupta et al., 2010, Microbiol 156: 2714-22 and Commandeur et al., 2011, Clin Vaccine Immunol. 18: 676-83). Particularly appropriate antigen(s) of the resuscitation phase is/are selected from the group consisting of RpfA, RpfB, RpfC, RpfD and RpfE and any combination thereof. A preferred immunogenic composition comprises or encodes at least RpfB and RpfD (e.g. immunogenic fragment thereof).

In a preferred embodiment, the immunogenic combination of the present invention comprises or encodes at least 5 mycobacterial antigens selected from the group consisting of ESAT-6 (Rv3875), CFP-10 (Rv3874), TB10.4 (Rv0288), Ag85A (Rv3804), Ag85B (Rv1886), Rv3619, Rv3620, RpfA, RpfB, RpfC, RpfD, RpfE, Rv0081, Rv0111, Rv0198, Rv0569, Rv1733c, Rv1735, Rv1737, Rv1806, Rv1807, Rv1813, Rv2005c, Rv2029c, Rv2032, Rv2626, Rv2627, Rv2628, Rv2660c, Rv3407 Rv3478, and Rv3812; preferably from the group consisting of ESAT-6 (Rv3875), TB10.4 (Rv0288), Ag85B (Rv1886), RpfB, RpfD, Rv0111, Rv0569, Rv1733c, Rv1807, Rv1813, Rv2029c, Rv2626, Rv3407 and Rv3478; and more preferably from the group of polypeptides comprising the amino acid sequences shown in SEQ ID NO: 1-14 or any variant or fragment thereof.

For illustrative purposes, SEQ ID NO: 1 represents the amino acid sequence of Rv0111; SEQ ID NO: 2 the amino acid sequence of TB10.4; SEQ ID NO: 3 the amino acid sequence of Rv0569; SEQ ID NO: 4 the amino acid sequence of RpfB; SEQ ID NO: 5 the amino acid sequence of Rv1733; SEQ ID NO: 6 the amino acid sequence of Rv1807; SEQ ID NO: 7 the amino acid sequence of Rv1813; SEQ ID NO: 8 the amino acid sequence of Ag85B; SEQ ID NO: 9 the amino acid sequence of Rv2029; SEQ ID NO: 10 the amino acid sequence of Rv2626; SEQ ID NO: 11 the amino acid sequence of RV2839c; SEQ ID NO: 12 the amino acid sequence of Rv3407; SEQ ID NO: 13 the amino acid sequence of Rv3478 and SEQ ID NO: 14 the amino acid sequence of ESAT-6.

Each modified mycobacterial antigen that can be envisaged in the context of the invention comprises one or more modifications with respect to the native counterpart, and especially one or more modifications which are beneficial to the synthesis, processing, stability and/or solubility of the resulting polypeptide and/or to its immunogenicity. Representative examples of suitable modifications include without limitation (a) the deletion of internal highly hydrophobic region(s), (b) the deletion of N-terminal signal peptide (replacement with heterologous ones if needed) and/or (c) the deletion of unfolded region that may interfere negatively with stability, immunogenicity and recombinant expression and/or (d) the deletion or mutation of a catalytic domain to abolish biological activity.

A particularly appropriate immunogenic composition comprises or encodes mycobacterial antigens selected from the group of polypeptides comprising an amino acid sequence as set forth in SEQ ID NO: 15-24. More specifically, SEQ ID NO: 15 represents the Rv0111 antigen (Rv0111*) modified with respect to the native counterpart by deletion of the hydrophobic N-terminal part (from the first residue to about position 393). SEQ ID NO: 16 represents a RpfB antigen modified with respect to the native counterpart by deletion of the signal peptide (from the first residue to approximately residue in position 29, and by deletion of the catalytic domain, thus retaining RfpB from approximately position 30 to position 283). SEQ ID NO: 17 represents the Rv1733 antigen (Rv1733*) modified with respect to the native counterpart by deletion of the N-terminal predicted TM domain (from the first residue to about position 61). SEQ ID NO: 18 represents the Rv1807 antigen (Rv1807*) modified with respect to the native counterpart by deletion of the unfolded C-terminal part (approximately the last 60 residues). SEQ ID NO: 19 represents the Rv1813 antigen (Rv1813*) modified with respect to the native counterpart by deletion of the N-terminal signal peptide (from the first residue to about position 34). SEQ ID NO: 20 represents the Ag85B (Ag85B*) modified with respect to the native counterpart by deletion of the N-terminal signal peptide (from the first residue to about position 39). SEQ ID NO: 21 represents the Rv2029 antigen (Rv2029*) modified with respect to the native counterpart by deletion of the C-terminal part (approximately the last 25 residue) and mutated at position 265 to abolish the Rv2029 enzymatic activity (e.g. D265N; Cabrera et al., 2010, Arch Biochem Biophys 502: 23-30). SEQ ID NO: 22 represents the RpfD antigen modified with respect to the native counterpart so as to retain the catalytic domain (also called LD for lysozyme domain) with three mutations aimed at abolishing the associated enzymatic activity (e.g. E292K, T315A and Q347A) and deletion of the last 7 residues. SEQ ID NO: 23 represents the Rv3407 antigen (Rv3407*) modified with respect to the native counterpart by deletion of the unfolded C-terminal part (approximately the last 33 residues). SEQ ID NO: 24 represents the Rv3478 antigen (Rv3478*) modified with respect to the native counterpart by deletion of the unfolded C-terminal part (approximately the last 40 residues).

In a preferred embodiment, the immunogenic combination of the invention comprises or encodes at least 5 mycobacterial antigens showing at least 80% identity (e.g. 80%, 85%, 90%, 92%, 94%, 95%, 96%, 97%, 98%, 99% or 100% identity) with an amino acid sequence set forth herein, in over the full length polypeptide or a fragment thereof (e.g. a fragment of 50 consecutive amino acid residues or more such as 60, 75, 80 or still 90 amino acid residues), and especially at least 5 Mtb antigens selected from the group of polypeptides comprising an amino acid sequence at least 80% homologous or identical to any of SEQ ID NO: 1-24 (with or without initiator Met).

In a more preferred embodiment, the immunogenic combination of the invention comprises or expresses at least Rv0111 with a specific preference for Rv0111* as illustrated in SEQ ID NO: 15.

In an even more preferred embodiment, the immunogenic combination of the invention comprises or expresses at least Rv0111, Rv2626, RpfB, RpfD, TB10.4 and Ag85B and with a specific preference for Rv0111* as illustrated in SEQ ID NO: 15, Rv2626 as illustrated in SEQ ID NO: 10, RpfB as illustrated in SEQ ID NO: 16, RpfD as illustrated in SEQ ID NO: 22, TB10.4 as illustrated in SEQ ID NO: 2 and Ag85B as illustrated in SEQ ID NO: 20.

As mentioned above, the immunogenic combination of the present invention encompasses any arrangement of its constitutive mycobacterial antigens and/or encoding nucleic acid molecules. Therefore the immunogenic combination of the invention may comprise or encode the mycobacterial antigens in the form of separate polypeptides (e.g. a mixture of recombinantly produced Mtb antigens) or in the form of one or more fusion polypeptides (covalent linkage of at least two of the mycobacterial antigens) or both separate antigen(s) and fusion(s).

On the same line, a combination of nucleic acid molecules encompasses either separate nucleic acid molecules or covalently linked nucleic acid molecules (e.g fusion-encoding nucleic acids) or both separate and fusionned nucleic acid molecules which can be carried by one or more vector(s). Given the number of mycobacterial antigens (from 5 up to 50), a preferred combination comprises one or more vector(s) encoding antigen fusions as described below. The vector combination may use the same type of vectors (e.g. two MVA) or different type of vectors (e.g. a plasmid DNA and a MVA) to express the various mycobacterial antigens or fusion as described herein.

Fusion Polypeptide

According to another aspect, the present invention also provides isolated fusion polypeptides comprising two or more mycobacterial antigens comprised or encoded by the immunogenic combination of the invention as well as compositions comprising such fusion polypeptides.

The term "fusion" or "fusion polypeptide" as used herein refers to the covalent linkage in a single polypeptide chain of two or more polypeptides and is performed by genetic means, i.e. by fusing in frame the nucleic acid molecules encoding each of said polypeptides. By "fused in frame", it is meant that the expression of the fused coding sequences results in a single polypeptide without any translational terminator between each of the fused polypeptides. The fusion can be direct (i.e. without any additional amino acid residues in between) or indirect (e.g. through a linker between the fused polypeptides) and can take place at the N or C terminus of a polypeptide or internally. The presence of a linker may facilitate correct folding and/or functioning of the fusion polypeptide. The present invention is not limited by the form, size or number of linker sequences employed. For illustrative purposes, typical linkers are 3 to 30 amino acids long and composed of repeats of amino acid residues such as glycine, serine, threonine, asparagine, alanine and/or proline.

As before, the mycobacterial antigens that make up the fusion polypeptide of the invention may be native, and/or modified (variants) and/or fragment(s) thereof as described above. Such combination of mycobacterial antigens for use in the form of a fusion polypeptide may provide improved immunogenicity as compared to the same antigen combination used in a mixture of separate antigens (or expressing vectors).

Preferably, the fusion polypeptide of the invention comprises at least two (e.g., 2, 3, 4, 5, 6, etc) mycobacterial antigens as described herein, and preferably at least 2 polypeptides selected from the group of polypeptides comprising an amino acid sequence at least 80% (e.g. 98 or 100%) identical to any of SEQ ID NO: 1-24.

In one embodiment, the fusion polypeptide of the invention comprises mycobacterial antigens of the same infection phase. An exemplary fusion of latent Mtb antigens comprises Rv2029, Rv2626, Rv1733 and Rv0111; an exemplary fusion of active Mtb antigens comprises Ag85B, TB10.4 and ESAT6; and an exemplary fusion of resuscitation Mtb antigens comprises RpfB and RpfD antigens.

In another embodiment, the fusion polypeptide of the invention comprises mycobacterial antigens from 2 different infection phases or even from the active, resuscitation and latent phases. Exemplary fusions of this type include without limitation a fusion of latent and active Mtb antigens comprising Rv2029, TB10.4, ESAT-6 and Rv011; a fusion of resuscitation and active Mtb antigens comprising RpfB, RpfD, Ag85B, TB10.4 and ESAT-6 as well as a fusion of latent, resuscitation and active Mtb antigens comprising Ag85B, Rv2626, RpfB, -RpfD and Rv1733.

In a preferred embodiment, the fusion polypeptide of the invention is selected from the group consisting of:
  A fusion polypeptide comprising Mtb antigen Rv0111 (with a specific preference for Rv0111 as illustrated in SEQ ID NO: 15);
  A fusion polypeptide comprising the Mtb antigens Rv2029, Rv2626, Rv1733 and Rv0111;
  A fusion polypeptide comprising the Mtb antigens Rv0569, Rv1813, Rv3407, Rv3478 and Rv1807;
  A fusion polypeptide comprising the Mtb antigens Ag85B, TB10.4 and ESAT6;
  A fusion polypeptide comprising the Mtb antigens RpfB and RpfD (e.g. as illustrated by the so-called RPFB-Dhyb which is a fusion between a LD-deleted RpfB antigen and the LD domain of RpfD with mutation abolishing enzymatic activity));
  A fusion polypeptide comprising the Mtb antigens RpfB, RpfD (e.g. RPFB-Dhyb), Ag85B, TB10.4 and ESAT6;
  A fusion polypeptide comprising the Mtb antigens Ag85B, Rv2626, RpfB, RpfD (e.g. RPFB-Dhyb) and Rv1733;
  A fusion polypeptide comprising the Mtb antigens Rv2029, TB10.4, ESAT6 and Rv0111; and
  A fusion polypeptide comprising the Mtb antigens Ag85B, Rv2626 and Rv1733.

In the context of the invention the mycobacterial antigens identified in the exemplary fusion polypeptides can be in any order from the N to the C terminus and not necessary in the recited order. Thus, a fusion comprising the Mtb antigens Ag85B, Rv2626 and Rv1733 encompasses Ag85B-Rv1733-Rv2626; Rv1733-Rv2626-Ag85B; Rv1733-Ag85B-Rv2626; Rv2626-Ag85B-Rv1733; Rv2626-Rv1733-Ag85B and Ag85B-TB10.4-Rv2626-Ag85B, etc fusions further to the recited Ag85B-Rv2626-Rv1733 fusion.

Further to the mycobacterial antigens, the immunogenic combination and/or the fusion polypeptide of the invention may optionally comprise other components that may derive from a *Mycobacterium* species (e.g. additional mycobacterial antigen(s)) or be heterologous (i.e. from a source different of a *Mycobacterium*). Such additional component(s) may be immunogenic or not. Representative additional components include without any limitation tag peptide(s), targeting peptide(s), oligomerization domain(s), immunoactivator peptide(s)/polypeptide(s) and nucleic acid molecule(s) encoding such element(s), etc.

In one embodiment, any of the mycobacterial antigen(s) present or encoded by the immunogenic combination or the fusion polypeptide of the invention may be operably linked to targeting peptides such as signal and/or trans-membrane peptides. Such targeting peptides are well known in the art (see for example WO99/03885). Briefly, signal peptides (SS) are generally present at the N-terminus of membrane-presented or secreted polypeptides and initiate their passage into the endoplasmic reticulum (ER). They comprise 15 or more essentially hydrophobic amino acids which are then removed by a specific ER-located endopeptidase to give the mature polypeptide. Trans-membrane peptides (TM) are usually highly hydrophobic in nature and serve to anchor the polypeptides in the cell membrane. The choice of the trans-membrane and/or signal peptides which can be used in the context of the present invention is vast. They may be obtained from any membrane-anchored and/or secreted polypeptide (e.g. cellular or viral polypeptides) such as those of immunoglobulins, tissue plasminogen activator (tPA), insulin, rabies glycoprotein, the HIV virus envelope glycoprotein or the measles virus F protein or may be synthetic. The preferred site of insertion of the signal peptide is the N-terminus downstream of the codon for initiation of translation and that of the trans-membrane peptide is the C-terminus, for example immediately upstream of the stop codon.

Alternatively or in addition, any of the mycobacterial antigen(s) present or encoded by the immunogenic combination or the fusion protein of the invention may be operably linked to tag peptides in order to facilitate its isolation and detection or to facilitate identification of host cells expressing such antigen or fusion. A vast variety of tag peptides can be used in the context of the invention including without limitation PK tag, FLAG tag (SEQ ID NO: 25), MYC tag (SEQ ID NO: 26), polyhistidine tag (usually a stretch of 5 to 10 histidine residues; e.g. SEQ ID NO: 27). Tag peptides can be detected by immunodetection assays using anti-tag antibodies as described in the appended examples. The tag peptide(s) may be independently positioned at the N-terminus of the mycobacterial antigen or fusion (tag-polypeptide) or alternatively at its C-terminus (polypeptide-tag) or alternatively internally or at any of these positions when several tags are employed.

Alternatively or in addition, any of the mycobacterial antigen(s) present or encoded by the immunogenic combination or the fusion polypeptide of the invention may be operably linked to one or more immunoactivator peptides/polypeptides capable of enhancing immunogenic properties. One may cite for example calreticulin (Cheng et al., 2001, J. Clin. Invest. 108: 669), Mtb heat shock protein 70 (HSP70) (Chen et al., 2000, Cancer Res. 60: 1035), ubiquitin (Rodriguez et al., 1997, J. Virol. 71: 8497), and T helper epitope(s) such as Pan-Dr peptide (Sidney et al., 1994, Immunity 1: 751), pstS1 GCG epitope (Vordermeier et al., 1992, Eur. J. Immunol. 22: 2631), tetanus toxoid peptides P2TT (Panina-Bordignon et al., 1989, Eur. J. Immunol. 19: 2237), P30TT (Demotz et al., 1993, Eur. J. Immunol. 23: 425), hemaglutinin epitope (Rothbard et al., 1989, Int. Immunol. 1: 479) and C4 bp oligomerization domain (Spencer et al., 2012, PLos One 7:e33555).

Depending of the mycobacterial antigen, the presence of such peptide(s) may be beneficial for enhancing expression and/or immunogenicity of the resulting combination or fusion polypeptide when compared with combination or fusion expressed without such peptides. Enhanced expression may be determined by conventional techniques such as Western blotting. Enhanced immunogenicity may be determined using conventional assays such as ELISpot assay.

In a preferred embodiment, the fusion polypeptide of the invention is operably linked to targeting and/or tag peptides. For example, fusions no 2, 3, 4 and 5, illustrated in the appended example section are operably linked to a signal peptide and a Flag tag positioned at the N-terminus immediately after the initiator Met and a myc tag, a trans-membrane peptide and a His tag at the C-terminus immediately before the STOP codon whereas fusions no 9, 10, 11 and 12 are operably linked to a Flag tag positioned at the N-terminus immediately after the initiator Met and a myc tag followed by a His tag at the C-terminus immediately before the STOP codon. On the other hand, fusions no 6, 8, 13 and 14 are operably linked to a signal peptide and a Flag tag positioned at the N-terminus immediately after the initiator Met and a myc tag and a His tag at the C-terminus immediately before the STOP codon.

Preferred examples of fusion polypeptides are selected from the group of polypeptides comprising, or alternatively consisting essentially of, or alternatively consisting of an amino acid sequence which exhibits at least 80% of identity, advantageously at least 85% of identity, desirably at least 90% of identity, preferably at least 95% of identity, and more preferably 98% identity and even more preferably 100% identity with any of the amino acid sequence shown in SEQ ID NO: 28-39. More specifically, SEQ ID NO: 28 and 29 comprise the fusion polypeptide comprising Ag85B, TB10.4 and ESAT6, with and without targeting peptides respectively (as illustrated by fusions no 2 and 10 in the appended examples). SEQ ID NO: 30 and 31 comprise the so-called RPFB-Dhyb fusion polypeptide comprising RpfB and RpfD, with and without targeting peptides respectively (as illustrated by fusions no 3 and 12 in the appended examples). SEQ ID NO: 32 and 33 comprise the fusion polypeptide comprising RPFB-Dhyb, Ag85B, TB10.4 and ESAT6, with and without targeting peptides respectively (as illustrated by fusions no 4 and 11 in the appended examples). SEQ ID NO: 34 and 35 comprise the fusion polypeptide comprising Rv0569 Rv1813, Rv3407, Rv3478 and Rv1807, with and without targeting peptides respectively (as illustrated by fusions no 5 and 9 in the appended examples). SEQ ID NO: 36 comprises the fusion polypeptide comprising Ag85B, Rv2626, RPFB-Dhyb and Rv1733, with a signal peptide (as illustrated by fusion no 6 in the appended examples). SEQ ID NO: 37 comprises the fusion polypeptide comprising Ag85B, Rv2626, and Rv1733, with a signal peptide (as illustrated by fusion no 8 in the appended examples). SEQ ID NO: 38 comprises the fusion polypeptide comprising Rv2029, Rv2626, Rv1733 and Rv0111, with a signal peptide (as illustrated by fusion no 13 in the appended examples). SEQ ID NO: 39 comprises the fusion polypeptide comprising Rv2029, TB10.4, ESAT-6 and Rv0111, with a signal peptide (as illustrated by fusion no 14 in the appended examples).

More preferred examples of fusion polypeptides are selected from the group of polypeptides comprising, or alternatively consisting essentially of, or alternatively consisting of an amino acid sequence which exhibits at least 80% of identity, advantageously at least 85% of identity, desirably at least 90% of identity, preferably at least 95% of identity, and more preferably 98% identity and even more preferably 100% identity with any of the following amino acid sequences:
- the amino acid sequence shown in SEQ ID NO: 28 from approximately position 32 to approximately position 506 (fusion Ag85B*-TB10.4-ESAT-6 as illustrated by fusion no 2 or 10 in the appended examples);
- the amino acid sequence shown in SEQ ID NO: 29 from approximately position 10 to approximately position 484 (fusion Ag85B*-TB10.4-ESAT-6 as illustrated by fusion no 2 or 10 in the appended examples);
- the amino acid sequence shown in SEQ ID NO: 30 from approximately position 32 to approximately position 380 (fusion RPFB-Dhyb as illustrated by fusions no 3 and 12 in the appended examples);
- the amino acid sequence shown in SEQ ID NO: 31 from approximately position 10 to approximately position 358 (fusion RPFB-Dhyb as illustrated by fusions no 3 and 12 in the appended examples);
- the amino acid sequence shown in SEQ ID NO: 32 from approximately position 32 to approximately position 855 (fusion RPFB-Dhyb-Ag85B*-TB10.4-ESAT-6 as illustrated by fusions no 4 and 11 in the appended examples);
- the amino acid sequence shown in SEQ ID NO: 33 from approximately position 10 to approximately position 833 (fusion RPFB-Dhyb-Ag85B*-TB10.4-ESAT-6 as illustrated by fusions no 4 and 11 in the appended examples);

the amino acid sequence shown in SEQ ID NO: 34 from approximately position 32 to approximately position 1115 (fusion Rv0569-Rv1813*-Rv3407-Rv3478-Rv1807 as illustrated by fusions no 5 and 9 in the appended examples);

the amino acid sequence shown in SEQ ID NO: 35 from approximately position 10 to approximately position 1093 (fusion Rv0569-Rv1813*-Rv3407-Rv3478-Rv1807 as illustrated by fusions no 5 and 9 in the appended examples);

the amino acid sequence shown in SEQ ID NO: 36 from approximately position 32 to approximately position 956 (fusion Ag85B*-Rv2626-RPFB-Dhyb-Rv1733* as illustrated by fusion no 6 in the appended examples);

the amino acid sequence shown in SEQ ID NO: 37 from approximately position 32 to approximately position 607 (fusion Ag85B*-Rv2626-Rv1733* as illustrated by fusion no 8 in the appended examples);

the amino acid sequence shown in SEQ ID NO: 38 from approximately position 37 to approximately position 932 (fusion Rv2029-Rv2626-Rv1733*-Rv0111* as illustrated by fusion no 13 in the appended examples); and the amino acid sequence shown in SEQ ID NO: 39 from approximately position 37 to approximately position 831 (fusion Rv2029*-TB10.4-ESAT-6-Rv0111*).

Of course, such amino acid sequences can be equipped with an initiator Met.

In a preferred embodiment, the fusion polypeptide of the invention further comprises appropriate targeting peptide(s) such as signal and/or trans-membrane peptides so as to allow its presentation at the cell membrane. Even more preferred fusion polypeptides are selected from the group of polypeptides comprising, or alternatively consisting essentially of, or alternatively consisting of an amino acid sequence which exhibits at least 80% of identity, advantageously at least 85% of identity, desirably at least 90% of identity, preferably at least 95% of identity, and more preferably 98% identity and even more preferably 100% identity with any of the following amino acid sequences:

the amino acid sequence shown in SEQ ID NO: 28 from position 1 (initiator Met) to approximately position 23 and from approximately position 32 to approximately position 506 and from approximately position 517 to approximately position 583 (fusion SS-Ag85B*-TB10.4-ESAT-6-TM as illustrated by fusions no 2 in the appended examples);

the amino acid sequence shown in SEQ ID NO: 30 from position 1 (initiator Met) to approximately position 23 and from approximately position 32 to approximately position 380 and from approximately position 391 to approximately position 457 (fusion SS-RPFB-Dhyb-TM as illustrated by fusion no 3 in the appended examples);

the amino acid sequence shown in SEQ ID NO: 32 from position 1 (initiator Met) to approximately position 23 and from approximately position 32 to approximately position 855 and from approximately position 866 to approximately position 932 (fusion SS-RPFB-Dhyb-Ag85B*-TB10.4-ESAT-6-TM as illustrated by fusion no 4 in the appended examples);

the amino acid sequence shown in SEQ ID NO: 34 from position 1 (initiator Met) to approximately position 23 and from approximately position 32 to approximately position 1115 and from approximately position 1126 to approximately position 1192 (fusion SS-Rv0569-Rv1813*-Rv3407-Rv3478-Rv1807-TM as illustrated by fusion no 5 in the appended examples);

the amino acid sequence shown in SEQ ID NO: 36 from position 1 (initiator Met) to approximately position 23 and from approximately position 32 to approximately position 956 (fusion SS-Ag85B*-Rv2626-RPFB-Dhyb-Rv1733* as illustrated by fusion no 6 in the appended examples);

the amino acid sequence shown in SEQ ID NO: 37 from position 1 (initiator Met) to approximately position 23 and from approximately position 32 to approximately position 607 (fusion SS-Ag85B*-Rv2626-Rv1733* as illustrated by fusion no 8 in the appended examples);

the amino acid sequence shown in SEQ ID NO: 38 from position 1 (initiator Met) to approximately position 28 and from approximately position 37 to approximately position 932 (fusion SS-Rv2029-Rv2626-Rv1733*-Rv0111* as illustrated by fusion no 13 in the appended examples); and the amino acid sequence shown in SEQ ID NO: 39 from position 1 (initiator Met) to approximately position 28 and from approximately position 37 to approximately position 831 (fusion SS-Rv2029*-TB10.4-ESAT-6-Rv0111* as illustrated by fusion no 14 in the appended examples).

Typically, the mycobacterial antigens and nucleic acid molecules encoding such antigens comprised in the immunogenic combination and fusion polypeptide of the invention can be isolated or prepared using standard techniques. They may be purified e.g. from bacteria culture or produced recombinantly in a host cell using any of the expression system available in the art or can be provided to the subject upon administration of suitable expression vector(s) such as those described herein.

Nucleic Acid Molecules and Nucleic Acid Combinations

The present invention also provides isolated nucleic acid molecules encoding the at least 5 mycobacterial antigens comprised in the immunogenic combination and the fusion polypeptides of present invention as well as compositions comprising such nucleic acid molecules.

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) (e.g., mRNA, antisense RNA) or mixed polyribo-polydeoxyribonucleotides. They encompass single or double-stranded, linear or circular, natural or synthetic nucleic acids.

As defined before, the nucleic molecules of the invention may be native nucleic acids (e.g. isolated from a genome or genomic fragment of a *Mycobacterium*) or may be modified by man to include substitution, deletion, addition and/or insertion of one or more nucleotide(s). The present invention encompasses any modifications aimed to improve cloning, expression, stability (e.g. introduction of appropriate restriction sites, degeneration and/or optimisation of nucleotide sequence to optimize translation in a given host cell and/or suppression of potentially negative elements that may destabilize the nucleic acid molecule or its transcript). When several modifications are contemplated, they can concern consecutive and/or non-consecutive nucleotide residues. The modification(s) contemplated by the present invention encompass silent modifications that do not change the amino acid sequence of the encoded mycobacterial antigens and fusion polypeptides, as well as modifications that are translated into the encoded mycobacterial polypeptide. Preferably the modifications do not decrease the immunogenic potential of encoded mycobacterial antigens and fusion polypeptides with respect to the non-modified ones.

In one embodiment, the nucleic acid molecule of the invention can be degenerated over the full length nucleotide sequence or portion(s) thereof so as to reduce sequence homology between nucleic acid molecule(s) used in the context of the invention or in the host cell. It is indeed advisable to degenerate the portions of nucleic acid sequences that show a high degree of nucleotide sequence identity and the skilled person is capable of identifying such portions by sequence alignment, to degenerate the nucleic acid molecules in the homologous portions so as to avoid stability problems during production process.

Alternatively or in addition, the nucleic acid molecule of the invention can be optimized for providing high level expression in a particular host cell or subject, e.g. avian (e.g. chicken embryonic fibroblast, *Cairina moschata* cell lines described in WO2010/130756 and WO2012/001075), mammalian, yeast (e.g. *Saccharomyces cerevisiae*, *Saccharomyces pombe* or *Pichia pastoris*) or bacteria (e.g. *E. coli*, BCG or *Listeria*). It has been indeed observed that, when more than one codon is available to code for a given amino acid, the codon usage patterns of organisms are highly non-random and the utilisation of codons may be markedly different between different hosts. As the nucleotide sequences used in the invention are mostly of bacterial origin, they may have an inappropriate codon usage pattern for efficient expression in host cells such as higher eukaryotic cells. Typically, codon optimisation is performed by replacing one or more "native" (mycobacterial) codon corresponding to a codon infrequently used in the host cell of interest by one or more codon encoding the same amino acid which is more frequently used. It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleic acid molecule.

Further to optimization of the codon usage, expression in the host cell or subject can further be improved through additional modifications of the nucleotide sequence. For example, the nucleic acid molecule of the invention can be modified so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; RNA secondary structures; and/or internal cryptic regulatory elements such as internal TATA-boxes, chi-sites, ribosome entry sites, and/or splicing donor/acceptor sites.

The present invention encompasses a nucleic acid molecule encoding any mycobacterial antigen selected from the group of polypeptides set forth in any of SEQ ID NO: 1-24.

Of particular interest is a nucleic acid molecule which encodes a fusion polypeptide comprising an amino acid sequence which exhibits at least 80% of identity (e.g. 80%, 85%, 90%, 95%, 98%, 100%) with any of the amino acid sequences shown in SEQ ID NO: 28-39 or any variant and fragment thereof (e.g. a fragment encoding the exemplary portion(s) of such SEQ ID NO: 28-39 cited above).

A particularly preferred embodiment of the present invention is directed to a nucleic acid molecule comprising, alternatively essentially consisting of or alternatively consisting of a nucleotide sequence which exhibits at least 80% of identity (i.e. a nucleic acid molecule that hybridizes to the recited nucleic acid molecule under stringent conditions), advantageously at least 85% of identity, preferably at least 90% of identity, more preferably at least 95% of identity, and even more preferably 100% identity with the nucleotide sequence shown in any of SEQ ID NO: 40-51 or any variant and fragment thereof (e.g. encoding the exemplary portions of SEQ ID NO: 28-39 cited above).

The nucleic acid molecules of the present invention can be generated using sequence data accessible in the art and the sequence information provided herein. For example, they may be isolated using routine techniques well known in the art, e.g. by PCR isolation and/or cloning by conventional molecular biology from a *Mycobacterium* genome of a particular species or genomic fragment thereof, cDNA and genomic libraries or any prior art vector known to include it. Alternatively, the nucleic acid molecules of the invention can also be generated by chemical synthesis in automatised process (e.g. assembled from overlapping synthetic oligonucleotides).

Another embodiment of the invention pertains to fragments of the nucleic acid molecules of the invention, e.g. restriction endonuclease and PCR-generated fragments. Such fragments can be used as probes, primers or fragments encoding relevant immunogenic portion(s).

Vectors

The present invention also concerns vectors comprising one or more nucleic acid molecule(s) of the present invention as well as compositions comprising such vector(s).

The term "vector" as used herein refers to a vehicle, preferably a nucleic acid molecule or a viral particle that contains the elements necessary to allow delivery, propagation and/or expression of any of the nucleic acid molecule(s) described herein within a host cell or subject. This term encompasses vectors for maintenance (cloning vectors) or vectors for expression in various host cells or subjects (expression vectors), extrachromosomal vectors (e.g. multicopy plasmids) or integration vectors (e.g. designed to integrate into the host cell genome and produce additional copies of the nucleic acid molecules when the host cell replicates) as well as shuttle vectors (e.g. functioning in both prokaryotic and/or eukaryotic hosts) and transfer vectors (e.g. for transferring nucleic acid molecule(s) in a viral genome). For the purpose of the invention, the vectors may be of naturally occurring genetic sources, synthetic or artificial, or some combination of natural and artificial genetic elements.

In the context of the invention, the term "vector" has to be understood broadly as including plasmid and viral vectors. A "plasmid vector" as used herein refers to a replicable DNA construct. Usually plasmid vectors contain selectable marker genes that allow host cells carrying the plasmid vector to be selected for or against in the presence of a corresponding selective drug. A variety of positive and negative selectable marker genes are known in the art. By way of illustration, an antibiotic resistance gene can be used as a positive selectable marker gene that allows a host cell to be selected in the presence of the corresponding antibiotic.

The term "viral vector" as used herein refers to a nucleic acid vector that includes at least one element of a virus genome and may be packaged into a viral particle or to a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject. Viral vectors can be replication-competent or -selective (e.g. engineered to replicate better or selectively in specific host cells), or can be genetically disabled so as to be replication-defective or replication-impaired.

Vectors which are appropriate in the context of the present invention, include, without limitation, bacteriophage, plasmid or cosmid vectors for expression in prokaryotic host cells such as bacteria (e.g. *E. coli*, BCG or *Listeria*); vectors for expression in yeast (e.g. *Saccharomyces cerevisiae, Schizosaccharomyces pombe, Pichia pastoris*); baculovirus vectors for expression in insect cell systems (e.g. Sf 9 cells); viral and plasmid vectors for expression in plant cell systems (e.g. Ti plasmid, cauliflower mosaic virus CaMV; tobacco mosaic virus TMV); as well as plasmid and viral vectors for expression in higher eukaryotic cells or subjects. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

Representative examples of suitable plasmid vectors include, without limitation, pREP4, pCEP4 (Invitrogen), pCI (Promega), pVAX (Invitrogen) and pGWiz (Gene Therapy System Inc).

Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In one embodiment, the viral vector employed in this invention is replication-defective or replication-impaired which means that it cannot replicate to any significant extent in normal cells (eg. normal human cells) or in the subject to whom it is administered (the impairment or defectiveness of replication functions can be evaluated by conventional means—eg. via measuring DNA synthesis and/or viral titre in non-permissive cells). Such replication-defective or impaired vectors typically require for propagation, permissive cell lines which bring up or complement the missing/impaired functions.

Examples of viral vectors that are useful in the context of the invention include adenoviral vectors which have a number of well-documented advantages for vaccination, immunotherapy, gene transfer or for recombinant production (for a review, see "Adenoviral vectors for gene therapy", 2002, Ed D. Curiel and J. Douglas, Academic Press). The adenoviral vectors of the present invention can be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. It may also be advantageous to use animal Ad with a special preference for chimp Ad, such as chimp Ad3 and Ad63. The cited adenovirus are available from ATCC or have been the subject of numerous publications describing their sequence, organization and methods of producing, allowing the artisan to apply them (see for example U.S. Pat. Nos. 6,136,594; 6,133,028; WO00/50573; WO00/70071; WO2004/083418; WO2004/097016 and WO2005/071093).

Preferred replication-defective adenoviral vectors are E1-defective with an E1 deletion extending from approximately positions 459 to 3328 or from approximately positions 459 to 3510 (by reference to the sequence of Ad5 disclosed in the GeneBank under the accession number M 73260). The cloning capacity can further be improved by deleting additional portion(s) of the adenoviral genome (all or part of the non-essential E3 region (e.g. deletion from approximately positions 27867 to 30743) or of other essential E2 and/or E4 regions as described in WO94/28152 and Lusky et al., 1998, J. Virol 72: 2022).

The nucleic acid molecules of the present invention can be independently inserted in any location of the adenoviral genome, with a specific preference for insertion in replacement of the E1 and/or E3 region. They may be positioned in sense or antisense orientation relative to the natural transcriptional direction of the region in question.

Other examples of viral vectors particularly appropriate in the context of the invention include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC (U.S. Pat. No. 5,494,807) and the modified Ankara (MVA) strain (Antoine et al., 1998, Virol. 244: 365; WO02/42480). The general conditions for constructing and producing recombinant poxvirus are well known in the art (see for example WO2010/130753; WO03/008533; U.S. Pat. No. 6,998,252; U.S. Pat. Nos. 5,972,597 and 6,440,422). The nucleic acid molecules of the present invention are preferably inserted within the poxviral genome in a non-essential locus. Thymidine kinase gene is particularly appropriate for insertion in Copenhagen vaccinia vectors and deletion II or III for insertion in MVA vector (WO97/02355).

Other viral vectors suitable in the context of the invention are morbillivirus which can be obtained from the paramyxoviridae family, with a specific preference for measles virus. Various attenuated strains are available in the art (Brandler et al, 2008, CIMID, 31: 271; Singh et al., 1999, J. virol. 73(6): 4823), such as and without limitation, the Edmonston A and B strains (Griffin et al., 2001, Field's in Virology, 1401-1441), the Schwarz strain (Schwarz A, 1962, Am J Dis Child, 103: 216), the S-191 or C-47 strains (Zhang et al., 2009, J Med Virol. 81 (8): 1477). Insertion between P and M genes or between H and L genes is particularly appropriate.

Suitable vector for use in the present invention also include bacterium cell which can be wild-type or mutant (e.g. avirulent). Well-known examples of such bacterium cells include without limitation avirulent *Mycobacterium* (e.g. *Mycobacterium bovis* BCG), *Lactobacillus* (e.g. *Lactococcus lactis*), *Listeria* (e.g. *Listeria monocytogenes*) and other microorganisms such as Salmonella and Pseudomona. A preferred embodiment is directed to a BCG vector into the genome of which has been incorporated nucleic acid molecule(s) encoding one or more mycobacterial antigen(s) or fusion polypeptide (s) as defined above in a manner allowing the BCG vector to express such element(s).

The present invention also encompasses vectors (e.g. plasmid DNA) complexed to lipids or polymers to form particulate structures such as liposomes, lipoplexes or nanoparticles.

In accordance with the present invention, the nucleic acid molecules comprised in the vector of the invention are in a form suitable for expression in a host cell or subject, which means that each of the nucleic acid molecules set forth herein is operably linked to appropriate regulatory sequences. As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA).

It will be appreciated by those skilled in the art that the choice of the regulatory sequences can depend on such factors as the vector itself, the host cell or subject, the level of expression desired, etc. The promoter is of special importance. In the context of the invention, it can be constitutive directing expression of the nucleic acid molecule in many types of host cells or specific to certain host cells (e.g. lung-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize vector production and circumvent potential toxicity of the expressed polypeptide(s).

Promoters suitable for constitutive expression in mammalian cells include but are not limited to the cytomegalovirus (CMV) immediate early promoter (U.S. Pat. No. 5,168,062), the RSV promoter, the adenovirus major late promoter, the phosphoglycero kinase (PGK) promoter, the thymidine kinase (TK) promoter of herpes simplex virus (HSV)-1 and the T7 polymerase promoter. Promoters such as the trp, lac, phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization. Vaccinia virus promoters are particularly adapted for expression in poxviral vectors. Representative example include without limitation the vaccinia 7.5K, H5R, 11K7.5 (Erbs et al., 2008, Cancer Gene Ther. 15: 18), TK, p28, p11 and K1L promoter, as well as synthetic promoters such as those described in Chakrabarti et al. (1997, Biotechniques 23: 1094-7; Hammond et al., 1997, J. Viol Methods 66: 135-8; and Kumar and Boyle, 1990, Virology 179: 151-8) as well as early/late chimeric promoters. Promoters suitable for measles-mediated expression include without limitation any promoter directing expression of measles transcription units (Brandler and Tangy, 2008, CIMID 31: 271).

Those skilled in the art will appreciate that the regulatory elements controlling the expression of the nucleic acid molecule(s) of the invention may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, Shine-Dalgarno sequences, etc.) into the host cell or subject and purification steps (e.g. a tag as described herein).

In one embodiment, the nucleic acid molecules encoding the mycobacterial antigens present in or encoded by the immunogenic combination and/or the fusion polypeptides of the invention are carried out by a single vector.

In an alternative embodiment, the nucleic acid molecules encoding the mycobacterial antigens present in or encoded by the immunogenic combination and/or the fusion polypeptides of the invention are carried out by two or more vectors. Each vector encodes one or more mycobacterial antigens among those cited above or one or more fusion polypeptides. The two or more vectors can be administered to the subject substantially simultaneously, or sequentially.

Particularly preferred embodiments of the invention are directed to a single vector (or viral particles) selected from the group consisting of:

i. A vector encoding a fusion polypeptide comprising Rv2029, Rv2626, Rv1733 and Rv011 and a fusion polypeptide comprising RpfB, RpfD, Ag85B, TB10.4 and ESAT-6 (exemplary vectors encoding fusions 13 and 4 and fusions 13 and 11, respectively);

ii. A vector encoding a fusion polypeptide comprising Rv2029, Rv2626, Rv1733 and Rv0111, a fusion polypeptide comprising RpfB, RpfD, Ag85B, TB10.4 and ESAT-6 and a fusion polypeptide comprising Rv0569, Rv1813, Rv3407, Rv3478 and Rv1807 (exemplary vectors encoding fusions 13, 4 and 5 and fusions 13, 11 and 9, respectively);

iii. A vector encoding a fusion polypeptide comprising Rv2029, Rv2626, Rv1733 and Rv0111, a fusion polypeptide comprising RpfB, RpfD, Ag85B, TB10.4 and ESAT-6 and a fusion polypeptide comprising Rv0569, Rv1813, Rv3407, Rv3478 and Rv1807 (exemplary vectors encoding fusions 13, 4 and 9 and fusions 13, 11 and 5, respectively);

iv. A vector encoding a fusion polypeptide comprising Ag85B, Rv2626 RpfB, RpfD and Rv1733 and a fusion polypeptide comprising Rv2029 TB10.4, ESAT-6 and Rv0111 (exemplary vectors encoding fusions 6 and 14);

v. A vector encoding a fusion polypeptide comprising Ag85B, Rv2626 RpfB, RpfD and Rv1733, a fusion polypeptide comprising Rv2029 TB10.4, ESAT-6 and Rv0111 and a fusion polypeptide comprising Rv0569, Rv1813, Rv3407, Rv3478 and Rv1807 (exemplary vectors encoding fusions 6, 14 and 5 and fusions 6, 14 and 9, respectively);

vi. A vector encoding a fusion polypeptide comprising RpfB, RpfD, Ag85B, TB10.4 and ESAT-6 and a fusion polypeptide comprising Rv0569, Rv1813, Rv3407, Rv3478 and Rv1807 (exemplary vectors encoding fusions 9 and 11 and fusions 5 and 4, respectively).

More preferably, the vector described above is a MVA vector.

If needed, the immunogenic combination, fusion polypeptide or vector of the invention can further comprise additional copies of the selected mycobacterial antigens, or additional antigens from a different *Mycobacterium* species, such as *M. bovis* or *M caprae*, and/or additional polypeptides from other sources (i.e. heterologous polypeptide), aimed to improve therapeutic or protective activity against a *Mycobacterium* infection or any disease or condition caused by or associated with a *Mycobacterium* infection. Suitable additional polypeptides include without limitation immunomodulators such as cytokines and any other antigen originating from a potentially co-infecting organism (e.g. HIV, HBV, etc).

According to a preferred embodiment, the vector of the invention is in the form of infectious viral particles. Typically, such viral particles are produced by a process comprising the steps of (i) introducing the viral vector of the invention into a suitable cell line, (ii) culturing said cell line under suitable conditions so as to allow the production of said infectious viral particle, (iii) recovering the produced viral particle from the culture of said cell line, and (iv) optionally purifying said recovered viral particle.

When the viral vector is replication-defective or replication-impaired, the particles are usually produced in a permissive cell line or via the use of a helper virus, which supplies in trans the missing/impaired functions. For example, suitable cell lines for complementing E1-deleted adenoviral vectors include the 293 cells (Graham et al., 1997, J. Gen. Virol. 36: 59-72) as well as the HER-96 and PER-C6 cells (e.g. Fallaux et al., 1998, Human Gene Ther. 9: 1909-17; WO97/00326) or any derivative of these cell lines. Avian cells are particularly suitable for propagating poxvirus vectors including without limitation primary chicken embryo fibroblasts (CEF) prepared from chicken embryos obtained from fertilized eggs, and duck cell lines (e.g. as described in WO03/076601, WO2009/004016, WO2010/130756 and US2011-008872).

The infectious viral particles may be recovered from the culture supernatant and/or from the cells after lysis. They can be further purified according to standard techniques (chromatography, ultracentrifugation techniques, etc).

The present invention also encompasses vectors or viral particles that have been modified to allow preferential targeting to a specific host cell. A characteristic feature of targeted vectors is the presence at their surface of a ligand capable of recognizing and binding to a cellular and surface-exposed component such as a cell-specific marker (e.g. a *mycobacterium*-infected cell), a tissue-specific marker (e.g. a lung-specific marker), etc. Examples of suitable ligands include antibodies or fragments thereof directed to a mycobacterial antigenic domain. Targeting can be carried out by genetically inserting the ligand into a polypeptide present on the surface of the virus (e.g. adenoviral fiber, penton, pIX or vaccinia p14 gene product).

Host Cells and Production Methods

In another aspect, the invention also relates to host cells which comprise the immunogenic combinations, the fusion polypeptides, the nucleic acid molecules or vectors (e.g. viral particles) of the invention as well as compositions comprising such a host cell.

As used herein, the term "host cell" should be understood broadly without any limitation concerning particular organization in tissue, organ, or isolated cells. Such cells may be of a unique type of cells or a group of different types of cells such as cultured cell lines, primary cells and proliferative cells. In the context of the invention, the term "host cells" include prokaryotic cells, lower eukaryotic cells such as yeast, and other eukaryotic cells such as insect cells, plant and mammalian (e.g. human or non-human) cells as well as cells capable of producing the vector of the invention (e.g. 293, HER96, PERC.6 cells, CEF, duck cell lines, etc). This term also includes cells which can be or has been the recipient of the vector described herein as well as progeny of such cells.

According to a specific embodiment of the invention, the host cell can be further encapsulated. Cell encapsulation technology is known in the art.

Still a further aspect of the present invention is a method for recombinant production of the mycobacterial antigens comprised in or encoded by the immunogenic combination or the fusion polypeptides of the invention, employing the vectors (or infectious viral particles) and/or host cells of the invention. Typically, the method comprises the steps of (i) introducing a vector into a suitable host cell to produce a transfected or infected host cell, (ii) culturing in-vitro said transfected or infected host cell under conditions suitable for growth of the host cell, (iii) recovering the cell culture, and (iv) optionally, purifying the mycobacterial antigen(s) or the fusion polypeptide from the recovered cell and/or culture supernatant.

It is expected that those skilled in the art are knowledgeable in the numerous expression systems available in the art for expressing polypeptides and of the methods for introducing a vector into a host cell. Such methods include, but are not limited to microinjection, $CaPO_4$— mediated transfection, DEAE-dextran-mediated transfection, electroporation, lipofection/liposome fusion, gene guns, transduction, viral infection as well as direct administration into a host organism via various means. The method may also be used in association with conventional transfection reagents that facilitate introduction of nucleic acids in host cells, such as polycationic polymers (e.g. chitosan, polymethacrylate, PEI, etc) and cationic lipids (e.g. DC-Chol/DOPE, transfectam, lipofectin, etc).

Host cells can be cultured in conventional fermentation bioreactors, flasks, and petri plates. Culturing can be carried out at a temperature, pH and oxygen content appropriate for a given host cell. No attempts will be made here to describe in detail the various prokaryotic and eukaryotic expression systems available in the art for such purposes.

In a preferred embodiment, the method employs an *E coli* host cell and in particular a *E. coli* strain carrying the D13 prophage in its genome for allowing inducible expression of T7 polymerase by lactose or analogue of lactose (e.g. IPTG: IsoPropyl b-D-1-Thio Galactopyranoside). Such strains are available for various manufacturers (e.g. Lucigen, Merck, etc). After plasmid introduction, the transformed *E. coli* cell can be cultured at a temperature comprised between approximately 18° C. to approximately 39° C. (specific preference for approximately 30° C. or approximately 37° C.) for a time period varying from 6 to 48 hours (specific preference from approximately 8 to approximately 24 h) in conventional medium adapted to the vector selection marker (e.g. presence of antibiotic) and to the host strain (e.g. in the presence of an inducer such as IPTG). The cell culture is recovered and can be lysed (e.g. chemical lysis with a detergent, sonication, etc). After centrifugation of the cell lysate, both the supernatant and the pellet can be collected for further analysis (e.g. by SDS PAGE) to evaluate the level of expression as well as the solubility of the expressed material (e.g. soluble material can be found in the cell lysate supernatant and insoluble material can be trapped in inclusion bodies).

The recovered mycobacterial antigen(s) or the fusion polypeptides can optionally be purified by well-known purification methods including ammonium sulfate precipitation, acid extraction, gel electrophoresis; filtration and chromatographic methods (e.g. reverse phase, size exclusion, ion exchange, affinity, hydrophobic-interaction, hydroxyapatite, high performance liquid chromatography, etc). The conditions and techniques to be used depend on factors such as net charge, molecular weight, hydrophobicity, hydrophilicity and will be apparent to those having skill in the art. Moreover, the level of purification will depend on the intended use. For example protein concentration can be evaluated by Bransdford assay (Biorad), endotoxin levels can be evaluated by techniques such as the Portable Test System (Charles River Laboratories) and the mass of the purified polypeptides can be measured using MALDI (Matrix-Assisted Laser Desorption/Ionisation) or electrospray methods.

Compositions

In another aspect, this invention provides a composition comprising at least one of the immunogenic combination, fusion polypeptide, nucleic acid molecule, vector (e.g. infectious viral particle), or host cell of the invention (also referred herein to "active agent") or any combination thereof (e.g. combination of different polypeptides or vectors/viral particles). Preferably, the composition is a pharmaceutical composition which comprises further to a therapeutically effective amount of the active agent(s), one or more pharmaceutically acceptable vehicle(s).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with administration in a subject and in particular in a human.

As used herein a "therapeutically effective amount" is a dose sufficient for the intended use. When prophylactic use is concerned, this term means a dose sufficient to prevent or to delay the onset and/or establishment of a *Mycobacterium* infection (e.g. Mtb infection). For "therapeutic" use, the composition is administered to a subject already infected with a *Mycobacterium* species with the goal of treating active disease or preventing reactivation in latently infected individuals, eventually in combination with one or more conventional therapeutic modalities as described herein. In particular, a therapeutically effective amount of the composition of the invention could be that amount necessary to cause induction or stimulation of the immune system in the administered subject (e.g. resulting in the development of an innate and/or specific response).

The subject to be treated may be a newborn, an infant, a young adult or an adult. The subject may have been previously immunized with *Bacillus* Calmette-Guerin (BCG) or previously treated for a *Mycobacterium* infection before being treated with the active agent(s) described herein. It may or not be co-infected with another pathogenic organism (e.g. the human immunodeficiency virus HIV).

In particular, the subject to be treated is infected with a virulent *Mycobacterium* species (e.g. Mtb) which may be a drug resistant (e.g. MDR, XDR or TDR) strain. The infecting *Mycobacterium* can be the same strain or isolate as any of the *Mycobacterium* from which originate the antigens comprised or encoded by the active agent used in the present invention or it can be from a different strain or isolate.

The composition of the invention is suitably buffered in order to be appropriate for human or animal use at a physiological or slightly basic pH (e.g. from approximately pH 7 to approximately pH 9). Suitable buffers include without limitation phosphate buffer (e.g. PBS), bicarbonate buffer and/or Tris buffer.

The composition of the invention can further comprise a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins).

Additional pharmaceutically acceptable excipients may be used for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. lung).

In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p 407-419), saponins such as QS21 (WO 98/56415), imidazo-quinoline compounds such as Imiquimod (WO2007/147529), cytosine phosphate guanosine oligodeoxynucleotides such as CpG and cationic peptides such as IC-31 (Kritsch et al., 2005, J. Chromatogr Anal. Technol Biomed Life Sci 822: 263) or any derivative thereof.

The pharmaceutically acceptable vehicles included in the composition of the invention must also permit to preserve its stability under the conditions of manufacture and long-term storage (i.e. at least one month with a preference for at least one year) at freezing (e.g. −70° C., −20° C.), refrigerated (e.g. 4° C.), ambient temperatures. Such "long term" formulations are known in the art (e.g. WO98/02522; WO03/053463). One may cite (a) 1M saccharose, 150 mM NaCl, 1 mM $MgCl_2$, 54 mg/l Tween 80, 10 mM Tris pH 8.5, (b) 10 mg/ml mannitol, 1 mg/ml HSA, 20 mM Tris, pH 7.2, and 150 mM NaCl and (c) physiological saline which are particularly adapted to the composition of the invention.

The composition of the invention can be in various forms, e.g. solid, liquid or frozen. Solid (e.g. dry powdered or lyophilized) compositions can be obtained by a process involving vacuum drying and freeze-drying. In a specific embodiment, the composition of the invention is formulated for delivery in the respiratory tract (e.g. by inhalation, intranasal or intrapulmonary route) in a spray-dried (see e.g. WO2010/135495) or droplet form (with a specific preference for droplets having an average diameter of 100-5000 μm).

The immunogenic combination, fusion polypeptide, nucleic acid molecule, vector, host cell or composition of the present invention is suitable for a variety of modes of administration. Any of the conventional administration routes are applicable in the context of the invention including systemic, topical or mucosal routes.

Systemic administration includes for example subcutaneous, intradermal, intramuscular, intravenous, intraperitoneal, intravascular, intraarterial injection as well as scarification. Injections can be made with conventional syringes and needles, or any other appropriate devices available in the art (e.g. electroporation). Mucosal administration includes without limitation oral/alimentary, intranasal, intratracheal, intrapulmonary, intravaginal or intra-rectal route. Administration in the respiratory tract can be performed through nebulisation or aerosolization of droplet, spray, or dry powdered compositions using appropriate dispenser. Topical administration can also be performed using transdermal means (e.g. patch and the like). Intramuscular, intradermal and subcutaneous routes are particularly preferred in the context of the invention as well as intranasal intratracheal and intrapulmonary administrations.

The appropriate dosage can be adapted as a function of various parameters, in particular the active agent(s) comprised in the composition, the mode of administration; the age, health, and weight of the subject; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances.

For general guidance, suitable dosage for a viral vector-comprising composition varies from about $10^4$ to about $10^{13}$ vp (viral particles), iu (infectious unit) or pfu (plaque-forming units) depending on the vector and the quantitative technique used. Techniques available to evaluate the quantity of vp, iu and pfu present in a sample are conventional in the art. For example, the number of adenoviral particles (vp) is usually determined by measuring the A260 absorbance or HPLC, iu titers by quantitative DBP immunofluorescence and pfu by counting the number of plaques following infection of permissive cells. Preferably, the vp/iu ratio is below 100 in accordance with FDA guidelines. A preferred dose contains from about $10^5$ to about $10^{12}$ vp of an adenoviral vector (e.g. about $5 \times 10^8$, about $10^9$, about $5 \times 10^9$, about $10^{10}$, about $5 \times 10^{10}$ vp or about $10^{11}$ vp). A dose from about $5 \times 10^5$ to about $10^9$ pfu are preferred for vaccinia (e.g. MVA)-based composition with a specific preference for about $5 \times 10^6$, about $10^7$, about $5 \times 10^7$, about $10^8$ or about $5 \times 10^8$ pfu. A dose from about $5 \times 10^4$ to about $10^7$ pfu are preferred for measles-based composition, with a specific preference for about $10^5$, $5 \times 10^5$, $10^6$ or $5 \times 10^6$ pfu. A composition based on plasmid vector may be administered in doses of between 10 μg and 20 mg, advantageously between 100 μg and 2 mg. A protein composition may be administered in doses of between 10 μg and 20 mg, with a special preference for about 0.1 mg to about 2 mg per kg body weight for each of the mycobacterial antigens comprised in the composition. The administration may take place in a single dose or repeated doses after a certain time interval.

Repeated administrations (2, 3, 4, 5, 6, 7, 8, 9, 10, etc) can be separated from each other by an appropriate period of time and carried out by the same route or by different routes of administration, either at the same site or at different sites. Moreover, each administration can use the same active agent(s) or different ones. For illustrative purposes, two or three subcutaneous administrations separated from each other by approximately one week (e.g. from 3 to 10 days) are particularly suitable for MVA-based compositions whereas one or two intramuscular administration(s) are particularly suitable for Ad-, measles- and plasmid-based compositions. One or more "recall" administration(s) can be performed following the first series of priming administration(s) (e.g. after 6 months to several years) so as to recall the primed anti-*Mycobacterium* immune response. It is also possible to proceed via sequential cycles of administrations (e.g. a cycle of weekly administrations) that are repeated after a rest period.

In a specific embodiment, the administrations can be carried out according to a prime boost modality which comprises sequential administrations of one or more priming composition(s) and one or more boosting composition(s). Typically, the priming and the boosting compositions use different active agents which comprise or encode at least a mycobacterial antigen, immunogenic domain or epitope in common. The priming and boosting compositions can be administered at the same site or at alternative sites by the same route or by different routes of administration. For example, compositions based on polypeptide can be administered by a mucosal route whereas compositions based on vectors are preferably injected, e.g. by subcutaneous or intramuscular route. For illustrative purposes, one may contemplate priming the host's response with a live attenuated bacterium (such as BCG) and boosting with at least one of the "active agent" described herein (e.g. the immunogenic combination, fusion polypeptide, nucleic acid molecule, vector (e.g. infectious viral particle), or host cell of the invention or any combination thereof).

Prophylactic and Therapeutic Use

The immunogenic combination, fusion polypeptide, nucleic acid molecule, vector, host cell or composition of the invention is preferably for use for preventing or treating a *Mycobacterium* infection or any disease and pathologic condition caused by or associated with it. Such use aims at inducing or stimulating protective immune responses against a mycobacterial antigen/epitope.

In one embodiment, the immunogenic combination, fusion polypeptide, nucleic acid molecule, vector, host cell or composition of the invention is for use in methods for preventing infection or delaying the risk of infection with a *Mycobacterium* in a subject in need thereof, especially a subject who has been in close contact with an infected individual having developed an active disease and thus at risk of developing a *Mycobacterium* infection (e.g. transmission by inhalation of bacilli in moist droplets coughed out by the individual with TB).

In another embodiment, the immunogenic combination, fusion polypeptide, nucleic acid molecule, vector, host cell or composition of the invention is for use in methods for treating an active disease in a subject infected with a *Mycobacterium* species and especially Mtb, the method comprising the step of administering to the infected subject having developed an active disease, a therapeutically effective amount of at least one of the immunogenic combination, fusion polypeptide, nucleic acid molecule, vector, host cell or composition described herein, so as to induce an immune response against the infecting *Mycobacterium* species, thereby delaying or reducing the risk of development of active disease.

An "active disease" refers to a *Mycobacterium* infection with manifested serious disease symptoms. For example, in a human subject, TB is characterized by general clinical signs (such as weight loss, asthenia, fever, night sweats), clinical signs and/or symptoms (such as cough, hemoptysis, thoracic pain in case of pulmonary TB), and/or in some cases extrapulmonary signs according to the sites of infection (such as lymph nodes, bone forms, meningitis, urologenital forms).

In still another embodiment, the immunogenic combination, fusion polypeptide, nucleic acid molecule, vector, host cell or composition of the invention is for use in methods for preventing or treating reactivation in a subject latently-infected with a *Mycobacterium* species and especially *M. tuberculosis*, the method comprising the step of administering to said latently-infected subject, a therapeutically effective amount of at least one of the immunogenic combination, fusion polypeptide, nucleic acid molecule, vector, host cell or composition described herein, so as to induce an immune response against the infecting *Mycobacterium* species, thereby preventing or delaying reactivation.

By "a latently infected subject" is understood an individual, who is already infected with a virulent *Mycobacte-*

*rium* species (e.g. Mtb), but shows no manifested disease symptoms or clinical signs. Typically, the latently-infected subject retains the *Mycobacterium* within his bodies, is not clinically ill but retains a risk of subsequent progression to clinical disease (reactivation), particularly in the context of immunosuppression (e.g. co-infection with another pathogen such as HIV or under immunosuppressive treatment such as TNFa inhibitors). A Mtb latently-infected subject will be expected to be positive if tested by any test permitting the diagnosis of a Mtb infection (e.g. tuberculin test, Mantoux test for PPD reactivity, and/or IFNg release assays).

The term "reactivation" refers to the later manifestation of manifested disease symptoms of a *Mycobacterium*-associated disease in a subject who tests positive for a *Mycobacterium* infection but did not manifest apparent disease symptoms. For example reactivation may occur in an infected subject which may or may not have previously manifested active disease symptoms or who had been treated sufficiently to bring the infection into a latent state. For example, a Mtb-infected subject was previously immunized with BCG or previously treated for the Mtb infection (e.g. with one or more "front line" chemotherapeutic drug(s).

In a specific embodiment, the immunogenic combination, fusion polypeptide, nucleic acid molecule, vector, host cell or composition of the invention is for use as BCG booster to increase efficacy of BCG vaccination in a vaccinated subject.

Association with Chemotherapy

The immunogenic combination, fusion polypeptide, nucleic acid molecule, vector, host cell or composition of the invention may be employed in association with one or more conventional therapy, e.g. one or more chemotherapeutic drug(s) effective against a *Mycobacterium* infection (e.g. Mtb infection).

The chemotherapy is typically determined by the treating physician using current practice. Examples of such chemotherapeutic drugs include without limitation antibiotic(s) as well as small direct and indirect inhibitor molecules, antibodies and immunotherapeutics as described in the art. Typically, "front-line" antibiotic chemotherapy currently used to treat a Mtb infection that is not drug resistant includes isoniazid, rifamycins (i.e., rifampin, rifapentine and rifabutin), ethambutol, streptomycin, pyrazinamide and fluoroquinolones. "Second-line" chemotherapy used to treat a Mtb infection that has demonstrated drug resistance to one or more "first-line" therapy includes ofloxacin, ciprofloxacin, ethionamide, aminosalicylic acid, cycloserine, amikacin, kanamycin and capreomycin. The one or more chemotherapeutic(s) is/are generally administered over an appropriate period of time, for example, for one or several months (e.g. 1, 2, 3, 4, 5, 6, 9 or 12 months) or longer. Daily administration of doses 200 to 600 mg (e.g. 300 or 400 mg) over a period of time ranging from 6 to 12 months is appropriate.

In one embodiment, the immunogenic combination, fusion polypeptide, nucleic acid molecule, vector, host cell or composition of the invention is for use for reducing the time course of chemotherapy against a *Mycobacterium* (e.g. Mtb) infection. Usually, administration of the active agent(s) described herein will allow to enhance the efficacy of chemotherapy, (e.g. decrease the duration and/or severity of the clinical signs, improve the sputum conversion rate, etc.), reduce the length of the chemotherapy and/or the number of chemotherapeutic drugs to be employed, especially when the infecting mycobacteria is drug resistant.

In accordance with the present invention, the immunogenic combination, fusion polypeptide, nucleic acid molecule, vector, host cell or composition of the invention can be administered before, concurrently with, or after administration of the one or more chemotherapeutic drug(s). In one embodiment, the active agent described herein is administered at least 2 weeks after starting administration of the chemotherapy.

In a preferred embodiment, the immunogenic combination, fusion polypeptide, nucleic acid molecule, vector, host cell and/or composition of the invention is for use for inducing or enhancing an immune response in the administered subject. Accordingly, the present invention also encompasses a method for inducing or stimulating an immune response against a mycobacterial antigen upon administration in a subject of the immunogenic combination, fusion polypeptide, nucleic acid molecule, vector, host cell and/or composition of the invention.

The induced or stimulated immune response can be specific (i.e. directed to a mycobacterial epitopes/antigen) and/or non-specific (innate), humoral and/or cellular. In the context of the invention, the immune response is preferably a T cell response CD4+ or CD8+-mediated or both, directed to a mycobacterial antigen/epitope.

The ability of the active agents(s) described herein to induce or stimulate an immune response can be evaluated either in vitro or in vivo using a variety of direct or indirect assays which are standard in the art. Testing and validation are also illustrated in the appended Example section.

For example, induction of non-specific immunity can be performed by measurement of the NK/NKT-cells (e.g. representativity and level of activation), as well as IFN-related cytokine and/or chemokine producing cascades, activation of TLRs and other markers of innate immunity (e.g. Riano et al., 2012, Tuberculosis 92: 148-59).

The ability to stimulate a humoral response can be determined by an increase in antibody titer that is specific for at least one of the antigens comprised in or encoded by the immunogenic combination and fusion polypeptides described herein. Exemplary techniques include without limitation antibody binding, binding competition as well as ELISA and Western blot.

Evaluation of cellular immunity can be estimated for example by an increased frequency in immune cells such as T lymphocytes specific for at least one of the mycobacterial antigens comprised in or encoded by the immunogenic combination and fusion polypeptide described herein. One may also monitor cell proliferation upon radioactive labelling (e.g. T cell proliferation assays by [$^3$H] thymidine incorporation assay). Another and sensitive method for detecting the immune response is ELISpot in which the frequency of IFNg-producing cells is determined. Cytotoxic capacity for antigen-specific T lymphocytes can also be evaluated in a sensitized subject or by immunization of appropriate animal models. It is also possible to proceed by quantification of the release of relevant Th1 and/or Th2 cytokine(s) produced by activated T cells using routine bioassays (e.g. by multiparameters flow cytometry (ICS), by cytokine profile analysis using multiplex technologies or ELISA, etc.). PCR techniques can also be used to determine the presence of mRNA coding for the relevant cytokines. It will be appreciated by a skilled person that a significant increase or decrease in the amount of such relevant cytokines can be used to assess the immunogenic activity of one or more of the active agent(s) described herein.

Finally, the protective immune response can be evaluated in vivo in appropriate experimental animal, e.g. a mouse, a rat or a guinea pig (see Ashwin et al., 2008, Am J Resp, 39: 503-8; Acosta et al., 2011, Malays J Med, 18: 5-12), e.g. by measuring a reduction in mycobacterial colony-forming unit (cfu) from the spleen, lung or other tissue homogenates isolated from the animals which have received a challenge infection with a virulent strain of a *Mycobacterium* species (e.g. Mtb) after previously having been immunized with one or more of the active agent(s) described herein, as compared to the mycobacterial cfu in a control group of experimental animals infected with the same virulent strain of *Mycobacterium*, but which have not previously been immunized. The comparison between treated and non-treated groups can also be assessed on animal survival (an increased survival in the treated group will correlate with a protective immune response).

Such immunological read out are good correlate of protective immune response against a *Mycobacterium* infection provided by the active agent(s) described herein.

The protective response provided by the immunogenic combination, fusion polypeptide, nucleic acid molecule, vector, host cell or composition of the invention can also be estimated upon administration in a human subject according to the modalities described herein, over the baseline status or over the expected status if not treated. The protective response can be evidenced by any relevant clinical measurement typically used by physicians or other skilled healthcare staff, including, for instance:

A diminishment of disease incidence and/or prevalence and/or frequency in a given population such as the Chinese population or a population of migrants in a given country (e.g. a lower proportion of new individuals who have been diagnosed with a *Mycobacterium* infection or at risk of developing a *Mycobacterium* infection or a disease associated with a *Mycobacterium* infection in the group having received the active agent(s) described herein);

A higher percentage of sputum conversion rate in the group of treated subjects;

A higher percentage of curing active disease in the group of treated subjects;

A diminishment of extent of *Mycobacterium* transmission after close contact with an infected subject (e.g. reduction or delay the risk of being infected or the risk of developing active disease and/or reduction or delay the risk reactivation in latently infected subjects);

An amelioration of a disease state (e.g. decrease of bacterial cfu in a target tissue or in a biological sample; diminishment of the disease symptoms or their severity (e.g. number and/or severity of lesions in a target organ) or stabilized (not worsening) disease state); and An improved response of the treated subject to concurrent treatment (reduction of the need, number, duration and/or doses of conventional chemotherapeutic drugs).

In the context of the invention, the protective response can be transient (for a couple of weeks after cessation of administration) or sustained (for several months or years). As the natural course of clinical status which may vary considerably from a subject to another, it is not required that the protective response be observed in each subject treated but in a significant number of subjects (e.g. statistically significant differences between two groups can be determined by any statistical test known in the art, such as a Tukey parametric test, the Kruskal-Wallis test the U test according to Mann and Whitney, the Student's t-test, the Wilcoxon test, etc).

Such measurements can be performed before the administration of the active agent(s) described herein (baseline) and at various time points during treatment and at least for some (e.g. 12) weeks after cessation of the treatment.

For general guidance, a *Mycobacterium*-infection and associated disease can be detected by various means. For example, Mtb infection can also be oriented by a number of methods in clinical use today such as the Mantoux tuberculin skin test (TST), the Quantiferon test as well as in vitro detection of responses to HBHA (heparin binding haemagglutinin; Hougardy et al., 2007; PLos One 2(10): e926) or the detection of IP10 after stimulation in vitro with ESAT6, CFP10 and TB7.7 (Ruhwald et al., 2008; Microbes Infect 9: 806-12). Subjects developing an active disease may be diagnosed according to current practice. For illustrative purposes, TB diagnosis is based on detection of the causative bacterium in clinical specimens by microscopy, cultural techniques, polymerase chain reaction (PCR) and its various derivatives. DNA fingerprinting methods and spoligotyping can also be implemented. Mycobacterial culture is the gold standard method for identification of an isolate of the *Mycobacterium tuberculosis* complex and drug susceptibility testing. X ray techniques and clinical observations can also be implemented to support findings of active pulmonary and/or extrapulmonary disease. On the other hand, numerous serological assays have been developed for diagnosis of Mtb infection using a variety of antigens to detect circulating antibodies including complement fixation tests, haemagglutination tests, radio immunoassay and enzyme-linked immunosorbent assays (ELISA).

Antibody

In a further aspect, the present invention relates to an antibody which selectively binds to at least one of the mycobacterial antigens comprised in or encoded by the immunogenic combination or the fusion polypeptide of the present invention.

As used herein, an "antibody" encompasses any polypeptide that comprises an antigen binding fragment or an antigen binding domain and selectively binds a target protein when it binds the target protein and does not significantly bind to unrelated protein. In certain cases, it would be understood that antibody binding to the target protein is still selective despite some degree of cross-reactivity. Typically, binding between an antibody and an antigen is considered to be specific when the association constant $K_A$ is higher than $10^{-6}$ M. The appropriate binding conditions, such as antibody concentration, ionic strength of the solution, temperature, time allowed for binding, concentration of a blocking agent (e.g., serum albumin, milk casein), etc., may be optimized by a skilled person using routine techniques.

The antibody of the present invention can be polyclonal, monoclonal, monospecific, polyspecific, human, humanized, single chain, chimeric, synthetic, recombinant antibodies, as well as any fragment of such antibodies that retain antigen binding, including, but not limited to, Fab, F(ab')$_2$, Fv and scFv fragments.

Antibodies of the present invention can be produced using conventional techniques in the art, e.g. following administering to an animal (e.g. rabbit, horse, etc.) an effective amount of any of the mycobacterial antigen, fusion protein described herein and/or a peptide fragment thereof, by display (e.g. phage, yeast or ribosome display) or hybridoma techniques. The general methodology for making monoclonal antibodies is well known in the art.

The antibody of the present invention may be provided in isolated form, in a solution (e.g. animal antisera) or in host cells (e.g. hybridomas). Moreover, it may be conjugated to appropriate labels (detectable or functional labels) including radioactive ($_{131}$I, or $_{99}$Tc, etc), enzymatic (horse radish peroxidase, alkaline phosphatase, etc.) and chemical (e.g. biotin, etc) labels.

Antibodies of the present invention have a variety of potential uses that are within the scope of the present invention. For example, such antibodies can be used (a) as reagents in assays to detect a mycobacterial antigen in use in the present invention, (b) as reagents in assays to detect the presence of a *Mycobacterium* in a biological sample, and/or (c) as tools to detect and/or recover the recombinantly-produced mycobacterial antigens and fusion polypeptide according to the method of the invention from a mixture of proteins and other contaminants (e.g. by permitting purification by affinity chromatography or immunoprecipitation from cultured host cells). They may also be used for therapeutic purposes, e.g. for treating a subject after exposure to a *Mycobacterium* (e.g. passive immunotherapy).

In one embodiment, the present invention relates to a method for the detection and/or quantification of a mycobacterial antigen in a biological sample (e.g. plasma, serum, sputum, etc) taken from a subject infected or susceptible to be infected by a *Mycobacterium* using the antibody of the invention which comprises the steps of bringing said biological sample into contact with the antibody of the invention as reagent under conditions allowing the formation of a complex between the mycobacterial antigen and the antibody reagent and detecting and/or quantifying the formation of said complex by any appropriate means. Detecting the presence of the target mycobacterial antigen is indicative of a *Mycobacterium* infection (e.g. Mtb).

In another embodiment, the present invention relates to a method for the detection and/or quantification of antibodies directed to a *Mycobacterium* in a biological sample (e.g. plasma, serum, etc taken from a subject infected or susceptible to be infected by a *Mycobacterium*), which comprises the steps of bringing said biological sample into contact with a reagent comprising any of the immunogenic combination, fusion polypeptide, nucleic acid molecules, vectors, infectious viral particles, host cells of the invention under conditions allowing the formation of a complex between the antibody and the mycobacterial antigen/epitope comprised or encoded by any of the above-cited reagents and detecting and/or quantifying the formation of said complex by any appropriate means. Detecting the presence of specific antibody is indicative of a *Mycobacterium* infection (e.g. Mtb).

A person skilled in the art will easily determine the quantity of reagent to be used in the methods of the invention. The means of detection and/or quantification of antigen/antibody complex are routine and well known to a person skilled in the art. By way of illustration, one may mention blots, ELISA, so-called sandwich techniques, competition techniques, and PCR techniques, in particular so called "real-time" techniques. The use of the above cited reagent can be facilitated by coupling (i.e., physically linking) to a detectable substance. Examples of detectable substances include various enzymes (e.g. horseradish peroxidase, alkaline phosphatase, beta-galactosidase or acetylcholinesterase), prosthetic groups (e.g. streptavidin/biotin, or avidin/biotin), fluorescent materials (e.g. umbelliferone, fluorescein, or fluorescein derivatives), luminescent materials, bioluminescent materials (e.g. luciferase, luciferin, or aequorin), and radioactive materials (e.g. $^{125}$I, $^{131}$I, $^{35}$S or $^{3}$H).

The present invention also concerns a kit of reagents for diagnosis a *Mycobacterium* (e.g. Mtb) infection for antigen assay comprising the antibody of the invention and for antibody assay comprising the immunogenic combination, fusion polypeptide, nucleic acid molecule, vector, host cell, composition of the invention.

All of the above cited disclosures of patents, publications and database entries are specifically incorporated herein by reference in their entirety to the same extent as if each such individual patent, publication or entry were specifically and individually indicated to be incorporated by reference.

DESCRIPTION OF THE DRAWINGS

FIG. 5A), pTG18296 (cytoplasmic Ag85B-TB10.4-ESAT6; FIG. 5B), a mixture of pTG18310, pTG18315 and pTG18308 plasmids encoding the individual Ag85B, TB10.4 and ESAT6 antigens (FIG. 5C) and pGWiz (FIG. 5D). Cellular immune response was evaluated 2 weeks following the last DNA injection by ELISpot IFNγ assays after ex vivo re-stimulation with specific peptide pools.

FIG. 6A), pTG18297 (cytoplasmic RPFB-Dhyb-Ag85B-TB10.4-ESAT6; FIG. 6B), a mixture of pTG18307, pTG18310, pTG18315 and pTG18308 plasmids encoding the individual RPFB-Dhyb, Ag85B, TB10.4 and ESAT6 antigens (FIG. 6C) and pGWiz (FIG. 6D). Cellular immune response was evaluated 2 weeks following the last DNA injection by ELISpot IFNγ assays after ex vivo re-stimulation with specific peptide pools.

FIG. 8A), pTG18295 (cytoplasmic Rv0569-Rv1813-Rv3407-Rv3478-Rv1807; FIG. 8B), a mixture of pTG18301, pTG18303, pTG18300, pTG18304 and pTG18302 plasmids encoding the individual Rv0569, Rv1813, Rv3407, Rv3478 and Rv1807 antigens (FIG. 8C) and pGWiz (FIG. 8D). Cellular immune response was evaluated 2 weeks following the last DNA injection by ELISpot IFNγ assays after ex vivo re-stimulation with specific peptide pools.

FIG. 9 illustrates SDS-PAGE analysis of the purified Rv2626 (FIG. 9A), RPFB-Dhyb fusion (FIG. 9B) and TB10.4 (FIG. 9C).

FIG. 10 illustrates the cellular immune response produced following immunization of animals with fusion-encoding plasmid pTG18323 (Rv2029-Rv2626-Rv1733-Rv0111; FIG. 10a) or pGWiz (FIG. 10b). IFNγ-producing cells were evaluated 2 weeks following the last DNA injection by IFNγ ELISpot assays after ex vivo re-stimulation with specific peptide pools. Each bar represents response of one mouse (7 mice/group).

FIG. 11 illustrates the cellular immune response induced following immunization of mice with (a) MVATG18365 (Rv2029-Rv2626-Rv1733-Rv0111+RpfB-Dhyb-Ag85B-TB10.4-ESAT6 W/O SS/TM) or (b) MVATG18364 (Rv2029-Rv2626-Rv1733-Rv0111+RpfB-Dhyb-Ag85B-TB10.4-ESAT6). IFNγ-producing cells were evaluated one week following the MVA injection by IFNγ ELISpot assays after ex vivo re-stimulation with specific peptide pools. Each bar represents response of individual mouse (5 mice/group).

FIG. 12 summarizes levels of IFNγ response in BALB/c mice vaccinated with all MVA candidates, produced according to TB disease phase or biochemical rational. IFNγ-producing cells were evaluated one week following the MVA injection by IFNγ ELISpot assays after ex vivo re-stimulation with specific peptide pools of the 14 Mtb antigens. Intensity of the detected responses is ranked according to fold increase of median value (spots/$10^6$ splenocytes) for each re-stimulation with respect to the cut-off value, using a colour code (see legend ranging from −, +, ++, +++). Hatched boxes mean that the antigen is lacking in the given MVA vaccine.

FIG. 15 summarizes levels of IFNγ response in transgenic HLA-A2, C57BL/6 and C3H/HeN mice vaccinated with the indicated MVA candidates. IFNγ-producing cells were evaluated one week following the MVA injection by IFNγELISpot assays after ex vivo re-stimulation with specific peptide pools of the 14 Mtb antigens. Intensity of the detected responses is ranked according to fold increase of median value (spots/$10^6$ splenocytes) for each re-stimulation with respect to the cut-off value, using a colour code (see legend ranging from −, +, ++, +++). Hatched boxes mean that the antigen is lacking in the given MVA vaccine.

MATERIALS AND METHODS

Analytical Methods

Figure 1:
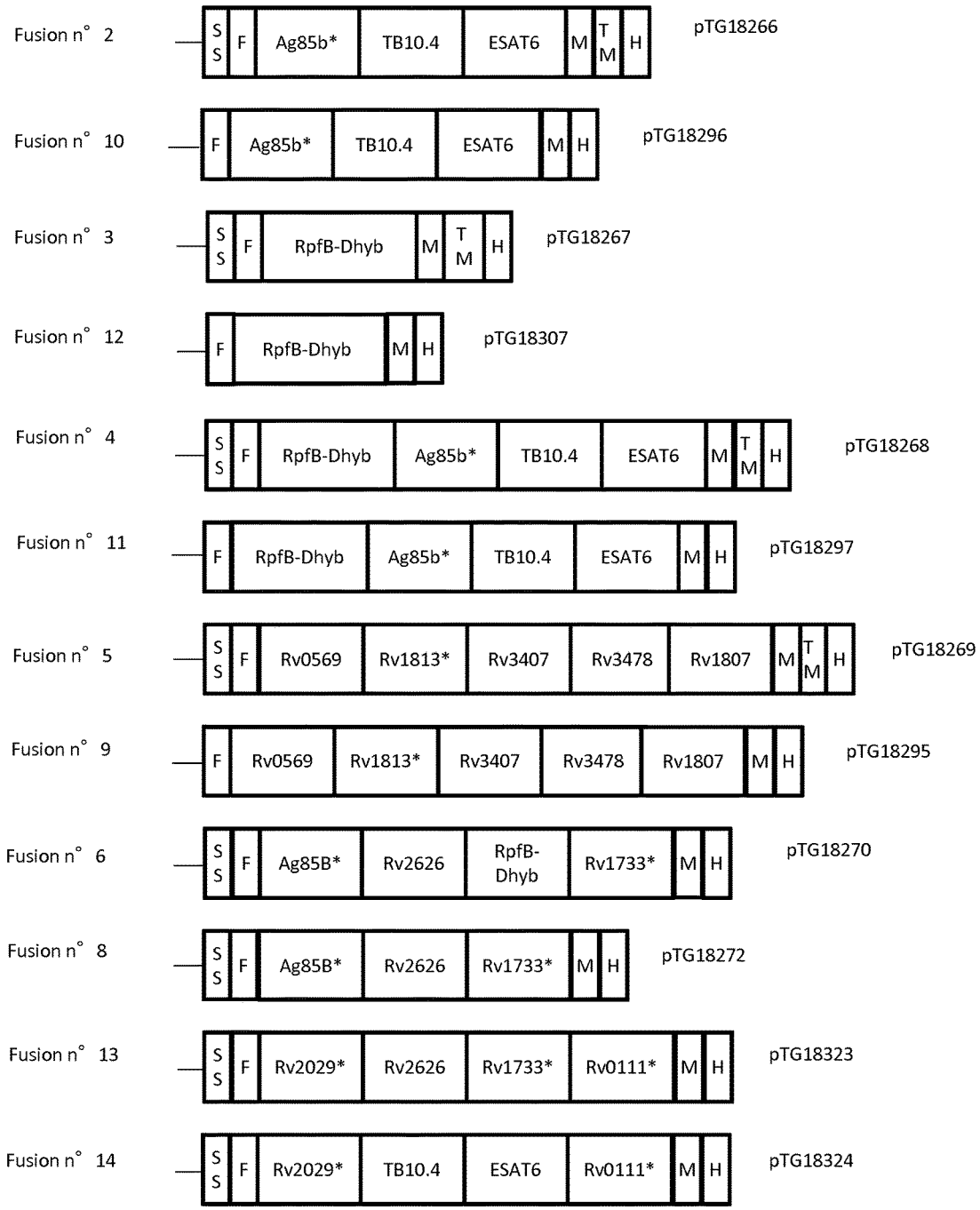
FIG. 1 shows a schematic representation of the various fusion polypeptides of Mtb antigens that were generated and used as described in the appended Example section. "SS" means signal peptide, "TM" Transmembrane domain, "F" Flag tag, "M" Myc tag and "H" his tag. A* is indicative of a modification of the Mtb antigen with respect to the native counterpart. The Figure also mentions the no of the fusion polypeptide and the reference of the expressing plasmid vector (pTGXXXXX) as used hereinafter.

Existing data on Mtb antigens were investigated from the available literature and data bases with the goal of identifying a first selection of Mtb genes/antigens that may be useful in an immunotherapeutic vaccine capable of raising anti-TB immunity during all phases of the natural course of infection.

The selected antigens were then submitted to a data-mining scoring system that was developed to transcribe and compare data from different sources. An overall final "score" was generated reflecting the value of each antigen. This score takes into account the immunogenic potential of the antigen as well as its capacity to protect against an infectious challenge in animal models and in humans (for example protection data in humans will be better scored than inducing immunogenicity in animal models). Once all data for a particular antigen were collected, a grade from 0 to 5 was attributed to each category, 0 being the worse possible grade while 5 being the best. The choice of the grade was also based on the quality of the data (e.g. right controls used in the experiments, rigorous interpretation) but also on the robustness of the data (e.g. number of times experiments were run, number of publications confirming/supporting the findings).

Antigen Biochemical in Silico Analyses

Biochemical and biological data are also key data for optimizing expression and fusion design permitting to anticipate potential expression problems. For example, the biological functions of a protein may lead to a potential toxicity resulting in genetic unstability and/or safety profile upon vector-mediated expression. Moreover, protein unfolding may impact stability and expression levels due to a higher cellular degradation rate.

An extensive bibliographic search was carried out for all Mtb antigens in order to better understand and characterize the structure and the functions of these proteins.

Additionally, biochemical and bioinformatic predictions were also performed for characterization of Mtb antigens. Bioinformatic prediction tools (Nielsen et al., 2007 PLos One 2: e796; Nielsen et al., 2008, PLoS Comput Biol 4: e1000107) were used to look at predicted epitopes for class I and II HLA molecules. Identification of these epitopic regions may be useful for optimization of the selected Mtb antigens or to facilitate the development of immune based assays.

Moreover, extensive in silico structure prediction analyses were performed in order to predict biochemical properties and/or biological functions and thus allow Mtb antigens selection and design (e.g. whether a full length native form is likely to be expressed or whether modifications appear to be required).

More specifically
Search for structural homologs in protein data bank (PDB). The program used was BLASTP with the default parameters and the selected database was NPS@ 3D SEQUENCES (from PDB). This search allows finding NMR or crystalline structures of the antigen or of proteins with sequence homologies higher than 25%. 3D structures were visualized using CN3D 4.1. or PDB viewer.

Search in UNIPROT-SWISSPROT and TB databases. Protein homologs to the Mtb antigens of interest were searched on UNIPROT-SWISSPROT database using primary structures as a query and BLAST search on NPS@. The program used was BLASTP with the default parameters and the selected database was UNIPROT-SWISSPROT; UNIPROT-SWISSPROT entries give access to general information on protein function, domains, potential signal peptide, posttranslational modifications as well as bibliographic references. General information (e.g. gene functions, genetic link between genes, phenotypes and mutations associated with genes, immunogenicity, as well as bibliographic references) about the selected Mtb antigens were retrieved using the Rv protein name as a query in the TB database.

Prediction of signal peptides: these short N-terminus sequences are often predicted as transmembrane domains but are not present in native and mature proteins. The presence of signal peptide was notified in the UNIPROT-SWISSPROT database for certain antigens or using the hidden Markov model of signal v3.0 algorithm. If no hit for homolog search, additional searches were undertaken:

Prediction of potential transmembrane domains TM using three different programs (e.g. dense Alignment surface (DAS) method, Algorithm TMHMM and Top-Pred0.01). It is our observations that the presence of such hydrophobic TM domains with may impair genetic stability of the corresponding antigen when expressed in viral vectors such as MVA.

Search for known protein motif associated with protein domains, families and functional sites using PROSITE SCAN Prediction of secondary structures using several prediction methods (namely: SOPM, MLRC, HNN, DSC, PHD, PREDATOR). A secondary structure was considered as highly probable if the 6 methods predicted it. A secondary structure was considered possible if 3 out of the 6 methods predicted it.

Hydrophobic cluster analysis (HCA). The HCA method is based on essential features of protein folding: the hydrophilic/hydrophobic dichotomy and the hydrophobic compactness of protein globular domains. HCA plots were used to identify hydrophobic clusters along the protein sequence. These clusters are characteristic of folded proteins with a hydrophobic buried core. An antigen was considered as probably having a folded state if hydrophobic clusters were present at least at some part of the protein.

Prediction of natively disordered regions that permit to identify unfolded regions (MetaPrDOS predictions). This analysis complements the HCA plot by predicting areas of the protein that are not folded. All areas above the threshold 0.5 (disordered tendency) were considered as unfolded parts of the protein. To be noted that most of the time, N- and C-terminus parts of proteins are non-folded in their native state. If such stretches at the extremities were present and smaller than 10 residues, they were kept as potential linkers for fusion.

Prediction of coiled coil (using the COILS program). Oligomerization state of the antigen could impact the antigen fusion design. A coiled coil domain was predicted if the output probability displayed a value of 1 for a part of the protein with at least 14 residues window analysis.

Further, sequence alignments were carried out to verify that the selected Mtb antigens are conserved among different Mtb strains and isolates. More precisely, multiple sequence alignments were performed using Clustal W2 (@.ebi.ac.uk/Tools/msa/clustalw2/) between the amino acid sequence of each selected antigen (the exemplified Mtb antigens originate from the H37Rv strain) and their equivalent of 11 other Mtb strains (clinical isolates) and *M bovis* that have been identified in protein databases (BLASTP search). As a result, the TB antigens showed high conservations among the 12 Mycobacteria strains analyzed with a percentage of identity ranging from 100% to 96% depending on the antigen and the *Mycobacterium* strain. The major exception was seen with Rv3478 for which only 88% identity was found between H37Rv and CDC1551 sequences.

Finally, another key criteria to reach final TB antigen selection was to ensure a balanced representativeness of antigens from the various phases of infection. For example, some latent antigens were selected despite lower final data mining score than most of the active phase antigens.

Construction of Fusion of Mtb Antigens 12 fusions of Mtb antigens were engineered as illustrated in FIG. 1. Five fusions were designed based on biochemical rationales (fusions 3, 5, 6, 8 and 14) whereas fusions 2, 4 and 13 were designed relative to the TB phase of the disease, with fusion 2 containing active antigens, fusion 4 active and resuscitation antigens and fusion 13 being constituted by latent antigens. In order to facilitate detection of the various gene fusions and avoid the need of specific antibodies for each Mtb antigen, TAG sequences were added in each fusion, respectively Flag TAG (DYKDDDDK; SEQ ID NO: 25) at the N-terminus, and c-myc (EQKLISEEDL; SEQ ID NO: 26) and His (HHHHHH; SEQ ID NO: 27) Tags at the C-terminus.

On the other hand, signal peptides (also called signal sequence or SS) and membrane-anchoring peptides (also called trans-membrane or TM peptide/domain) were added respectively at the N-terminus and C-terminus of the Mtb fusion proteins to ensure anchorage at the cell surface which is assumed to optimize immunogenic activity in certain cases. However, addition of TM domain was not necessary for fusions ending with Rv0111 or Rv1733, as these proteins already contain membrane-anchoring peptides. For comparative purposes, four fusions were also engineered without any signal sequence (SS) and TM domain so as to study the influence of cell location (membrane presentation in the presence of SS and TM peptides versus cytoplasmic location in the absence of such peptides) on expression level and immunogenic activity. For example, pTG18269 encodes the same Mtb antigens (Rv0569-Rv1813*-Rv3407-Rv3478-Rv1807) as pTG18295 except that the pTG18269-encoded fusion is equipped with a SS at its N-terminus and a TM—at its C terminus between Myc and His tags whereas the pTG18295-encoded fusion is devoid of such SS and TM peptides.

Synthetic genes coding for the different Mtb antigens and fusions were synthesized by Geneart (Regensburg, Germany). The sequences were optimized for human codon usage and a Kozak sequence (ACC) was added before the ATG starting codon. Moreover some motives were excluded: TTTTTNT, GGGGG, CCCCC which are deleterious for expression in poxvirus vector and AAAGGG, AAAAGG, GGGAAA, GGGGAA, (and complementary sequences TTCCCC, TTTCCC, CCTTTT, CCCCTT) which can be deleterious for expression in some others vectors.

The fusions were cloned in pGWiz plasmid (Gelantis) digested by NotI and BamH. This plasmid contains a modified CMV promoter, followed by intron A from the CMV immediate early gene, and a high-efficiency artificial transcription terminator.

Construction of pTG18266 (Fusion No 2)

The amino acid sequence of the fusion no 2 is shown in SEQ ID NO: 28. Amino acids 1 to 23 correspond to the signal peptide present at the N-terminus of the glycoprotein precursor of rabies virus ERA strain (described in Genbank no M38452), amino acids 24 to 31 correspond to the Flag TAG, amino acids 32 to 317 correspond to Ag85B*, amino acids 318 to 412 correspond to TB10.4, amino acids 413 to 506 correspond to ESAT6, amino acids 507 to 516 correspond to the c-myc TAG, a Ser linker, amino acids 518 to 583 correspond to the membrane-anchoring peptide derived from the rabies glycoprotein of ERA strain and amino acids 584 to 589 correspond to the His TAG. The fusion no 2-encoding nucleotide sequence shown in SEQ ID NO: 40 was generated by synthetic way and the synthetic gene was cloned in pGWiz restricted by NotI and BamH1 to give pTG18266.

Construction of pTG18267 (Fusion No 3)

The amino acid sequence of the fusion no 3 is shown in SEQ ID NO: 30. Amino acids 1 to 23 correspond to the signal peptide present at the N-terminus of the glycoprotein precursor of rabies virus PG strain (described in Genbank no ay009097 and SEQ ID NO: 2 in WO2008/138649), amino acids 24 to 31 correspond to the Flag TAG, amino acids 32 to 380 correspond to RPFB-Dhyb*, amino acids 381 to 390 correspond to the c-myc TAG, a Ser linker, amino acids 392 to 457 correspond to the membrane-anchoring peptide derived from the rabies glycoprotein of PG strain (SEQ ID NO: 3 in WO2008/138649) and amino acids 458 to 463 correspond to the His TAG. The fusion no 3-encoding nucleotide sequence shown in SEQ ID NO: 42 was generated by synthetic way and the synthetic gene was cloned in pGWiz restricted by Nod and BamH1 to give pTG18267.

Construction of pTG18268 (Fusion No 4)

The amino acid sequence of the fusion no 4 is shown in SEQ ID NO: 32. Amino acids 1 to 23 correspond to the signal peptide present at the N-terminus of the glycoprotein precursor of rabies virus PG strain (described in Genbank no ay009097), amino acids 24 to 31 correspond to the Flag TAG, amino acids 32 to 380 correspond to RPFB-Dhyb*, amino acids 381 to 666 correspond to Ag85B*, amino acids 667 to 761 correspond to TB10.4, amino acids 762 to 855 correspond to ESAT6, amino acids 856 to 865 correspond to the c-myc TAG, a Ser linker, amino acids 867 to 932 correspond to the membrane-anchoring peptide derived from the rabies glycoprotein of PG strain and amino acids 933 to 938 correspond to the His TAG. The fusion no 4-encoding nucleotide sequence shown in SEQ ID NO: 44 was generated by synthetic way and the synthetic gene was cloned in pGWiz restricted by NotI and BamH1 to give pTG18268.

Construction of pTG18269 (Fusion No 5)

The amino acid sequence of the fusion no 5 is shown in SEQ ID NO: 34. Amino acids 1 to 23 correspond to the signal peptide present at the N-terminus of the glycoprotein precursor of rabies virus ERA strain (described in Genbank no M38452), amino acids 24 to 31 correspond to the Flag TAG, amino acids 32 to 118 correspond to Rv0569, amino acids 119 to 227 correspond to Rv1813*, amino acids 228 to 325 correspond to Rv3407, amino acids 326 to 717 correspond to Rv3478, amino acids 718 to 1115 correspond to Rv1807, amino acids 1116 to 1125 correspond to the c-myc TAG, a Ser linker, amino acids 1127 to 1192 correspond to the membrane-anchoring peptide derived from the rabies glycoprotein of PG strain (SEQ ID NO: 3 in WO2008/138649) and amino acids 843 to 848 correspond to the His TAG. The fusion no 5-encoding nucleotide sequence shown in SEQ ID NO: 46 was generated by synthetic way and the synthetic gene was cloned in pGWiz restricted by NotI and BamH1 to give pTG18269.

Construction of pTG18270 (Fusion No 6)

The amino acid sequence of the fusion no 6 is shown in SEQ ID NO: 36. Amino acids 1 to 23 correspond to the signal peptide present at the N-terminus of the glycoprotein precursor of rabies virus ERA strain (described in Genbank no M38452), amino acids 24 to 31 correspond to the Flag TAG, amino acids 32 to 317 correspond to Ag85B*, amino acids 318 to 459 correspond to Rv2626, amino acids 460 to 808 correspond to RPFB-Dhyb*, amino acids 809 to 956 correspond to Rv1733*, amino acids 957 to 966 correspond to the c-myc TAG, a Ser linker, and amino acids 968 to 973 correspond to the His TAG. The fusion no 6-encoding nucleotide sequence shown in SEQ ID NO: 48 was generated by synthetic way and the synthetic gene was cloned in pGWiz restricted by NotI and BamH1 to give pTG18270.

Construction of pTG18272 (Fusion No 8)

The amino acid sequence of the fusion no 8 is shown in SEQ ID NO: 37. Amino acids 1 to 23 correspond to the signal peptide present at the N-terminus of the glycoprotein precursor of rabies virus ERA strain (described in Genbank no M38452), amino acids 24 to 31 correspond to the Flag TAG, amino acids 32 to 317 correspond to Ag85B*, amino acids 318 to 459 correspond to Rv2626, amino acids 460 to 607 correspond to Rv1733*, amino acids 608 to 617 correspond to the c-myc TAG, a Ser linker and amino acids 619 to 624 correspond to the His TAG. The fusion no 8-encoding nucleotide sequence shown in SEQ ID NO: 49 was generated by synthetic way and the synthetic gene was cloned in pGWiz restricted by NotI and BamH1 to give pTG18272.

Construction of pTG18323 (Fusion No 13)

The amino acid sequence of the fusion no 13 is shown in SEQ ID NO: 38. Amino acids 1 to 28 correspond to the signal peptide present at the N-terminus of the F protein of measles virus (Hallé strain, described in Genbank no X05597-1), amino acids 29 to 36 correspond to the Flag TAG, amino acids 37 to 349 correspond to Rv2029*, amino acids 350 to 491 correspond to Rv2626, amino acids 492 to 639 correspond to Rv1733*, amino acids 640 to 932 correspond to Rv0111*, amino acids 933 to 942 correspond to the c-myc TAG, a Ser linker and amino acids 944 to 949 correspond to the His TAG. The fusion no 13-encoding nucleotide sequence shown in SEQ ID NO: 50 was generated by synthetic way and the synthetic gene was cloned in pGWiz restricted by NotI and BamH1 to give pTG18323.

Construction of pTG18324 (Fusion No 14)

The amino acid sequence of the fusion no 14 is shown in SEQ ID NO: 39. Amino acids 1 to 28 correspond to the signal peptide present at the N-terminus of the F protein of measles virus (Hallé strain, described in Genbank no X05597-1), amino acids 29 to 36 correspond to the Flag TAG, amino acids 37 to 349 correspond to Rv2029*, amino acids 350 to 444 correspond to TB10.4, amino acids 445 to 538 correspond to ESAT6, amino acids 539 to 831 correspond to Rv0111*, amino acids 832 to 841 correspond to the c-myc TAG, a Ser linker and amino acids 843 to 848 correspond to the His TAG. The fusion no 14-encoding nucleotide sequence shown in SEQ ID NO: 51 was generated by synthetic way and the synthetic gene was cloned in pGWiz restricted by NotI and BamH1 to give pTG18324.

Construction of Fusions 9-12

The targeting sequences were deleted from plasmids pTG18267, pTG18269, pTG18266 and pTG18268 by directed mutagenesis (Quick Change Site-Directed mutagenesis kit, Stratagene) using appropriate pairs of primers, OTG20188 (CGCGGCCGCACCATGGATTACAAGGATGACGACG; SEQ ID NO: 52) and OTG20189 (CGTCGTCATCCTTGTAATCCATGGTGCGGCCGCG; SEQ ID NO: 53) for deleting signal peptide sequence and OTG20190 (CATCTCAGAAGAGGATCTG-CATCATCATCATCATTG; SEQ ID NO: 54) and OTG20191 (CAATGATGATGAT-GATGATGCAGATCCTCTTCTGAGATG; SEQ ID NO: 55) for deleting TM sequence. The resulting plasmids were respectively pTG18307 (fusion no 12=cytoplasmic fusion no 3), pTG18295 (fusion no 9=cytoplasmic fusion no 5), pTG18296 (fusion no 10=cytoplasmic fusion no 2) and pTG18297 (fusion no 11=cytoplasmic fusion no 4), corresponding to amino acid sequences SEQ ID NO: 31, 35, 29 and 33 encoded by the nucleotide sequences SEQ ID NO: 43, 47, 41 and 45.

Construction of Individual Mtb Gene Expression Plasmids

The Flag sequence and c-myc-His sequences separated by a NheI restriction site were introduced downstream the CMV promoter in pGWiz plasmid. A synthetic DNA fragment containing the end of CMV promoter, Flag and c-myc-His sequences was synthesized by Geneart and inserted into the plasmid FLAG_TAG_1. This plasmid was digested by PvuII and BglII and the resulting fragment was inserted in pGWiz restricted by the same enzyme, giving rise to pTG18282. The individual Rv3407, Rv0569, Rv1807, Rv1813*, Rv3478 and Rv2626 genes were then amplified by PCR from pTG18269 except Rv2626 for which the pTG18323 was used as template.

The amplification primer pairs used for isolation of each TB gene are illustrated in Table 1.

TABLE 1

| TB gene | Primer name | Primer sequence |
|---|---|---|
| Rv3407 | OTG20232 | GATGACGACGATAAGGCTAGCA |
|  | SEQ ID NO: 56 | GAGCCACCGTGGGACTGG |
|  | OTG20233 | GATGAGTTTTTGTTCGCTAGCC |
|  | SEQ ID NO 57 | TGTTCATCCCGCATCTCGT |
| Rv0569 | OTG20234 | GATGACGACGATAAGGCTAGCA |
|  | SEQ ID NO: 58 | AGGCCAAAGTCGGCG |
|  | OTG20235 | GATGAGTTTTTGTTCGCTAGCT |
|  | SEQ ID NO: 59 | GTTCCTCTGGCGTGC |

TABLE 1-continued

| TB gene | Primer name | Primer sequence |
|---|---|---|
| Rv1807 | OTG20236 | GATGACGACGATAAGGCTAGCG |
|  | SEQ ID NO: 60 | ATTTTGCCACCCTCCCACC |
|  | OTG20237 | GAGATGAGTTTTTGTTCGCTAG |
|  | SEQ ID NO: 61 | CGCCAGCTGCAGGAGGTCTGG |
| Rv1813* | OTG20238 | GATGACGACGATAAGGCTAGCG |
|  | SEQ ID NO: 62 | CCAACGGCAGCATGAGCG |
|  | OTG20239 | GAGATGAGTTTTTGTTCGCTAG |
|  | SEQ ID NO: 63 | CGTTGCAGGCCCAGTTCACGA |
| Rv3478 | OTG20240 | GATGACGACGATAAGGCTAGCG |
|  | SEQ ID NO: 64 | TGGACTTCGGCGCCCTGC |
|  | OTG20241 | GAGATGAGTTTTTGTTCGCTAG |
|  | SEQ ID NO: 65 | CGCCAGCGGCTGGAGTTCTGG |
| Rv2626 | OTG20242 | GATGACGACGATAAGGCTAGCA |
|  | SEQ ID NO: 66 | CAACCGCCAGAGACATCATG |
|  | OTG20243 | GATGAGTTTTTGTTCGCTAGCA |
|  | SEQ ID NO: 67 | GAGGCCAGGGCCATGGG |

The resulting amplicons were cloned by "In fusion Advantage" PCR cloning method (Clontech) in pTG18282 linearized by NheI. This allows the fusion of Tag sequences with Mtb genes. The generated plasmids were named respectively pTG18300 (Rv3407), pTG18301 (Rv0569), pTG18302 (Rv1807), pTG18303 (Rv1813*), pTG18304 (Rv3478) and pTG18305 (Rv2626).

Six plasmids containing expression cassettes for ESAT6, Rv1733*, Ag85B*, TB10-4, Rv0111* and Rv2029* fused to Flag in 5' and c-myc-His sequences in 3' were synthesized by Geneart and inserted in pGWiz. They were named respectively pTG18308 (ESAT6), pTG18309 (Rv1733*), pTG18310 (Ag85B*), pTG18315 (TB10.4), pTG18329 (Rv0111*), pTG18317 (Rv2029*). As Rv1733* and Rv0111* proteins contain a TM domain, the signal peptide presents at the N-terminus of the glycoprotein precursor of rabies virus ERA strain was fused upstream to the Flag sequence to avoid expression issues.

Whether encoding individual or fused Mtb genes, plasmids used for immunization were produced in endotoxin-free conditions.

Construction of Recombinant MVA

Deletion of TAG Sequences

TAG sequences were removed from the Mtb antigen fusions to avoid their presence in the MVA vectors. TAG sequences located inside the Mtb fusion cassettes (i.e. Flag present between the signal peptide and the first amino acid of the Mtb fusion and cmyc TAG present between the last amino acid of the Mtb fusion and membrane-anchoring peptide) were deleted by directed mutagenesis using the QuikChange Site-directed Mutagenesis kit (Stratagene) and appropriate primers pairs as illustrated in the following Table 2. TAG sequences located outside the Mtb fusion cassettes (for cytoplasmic fusion and His TAG) were deleted by PCR using primers allowing the addition of an initiator Met and a terminator codon on both extremity of the fusions.

TABLE 2

| Fusion | Primer pairs for deletion of Flag | Primer pairs for deletion of cmyc | Resulting plasmid |
|---|---|---|---|
| 4 | OTG20313 (SEQ ID NO: 68) | OTG20315 (SEQ ID NO: 70) | pTG18339 |
|  | OTG20314 (SEQ ID NO: 69) | OTG20316 (SEQ ID NO: 71) |  |
| 5 | OTG20317 (SEQ ID NO: 72) | OTG20319 (SEQ ID NO: 74) | pTG18340 |
|  | OTG20318 (SEQ ID NO: 73) | OTG20320 (SEQ ID NO: 75) |  |
| 6 | OTG20321 (SEQ ID NO: 76) | NA | pTG18341 |
|  | OTG20322 (SEQ ID NO: 77) |  |  |

TABLE 2-continued

| Fusion | Primer pairs for deletion of Flag | Primer pairs for deletion of cmyc | Resulting plasmid |
|---|---|---|---|
| 13 | OTG20333 (SEQ ID NO: 78) OTG20334 (SEQ ID NO: 79) | NA | pTG18342 |
| 14 | OTG20333 (SEQ ID NO: 78) OTG20334 (SEQ ID NO: 79) | NA | pTG18343 |

Construction of MVATG18355 (Fusion No 13)

The nucleotide sequence encoding fusion no 13 (SF-Rv2029*-Rv2626-Rv1733*-Rv0111* as illustrated by the portion of SEQ ID NO: 38 from 1 to 28 and 37 to 932) was placed under the control of the p7.5K promoter (SEQ ID NO: 80; CCACCCACTTTTTATAGTAAGTTTTTCAC-CCATAAATAATAAATACAATAATTAA TTTCTCG-TAAAAGTAGAAAATATATTCTAATTTATTGCACGG-TAAGGAAGTAGA ATCATAAAGAACAGT). This latter was amplified by PCR from VV (Vaccinia virus) Copenhagen strain DNA using a pair of appropriate primers OTG20405 (SEQ ID NO: 81) and OTG20406 (SEQ ID NO: 82) while the fusion no 13 sequence was amplified from plasmid pTG18342 by PCR with OTG20407 (SEQ ID NO:83) and OTG20408 (SEQ ID NO: 84). Then p7.5K and fusion no 13-encoding sequence were reassembled by double PCR using the primers OTG20405 (SEQ ID NO: 81) and OTG20408 (SEQ ID NO: 84). The resulting fragment was inserted into the BglII and NotI restriction sites of a vaccinia transfer plasmid, pTG17960, resulting in pTG18355.

The MVA transfer plasmid, pTG17960, is designed to permit insertion of the nucleotide sequence to be transferred by homologous recombination in deletion III of the MVA genome. It originates from the plasmid pTG1E (described in Braun et al., 2000, Gene Ther. 7:1447) into which were cloned the flanking sequences (BRG3 and BRD3) surrounding the MVA deletion III (Sutter and Moss, 1992, Proc. Natl. Acad. Sci. USA 89:10847). The transfer plasmid also contains a fusion between the *Aequorea victoria* enhanced Green Fluorescent Protein (eGFP gene, isolated from pEGP-C1, Clontech) and the *Escherichia coli* xanthine-guanine phosphoribosyltransferase gene (gpt gene) under the control of the early late vaccinia virus synthetic promoter p11K7.5 (kindly provided by R. Wittek, University of Lausanne). Synthesis of xanthine-guanine phosphoribosyltransferase enables GPT$^+$ recombinant MVA to grow in a selective medium containing mycophenolic acid, xanthine, and hypoxanthine (Falkner et al, 1988, J. Virol. 62, 1849-54) and eGFP enables the visualisation of recombinant MVA plaques. The selection marker eGFP-GPT is placed between two homologous sequences in the same orientation. After clonal selection, the selection marker can be easily eliminated by several passages without selection allowing the growth of eGFP-GPT recombinant MVA.

Generation of MVATG18355 was performed by homologous recombination in primary chicken embryos fibroblasts (CEF) infected with MVA and transfected by nucleofection with pTG18355 (according to Amaxa Nucleofector technology). Viral selection was performed by plaque purification after growth in the presence of a selective medium containing mycophenolic acid, xanthine and hypoxanthine. As mentioned above, the selection marker was then eliminated by passage in a non-selective medium. Absence of contamination by parental MVA was verified by PCR.

Construction of MVATG18364 (Fusion No 13+Fusion No 4)

The nucleotide sequence encoding fusion no 4 (SR-RPFB-Dhyb*-Ag85B*-TB10.4-ESAT6-TMR as illustrated by the portion of SEQ ID NO: 32 from 1 to 23 followed by 32 to 855 and 866 to 932) was placed under the control of pH5R promoter (SEQ ID NO: 85, TTTATTCTATACT-TAAAAAATGAAAATAAATACAAAGGTTCTT-GAGGGTTGTGTT AAATTGAAAGCGAGAAATAAT-CATAAATTATTTCATTATCGCGATATCCGTTAA GTTTG) cloned from genomic DNA of wild type MVA by PCR with primer pair OTG20445 (SEQ ID NO: 86) and OTG20446 (SEQ ID NO: 87). The amplified product was digested by NotI and PacI. The fusion no 4-encoding sequence was amplified from pTG18339 by PCR using OTG20447 (SEQ ID NO: 88) and OTG20380 (SEQ ID NO: 89) primers. The amplified product was digested by PacI and XhoI. Both fragments were cloned together into pTG18355 restricted by NotI and XhoI, resulting in pTG18364.

Generation of MVATG18364 virus was performed in CEF by homologous recombination as described above.

Construction of MVATG18365 (Fusion No 13+Fusion No 11)

The nucleotide sequence encoding fusion no 11 (RPFB-Dhyb*-Ag85B*-TB10.4-ESAT6 as illustrated by the portion of SEQ ID NO: 33 from position 10 to position 833 preceded with the Met initiator in position 1) was placed under the control of pH5R promoter. The promoter was obtained from pTG18364 by PCR with OTG20445 (SEQ ID NO: 86) and OTG20446 (SEQ ID NO: 87) primers and the amplified fragment digested by NotI and PacI. The fusion no 11-encoding sequence was cloned from pTG18297 by PCR using primer pair OTG20448 (SEQ ID NO: 90) and OTG20382 (SEQ ID NO: 91) and the amplified product digested by PacI and XhoI. Both fragments were cloned together into pTG18355 restricted by NodI and XhoI to give pTG18365.

Generation of MVATG18365 virus was performed in CEF by homologous recombination as described above.

Construction of MVATG18376 (Fusion No 13+Fusion No 4+Fusion No 5)

The nucleotide sequence encoding the fusion no 5 (SR-Rv0569-Rv1813*-Rv3407-Rv3478-Rv1807-TMR as illustrated by the portion of SEQ ID NO: 34 from positions 1 to 23 followed by 32 to 1115 and 1126 to 1192) was placed under the control of the B2R promoter (SEQ ID NO: 92, TATATTATTAAGTGTGGTGTTTGGTCGATG-TAAAATTT-TTGTCGATAAAAATTAAAAAATAACT-TAATTTATTATTGATCTCGTGTGTACAAC CGAAATC). The promoter was amplified from VV Western Reserve strain DNA by PCR using primer pair OTG20469 (SEQ ID NO: 93) and OTG20470 (SEQ ID NO: 94) and the amplified fragment was digested by XhoI and NheI. The fusion no 5-encoding sequence was amplified from pTG18340 using primer pair OTG20472 (SEQ ID NO: 95) and OTG20473 (SEQ ID NO: 96) before being restricted by NheI and BamHI. Both digested fragments were cloned together into pTG18364 linearized by XhoI and BamHI to generate pTG18376.

Generation of MVATG18376 virus was performed in CEF by homologous recombination as described above.

Construction of MVATG18377 (Fusion No 13+Fusion No 11+Fusion No 5)

The B2R promoter was amplified from pTG18376 using primer pair OTG20469 and OTG20470 described above and digested by XhoI and NheI. The nucleotide sequence encoding the fusion no 5 (SR-Rv0569-Rv1813*-Rv3407-Rv3478-Rv1807-TMR) was amplified as described above and cloned under the control of the B2R promoter into pTG18364 linearized by XhoI and BamHI to generate pTG18377.

Generation of MVATG18377 virus was performed in CEF by homologous recombination as described above.

Construction of MVATG18378 (Fusion No 13+Fusion No 4+Fusion No 9)

The nucleotide sequence encoding the fusion no 9 (Rv0569-Rv1813*-Rv3407-Rv3478-Rv1807 as illustrated by the portion of SEQ ID NO: 35 from positions 10 to 1093 preceded with the Met initiator in position 1) was amplified from pTG18295 by PCR using primer pair OTG20483 (SEQ ID NO: 97) and OTG20474 (SEQ ID NO: 98). The amplified product was digested by NheI and BamHI and cloned with the XhoI and NheI-restricted B2R promoter (amplified from pTG18376 as described above) into pTG18364 linearized by XhoI and BamHI, resulting in pTG18378.

Generation of MVATG18378 virus was performed in CEF by homologous recombination as described above.

Construction of MVATG18379 (Fusion No 13+Fusion No 11+Fusion No 9)

The nucleotide sequence encoding the fusion no 9 (Rv0569-Rv1813*-Rv3407-Rv3478-Rv1807) and the B2R promoter were both amplified as described above and cloned together into pTG18365 linearized by XhoI and BamHI, resulting in pTG18378.

Generation of MVATG18379 virus was performed in CEF by homologous recombination as described above.

Construction of MVATG18404 (Fusion No 14+Fusion No 6)

The nucleotide sequence encoding the fusion no 14 (SF-Rv2029*-TB10.4-ESAT6-Rv0111* as illustrated by the portion of SEQ ID NO: 39 from positions 1 to 28 and 37 to 831) was amplified from pTG18343 by PCR using primer pair OTG20407 (SEQ ID NO: 83) and OTG20525 (SEQ ID NO: 99). The p7.5K promoter was obtained from pTG18355 by PCR with OTG20524 (SEQ ID NO: 100) and OTG20406 (SEQ ID NO: 82) primers. The fusion no 14-encoding sequence was then cloned under the control of the p7.5K promoter by double PCR using OTG20524 (SEQ ID NO: 100) and OTG20525 (SEQ ID NO: 99). The resulting fragment was restricted with BamHI and NotI and inserted into the BglII and NotI restriction sites of the vaccinia transfer plasmid, pTG17960, resulting in pTG18395.

The nucleotide sequence encoding the fusion no 6 (SS-Ag85B*-Rv2626-RPFB-Dhyb*-Rv1733* as illustrated by the portion of SEQ ID NO: 36 from positions 1 to 23 and 32 to 956) was amplified from pTG18341 by PCR using primer pair OTG20527 (SEQ ID NO. 101) and OTG20376 (SEQ ID NO: 102) and the amplification product was digested with PacI and XhoI. The pH5R promoter was amplified from pTG18355 as described above and digested by NotI and PacI. Both digested fragments were cloned together into pTG18395 linearized by NotI and XhoI, resulting in plasmid pTG18404.

Generation of MVATG18404 virus was performed in CEF by homologous recombination as described above.

Construction of MVATG18417 (Fusion No 14+Fusion No 6+Fusion No 5)

The nucleotide sequence encoding the fusion no 5 (SR-Rv0569-Rv1813*-Rv3407-Rv3478-Rv1807-TMR) placed under the control of B2R promoter was obtained by digestion of pTG18376 with XhoI and BamHI. The resulting fragment was inserted in pTG18404 restricted by the same enzymes, giving rise to pTG18417.

Generation of MVATG18417 virus was performed in CEF by homologous recombination as described above.

Construction of MVATG18418 (Fusion No 14+Fusion No 6+Fusion No 9)

The nucleotide sequence encoding the fusion no 9 (Rv0569-Rv1813*-Rv3407-Rv3478-Rv1807) placed under the control of B2R promoter was obtained by digestion of pTG18379 with XhoI and BamHI. The resulting fragment was inserted in pTG18404 restricted by the same enzymes, giving rise to pTG18418.

Generation of MVATG18418 virus was performed in CEF by homologous recombination as described above.

Production and Protein Purification

Four *E. coli* strains have been tested for the expression of the individual Mtb antigens. All the strains carry the DE3 prophage in their genome that allows the induction of expression of T7 polymerase by lactose or analogue of lactose (i.e. IPTG). The four strains were B121(DE3) (Lucigen) as a classic strain for protein expression, C41(DE3) (Lucigen) for the expression of toxic protein, B121(DE3) Rosetta (Merck Chemical) for expression of protein with a codon usage that is different of the *E. coli* one, and C43 (DE3) (Lucigen) for the expression of protein with transmembrane peptides (e.g. Rv1733). Moreover, three different temperatures and production time were tested for optimizing antigen production.

Expression Assays for Determining Optimal Conditions

Each *E. coli* strain was transformed with the plasmid encoding the Mtb antigen to be produced. Five colonies were isolated from a freshly transformed plate, inoculated in 50 ml of LB (Luria Broth) medium in the presence of ampicillin and allowed to grow overnight at 37° C. under shaking A flask of autoinducible medium (AI medium containing glucose/lactose and antibiotic; Studier, 2005, Protein Expr Purif. 41: 207-34) was inoculated with preculture specimen and was then cultured at either 18° C., 30° C. and 37° C. for 24, 8 and 8 hours, respectively. At the end of incubation, the absorbance at 600 nm was measured and the cells were harvested by centrifugation. The cell pellet was resuspended in PBS and the OD 600 nm adjusted around 50 for each culture condition tested before lysing the cells by sonication. The cell lysate was then centrifuged at 10,000 g for 10 minutes at 4° C. and a specimen (typically 10 µL) of the supernatant and the pellet were then loaded on a SDS-PAGE to estimate optimal conditions.

Production and Purification of Mtb Antigens

Purification of His tag-containing Mtb antigens was undertaken from 500 mL culture grown in 2 L flasks applying the optimal conditions determined previously. The cells were harvested by centrifugation and pellets corresponding to 250 mL of culture were kept at −20° C. until use. The harvested bacteria were resuspended in PBS or in guanidine depending of the solubility of the antigen, submitted to sonication for cell lysis and purified by IMAC affinity chromatography on Ni sepharose 6 fast Flow resin (GE Healthcare; reference 17-5318) either in native or denaturing conditions according to the provider's recommendations. Proteins were eluted by applying increasing concentrations of Imidazole (50 mM, 100 mM and 250 mM). Fractions containing the pure protein were pooled and dialysed against PBS or Urea depending of the solubility of the antigen.

Protein Characterization

A variety of tests can be performed to estimate the quantity and quality of the purified Mtb antigens present in the eluted fractions.

Endotoxin levels were measured using Portable Test System (PTS) from Charles River Laboratories. Cartridges with a range of detection of 0.005 to 0.5 EU/mL were used according to the manufacturer's recommendations.

Protein concentrations were determined by Bradford assay (Bioroad) according to the manufacturer's recommendations. Bovine serum albumin (BSA) diluted in the sample buffer was used as a standard.

Purity of the eluted fractions and dialysed solution can be evaluated by electrophoresis on SDS-PAGE (4-12% Invitrogen).

Mass of the purified proteins was measured using MALDI (Matrix-Assisted Laser Desorption/ionization) or electrospray methods. Measured and calculated masses were compared in order to determine if the protein is intact or not. Identity of the protein either in solution or in a band of gel was checked by mass measurement of peptides generated after trypsin digestion. Masses of peptides were determined by MALDI and/or liquid chromatography coupled to tandem mass Spectrometry (LC/MS/MS). Measured and calculated masses of peptides were compared in order to verify the identity of the protein.

Production of Antibodies Against Mtb Antigens

Antibodies directed against the various Mtb antigens were produced following immunization of rabbits with a mixture of two different antigen-specific peptides (Eurogentec; Seraing, Belgium). Such peptides of 15 or 16 amino acid residues were selected after running epitope B prediction programs. Antisera against Rv1733*, Rv2029*, Rv0569, Rv1807, Rv0111, RPFB-Dhyb*, Rv1813* and Rv3407 antigens were generated following rabbits immunization with the two specific peptides at day 0 and three boosts at day 7, 10 and 18. Blood samples were taken before first peptide injection and at day 21. Final bleeding of rabbits was done at day 29. For Rv3478, the rabbits were injected at day 0, 22, 49 and 77 with the two specific 16 mer peptides. Blood samples were taken before first peptide injection and at day 31 and 59. Final bleeding of rabbits was done at day 87.

The final sera were evaluated by ELISA using the specific peptides and by Western-blot analysis using the individual Mtb gene expression plasmids.

In Vitro Testing of the Mtb Fusion Proteins

Western Blot on DNA-Mediated Expression Products $2 \times 10^6$ HEK293 cells were transfected with 5 µg of the various plasmids encoding Mtb antigen fusions or individual genes using Lipofectamine 2000 (Invitrogen; #11668-019) in presence of proteasome inhibitor MG132 (10 µM) added to growth medium 18 h after transfection. pGWIZ plasmid was used as negative control After 48 hours medium was discarded and cells were lysed with 450 µL/dish of Tris-Glycin-SDS 2+ buffer (ref: LC2676; Novex) supplemented with β-mercaptoethanol (5% v:v). The lysate was then sonicated and boiled for 5 min at 95° C. Thirty microliters of cell lysates were submitted to electrophoresis onto precasted 10% Criterion gel using the Criterion Precast gel system (Biorad). Following electrophoresis, proteins were transferred onto a PVDF membrane (Macherey Nagel, 741260). Immunodetection was performed with 1/500 diluted monoclonal anti-Flag M2 peroxydase (HRP) antibody (Sigma; #A8592) or with 1/5000 diluted monoclonal anti-His peroxydase antibody (Invitrogen; #R931-25). Immune-complexes were revealed using the ImmunStar WesternC kit (Biorad, ref 170.5070).

Sera (diluted 1/1000) obtained after immunization of rabbit, as described above, were also used for Western Blot detection of Rv1733*, Rv2029*, Rv0569, Rv1807, Rv0111*, Rpf-B-D, Rv1813*, Rv3407 and Rv3478. Commercial antibodies were used for detecting ESAT6, Ag85B*, TB10.4 and Rv2626, respectively, mouse monoclonal antibody HYB076-08 (Santa-Cruz; #sc-57730, diluted 1/500) for ESAT6, rabbit polyclonal anti-serum NR-13800 (BEI, diluted 1/5000) for Ag85B*, mouse monoclonal antibody 26A11 (Lifespan-Biosciences; #LS-C91052 diluted 1/1000) for Rv2626 and polyclonal rabbit antibody ABIN361292 (Antibodies-online, diluted 1/1000) for TB10.4.

Western Blot on MVA-Mediated Expression Products $10^6$ A549 cells were infected at MOI 1 with the various MVA producing Mtb antigen fusions in presence of proteasome inhibitor MG132 (10 µM) added to growth medium 30 min after infection. MVATGN33.1 empty vector was used as negative control. After 24 hours, medium was discarded and cells were lysed with 300 µL/dish of Tris-Glycin-SDS 2× buffer (ref: LC2676; Novex) supplemented with β-mercaptoethanol (5% v:v). The lysate was then sonicated and heated for 5 min at 95° C. Twenty microliters of cell lysates were submitted to electrophoresis onto precasted 4-15% Criterion gel using the Criterion Precast gel system (Biorad). Following electrophoresis, proteins were transferred onto a PVDF membrane (Trans-Blot® Turbo™ Transfer System (#170-4155, Biorad)). Immunodetection was performed with Mtb specific antibodies, as described above in connection with expression products of DNA plasmids. Immune-complexes were revealed using the ImmunStar WesternC kit (Biorad, ref 170.5070).

Immunogenicity Evaluation in a Mouse Model

DNA Immunization Protocols

Mice were immunized three times at 2 or 3-week interval either with the fusion encoding plasmid or with a mix of plasmids encoding the individual Mtb antigens included in the fusion. 100 µg of DNA in 100 µL of sterile PBS were injected via intramuscular route in the tibialis anterior muscle. Cellular immune response was evaluated 2 weeks following the last DNA injection by ELISpot IFNγ assays.

MVA Immunization Protocols

Immunogenicity of MVA TB candidates was evaluated in BALB/c, transgenic HLA-A2, C57BL/6 and C3H/HeN mice. Each MVA vector was administered subcutaneously at the base of the tail once at a dose of $1 \times 10^7$ pfu in 100 µL of a Tris-HCl-buffered and sucrose-containing buffer. Cellular immune responses were evaluated 7 days after MVA injection by ELISpot IFNγ assay.

Peptide Libraries

A peptide library was used to restimulate ex-vivo the splenocytes from immunized mice. More precisely, 679 peptides (15 mers overlapping by 11 amino acids) covering all 14 Mtb antigens contained in the fusions described above were synthesized (ProImmune). Pools of peptides were prepared in DMSO with a final concentration of 1 µmol/L. One to 4 pools were needed so as to cover the full length of each Mtb antigen.

Rv1733 was covered by 2 pools of 18 and 17 peptides. Pool 1: 18 peptides covering Rv1733 residues 62 to 144; Pool 2: 17 peptides covering Rv1733 residues 134 to 210.

Rv2029 was covered by 4 pools of 19 peptides. Pool 1: 19 peptides covering Rv2029 residues 1 to 87; Pool 2: 19 peptides covering Rv2029 residues 77 to 163; Pool 3: 19 peptides covering Rv2029 residues 153 to 239; Pool 4: 19 peptides covering Rv2029 residues 229 to 314.

Rv0569 was covered by 1 pool of 20 peptides covering Rv0569 from residues 1 to 88.

Rv1807 was covered by 4 pools of 25 peptides for the first 3 pools and 22 peptides for the fourth pool. Pool 1: 25 peptides covering Rv1807 residues 1 to 111; Pool 2: 25 peptides covering Rv1807 residues 101 to 211; Pool 3: 25 peptides covering Rv1807 residues 201 to 311; Pool 4: 22 peptides covering Rv1807 residues 301 to 399.

Rv0111 was covered by 4 pools of 20 peptides for the first 3 pools and 19 peptides for the fourth pool. Pool 1: 20 peptides covering Rv0111 residues 361 to 451; Pool 2: 20 peptides covering Rv0111 residues 441 to 531; Pool 3: 20 peptides covering Rv0111 residues 521 to 611; Pool 4: 19 peptides covering Rv0111 residues 601 to 685.

RpfB-Dhyb was covered by 4 pools of 22 peptides for the first 3 pools and 19 peptides for the fourth pool. Pool 1: 22 peptides covering RpfB residues 30 to 127; Pool 2: 22 peptides covering RpfB residues 117 to 215; Pool 3: 22 peptides covering RpfB residues 205 to 284 and RpfD residues 53 to 71; Pool 4: 19 peptides covering RpfD residues 61 to 146.

Rv1813 was covered by 1 pool of 25 peptides covering Rv1813 residues 34 to 143.

Rv3407 was covered by 1 pool of 22 peptides covering Rv3407 residues 1 to 99.

Rv3478 was covered by 4 pools of 24 peptides. Pool 1: 24 peptides covering Rv3478 residues 1 to 107; Pool 2: 24 peptides covering Rv3478 residues 97 to 203; Pool 3: 24 peptides covering Rv3478 residues 193 to 299; Pool 4: 24 peptides covering Rv3478 residues 289 to 393.

Rv2626 was covered by 2 pools of 17 and 16 peptides. Pool 1: 17 peptides covering Rv2626 residues 1 to 79; Pool 2: 16 peptides covering Rv2626 residues 69 to 143.

Ag85B was covered by 3 pools of 23 peptides. Pool 1: 23 peptides covering Ag85B residues 39 to 141; Pool 2: 23 peptides covering Ag85B residues 131 to 233; Pool 3: 23 peptides covering Ag85B residues 223 to 325.

ESAT-6 was covered by 1 pool of 21 peptides covering ESAT-6 from residues 1 to 95.

TB10.4 was covered by 1 pool of 21 peptides covering TB10.4 from residues 1 to 95.

IFNγELISpot Assays

Splenocytes from immunized mice were collected and red blood cells were lysed (Sigma, R7757). $2 \times 10^5$ cells per well were cultured in triplicate for 40 h in Multiscreen plates (Millipore, MSHA S4510) coated with an anti-mouse IFNγ monoclonal antibody (BD Biosciences; 10 μg/mL, 551216) in αMEM culture medium (Gibco, 22571) supplemented with 10% FCS (JRH, 12003-100M), 80 U/mL penicillin/80 μg/mL streptomycin (PAN, P06-07-100), 2 mM L-glutamine (Gibco, 25030), 1× non-essential amino acids (Gibco, 11140), 10 mM Hepes (Gibco, 15630), 1 mM sodium pyruvate (Gibco, 31350) and 50 μM β-mercaptoethanol (Gibco, 31350) and in presence of 10 units/mL of recombinant murine IL2 (Peprotech, 212-12), alone as negative control, or with:

The above-described pool of peptides at a final concentration of 1 μmol/L

5 μg/ml of Concanavalin A (Sigma, C5275) for positive control.

Irrelevant peptide

IFNγ-producing T cells were quantified by ELISpot (cytokine-specific enzyme linked immunospot) assay as previously described (Himoudi et al., 2002, J. Virol. 76: 12735-46). Results are shown as the mean value obtained for triplicate wells. An experimental threshold of positivity for observed responses (or cut-off) was determined by calculating a threshold value which corresponds to the mean value of spots observed with medium alone +2 standard deviations, reported to $10^6$ cells. A technical cut-off linked to the CTL ELISpot reader was also defined as being 50 spots/$10^6$ cells (which is the value above which the CV (coefficient of variation) of the reader was systematically less than 20%). Statistical analyses of ELISpot responses were conducted by using a Kruskal-Wallis test followed, when a significant difference was obtained, by a Mann-Whitney test. P value equal or inferior to 0.05 will be considered as significant.

Evaluation of Therapeutic Efficacy of Mtb Antigens-Containing Vaccines Against *Mycobacterium tuberculosis* Infection in Mice Female C57BL/6 mice (6 to 8 weeks old) were aerosol challenged at week 0 using a contained Henderson apparatus in conjunction with an Aero control unit (Hartings et al., 2004, J Pharmacol Toxicol Methods 49: 39-55). *Mycobacterium tuberculosis* challenge strain H37Rv (NCTC 7416) was cultured in a chemostat (James et al., 2000, J Appl Microbiol 88: 669-77) and fine particles of a mean diameter of 2 μm were generated in a Collison nebulizer and delivered directly to the animal snout. The suspension in the Collison nebulizer was adjusted to deliver an estimated inhaled dose of approximately 100 CFU/lung to each group of mice.

Mice were immunized at 10 and 14 weeks post-infection with MVATG18364, MVATG18376 or MVATG18377 given subcutaneously at the base of tail in one site ($10^7$ pfu/100 μL/mouse). A group of mice was injected with MVATGN33.1 as negative control ($10^7$ pfu/100 μL/mouse).

Mice were treated with isoniazid (INH, 25 mg per kg body weight) and rifapentine (RIF, 10 mg per kg body weight) once a week by oral gavage for 10 weeks, from week 6 to week 15 (protocol adapted from Aagaard et al., 2011, Nat Med, 17: 189-194). 5 mice were sacrificed at week 6 before drug treatment.

Mice from each of group were sacrificed, five at the end of the antibiotic treatment (15 weeks post-infection) to determine clearance at the end of the treatment phase and the others at week 21. Organs (e.g. spleen) were aseptically removed, frozen on the day of necropsy and processed for bacterial load analysis. Serial dilutions of samples of organ homogenates were plated onto 7H11 Middlebrook OADC selective agar and incubated for up to 3 weeks for enumeration of viable mycobacteria (CFU). Bacterial load data was expressed as Log 10 total Colony Forming Unit (CFU).

The therapeutic efficacies of the MVA candidates were compared and ranked using the Mann-Whitney test. A p value inferior to 0.05 was considered significant.

Results

Example 1: Selection of Suitable Mtb Antigens for Immunogenic Combination

The Mtb genome expresses approximately 4000 genes but the function and role in Mtb life cycle of the great majority of the gene products have not yet been characterized. As described in Materials and Methods, existing data on Mtb antigens were investigated from the available literature and data bases with the goal of identifying the most appropriate set of genes/antigens from Mtb genome for providing an immunotherapeutic vaccine capable of raising anti-TB immunity during all phases of the natural course of infection.

These bibliographic analyses permit to "pre-select" a set of 33 Mtb antigens belonging to all three phases of infection, namely seven antigens of the active phase, five resuscitation (Rpf) antigens and 19 latent antigens as well as two PE/PPE antigens.

Antigens of the active phase: ESAT-6 (Rv3875), CFP-10 (Rv3874), TB10.4 (Rv0288), Ag85A (Rv3804), Ag85B, (Rv1886) and two "ESAT-6 like antigens" (Rv3620 and Rv3619);

Two PE/PPE antigens (Rv2608 and Rv3478) which appear to be associated with virulence.

Antigens of the resuscitation phase: the five existing Rpfs genes (RpfA (Rv0867c), RpfB (Rv1009), RpfC (Rv1884c), RpfD (Rv2389), RpfE (Rv2450c)) were preselected. Rpfs are secreted or membrane bound muralytic enzymes which expression is required for the resuscitation of the dormant cells.

Nineteen latent antigens were preselected from the more than 150 existing latent genes described. More precisely, twelve belong to the DosR regulon, a set of 45 genes which expression is increased during latency period and five were selected among genes which expression was modulated during culture condition thought to mimic the latency condition that Mtb encounters in vivo. Three latent antigens were also selected based on preclinical and early clinical phases recently described (Bertholet et al., 2008, J. Immunol. 181: 7948-57; Bertholet et al., 2010, Sci Transl Med 2: 53ra74, Mollenkopf et al., 2004, Infect Immun 72: 6471-9). In summary, the 19 latent antigens preselected were Rv1733c, Rv2029c, Rv1735, Rv1737, Rv2628, Rv0569, Rv2032, Rv2627c, Rv0111, Rv3812, Rv1806, Rv1807, Rv0198, Rv2626, Rv0081, Rv2005c, Rv2660, Rv3407 and Rv1813.

Then, a second selection was undertaken in order to rank the 33 preselected Mtb antigens. The second selection of Mtb antigens was based on a data mining-based selection process (see Materials and Methods) reflecting their immunological and protective potential (highest score retained) as well as biochemical prediction.

The following antigens were chosen:

Latent phase antigens: Rv1733, Rv2029, Rv0569, Rv0111, Rv1807 and Rv3407. Rv2626 and Rv1813 were also chosen due to their very good data mining score and biochemical prediction score.

Active phase antigens: ESAT-6 (Rv3875), TB10.4 (Rv0288), Ag85B (Rv1886) and Rv3478. It has to be noted that the pre-selected active phase Rv3619 antigen had a good data mining score, but being an ESAT-6 like protein while not showing better score than ESAT-6 itself, it was not retained in the selected list. As another example, active Rv2608 and Rv3478 antigens had the same data mining score but Rv3478 was selected on the basis of its capacity of inducing a stronger percentage of responders in human cohort studies.

Resuscitation phase antigens: RpfB and RpfD. Among the 5 resuscitation gene products, three Rpfs stood out (RpfB, D and E) with very similar score after the running data mining scoring process but only RpfB and D were selected for 2 main reasons. Firstly, the reported cross-reactivity in term of cellular and humoral responses between 4 out of 5 Rpfs (Yeremeev et al., 2003, Infect Immun 71: 4789-94), except for RpfB justified in our view the selection of the latter. Secondly, RpfD was chosen instead of RpfE after sequence analysis based on a lower sequence homology in the lysozyme domain (LD) between RpfB and D than between RpfB and E. It is thus assumed that keeping Rpfs B and D would be sufficient to generate immune response toward the 5 Rpfs.

Example 2: Fusion Design

Extensive in silico structure prediction and bibliographical analyses were performed in order to predict biochemical properties and/or biological functions of the selected Mtb antigens as described in Materials and Methods.

The selected 14 antigen candidates were classified into three groups that required different types of analysis.

Antigens with available data concerning their expression in various viral vectors namely Ag85B ESAT-6 and TB10-4 in MVA (Kolilab et al. 2010, Clin Vaccine Immunol 17: 793-801); vaccinia virus (Malin et al. 2000, Microbes Infect 2: 1677-85) and adenovirus (Mu et al., 2009, Mol Ther 17: 1093-100; Dietrich et al. 2005, J Immunol 174: 6332-9; and Havenga et al. 2006; J Gen Virol 87: 2135-43). In these cases, analysis of the bibliography was the main source of information to design the sequence to insert in vector constructions.

Antigens with no data reported on viral vectorization but identical or homologous to a protein with a known structure. In these cases, structural data were the main source of information to design the Mtb sequence to insert in vector constructions (Rv2626, Rv2029, RpfB, RpfD and Rv0569).

Antigens with no data reported on viral vectorization and with no homology with any protein with a known structure. In these cases, in silico biochemical analyses and predictions were used to characterize the antigens, and to design the Mtb sequence to insert in vector constructions (Rv0111, Rv3407, Rv3478, Rv1807 and Rv1813).

Design of Ag85B Antigen

Ag85B displays a 40 residues long peptide signal that was conserved in the Kolilab's MVA vector but not in the Malin's vaccinia virus and the adenovirus constructs. As Ag85B signal peptide was predicted as a TM domain, the inventors recommended not to keep the Ag85B peptide signal in the vector constructions of this invention. The recommended primary structure of Ag85B* to be used in vector constructions described herein corresponds to the amino acid sequence shown in SEQ ID NO: 20.

Design of ESAT-6 Antigen

ESAT-6 forms a heterodimeric complex with CFP-10 and this heterodimeric interaction is expected to induce the folding of both proteins. Alone ESAT-6 adopts a molten globule-like state and a helix-turn-helix when complexed with CFP10. Thus, ESAT-6 bound to its partner could be more stable than ESAT-6 expressed alone. However, the recommended primary structure of ESAT-6 to be used in vector constructions described herein corresponds to the full length protein, (amino acid sequence shown in SEQ ID NO: 14) eventually without its initiator Met (e.g. if internal position in the fusion).

Design of TB10-4 (Rv0288)

TB10-4 belongs to the same family of protein as ESAT-6. NMR structure of TB10-4 showed that it forms a heterodimeric complex with Rv0287 that is expected to stabilize the structure. There is no publication reporting TB10-4 expression by poxviruses whereas expression of the full length TB10-4 was reported in adenovirus vectors in a form fused to the C-terminus part of either Ag85A or Ag85B. On this basis, the recommended primary structure of TB10.4 to be used in vector constructions described herein corresponds to the full length protein (amino acid sequence shown in SEQ ID NO: 2), eventually without its initiator Met.

Design of Rv2626

Crystallization of Rv2626 (Sharpe et al., 2008, J Mol Biol 383: 822-36) showed that it is expressed as a homodimer with an intra and an inter subunit disulfide bonds. No signal peptide was predicted for Rv2626. Since Rv2626 has a very well defined fold, the recommended primary structure of Rv2626 to be used in vector constructions described herein corresponds to the full length protein (amino acid sequence shown in SEQ ID NO: 10), eventually without its initiator Met.

Design of Rv0569

Rv0569 structure is not known but this protein displays a 62% identity (81% similarity) with Rv2302 in a 76 amino acid overlap region (out of 88 residues). The structure of this latter has been solved by NMR (Buchko et al., 2006, Bacteriol 188: 5993-6001) and showed a very well folded structure in solution with antiparallel β-sheet core and a C-terminal α-helix. No coiled coil prediction is associated with this protein. No known function is associated with Rv0569 protein. Due to the potential very well defined fold, the recommended primary structure of the Mtb Rv0569 to be used in vector constructions described herein corresponds to the full length protein (amino acid sequence shown in SEQ ID NO: 3, eventually without its initiator Met.

Design of Rv2029

Rv2029 structure is not known, but this protein displays a 35% identity with phosphofructokinase-2 (pfk2) of $Escherichia\ coli$ in a 310 aa overlap region (out of 339). Moreover, PROSCAN search yielded to the identification of a fully conserved carbohydrate kinases signature. Therefore, Rv2029 has probably a phosphofructokinase activity in Mtb. Phosphofructokinase catalyzes the phosphorylation of fructose-6-phosphate during glycolysis. $E.\ coli$ pfk2 structure is tetrameric when ATP is bound and dimeric when ATP is not present in the medium (allosteric regulation of the enzyme activity). In the $E.\ coli$ enzyme, deletion of the last C-terminal 4 residues completely inhibits ATP induced tetramerization. Thus, in order to avoid oligomerization heterogeneity of Rv2029 (mix of dimeric and tetrameric forms), the deletion of the C-terminus part is recommended (i.e. deletion of the last 25 residues). Moreover, in order to abolish enzymatic activity of Rv2029, the mutation D265N (position 265 starting from the Met initiator or 264 without Met) is recommended since it abolishes almost totally the enzymatic activity in $E.\ coli$ pfk-2 (Cabrera et al., 2010, Arch Biochem Biophys 502: 23-30). On this basis, the recommended primary structure of the Rv2029 antigen (Rv2029*) to be used in vector constructions described herein corresponds to the amino acid sequence shown in SEQ ID NO: 21.

Design of RpfB and RpfD

The Resuscitation Promoting Factors (Rpf) are secreted proteins that are produced during the reactivation phase of the bacteria (transition from dormancy to growth). $M.\ tuberculosis$ has five different Rpf (A to E) that all contain a conserved catalytic domain (lysozyme like domain). Apart from this domain, there is no significant similarity among these five proteins. RpfB structure has been obtained for about half of the molecule (residues 194-362) and a signal peptide was predicted (residues 1-29; Ruggiero et al. 2009, J Mol Biol 385: 153-62). The full length protein (without its signal peptide) behaves as a monomer when expressed in $E.\ coli$.

In silico predictions and analyses were performed on RpfB to analyse the part of the protein (30-193) for which no structure was available. Except for the signal peptide, no transmembrane domain was predicted. HCA plots, secondary structure prediction and natively disordered regions predictions are in agreement with a well-defined fold of the 30-193 region. Coiled coils predictions and search for known motifs using PROSCAN did not yield any significant result.

Activity of the catalytic domain has been shown to depend on a conserved residue essential in the resuscitation activity of $Micrococcus\ luteus$ Rpf in a $Mycobacterium\ smegmatis$ resuscitation assay (mutation E292K; Mukamolova et al. 2006, Mol Microbiol 59: 84-98). Furthermore, the two residues T315 and Q347 are involved in substrate binding in lysozyme, and conserved in RpfB (Cohen-Gonsaud, et al. 2005, Nat Struct Mol Biol 12, 270-3).

In addition, it has been chosen to design a RPFB-D hybrid that corresponds to the RpfB molecule with its catalytic domain replaced by the most divergent catalytic domain among Rpfs (i.e. RpfD catalytic domain). Therefore, the RPFB-D hybrid to be expressed in viral vectors is a hybrid protein with a neutralized catalytic activity by three mutations (E292K, T315A and Q347A) and without signal peptide. The recommended primary structure for this RPFB-D hybrid protein used in fusions corresponds to the amino acid sequence shown in SEQ ID NO: 31 from residue 10 to residue 283 of RpfB fused to residue 51 to residue 147 of RpfD, eventually with a initiator Met.

Design of Rv1807

Rv1807 structure is not publicly available, but a BLAST search against the PDB database yielded a match with only the first 150 residues of a Mtb PPE protein (Rv2430). PE/PPE is a large family of Mtb proteins (around 100 PE and 60 PPE members) that have in common a PE (Proline, Glutamic acid) or PPE (Proline, Proline, Glutamic acid) motif, at their N-terminus parts. PE proteins are expressed as heterodimers with PPE, and their function is not known yet. BLAST search against UNIPROT-SWISSPROT yielded several matches but all of them were additional Mtb PPE that did not allow to gain additional information.

In $E.\ coli$, expression of a soluble PPE (Rv2430) or PE (Rv2431) is apparently possible only when expressed as a heterodimer (Strong et al. 2006, Proc Natl Acad Sci 103: 8060-5). These authors reported that Rv1807 expressed alone in $E.\ coli$ forms inclusion bodies. PROSCAN search did not yield any significant match with a known motif. No signal peptide or transmembrane domain were reported or predicted for this protein. HCA plots, as well as secondary structure predictions were in agreement with a well-defined fold of the whole protein except the last 60-70 residues region. Moreover, the last 60 residues are predicted to be unfolded using natively disordered regions predictions whereas coiled coils predictions on Rv1807 did not yield any significant result.

As for ESAT6 and TB10-4, the coexpression of Rv1807 with its partner (i.e. Rv1806) would probably favourably impact the protein stability and therefore potentially its immunogenicity. The expression of a misfolded protein (a monomeric one) could impair the recombinant vector stability (protein toxicity). Moreover, the unfolded C-terminus part of Rv1807 could also have an unfavourable impact on either immunogenicity and/or on the recombinant virus stability. The recommended primary structure for Rv1807 used in fusions corresponds to the full length protein (SEQ ID NO: 6). In case of problem encountered with the full length antigen, one may use a C-terminus truncated antigen deleted of the last 60 residues (as shown in SEQ ID NO: 18).

Design of Rv3478

Rv3478 is another PPE protein. Its PPE domain is 57% identical to the PPE domain of Rv1807 (41% identity between the two whole proteins). BLAST search against UNIPROT-SWISSPROT yielded several matches that were all other Mtb PPE. HCA plot demonstrated the presence of hydrophobic patches all along the protein sequence. In other words, HCA plot does not indicate unfolded hydrophilic region in Rv3478. But, as for Rv1807, the last 40 to 50 residues of Rv3478 are predicted to be unfolded (based on both secondary structure and natively disordered predictions). No signal peptide or transmembrane domain were reported or predicted for this protein. Coiled coils predictions on Rv3478 did not yield any significant result. As for Rv1807, the recommended primary structure is the full length protein (SEQ ID NO: 13) or, if problem are encountered, a C-terminus truncated antigen deleted of the last 40 residues (as shown in SEQ ID NO: 24).

Design of Rv0111

Rv0111 is predicted to be a membrane protein with a possible acyltransferase activity. Ten transmembrane domains are predicted by DAS, TMHMM and TopPred spanning from residues 58 to 427. No signal peptide was predicted. Secondary structures are predicted all along the primary structure, with a gap at 449-469 that corresponds to a predicted natively disordered region. Coiled coils predictions on Rv0111 did not yield any significant result.

Proscan analysis yielded four hits with ≥80% similarity: Aldo/keto reductase enzyme site, acyltransferase lipoyl binding site, sugar transport protein signature and the eukaryote lipocalin proteins. As the three first signatures are in the first 300 residues of the protein, it is thus recommended to remove at least this part of the protein in order to avoid any potential biological activity. This would also allow to get rid of the majority of the transmembrane domains of the protein. Therefore the recommended primary structure of Rv0111 to be used in viral vectors is the C terminus part of the protein (e.g. residues 393-685 of the native antigen as shown in SEQ ID NO: 15) with only one TM for plasmatic membrane anchorage in case of secreted construction. If expression problems are encountered, one may use an even more truncated antigen without any TM domain (residues 429-685 of the native Rv0111 starting at residue 37 of SEQ ID NO: 15).

Design of Rv1813

Rv1813 structure is not publicly available and BLAST search against PDB yielded no match. Rv1813 is a small protein (143 residues), that is predicted to contain a signal peptide (1-32) and no transmembrane domain. It displays no significant homology with other proteins in the Uniprot-Swissprot database. HCA plots, secondary structure prediction and natively disordered regions predictions are all in agreement with a well-defined fold of the whole protein. Coiled coils predictions did not yield any significant result. No function is reported in the TB base and a PROSCAN search yielded no significant match with a known motif. Therefore the recommended primary structure of Rv1813 to be used in viral vectors is the full-length protein without its signal peptide (residues 1 to 34) which amino acid sequence is shown in SEQ ID NO: 19.

Design of Rv3407

Rv3407 structure is not publicly available and a BLAST search against PDB did not yield any match. Rv3407 is a small protein (99 residues) with no significant homology with other protein in Uniprot-Swissprot database. No signal peptide or transmembrane domain was reported or predicted for this protein. HCA plot and secondary structure predictions were in agreement with a well-defined fold of the whole protein. However, natively disordered regions predictions indicated that the last 33 residues may not be folded in a defined structure. This last result that is not in agreement with HCA and secondary structure predictions could be the signature of a MORE ("Molecular Recognition Element") that folds upon binding to a partner protein. In the case of Rv3407 a C-terminal alpha helix could be present only when Rv3407 is bound to its partner. Coiled coils predictions did not yield any significant result. No function is reported in TB base for this protein and PROSCAN search did not yield any significant match with a known motif. The recommended primary structure of Rv3407 is the full length protein (SEQ ID NO: 12). If stability issue are encountered, one may use a C-terminus truncated antigen deleted of the last 33 residues (as shown in SEQ ID NO: 23).

Design of Rv1733

Rv1733 is predicted to be a membrane protein according to UNIPROT-SWISSPROT and TB base, with two transmembrane domains (that are also predicted using DAS, TMHMM and TopPred). The first TM domain was predicted as a signal peptide. Apart from these transmembrane domains, few secondary structures are predicted for this protein. HCA plot demonstrates the presence of few hydrophobic patches between the two transmembrane helices. Finally, a natively disordered region (about 20 residues long) was predicted between the two transmembrane helices. All together, theses results indicate a probably loose fold beside the transmembrane domains. PROSCAN search on Rv1733 without its signal peptide did not yield any significant match with a known motif Coiled coil prediction on Rv1733 did not yield any significant result. Therefore the recommended primary structure of Rv1733 to be used in viral vectors is the whole protein minus its signal peptide (62 first residues) as shown in SEQ ID NO: 17. Alternatively, one may also use the full length Rv1733 (SEQ ID NO: 5).

Example 3: Construction of Mtb Gene Fusions

Twelve different fusion proteins were engineered as illustrated in FIG. 1 and Table 3. More specifically, 5 fusions were designed based on biochemical rationales as described below, respectively:

- Fusion no 3 (RPFB-Dhyb*);
- Fusion no 5 (Rv0569-Rv1813*-Rv3407-Rv3478-Rv1807);
- Fusion no 6 (Ag85B*-Rv2626-RPFB-Dhyb*-Rv1733*);
- Fusion no 8 (Ag85B*-Rv2626-Rv1733*); and
- Fusion no 14 (Rv2029*-TB10.4-ESAT6-Rv0111*).

The following biochemical rationales have been followed to design the fusions

- Two dimeric proteins (i.e. Rv2626 and Rv2929*) should not be fused in the same fusion to avoid any steric clashes.
- Two membrane proteins should not be used in the same fusion (i.e. Rv1733* and Rv0111*) to avoid potential toxicity issue.
- Proteins with TM (Rv1733* and Rv0111*) should be inserted at the end of the fusion to allow plasmatic membrane anchorage for secreted constructions.
- If possible, the fusion protein should start with a well folded protein (i.e. Ag85B*, Rv2029*, Rv2626, Rv0569, RPFB-D hybrid*) to have a «chaperone» effect on the rest of the fusion.

Make three fusions, two of which with the minimal set of antigens (i.e. Ag85B*, Rv2029*, Rv2626, Rv0111*, Rv1733*, TB10-4, ESAT-6, RPFB-D hybrid*) and the last fusion with the rest (optional) of the antigens (i.e. Rv0569, Rv1813*, Rv3407, Rv1807, Rv3478).

On the other hand, fusions were also designed relative to the phase of TB disease. Fusion no 2 contains active antigens (Ag85B*-TB10.4-ESAT6) while fusion no 4 contains active and resuscitation antigens (RPFB-Dhyb*-Ag85B*-TB10.4-ESAT6). The fusion no 13 is constituted by latent antigens (Rv2029*-Rv2626-Rv1733*-Rv0111*).

As described in Materials and Methods, a series of peptides were added to the Mtb antigen fusion, respectively a N-terminal Flag Tag and C-terminal c-myc and His Tag peptides aimed to facilitate detection of the encoded gene products as well as N-terminal signal and C-terminal membrane-anchoring peptides to enhance immunogenic activity (to be noted that addition of a TM domain was not necessary for fusions ending with Rv0111* or Rv1733*, as these proteins already contain such domains).

For comparative purposes, fusions were also constructed without any SS and TM peptides in order to evaluate cytoplasmic expression of the encoded Mtb antigens. The fusions no 3 (pTG18267), no 5 (pTG18269), no 2 (pTG18266) and no 4 (pTG18268) were deleted from the SS and TM peptides, giving fusions no 12 (pTG18307), no 9 (pTG18295), no 10 (pTG18296) and no 11 (pTG18297). The N-terminus Flag TAG and the C-terminus c-myc and His TAG were kept in these constructions.

Table 3 provides a summary of the various fusions constructed in this study

|  | Fusion # | TB antigens | plasmids |
|---|---|---|---|
| Fusion by phase | 13 | Rv2029*-Rv2626-Rv1733*-Rv0111* | pTG18323 |
|  | 2 | Ag85B*-TB10.4-ESAT6 | pTG18266 |
|  | 4 | RPFB-Dhyb-Ag85B*-TB10.4-ESAT6 | pTG18268 |
| Max list | 5 | Rv0569-Rv1813*-Rv3407-Rv3478-Rv1807 | pTG18269 |
| Fusion by biochemistry rules | 6 | Ag85B*-Rv2626-RPFB-Dhyb-Rv1733* | pTG18270 |
|  | 14 | Rv2029-TB10.4-ESAT6-Rv0111* | pTG18324 |
|  | 8 | Ag85B*-Rv2626-Rv1733* | pTG18272 |
|  | 3 | RPFB-Dhyb | pTG18267 |
| Fusion without SS and TM | 9 | Rv0569-Rv1813*-Rv3407-Rv3478-Rv1807 | pTG18295 |
|  | 10 | Ag85B*-TB10.4-ESAT6 | pTG18296 |
|  | 11 | RPFB-Dhyb-Ag85B*-TB10.4-ESAT6 | pTG18297 |
|  | 12 | RPFB-Dhyb | pTG18307 |

For comparative purposes, plasmids encoding the individual Mtb genes used in the above-described fusions were amplified by PCR or gene sequence synthesized by Geneart. More precisely, pTG18269 was used as template to amplify Rv3407, Rv0569, Rv1807, Rv1813* and Rv3478 whereas pTG18323 was used to amplify Rv2626. ESAT6, Rv1733*, Ag85B*, TB10-4, Rv0111* and Rv2029* were produced as synthetic genes.

The individual genes were placed in the same context as the fusions, i.e. inserted in pGWiz downstream the CMV promoter and fused to Flag in 5' and c-myc-His sequences in 3'. As Rv1733* and Rv0111* proteins contain a TM domain, the signal peptide presents at the N-terminus of the glycoprotein precursor of rabies virus ERA strain was fused upstream to the Flag sequence to avoid expression issues. The generated plasmids were named respectively pTG18300 (Rv3407), pTG18301 (Rv0569), pTG18302 (Rv1807), pTG18303 (Rv1813*), pTG18304 (Rv3478), pTG18305 (Rv2626), pTG18308 (ESAT6), pTG18309 (Rv1733*), pTG18310 (Ag85B*), pTG18315 (TB10.4), pTG18329 (Rv0111*), pTG18317 (Rv2029*).

The various fusion proteins was assessed in eukaryotic expression system after introduction of the corresponding expression plasmids. Expression was assessed by Western Blot whereas immunogenic activity was evaluated by ELISpot IFNγ assays after DNA immunization of mice. When possible, expression and immunogenicity of the cytoplasmic (without SS and TM) and membrane-anchored versions were compared as well as immunogenicity provided by the fusions with that obtained with a mix of plasmids expressing the individual Mtb antigens.

Example 4: Analysis of Expression of Mtb Antigens and Fusions

Whether expressed individual or in fusion, expression of Mtb genes was analyzed by Western Blot from cell lysates obtained from transfected HEK293 cells.

4.1 Western Blot Analysis of Cell Lysate Transfected with Plasmids Encoding Individual Mtb Antigens.

Immunodetection of the individual Mtb antigens was performed with either antibodies directed to the tag peptides included in the expression cassettes (e.g. anti-Flag M2 peroxydase (HRP) antibody, monoclonal anti-c-myc peroxidase antibody and monoclonal anti-His peroxydase antibody) or antibodies specific for Mtb antigens. Specifically, the sera obtained after immunization of rabbits (see Materials and Methods) were used for detection of Rv1733*, Rv2029*, Rv0569, Rv1807, Rv0111*, Rpf-B-D, Rv1813*, Rv3407, and Rv3478 whereas commercial antibodies were used for the detection of ESAT6, Ag85B*, TB10.4 and Rv2626.

Figure 2D:
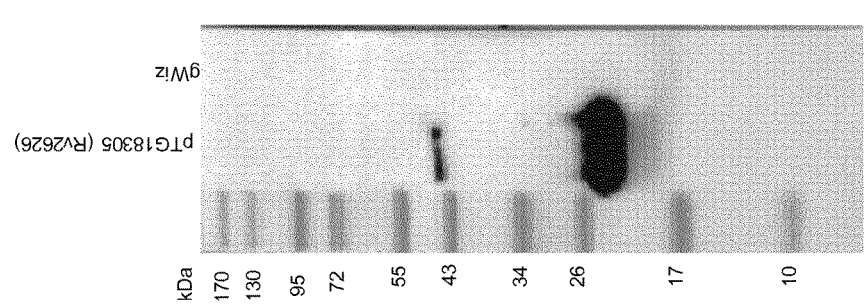
FIG. 2 illustrates expression of the individual Mtb genes by Western blot following immunodetection with specific antibodies. 2×10$^6$ HEK293 cells were transfected with 5 µg of DNA using Lipofectamine 2000. Proteasome inhibitor MG132 was added to the culture medium 18 h after the transfection. Lysates of cells harvested after 48 h of culture were analysed by electrophoresis on 10% gel criterion and immunodetection was performed with rabbit anti-sera diluted 1/1000 recognizing Rv2029* (FIG. 2A), RPFB-Dhyb (FIG. 2B), and commercial antibodies recognizing ESAT-6 (FIG. 2C) and Rv2626 (FIG. 2D).
Figure 2C:
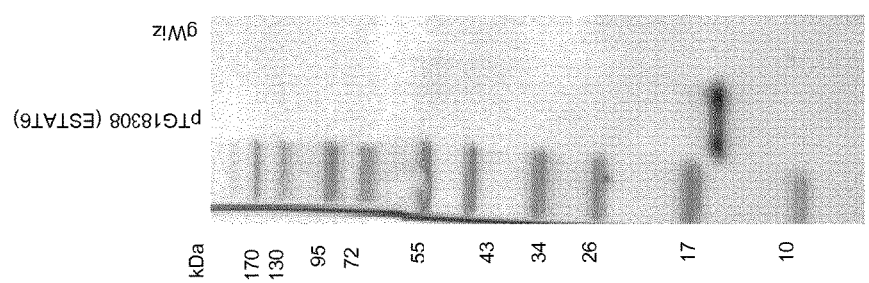
Figure 2B:
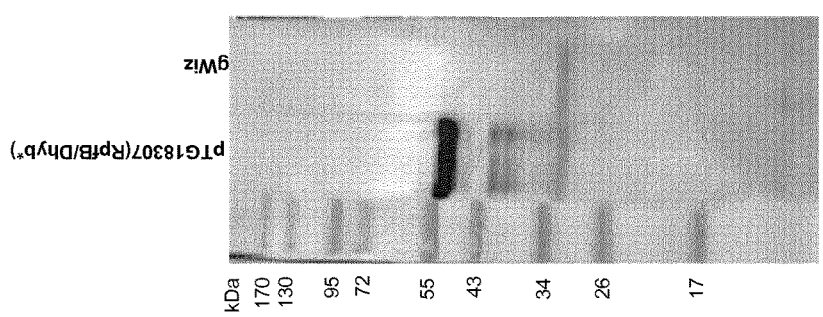
Figure 2A:
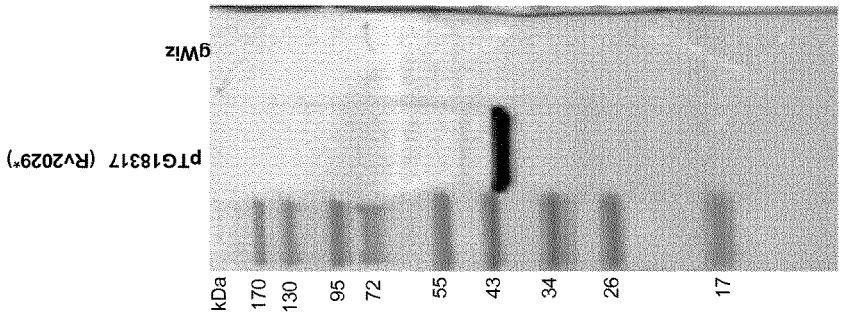

The results are summarized in Table 4. More specifically, a band corresponding to the expected size was detected for all individual proteins, whatever the immunodetection system used (anti-Flag, anti-His antibodies, specific rabbit sera and commercial antibodies). Additional products were also detected for some proteins and depending on the immunodetection system used. Moreover, high levels of expression were detected, except for Rv3407 and, to a lesser extend TB10.4 and ESAT6. Examples of expression detection are shown in FIG. 2 for a panel of representative Mtb antigens, namely Rv2029* (FIG. 2A), RPFB-Dhyb (FIG. 2B), ESAT6 (FIG. 2C) and Rv2626 (FIG. 2D).

TABLE 4

| TB antigen (plasmid) | Expected size (level expr.) | Additional products with anti Flag and anti-His antibodies | Additional products with anti Mtb antibodies |
|---|---|---|---|
| Rv3407 (pTG18300) | 14.4 kDa (+) | | |

TABLE 4-continued

| TB antigen (plasmid) | Expected size (level expr.) | Additional products with anti Flag and anti-His antibodies | Additional products with anti Mtb antibodies |
|---|---|---|---|
| Rv0569 (pTG18301) | 12.9 kDa (+++) | | 1 weak band ≈ 10 kDa |
| Rv1807 (pTG18302) | 43.3 kDa (++) | | |
| Rv1813* (pTG18303) | 15.1 kDa (+++) | | |
| Rv3478 (pTG18304) | 42.8 kDa (+++) | 2 N-terminal clived products (recognized by anti-Flag antibody) of about 16 and 26 kDA | 1 band ≈ 30 kDa |
| Rv2626 (pTG18305) | 18.9 kDa (+++) | Additional band corresponding to Rv2626 dimers | Dimer ≈ 43 kDa |
| ESAT6 (pTG18308) | 13.0 kDa (++) | | |
| Rv1733* (pTG18309) | 21.2 kDa (+++) | One N-terminal clived product of about 20 kDa and 3 C-terminal products comprised between 8 and 10 kDa | 2 bands ≈ 10 and 20 kDa |
| Ag85B* (pTG18310) | 33.9 kDa (+++) | 5 minor N-terminal clived products of about 26, 24, 20, 17 and 12 kDa as well as a C-terminal clived product (detected with anti-His antibody) of about 34 kDa. | 3 weak bands ≈ 26, 28 and 34 kDa |
| TB10.4 (pTG18315) | 13.5 kDa (++) | | |
| Rv0111* (pTG18329) | 37.6 kDa (+++) | one N-terminal clived product of about 8 kDa and one C-terminal products of about 34 kDa | 1 band ≈ 34 kDa and 2 very weak bands ≈ 18 and 20 kDa |
| Rv2029* (pTG18317) | 35.8 kDa (+++) | | |
| RfpB-Dhyb* (pTG18307) | 39.4 kDa (+++) | | 2 weak bands ≈ 40 kDa |

4.2 Western Blot Analysis of Cell Lysate Transfected with Plasmids Encoding Mtb Antigen Fusions.

HEK293 cells were transfected with the plasmids expressing the different Mtb gene fusions and expression products were analysed by Western blot in the same conditions as above. Transfections were done in the presence, but also in the absence of proteasome inhibitor MG132. Here again, immunodetection was performed with anti-Flag M2 peroxydase (HRP) antibody, monoclonal anti-c-myc peroxidase antibody and monoclonal anti-His peroxydase antibody as well as anti-Mtb specific antibodies.

Figure 3:
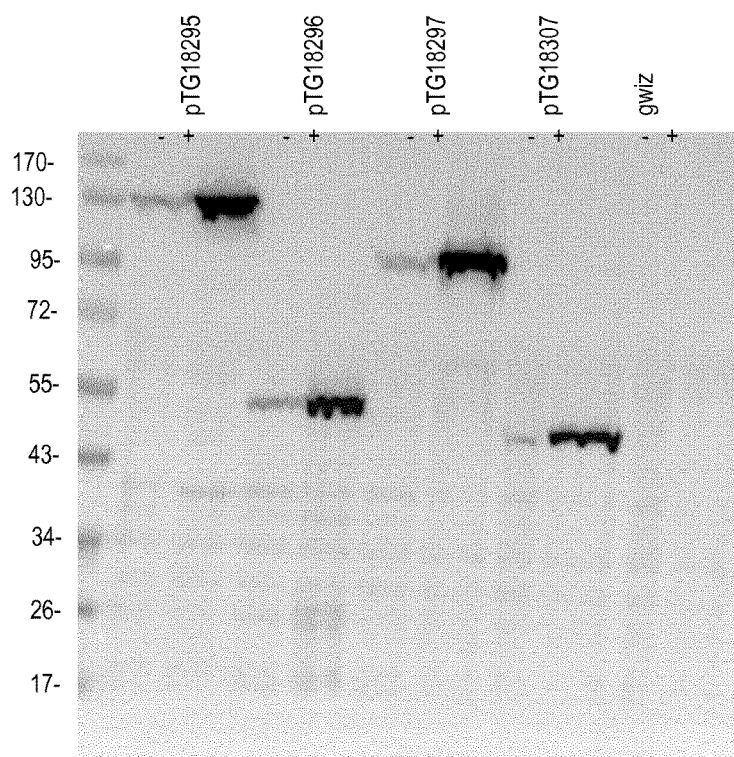
FIG. 3 illustrates Western blot analysis of Mtb fusions encompassing latent antigens (pTG18295 encoding fusion no 9), active antigens (pTG18296 encoding fusion no 10) resuscitation antigens (pTG18307 encoding fusion no 12) and both resuscitation and active antigens (pTG18297 encoding fusion no 11) following anti Flag immunodetection. +/− represents with and without MG132.

The expected sizes of the tagged fusions are indicated below:
fusion no 2 (pTG18266): 63.6 kDa
fusion no 3 (pTG18267): 49.0 kDa
fusion no 4 (pTG18268): 99.7 kDa
fusion no 5 (pTG18269): 122.0 kDa
fusion no 6 (pTG18270): 103.5 kDa
fusion no 8 (pTG18272): 67.3 kDa
fusion no 9 (pTG18295): 112.9 kDa
fusion no 10 (pTG18296): 53.8 kDa
fusion no 11 (pTG18297): 90.0 kDa
fusion no 12 (pTG18307): 39.3 kDa
fusion no 13 (pTG18323): 101.5 kDa
fusion no 14 (pTG18324): 90.6 kDA All the Mtb antigen fusions were detected with the anti-Flag and anti-His monoclonal antibodies. Mtb fusion products were also detected with the anti-c myc monoclonal antibody except for pTG18266, pTG18267, pTG18268 and pTG18269. The c-myc epitope might be inaccessible in these fusions due to adjacent TM domains since the cytoplasmic counterparts (pTG18296, pTG18307, pTG18297 and pTG18295) are well detected with the anti-myc antibody. FIG. 3 illustrates Western blot analysis of Mtb fusions encompassing latent antigens (pTG18295 encoding fusion no 9), active antigens (pTG18296 encoding fusion no 10), resuscitation antigens (pTG18307 encoding fusion no 12) and both resuscitation and active antigens (pTG18297 encoding fusion no 11) following anti Flag immunodetection. Immunodetection with anti-His antibodies gave the same expression pattern.

Figure 4A:
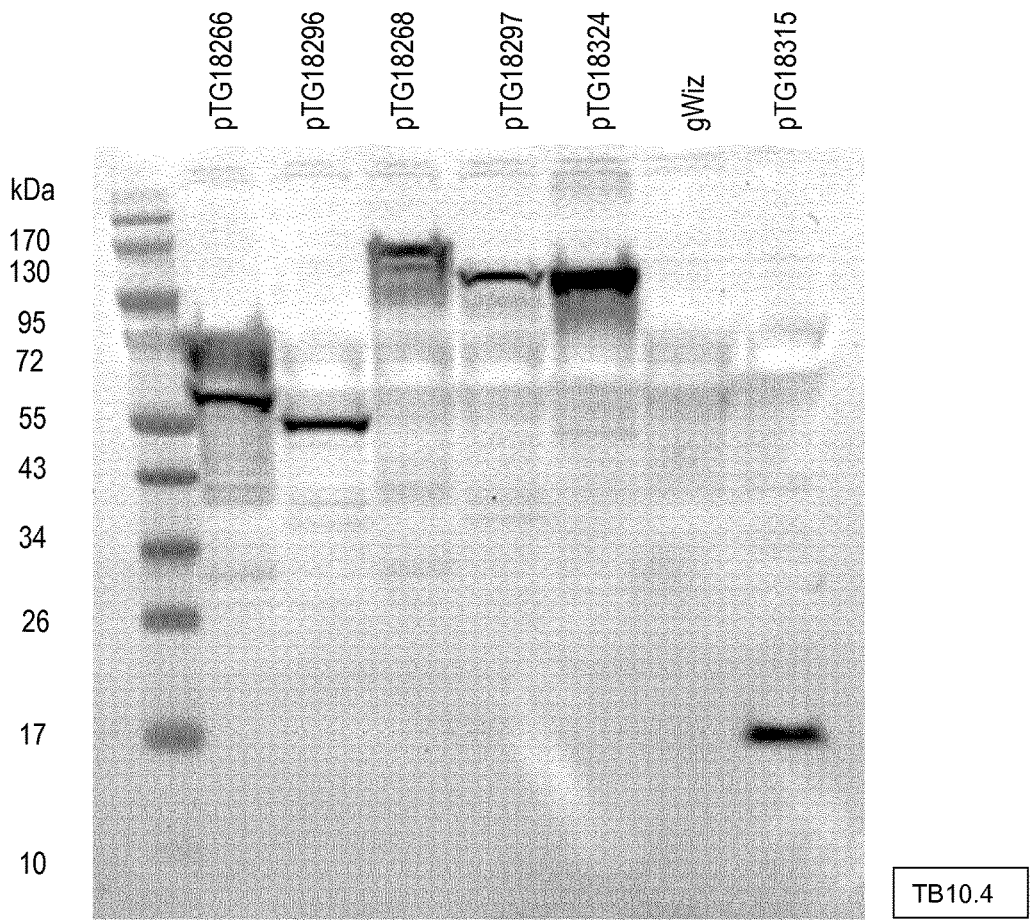
FIG. 4 illustrates Western blot analysis of Mtb fusions including TB10.4 (FIG. 4A), Rv0569 (FIG. 4B) and Rv2626 (FIG. 4C) respectively, following immunodetection with commercial anti-TB10.4 antibody (ABIN361292), anti-Rv0569 rabbit antisera and anti-Rv2626 mouse monoclonal antibody 26A11.

FIG. 4 illustrates Western blot analysis of Mtb fusions including TB10.4 (FIG. 4A), Rv0569 (FIG. 4B) and Rv2626 (FIG. 4C) following immunodetection with the corresponding specific sera, respectively TB10.4-containing fusions no 2 (pTG18266), no 10 (pTG18296), no 4 (pTG18268), no 11 (pTG18297), no 14 (pTG18324); Rv0569-containing fusions no 5 (pTG18269) and no 9 (pTG18295) and Rv2626-containing fusions no 13 (pTG18323), no 6 (pTG18270) and no 8 (pTG18272). pGWiz is shown as negative control and TB10.4-encoding pTG18315 as positive control.

Whatever the immunodetection system, a band corresponding to the expected size was highlighted for all fusions and, in some cases, additional fusion products were also observed. In particular, dimers were detected for pTG18270, pTG18272 and pTG18323. These three fusions contain Rv2626 which has the ability to form dimers resistant to reducing conditions. Immunodetection with anti-Flag and anti-His antibodies highlighted some additional minor proteolytic products for pTG18323 and pTG18269. Moreover, additional products higher than the expected size were detected for pTG18266, pTG18268, pTG18269, pTG18270, pTG18272, pTG18323 and pTG18324 with anti-Flag and anti-His antbodies. These bands correspond to N-glycosylated products as it was demonstrated by in vitro treatment with N-Glycosidase F (i.e. expression products at the expected size were obtained after N-glycosidase treatment of cellular extracts). All fusions containing a signal peptide lead to N-glycosylated products, except fusion no 4 (pTG18267, RpfB-D*). N-glycosylated products were also detected with antigen-specific antibodies as well as dimers for Rv2626-containing fusions pTG18270, pTG18272 and pTG18323. Proteolytic products were also evidenced for some fusions with specific sera (data not shown) depending on the fusions and the sera. For example, additional bands of ≈40 kDa for pTG18269 and ≈36 and 38 kDa for pTG18295 were detected with Rv3407 specific serum but are not seen with Rv0569 specific serum.

Similar and high levels of expression were obtained for all fusions and higher amounts of products were detected in the presence of MG132. The expression levels of membrane-anchored fusions (pTG18269, pTG18268) were comparable to those detected with their cytoplasmic counterparts (pTG18295, pTG18297), except for pTG18266 which was better expressed than the cytoplasmic fusion (pTG18296). Fusion no 5 (pTG18269) was very weakly detected with Rv1807 specific antibody while it is not the case for the cytoplasmic fusion (pTG18295). Rv1807 specific epitopes might be inaccessible in this fusion due to adjacent TM sequence.

Example 5: DNA Immunization Evaluation

Immunogenic activity of the various Mtb antigen fusions was evaluated in various mouse models following DNA immunization.

5.1. Evaluation of the Immunogenicity Induced by Fusions Based on Mtb Antigens of the Active Phase.

BALB/c mice were immunized three times at 3-week interval via intramuscular route with the plasmid expressing the fusion "Ag85B-TB10.4-ESAT6" either in an anchored form at the cell membrane (SS/TM: pTG18266) or cytoplasmic form (pTG18296). For comparative purposes, mice were also immunized with a mix of plasmids encoding the individual Mtb antigens included in the fusion (pTG18310 (Ag85B)+pTG18315 (TB10.4)+pTG18308 (ESAT6)) and with empty pGWiz as negative control. Cellular immune response was evaluated 2 weeks following the last DNA injection by ELISpot IFNγ assays after ex vivo re-stimulation with the various peptide pools described in Materials and Methods.

Figure 5:
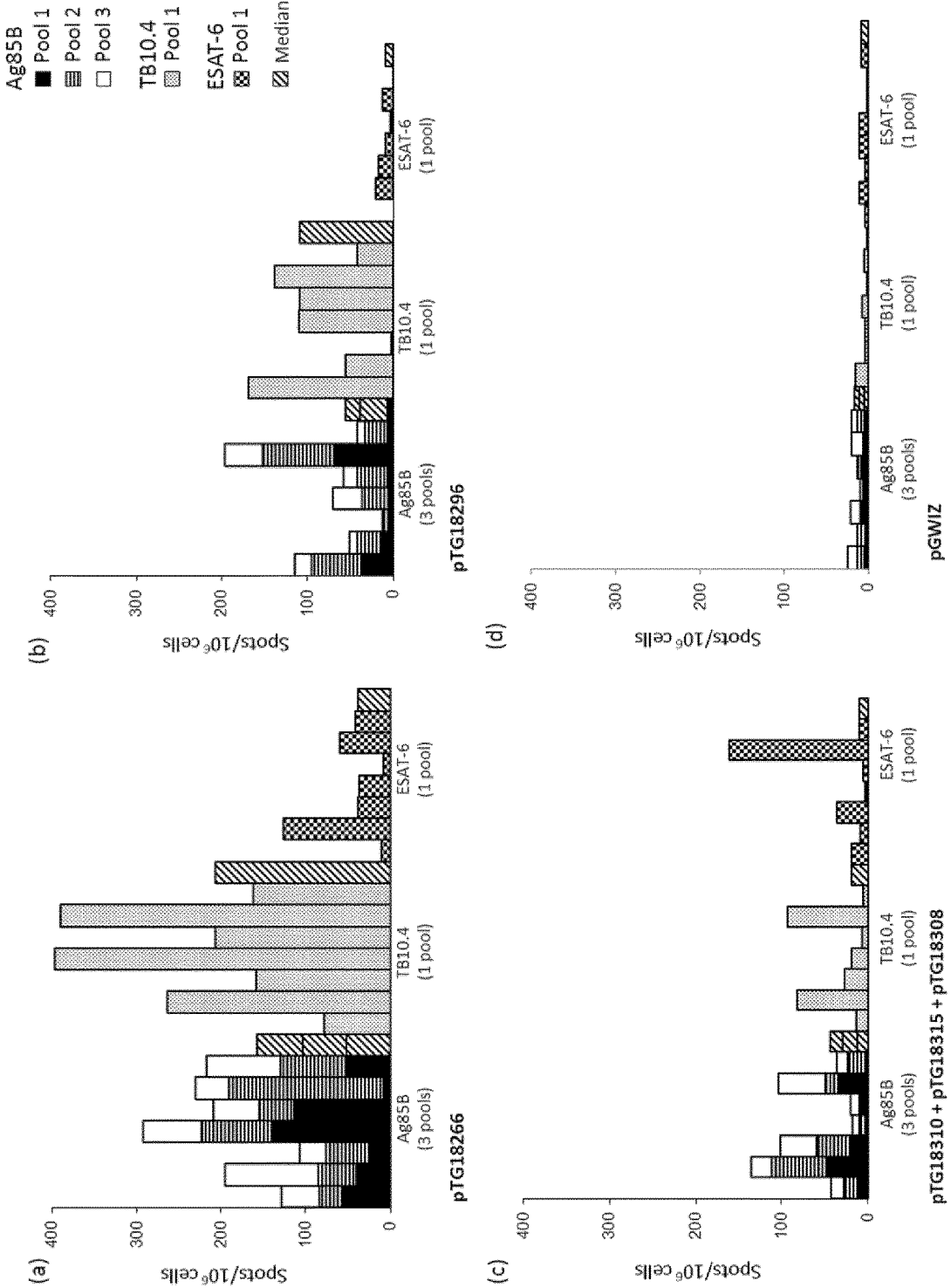
FIG. 5 illustrates IFNg-producing cells induced following immunization of animals with fusion-encoding plasmids pTG18266 (SS-Ag85B-TB10.4-ESAT6-TM.

As illustrated in FIG. 5, a strong cellular response against Ag85B and TB10.4 antigens was induced in all the mice immunized with pTG18266 (expressing the anchored version of the Ag85B-TB10.4-ESAT fusion) whereas IFNγ producing cells against ESAT-6 were generated in 6 out of 8 animals (FIG. 5a). In mice immunized with pTG18296 (expressing the cytoplasmic version of the Ag85B-TB10.4-ESAT fusion), activation of IFNγ producing cells against Ag85B and TB10.4 antigens was also detected but to a lesser level compared to that induced by the anchored fusion whereas very weak responses were detected against ESAT-6 (FIG. 5b). Very interestingly, when comparing FIGS. 5a/5b and FIG. 5c, strongest responses against all three antigens were detected when Ag85B, TB10.4 and ESAT-6 are expressed as a fusion protein (pTG18266 and pTG18296) rather than being independently expressed from individual plasmids (mix of pTG18310, pTG18315 and pTG18308). As expected, immunization with the empty plasmid did not induce any specific immune response (FIG. 5d).

Thus, at least for Mtb antigens of the active phase, these results highlight the benefit of designing antigen fusions expressed at the cell surface (with SS and TM peptides) to optimize the immunogenic activity of the resulting Mtb antigen fusions.

5.2. Evaluation of the Immunogenicity Induced by Fusions Based on Mtb Antigens of the Active and Resuscitation Phases.

BALB/c mice were immunized three times at 3-week interval via intramuscular route with the plasmid expressing the fusion "RpfB-Dhyb-Ag85B-TB10.4-ESAT6" either in an anchored form at the cell membrane (SS/TM: pTG18268) or cytoplasmic form (pTG18297). For comparative purposes, mice were also immunized with a mix of plasmids encoding the individual TB antigens included in the fusion (pTG18307 (RpfB-Dhyb)+pTG18310 (Ag85B)+pTG18315 (TB10.4)+pTG18308 (ESAT6)) and with empty pGWiz as negative control. Cellular immune response was evaluated 2 weeks following the last DNA injection by ELISpot IFNγ assays after ex vivo re-stimulation with the various peptide pools described in Materials and Methods.

Figure 6:
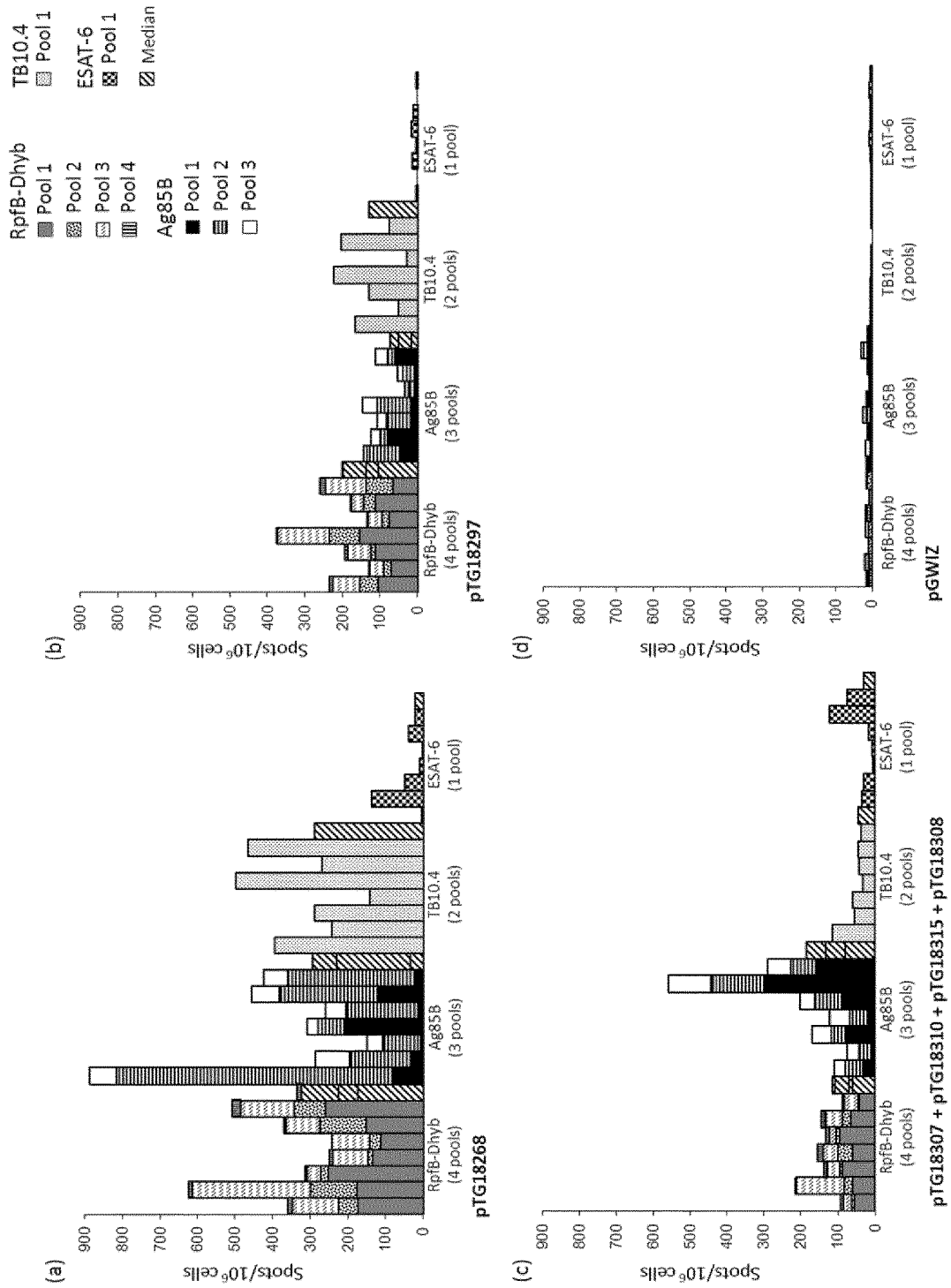
FIG. 6 illustrates IFNg-producing cells induced following immunization of animals with fusion-encoding plasmids pTG18268 (SS-RPFB-Dhyb-Ag85B-TB10.4-ESAT6-TM.

As illustrated in FIG. 6, immunization with pTG18268 plasmid (expressing the anchored version of the RpfB-DHyb-Ag85B-TB10.4-ESAT-6 fusion) resulted in a strong response specific of RpfB-DHyb, Ag85B and TB10.4 antigens characterized by detection of high levels of IFNγ producing cells after ex vivo re-stimulation with the corresponding peptide pools whereas IFNγ producing cells against ESAT-6 were induced in fewer animals and at lower levels (FIG. 6a). In mice immunized with pTG18297 (expressing the cytoplasmic version of the RpfB-DHyb-Ag85B-TB10.4-ESAT-6 fusion), activation of IFNγ producing cells against RpfB-DHyb, Ag85B and TB10.4 antigens was also detected but to a lesser level compared to that induced by the anchored fusion whereas very weak responses were generated against ESAT-6 (FIG. 6b). With the exception of ESAT-6, as illustrated in FIG. 6c, strongest anti Mtb responses were obtained against RpfB-DHyb, Ag85B and TB10.4 when expressed as a fusion protein (pTG18268 and pTG18297 FIGS. 6a and 6b) rather than being independently expressed from individual plasmids (mix of pTG18307+pTG18310+pTG18315+pTG18308). As expected, immunization with the empty plasmid did not rise any specific immune response (FIG. 6d).

5.3. Evaluation of the Immunogenicity Induced by Fusions Based on Mtb Antigens of the Resuscitation Phase.

BALB/c mice were immunized three times at 3-week interval via intramuscular route with the plasmid expressing the fusion "RpfB-Dhyb" either in an anchored form at the cell membrane (SS/TM: pTG18267) or cytoplasmic form (pTG18307). Empty pGWiz was used as a negative control. Cellular immune response was evaluated 2 weeks following the last DNA injection by ELISpot IFNγ assays after ex vivo re-stimulation with the four peptide pools described in Materials and Methods.

Figure 7A:
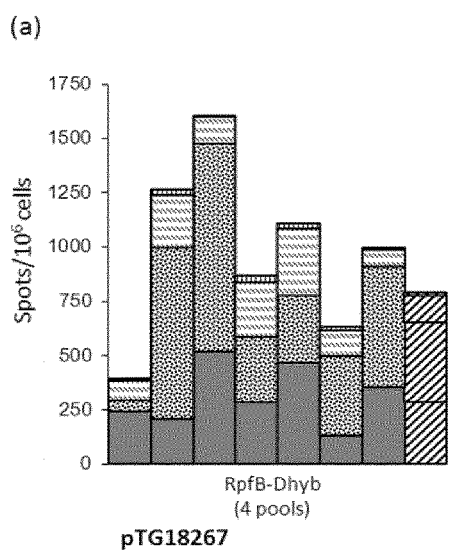
FIG. 7A), pTG18307 (cytoplasmic RPFB-Dhyb.
Figure 7B:
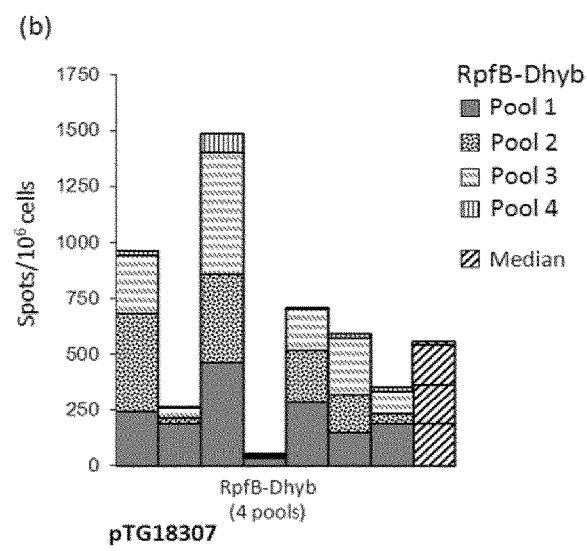
FIG. 7B) and pGWiz (FIG. 7C). Cellular immune response was evaluated 2 weeks following the last DNA injection by ELISpot IFNγ assays after ex vivo re-stimulation with specific peptide pools covering RpfB and RpfD antigens.
Figure 7C:
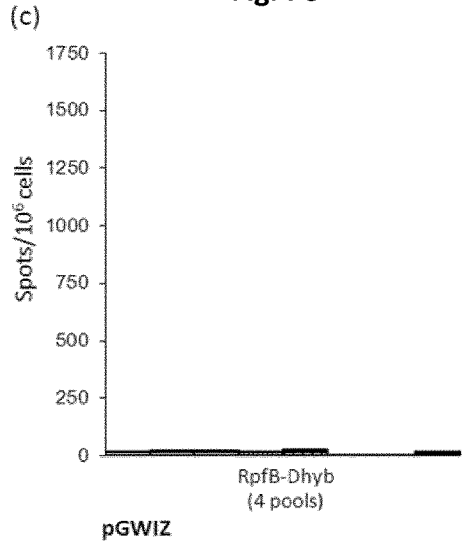
FIG. 7 illustrates IFNg-producing cells induced following immunization of animals with fusion-encoding plasmids pTG18267 (SS-RPFB-TM.

As illustrated in FIG. 7, high levels of IFNγ producing cells were observed in mice vaccinated with pTG18267 (expressing the anchored version of the RpfB-DHyb fusion with SS/TM peptides), indicating that these mice mounted a strong specific cellular response (FIG. 7a). Immunization with pTG18307 (expressing the cytoplasmic version of the RpfB-DHyb fusion), also resulted in activation of IFNγ producing cells but to a slightly lesser extend (FIG. 7b). Moreover, the response seemed more homogeneous within the group of animals treated with pTG18267 than within the group treated with pTG18307. As expected, immunization with the empty plasmid did not rise any specific immune response (FIG. 7c).

5.4. Evaluation of the Immunogenicity Induced by Fusions Based on Mtb Antigens of the Latent Phase.

BALB/c mice were immunized three times at 3-week interval via intramuscular route with the plasmid expressing the fusion "Rv0569-Rv1813-Rv3407-Rv3478-Rv1807" either in an anchored form at the cell membrane (pTG18269) or cytoplasmic form (pTG18295). For comparative purposes, mice were also immunized with a mix of plasmids encoding the individual Mtb antigens included in the fusion (pTG18300 (Rv3407)+pTG18301 (Rv0569)+pTG18302 (Rv1807)+pTG18303 (Rv1813)+pTG18304

(Rv3478)) and with empty pGWiz as a negative control. Cellular immune response was evaluated 2 weeks following the last DNA injection by ELISpot IFNγ assays after ex vivo re-stimulation with the various peptide pools described in Materials and Methods.

Figure 8:
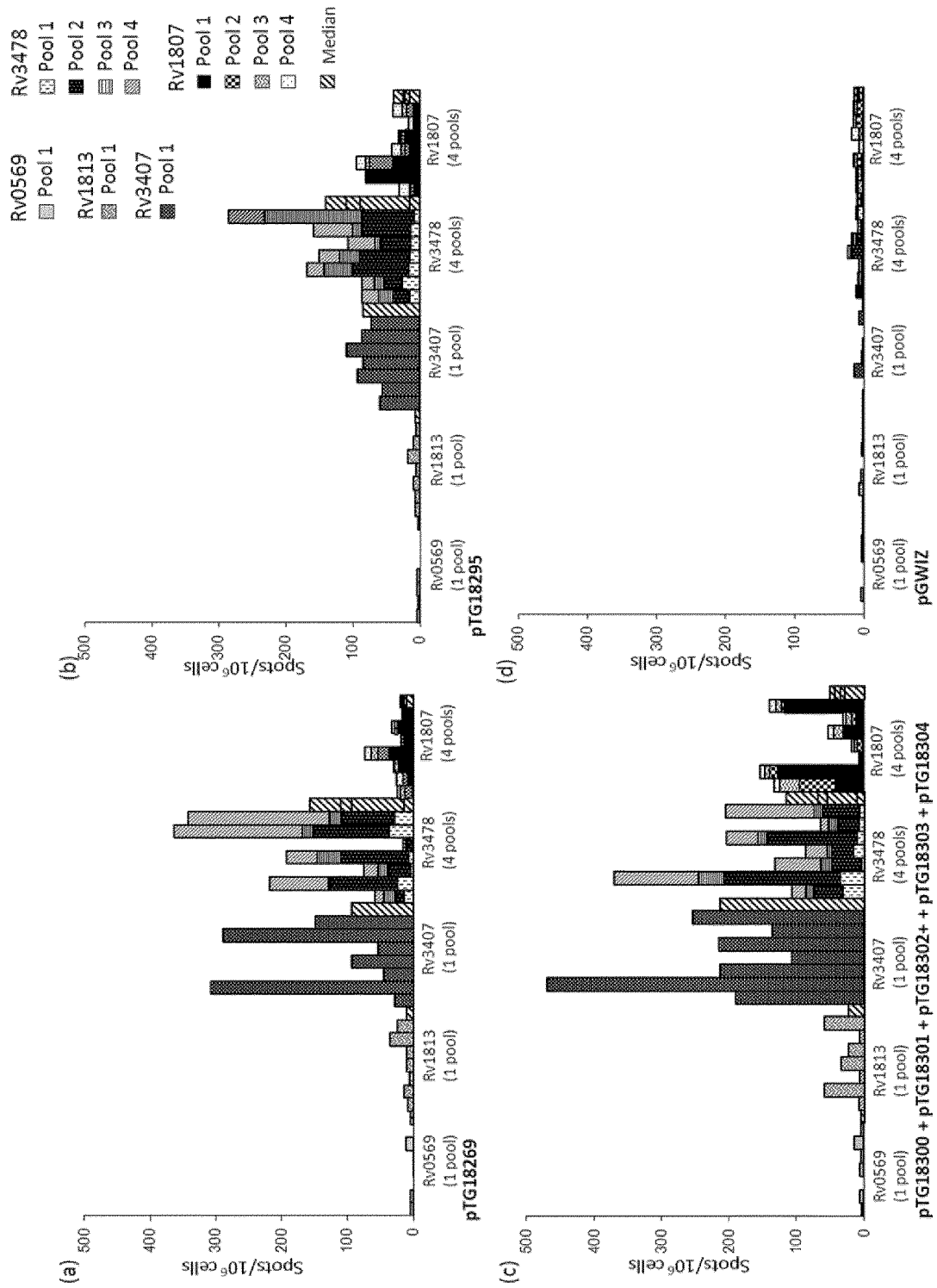
FIG. 8 illustrates IFNg-producing cells induced following immunization of animals with fusion-encoding plasmids pTG18269 (SS-Rv0569-Rv1813-Rv3407-Rv3478-Rv1807-TM.

As illustrated in FIG. 8, immunization with pTG18269 plasmid (expressing the anchored version of the Rv0569-Rv1813-Rv3407-Rv3478-Rv1807 fusion) resulted in a strong response specific for Rv3407 and Rv3478 antigens and to a lower extend for Rv1807 (FIG. 8a). Similar levels of IFNγ producing cells against these three antigens were obtained in mice immunized with pTG18295 (expressing the cytoplasmic version of the Rv0569-Rv1813-Rv3407-Rv3478-Rv1807 fusion) (FIG. 8b). The responses were within the same order in mice injected with the plasmid mix (FIG. 8c). On the other hand, no significant responses could be detected against Rv1813 and Rv0569 in all cases (FIGS. 8a, b and c). As expected, immunization with the empty plasmid did not rise any specific immune response (FIG. 8d).

Other strains of mice were also used for investigation of the anti Mtb antigen responses in order to cover different MHC haplotypes: BALB/c mice are H-2$^d$, C57BL/6 mice are H-2$^b$, CBA/J and C3H/HeN mice are H-2$^k$.

Mice were immunized three times at 2-week interval via intramuscular route with pTG18323 expressing the antigens from the latent phase "Rv2029-Rv2626-Rv1733-Rv0111" or with empty pGWiz as a negative control. Cellular immune response was evaluated 2 weeks following the last DNA injection by ELISpot IFNγ assays after ex vivo re-stimulation with the various peptide pools described in Materials and Methods section. As illustrated in FIG. 10, immunization of C3H/HeN mice with pTG18323 plasmid resulted in a strong immune response specific for Rv2029 (positive pool of peptides no 1), Rv2626 (positive pool no 2) and Rv1733 antigens (positive pool no 2) (FIG. 10a). Unspecific background response was detected following immunization with pGWiz and ex vivo re-stimulation with Rv0111 peptide pools (FIG. 10b), thus complicating the detection of anti-Rv0111 specific response following vaccination with pTG18323.

Immune responses specific for Rv2029, Rv2626 and Rv1733 antigens were also detected to similar levels as seen in H-2$^k$ CBA/J mice immunized with pTG18323. In contrast, in BALB/c mice, IFNγ producing cells were specifically detected only after re-stimulation with Rv2626 peptides while in C57BL/6 mice no signal was detected.

Overall, these results highlight the fact that the tested Mtb antigen fusion sequences are able to induce robust cell-based immune responses in different haplotype of mice.

5.5. Evaluation of the Immunogenicity Induced by Fusions Based on Biochemistry Rules.

BALB/c mice or C57BL/6 mice were immunized three times at 2-week interval via intramuscular route with plasmids coding for the fusion number 6, 8 or 14, designed according to biochemistry properties of Mtb antigens, i.e. pTG18270 (Ag85B-Rv2626-RpfB-Dhyb-Rv1733), pTG18272 (Ag85B-Rv2626-Rv1733) and pTG18324 (Rv2029-TB10.4-ESAT-6-Rv0111). For comparative purposes, mice were also immunized with empty pGWiz as negative control. Cellular immune response was evaluated 2 weeks following the last DNA injection by ELISpot IFNγ assays after ex vivo re-stimulation with the various peptide pools described in Materials and Methods section.

A strong cellular response specific of Ag85B and RpfB-Dhyb antigens was induced in both BALB/c and C57BL/6 mice immunized with pTG18270, whereas high level of IFNγ producing cells specific of Rv2626 were detected only in BALB/c mice. Immunization with pTG18272 resulted in activation of IFNγ producing cells specific of Ag85B in BALB/c mice and specific of Ag85B and Rv2626 antigens in C57BL/6 mice, but to a lower level compared to response induced by pTG18270. In mice immunized with pTG18324, high levels of IFNγ producing cells specific of TB10.4 and ESAT-6 antigens was detected, whereas IFNγ producing cells specific of Rv2029 and Rv0111 were also induced but to lower levels. As expected, immunization with the empty plasmid did not induce any specific immune response.

Overall, the tested fusions, designed according a biochemical-based rationale in order to increase stability and production of the fusions, display a good immunogenic response specific of the Mtb antigens from the different phases of infection.

5.6. Evaluation of the Anti-Rv1733 Humoral Response Induced by Mtb Antigen Fusions.

BALB/c mice were immunized three times at 3-week interval via intramuscular route with the plasmids expressing the fusion "Ag85B*-Rv2626-Rv1733*" (pTG18270) and the fusion "Ag85B*-Rv2626-RPFB-Dhyb*-Rv1733*" (pTG18272). For comparative purposes, mice were also immunized with a mix of plasmids encoding the individual Mtb antigens included in the fusion (pTG18310 (Ag85B*)+pTG18305 (Rv2626)+pTG18309 (Rv1733*)) and with empty pGWIZ as negative control. Humoral immune response was evaluated 2 weeks following the last DNA injection. Sera of immunized-mice were pooled and analysed by Western-blot. More specifically, 100 ng/lane of recombinant protein Rv1733 (produced in E. coli, see example no 8) were loaded on an acrylamide gel and immunodetection was performed with 1/200 diluted sera. As a result, specific detection on Rv1733 protein was observed with the sera of mice immunised with pTG18270, pTG18272 and the mix of plasmids encoding the individual Mtb antigens.

5.7. Evaluation of the Anti-Rv1813 Humoral Response Induced by Mtb Antigen Fusions.

BALB/c mice were immunized three times at 3-week interval via intramuscular route with the plasmid expressing the fusion "Rv0569-Rv1813-Rv3407-Rv3478-Rv1807" either in an anchored form at the cell membrane (SS/TM: pTG18269) or cytoplasmic form (pTG18295). For comparative purposes, mice were also immunized with a mix of plasmids encoding the individual Mtb antigens included in the fusion (pTG18300 (Rv3407)+pTG18301 (Rv0569)+pTG18302 (Rv1807)+pTG18303 (Rv1813)+pTG18304 (Rv3478)) and with empty pGWiz as a negative control. Humoral immune response was evaluated 2 weeks following the last DNA injection. Sera of immunized mice were pooled and analysed by Western-blot with 100 ng/lane of recombinant protein Rv1813 (produced in E. coli, see example no 8) loaded on an acrylamide gel. Immunodetection was performed with 1/200 diluted sera. As a result, Rv1813 protein was specifically detected with the sera of mice immunised with pTG18269 (encoding fusion in an anchored form at the cell membrane).

Example 6: Generation of Recombinant MVA Expressing Mtb Antigens

A total of 10 MVA vaccine candidates were engineered for expression of one or up to three Mtb fusions and expression of the various Mtb antigens was analyzed by Western Blot from cell lysates obtained from infected A549 cells.

6.1 Generation of Recombinant MVA by Phase of the TB Disease

Seven recombinant MVA candidates were engineered so as to contain one, two or three cassettes for expression of Mtb fusions representative of the various phases of TB disease. Fusion no 4 and fusion no 11 both contain active and resuscitation antigens (RPFB-Dhyb*-Ag85B*-TB10.4-ESAT6) either expressed anchored in the cell membrane (fusion no 4 equipped with N-terminal signal and C-terminal membrane anchoring peptides) or in the cytoplasm (fusion no 11 corresponds to the cytoplasmic version of fusion no 4). Fusion no 13 contains latent antigens (Rv2029*-Rv2626-Rv1733*-Rv0111*). Fusion no 5 and fusion no 9 both contain additional latent antigens (Rv056-Rv1813*-Rv3407-Rv3478-Rv1807) expressed at different cell location either anchored in the cell membrane (fusion no 5 contains N-terminal signal and C-terminal membrane anchoring peptides) or in the cytoplasm (fusion no 9).

All together, the seven MVA candidates are the followings:

- MVATG18355 contains the fusion no 13 under the control of p7.5K promoter.
- MVATG18364 contains the fusion no 13 under the control of p7.5K promoter and the fusion no 4 under the control of pH5R promoter.
- MVATG18365 contains the fusion no 13 under the control of p7.5K promoter and the fusion no 11 under the control of pH5R promoter.
- MVATG18376 contains the fusion no 13 under the control of p7.5K promoter, the fusion no 4 under the control of pH5R promoter and the fusion no 5 under the control of B2R promoter.
- MVATG18377 contains the fusion no 13 under the control of p7.5K promoter, the fusion no 11 under the control of pH5R promoter and the fusion no 5 under the control of B2R promoter
- MVATG18378 contains the fusion no 13 under the control of p7.5K promoter, the fusion no 4 under the control of pH5R promoter and the fusion no 9 under the control of B2R promoter.
- MVATG18379 contains the fusion no 13 under the control of p7.5K promoter, the fusion no 11 under the control of pH5R promoter and the fusion no 9 under the control of B2R promoter.

6.2 Generation of Recombinant MVA on Biochemical Rational

Three recombinant MVA candidates were engineered so as to contain two or three cassettes for expression of Mtb fusions designed relative to biochemical rationales. Fusion no 6 contains the following antigens Ag85B*-Rv2626-RPFB-Dhyb*-Rv1733* while fusion no 14 contains Rv2029*-TB10.4-ESAT6-Rv0111*. N-terminal signal peptides were added for both fusions while no TM domain were added since these fusions end with Rv0111 or Rv1733 which already contain membrane-anchoring peptides.

- MVATG18404 contains the fusion no 14 under the control of p7.5K promoter and the fusion no 6 under the control of pH5R promoter.
- MVATG18417 contains the fusion no 14 under the control of p7.5K promoter, the fusion no 6 under the control of pH5R promoter and the fusion no 5 under the control of B2R promoter.
- MVATG18418 contains the fusion no 14 under the control of p7.5K promoter, the fusion no 6 under the control of pH5R promoter and the fusion no 9 under the control of B2R promoter.

6.3 Western Blot Analysis of MVA-Expressed Mtb Antigens and Fusions

A549 cells were infected (MOI 1) with the various MVA candidates described above and expression products were analyzed by Western blot under the conditions described in Materials and Methods. Immunodetection was performed with antibodies specific of the various Mtb antigens described herein. Specifically, the sera obtained after immunization of rabbits (see Materials and Methods) were used for detection of Rv1733*, Rv2029*, Rv0569, Rv1807, Rv0111*, RPFB-Dhyb*, Rv1813*, Rv3407, and Rv3478 whereas commercial antibodies were used for the detection of ESAT6, Ag85B*, TB10.4 and Rv2626.

As a result, a band corresponding to the expected size was highlighted for all fusions whatever the recombinant MVA tested. More specifically, a band of approximately 98.4 kDa (expected size for fusion no 13) was detected following anti-Rv2626 and anti-Rv0111 immunodetection in the cell lysates originating from cells infected with MVATG18355, MVATG18364, MVATG18365, MVATG18376, MVATG18377, MVATG18378 and MVATG18379. A band of approximately 96.7 kDa (expected size for fusion no 4) and a band of approximately 87 kDa (expected size for fusion no 11) were detected following anti-ESAT6 immunodetection in the cell lysates originating from cells infected respectively with fusion no 4-containing MVATG18364, MVATG18376 and MVATG18378 and fusion no 11-containing MVATG18365, MVATG18377 and MVATG18379. Moreover a band of approximately 119.7 kDa (expected size for fusion no 5) and a band of approximately 109.9 kDa (expected size for fusion no 9) were detected following anti-Rv3407 immunodetection in the cell lysates originating from cells infected respectively with fusion no 5-containing MVATG18376 and MVATG18377 and fusion no 9-containing MVATG18378 and MVATG18379. Finally, a band of approximately 100.4 kDa (expected size for fusion no 6) and a band of approximately 87.5 kDa (expected size for fusion no 14) were detected in the cell lysates originating from cells infected with MVATG18404 following anti-Rv2626 and anti-Rv0111 immunodetection, respectively.

Moreover, in some case, additional fusion products were also observed. In particular, dimers were detected for fusion no 13 and fusion no 6 likely resulting of the ability of Rv2626 to form dimers resistant to reducing conditions. Concerning fusion no 13, expression of the entire fusion no 13 (expected size 98.4 kDa) was indeed detected but at low level. Major proteolytic products were observed with anti-Rv2626 (around 70 kDa) and with anti-Rv0111 (around 30 kDa), suggesting a proteolytic cleavage of the fusion no 13.

Similar level of expression was detected for fusions no 4 and no 11 which contain the same antigens (RPFB-Dhyb*-Ag85B*-TB10.4-ESAT6) but either membrane-anchored (fusion no 4) or cytoplasmic (fusion no 11). A higher band than the expected size (115 kDa instead of 96.7 kDa) was observed for fusion no 4, corresponding probably to N-glycosylated products. Minor proteolytic products were also detected for both fusions.

Similar level of expression was also revealed with anti-Rv3407 in cell lysates of MVA expressing fusions no 5 and no 9 (both corresponding to the fusion of Rv0569-Rv1813*-Rv3407-Rv3478-Rv1807 antigens but expressed in membrane anchored form (fusion no 5) or in cytoplasmic (fusion no 9)). A higher band than the expected size (120 kDa instead of 98.4 kDa) was present in fusion no 5-expressing cell lysates, corresponding probably to N-glycosylated products. On the other hand, fusion no 5 was very weakly detected with anti-Rv1807 antibody while it is not the case for the cytoplasmic version. It is assumed that Rv1807 specific epitopes might be inaccessible in the membrane-anchored fusion due to the adjacent TMR sequence.

Example 7: Evaluation of the Immunogenicity of MVA Candidate Vaccines Expressing Mtb Antigens 7.1 Evaluation of Immunogenicity of MVA Candidate Vaccines Expressing Mtb Antigens in BALB/c Mice BALB/c mice were immunised with MVATG18365 and MVATG18364 both expressing «Rv2029-Rv2626-Rv1733-Rv0111» (corresponding to fusion no 13) as well as «RpfB-Dhyb-Ag85B-TB10.4-ESAT6» (corresponding to fusion no 4 or no 11). In the fusion no 13, a SS domain is present at the N-terminus and Rv1733 and Rv0111 are expressed with a TM domain which should direct expression of the fusion to the cell surface. Fusion no 4 expressed by MVATG18364 contains both a SS and a TM domain whereas fusion no 11 (MVATG18365) does not and should theoretically retain a bcytoplasmic expression. Specific-cellular immune responses were evaluated one week after injection by IFNγ ELISpot assays following restimulation with peptide pools described herein. Mice were also immunized with empty MVA vector (MVATGN33.1) as a negative control.

As illustrated in FIGS. 11a and b respectively, both vectors MVATG18365 and MVATG18364 induced IFNγ positive responses specific of Rv2626, Rv0111, RpfB-Dhyb, Ag85B and TB10.4 in BALB/c mice when compared with MVATGN33.1 vector. These responses were systematically stronger with the MVATG18364 (anchored fusion) as compared with MVATG18365 (cytoplasmic fusion) except for Rv2626 showing similar responses. Weaker and sporadic responses specific of Rv2029, Rv1733 and ESAT6 were detected.

In addition, all recombinant MVA candidate vaccines described in "Example 6" section were injected in BALB/c mice and cellular immune responses specific of all Mtb antigens were assessed by IFNγ ELISpot assays as described in Materials and Methods section. A summary of the scope and intensity of responses induced by each MVA candidate in BALB/c mice is described in FIG. 12. All MVA vaccines, with Mtb antigens fusions designed according to phase of TB disease or biochemical rationale, were able to induce an IFNγ response specific of 12 out of 14 antigens in BALB/c mice. No positive cellular response specific of the two latent antigens, Rv1733 and Rv0569, was detected.

Figure 13:
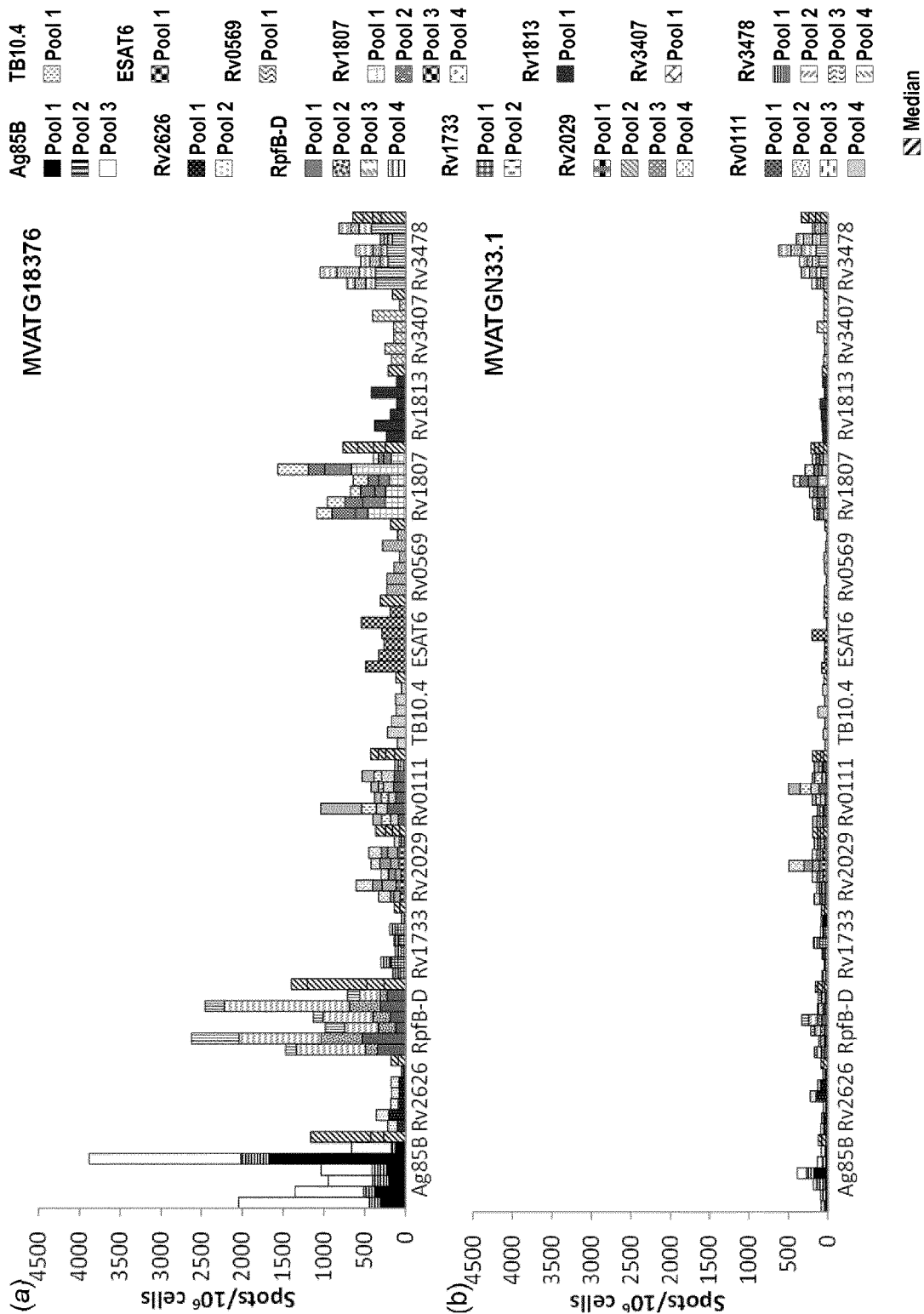
FIG. 13 illustrates the cellular immune response induced following immunization of transgenic HLA-A2 mice with (a) MVATG18376 (Rv2029-Rv2626-Rv1733-Rv0111+RpfB-Dhyb-Ag85B-TB10.4-ESA T6+Rv0569-Rv1813-Rv3407-Rv3478-Rv1807) or (b) the empty MVATGN33.1. IFNγ-producing cells were evaluated one week following the MVA injection by IFNγELISpot assays after ex vivo re-stimulation with specific peptide pools. Each bar represents response of individual mouse (6 mice/group).

7.2 Evaluation of Immunogenicity of MVA Candidate Vaccines Expressing Mtb Antigens in Transgenic HLA-A2 Mice As we have observed in the DNA-based studies, the mice haplotype has an influence on immunogenicity of the selected Mtb antigens (see section 5). In order to further analyze immunogenicity of Rv1733 and Rv0569 antigens induced by MVA candidates, transgenic mice expressing human MHC class I molecule, HLA-A2, were injected with recombinant MVAs expressing both antigens. Cellular immune response was evaluated one week after injection by IFNγ ELISpot assay after restimulation with the peptide pools described herein. Mice were also immunized with empty MVA vector (MVATGN33.1) as a negative control. Specifically, HLA-A2 mice were immunized with MVATG18376 or MVATG18378 vaccines expressing «Rv2029-Rv2626-Rv1733-Rv0111» (corresponding to fusion no 13), «RpfB-Dhyb-Ag85B-TB10.4-ESAT6» (corresponding to fusion no 4) as well as «Rv0569-Rv1813-Rv3407-Rv3478-Rv1807» (corresponding to fusion no 5 or no 9). In the fusion no 5 expressed by MVATG18376, SS and TM domains were expressed at the N-terminus and C-terminus part, respectively. FIG. 13 illustrates IFNγ response induced in HLA-A2 mice immunized with MVATG18376 vaccine. Immune response specific of 7 out of 14 antigens was detected (FIG. 13a). High levels of IFNγ-producing cells were detected when splenocytes were restimulated with peptides specific of RpfB-Dhyb and Ag85B antigens (1397 spots/$10^6$ cells and 1160 spots/$10^6$ cells, respectively). In contrast, lower levels of cellular responses specific of Rv1807, Rv1813, Rv3407 and ESAT6 were induced by the MVATG18376 vaccine. In addition, a low (1× cut-off median <2× cut-off, 186 spots/$10^6$ cells, FIG. 13a) but significant level of IFNγ-producing cells was detected when cells were restimulated with Rv0569-specific peptides as compared with signal detected with the MVATGN33.1 empty vaccine (36 spots/$10^6$ cells, FIG. 13b). Similar results were also induced in HLA-A2 mice vaccinated with the MVATG18378 candidate which induced additional weak responses specific of Rv0111 and TB10.4 antigens. IFNγ responses induced by both MVATG18376 and MVATG18378 vaccines are summarized in FIG. 15. Whatever the MVA candidate injected, no detectable response specific of Rv1733, Rv2029, Rv2626 and Rv3478 could be observed in HLA-A2 transgenic mice.

7.3 Evaluation of Immunogenicity of MVA Candidate Vaccines Expressing Mtb Antigens in C57Bl/6 Mice H-$2^b$ haplotype C57BL/6 mice were immunized with MVATG18377 or MVATG18379 vaccines expressing «Rv2029-Rv2626-Rv1733-Rv0111» (corresponding to fusion no 13), «RpfB-Dhyb-Ag85B-TB10.4-ESAT6» (corresponding to fusion no 11) as well as «Rv0569-Rv1813-Rv3407-Rv3478-Rv1807» (corresponding to fusion no 5 or no 9) in order to demonstrate immunogenicity of Rv0569 and Rv1733 antigens. Cellular immune response was evaluated one week after injection by IFNγ ELISpot assays after restimulation with the peptide pools described herein. Mice were also immunized with empty MVA vector (MVATGN33.1) as a negative control. Cellular IFNγ responses are summarized in FIG. 15. Both MVA vaccines were able to trigger strong immune response specific of Rv1807, RpfB-Dhyb, Rv3478, Ag85B and ESAT6 antigens (ranging from 92 to 861 spots/$10^6$ cells) while a positive IFNγ response specific of TB10.4 and Rv0569 antigens was only detected in mice immunized with MVATG18379 candidate (78 and 58 spots/$10^6$ cells, respectively). No positive response specific of Rv1733, Rv2029, Rv2626, Rv0111, Rv1813 and Rv3407 was detected in immunized C57BL/6 mice.

Figure 14:
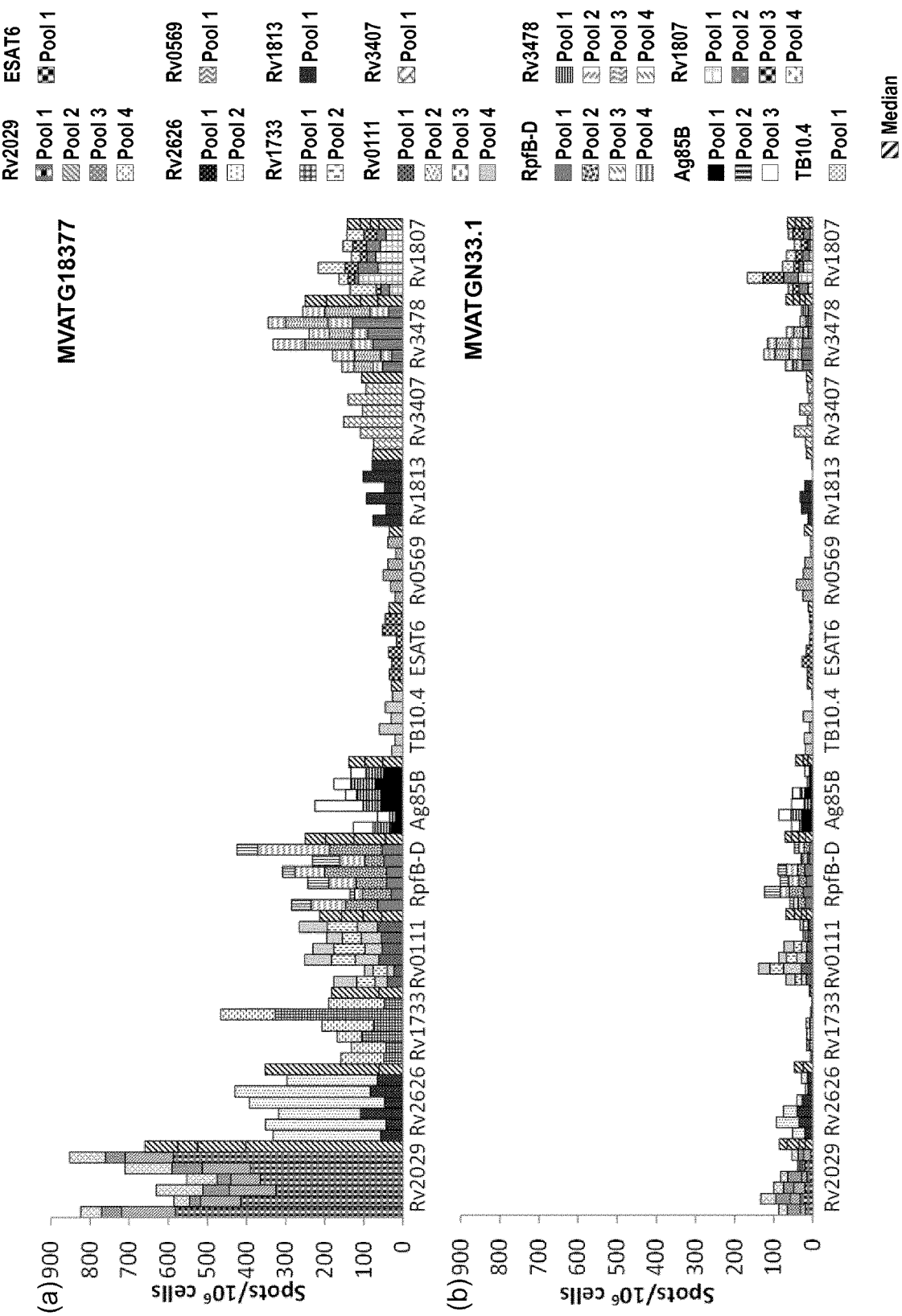
FIG. 14 illustrates the cellular immune response induced following immunization of C3H/HeN mice with (a) MVATG18377 (Rv2029-Rv2626-Rv1733-Rv0111+RpfB-Dhyb-Ag85B-TB10.4-ESAT6 W/O SS/TM+Rv0569-Rv1813-Rv3407-Rv3478-Rv1807) or (b) the empty MVATGN33.1. IFNγ-producing cells were evaluated one week following the MVA injection by IFNγELISpot assays after ex vivo re-stimulation with specific peptide pools. Each bar represents response of individual mouse (6 mice/group).

7.4 Evaluation of Immunogenicity of MVA Candidate Vaccines Expressing Mtb Antigens in C3H/HeN Mice As immunogenicity specific of Rv1733 has been demonstrated in H-$2^k$ haplotype C3H/HeN mice vaccinated with plasmids (see section 5.4), MVATG18376, MVATG18378, MVATG18377 and MVATG18379 expressing fusions containing the Rv1733 protein were injected to this mouse strain. Cellular immune response was evaluated one week after injection by IFNγELISpot assays after restimulation with the peptide pools described herein. Mice were also immunized with empty MVATGN33.1 vector as a negative control. As illustrated in FIG. 14, MVATG18377 vaccine induced IFNγ responses in C3H/HeN mice as compared with MVATGN33.1. High levels of IFNγ-producing cells were detected upon splenocytes restimulation with Rv2029 and Rv2626 peptides (660 and 353 spots/$10^6$ cells, respectively). A low cellular immune response specific of RpfB-Dhyb, Rv1813, Rv3407 and Rv3478 antigens, ranging from 78 to 250 spots/$10^6$ cells, was also induced in immunized C3H/

HeN mice. As demonstrated in DNA-vaccinated C3H/HeN mice, Rv1733-specific IFNγ response (183 spots/$10^6$ cells) was triggered in this mouse strain as compared with signals resulting from mice injected with empty MVATGN33.1 vaccine (9 spots/$10^6$ cells, FIG. 14b). Unspecific background response was detected following immunization with MVATGN33.1 and ex vivo restimulation with Rv0111, Ag85B and Rv1807 peptide pools (FIG. 14b), rendering difficult the detection of response specific of these antigens following vaccination with MVATG18377.

In addition to MVATG18377, immune responses induced by MVATG18376, MVATG18378 and MVATG18379 in C3H/HeN mice are illustrated in FIG. 15. Among the four MVA candidates tested, MVATG18377 was the most immunogenic (7 out of 14 antigens). MVATG18376 and MVATG18378 induced cellular immune responses specific of only 2 (Rv2029 and Rv2626) out of 14 antigens, while MVATG18379 was able to trigger response to not only both antigens but also Rv1733. MVATG18377 and MVATG18379 express the same fusion proteins except the fusion «Rv0569-Rv1813-Rv3407-Rv3478-Rv1807». In MVATG18377, SS and TM domains are expressed at the N-terminus and C-terminus part respectively of fusion no 5 while in MVATG18379 both domains are not present. 3 out of 5 antigens present in this fusion were immunogenic in MVATG18377, while none was in MVATG18379. These results show that addressing fusion protein to cell membrane improve their immunogenicity.

Overall, immunization with MVA vectors as well as with DNA plasmids leads to induction of strong and specific cellular responses targeting all Mtb antigens included in the fusions described in the present application. Humoral immune responses specific of two tested antigens were also detected in DNA-immunized mice. As with DNA plasmids, membrane-anchorage of the MVA-expressed Mtb fusions improves to some extent the level of induction of specific immune responses.

Example 8: Production and Purification of the Mtb Antigens 8.1 Optimal Conditions for Biomass Production of the Selected Mtb Antigens Four E. coli strains have been tested for the expression of the individual Mtb antigens as well as different culture conditions (e.g. temperature).

These assays highlight that all the 14 selected antigens could be expressed at least in one bacterial strain at one defined temperature but significant differences were observed from one Mtb antigen to another. Indeed, some Mtb antigens could be easily produced in various E. coli strains and whatever the culture conditions (e.g. Rv0111, Rv0569, Rv1807, Rv2029, Rv2626, RpfB-D fusion) while other antigens require very specific host cells and conditions (e.g. Rv1733, Rv1813, TB10-4). On the other hand, high expression levels could be obtained for most of Mtb antigens in the different E. coli strains except Rv3407, Ag85B and Rv1813 expressed at lower but detectable levels. Moreover, certain Mtb antigens are produced as soluble material (e.g. Rv2626, Rv3407 and Ag85B that could be collected directly from cell lysate supernatants) while others are in insoluble material (e.g. RPFB-D, Rv0111, Rv1733, Rv2029, Rv3478, Rv1807, ESAT6 and TB10.4 that are collected from the pellet after cell lysis). Interestingly, Rv0569 is soluble when produced from transformed B121 cells cultured at 18° C. and both in soluble and insoluble material (in supernatant and pellet after lysis) when the B121 cells are cultured at 37° C.

8.2 Purification of the Mtb Antigens

As described in Materials and Methods, Mtb antigens were purified by IMAC chromatography on nickel columns, eventually followed by gel filtration columns.

Representative purification assays are shown for Rv2626 (purified from soluble material produced in C41 (DE3) cells at 37° C.), RPFB-D fusion (denatured RpfB-D purified from solubilized inclusion bodies produced in B121 (DE3) at 37° C.) and for TB10.4 (purified from soluble and insoluble material produced in C41 (DE3) cells at 37° C. The eluted fractions were assayed on SDS-PAGE as shown in FIGS. 9a, b and c, respectively.

As illustrated in FIG. 9A, the Rv2626 purified pool did not show any visible contaminant. A major band was seen at the expected Rv2626 molecular weight as well as a minor band (the so-called band B) which has been identified by MS as Rv2626. Rv2626 is known to form dimers that are partially resistant to denaturation and reduction. Therefore, it is assumed that minor band B corresponds to the dimeric form of Rv2626.

When visualized on SDS-PAGE (lanes 1 to 8 represent intermediate purification fractions and lanes 9 to 11 5, 10 and 15 µL of purified pool), the RPFB-Dhyb purified pool did not show any visible contaminant (see FIG. 9B).

TB10-4 was purified in denaturing conditions followed by a final step in native conditions. As illustrated in FIG. 9C, the gel analysis of the purified pool did not show any visible contaminant (lanes 2 to 6 represent intermediate purification fractions and lanes 7 to 9 1, 3 and 6 µL of purified pool).

In the three cases, endotoxin levels were measured in the purified pools and showed to be at a maximum level of 10 EU/mg protein.

Therefore, the three proteins have been purified with acceptable amount, purity and endotoxin level.

As a summary, the present invention provides an optimized combination of Mtb antigens. 14 Mtb antigens were selected after extensive bibliographic, data mining scoring and biochemical in silico analyses and cloned in plasmid vectors either individually or in the form of fusions. As demonstrated by Western blotting, all fusions were expressed at high levels and detected at the correct expected size following immunodetection with a series of antibodies directed against tags present at the N and C termini or against each Mtb antigen present in the fusion. Immunization assays in BALB/c mice support the immunogenic potential of the selected Mtb antigen combinations and fusions for inducing T cell responses.

Moreover, the selected Mtb antigens (RpfB and RpfD in fusion) were individually produced in bacteria by recombinant means. Conditions for expression in E. coli were optimized by studying criteria such as bacterial strains and culture conditions (e.g. growth temperature). All proteins have been successfully expressed and produced at a litter scale.

Example 9: Evaluation of Therapeutic Efficacy of Mtb Antigen-Containing Vaccines Against *Mycobacterium tuberculosis* Infection in Mice Therapeutic efficacies of three Mtb-expressing MVA candidates, MVATG18364, MVATG18376 and MVATG18377 were investigated in a therapeutic setting co-administered with antibiotics in mice that were previously infected with Mtb strain H37Rv. As negative control, MVATGN33.1 was also injected in one group. Bacterial load was evaluated in spleens collected from the treated mice at the end of antibiotic treatment (at week 15 post-infection) and 6 weeks after (at week 21 post-infection). Groups of mice, drug regimen and immunization schedule are described in Table 5.

TABLE 5

| Group | N mice | Treatment | Pre-treat Week 0 Aerosol challenge | CFU (day 1, Week 6) | INH/RIF Treatment (week 6 to week 15) | | | CFU (relapse) Week 21 |
|---|---|---|---|---|---|---|---|---|
| | | | | | MVA Week 10 | MVA Week 14 | CFU Week 15 | |
| 1 | 5 | None | 5 | 5 | | | | |
| 2 | 20 | INH/RIF | 20 | — | | | 5 | 15 |
| 3 | 20 | INH/RIF + MVATG18376 | 20 | — | 20 | 20 | 5 | 15 |
| 4 | 20 | INH/RIF + MVATG18377 | 20 | — | 20 | 20 | 5 | 15 |
| 5 | 20 | INH/RIF + MVATG18364 | 20 | — | 20 | 20 | 5 | 15 |
| 6 | 20 | INH/RIF + MVATGN33.1 | 20 | | 20 | 20 | 5 | 15 |

Six weeks post-Mtb infection and before starting chemotherapy and MVA immunization, the mycobacteria developed in the spleen of all mice groups (2.64 $\log_{10}$ total cfu). As expected, mycobacterial load decreased during chemotherapy treatment. In group 2 treated only with chemotherapy, the Mtb level decreased progressively to reach 1.18 $\log_{10}$ total cfu at week 15 and 0.70 $\log_{10}$ total cfu at week 21. Interestingly, at week 15, the mycobacterial loads were lower in mice co-treated with antibiotics and Mtb antigens-expressing MVA (0.70 $\log_{10}$ total CFU at week 15 in groups 3-5) than in mice treated with antibiotics only (group 2) and with the control empty MVA in combination with antibiotics (group 6), suggesting that Mtb-expressing MVA contributed to a stronger antibacterial effect. It is noteworthy that 6 weeks after the end of treatment (week 21), mycobacteria did not proliferate and loads were controlled in MVA-vaccinated mice (ranging from 0.70 to 0.85 $\log_{10}$ total cfu) at a level similar to the one observed in antibiotics therapy alone-treated mice. As control, the empty MVATGN33.1 vector combined with drugs therapy did not induce any anti-mycobacterial effect better than antibiotic regimen only at week 15 and week 21.

The invention claimed is:

1. An immunogenic combination comprising a viral vector or a combination of two or more viral vectors comprising one or more nucleic acid molecules encoding at least 5 antigens, wherein said antigens are independently obtained from a *Mycobacterium* species and wherein said at least 5 mycobacterial antigens are selected from the group consisting of ESAT-6 (Rv3875), TB10.4 (Rv0288), Ag85B (Rv1886), RpfB, RpfD, Rv0111, Rv0569, Rv1733c, Rv1807, Rv1813, Rv2029c, Rv2626, Rv3407, and Rv3478.

2. The immunogenic combination according to claim 1, wherein the mycobacterial antigens are obtained from a *Mycobacterium* species of the tuberculosis complex selected from the group consisting of *M. tuberculosis* (Mtb), *M. bovis*, *M. bovis* BCG, *M. africanum*, *M. canetti*, *M. caprae*, and *M. microti*.

3. The immunogenic combination according to claim 1, wherein said immunogenic combination encodes mycobacterial antigens from at least 2 different infection phases selected from the group consisting of active, resuscitation, and latent phases.

4. The immunogenic combination according to claim 3, wherein said immunogenic combination is multiphasic encoding at least one antigen from the active infection phase, at least one antigen from the resuscitation infection phase, and at least one antigen from the latent infection phase.

5. The immunogenic combination according to claim 3, wherein said immunogenic combination expresses at least ESAT-6 (Rv3875), Ag85B (Rv1886), and TB10.4 (Rv0288).

6. The immunogenic combination according to claim 3, wherein said antigen(s) of the latent phase is/are selected from the group consisting of Rv0111, Rv0569, Rv1733, Rv1807, Rv1813, Rv2029, Rv2626, Rv3407, and Rv3478.

7. The immunogenic combination according to claim 3, wherein said immunogenic combination expresses at least RpfB and RpfD.

8. The immunogenic combination according to claim 1, wherein the at least 5 mycobacterial antigens are selected from polypeptides comprising an amino acid sequence at least 80% homologous or identical to any one of SEQ ID NO: 1-24.

9. The immunogenic combination according to claim 1, wherein said immunogenic combination encodes the mycobacterial antigens in the form of separate polypeptides or in the form of one or more fusion polypeptides or both in the form of separate antigen(s) and fusion(s) polypeptides.

10. A vector, or a combination of vectors, comprising one or more nucleic acid molecule(s) encoding a fusion polypeptide comprising at least two mycobacterial antigens selected from the group consisting of ESAT-6 (Rv3875), TB10.4 (Rv0288), Ag85B (Rv1886), RpfB, RpfD, Rv0111, Rv0569, Rv1733c, Rv1807, Rv1813, Rv2029c, Rv2626, Rv3407, and Rv3478.

11. The vector of claim 1 or claim 10, wherein said vector is a viral vector selected from the group consisting of retrovirus, adenovirus, adenovirus-associated virus (AAV), poxvirus, herpes virus, measles virus, foamy virus, alphavirus, and vesicular stomatis virus.

12. The vector of claim 11, wherein said vector is a E1-defective adenoviral vector or a poxvirus vector selected from the group consisting of fowlpox, canarypox, and vaccinia virus vector.

13. The vector of claim 12, wherein said vaccinia virus vector is selected from Copenhagen, Wyeth, NYVAC, and modified Ankara (MVA) strains.

14. The vector according to claim 10, which is in the form of infectious virus particles.

15. A composition comprising at least one of the immunogenic combinations of claim 1, the vector of claim 10, or any combination thereof.

16. The composition of claim 15, which further comprises a pharmaceutically acceptable vehicle.

* * * * *